(12) United States Patent
Marugan et al.

(10) Patent No.: US 9,452,973 B2
(45) Date of Patent: Sep. 27, 2016

(54) MODULATORS OF THE RELAXIN RECEPTOR 1

(71) Applicants: The United States of America, as Represented by the Secretary, Department of Health and Human Service, Washington, DC (US); The Florida International University Board of Trustees, Miami, FL (US)

(72) Inventors: Juan Jose Marugan, Gaithersburgh, MD (US); Jingbo Xiao, Rockville, MD (US); Marc Ferrer-Alegre, Potomac, MD (US); Catherine Chen, Germantown, MD (US); Noel Southall, Potomac, MD (US); Wei Zheng, Potomac, MD (US); Alexander Agoulnik, Miami, FL (US); Irina Agoulnik, Miami, FL (US)

(73) Assignees: THE UNITED STATES OF AMERICA, AS REPRESENTED BY THE SECRETARY DEPARTMENT OF HEALTH AND HUMAN SERVICES, Washington, DC (US); THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 14/398,830

(22) PCT Filed: Mar. 15, 2013

(86) PCT No.: PCT/US2013/032231
§ 371 (c)(1),
(2) Date: Nov. 4, 2014

(87) PCT Pub. No.: WO2013/165606
PCT Pub. Date: Nov. 7, 2013

(65) Prior Publication Data
US 2015/0119426 A1    Apr. 30, 2015

Related U.S. Application Data

(60) Provisional application No. 61/642,986, filed on May 4, 2012.

(51) Int. Cl.
*A61K 31/166* (2006.01)
*C07C 233/64* (2006.01)
(Continued)

(52) U.S. Cl.
CPC .......... *C07C 237/42* (2013.01); *C07C 233/63* (2013.01); *C07C 235/64* (2013.01); *C07C 237/30* (2013.01); *C07C 237/40* (2013.01); *C07C 255/57* (2013.01); *C07C 255/60* (2013.01); *C07C 257/04* (2013.01); *C07C 257/18* (2013.01); *C07C 271/28* (2013.01); *C07C 311/29* (2013.01); *C07C 317/36* (2013.01); *C07C 317/40* (2013.01); *C07C 317/44* (2013.01); *C07C 323/42* (2013.01); *C07C 323/62* (2013.01); *C07D 209/08* (2013.01); *C07D 209/46* (2013.01); *C07D 213/75* (2013.01); *C07D 213/79* (2013.01); *C07D 213/80* (2013.01); *C07D 213/81* (2013.01); *C07D 213/82* (2013.01); *C07D 235/06* (2013.01); *C07D 235/18* (2013.01); *C07D 261/18* (2013.01); *C07D 295/088* (2013.01); *C07D 295/135* (2013.01); *C07D 295/205* (2013.01); *C07D 307/52* (2013.01); *C07D 307/68* (2013.01); *C07D 317/66* (2013.01); *C07D 317/68* (2013.01); *C07D 333/20* (2013.01); *C07D 333/38* (2013.01); *C07D 333/40* (2013.01); *C07D 403/10* (2013.01); *C07D 487/04* (2013.01); *C07C 2101/02* (2013.01); *C07C 2101/04* (2013.01); *C07C 2101/10* (2013.01); *C07C 2101/14* (2013.01); *C07C 2101/16* (2013.01); *C07C 2101/18* (2013.01); *C07C 2102/08* (2013.01); *C07C 2103/74* (2013.01)

(58) Field of Classification Search
USPC ................................ 514/616; 564/155, 154
See application file for complete search history.

(56) References Cited

U.S. PATENT DOCUMENTS

| 5,166,191 A | 11/1992 | Cronin et al. |
| 2002/0120007 A1 | 8/2002 | Beight et al. |

(Continued)

FOREIGN PATENT DOCUMENTS

| EP | 1839655 A1 | 10/2007 |
| WO | 9809630 A1 | 3/1998 |

OTHER PUBLICATIONS

Gelling et al., "Pyridopyrimidines. Part V. Syntheses and Properties of Pyrido[3,4-d]-pyrimidin-4(3H)-ones and—pyrimidine-2,-4-(1H,3H)-diones", Journal of the Chemical Society (C), No. 6, Jan. 1, 1969, pp. 931-934.

(Continued)

*Primary Examiner* — Charanjit Aulakh
(74) *Attorney, Agent, or Firm* — Cantor Colburn LLP

(57) ABSTRACT

Disclosed are modulators of the human relaxin receptor 1, for example, of formula (I), wherein A, $R^1$, and $R^2$ are as defined herein, that are useful in treating mammalian relaxin receptor 1 mediated facets of human health, e.g., cardiovascular disease. Also disclosed is a composition comprising a pharmaceutically suitable carrier and at least one compound of the disclosure, and a method for therapeutic intervention in a facet of mammalian health that is mediated by a human relaxin receptor 1.

18 Claims, 9 Drawing Sheets

(51) Int. Cl.

| | |
|---|---|
| C07C 237/42 | (2006.01) |
| C07C 255/57 | (2006.01) |
| C07D 213/75 | (2006.01) |
| C07C 255/60 | (2006.01) |
| C07C 257/18 | (2006.01) |
| C07D 213/79 | (2006.01) |
| C07D 213/80 | (2006.01) |
| C07D 213/81 | (2006.01) |
| C07D 213/82 | (2006.01) |
| C07C 271/28 | (2006.01) |
| C07D 317/68 | (2006.01) |
| C07D 333/20 | (2006.01) |
| C07D 333/38 | (2006.01) |
| C07D 333/40 | (2006.01) |
| C07C 311/29 | (2006.01) |
| C07D 235/18 | (2006.01) |
| C07C 323/62 | (2006.01) |
| C07C 257/04 | (2006.01) |
| C07C 233/63 | (2006.01) |
| C07D 261/18 | (2006.01) |
| C07C 235/64 | (2006.01) |
| C07C 237/30 | (2006.01) |
| C07C 237/40 | (2006.01) |
| C07D 209/08 | (2006.01) |
| C07D 209/46 | (2006.01) |
| C07D 295/088 | (2006.01) |
| C07D 295/205 | (2006.01) |
| C07D 307/52 | (2006.01) |
| C07D 307/68 | (2006.01) |
| C07D 317/66 | (2006.01) |
| C07D 235/06 | (2006.01) |
| C07D 403/10 | (2006.01) |
| C07D 487/04 | (2006.01) |
| C07D 295/135 | (2006.01) |
| C07C 317/36 | (2006.01) |
| C07C 317/40 | (2006.01) |
| C07C 317/44 | (2006.01) |
| C07C 323/42 | (2006.01) |

(56) References Cited

U.S. PATENT DOCUMENTS

| | | |
|---|---|---|
| 2003/0195223 A1 | 10/2003 | Beight et al. |
| 2008/0206287 A1 | 8/2008 | Reed et al. |
| 2011/0144135 A1 | 6/2011 | Chong et al. |
| 2011/0294807 A1 | 12/2011 | Hansen et al. |

OTHER PUBLICATIONS

Haugaard-Kedstrom et al., "Design, Synthesis, and Characterization of a Single-Chain Peptide Antagonist for the Relaxin-3 Receptor RXFP3", Journal of the American Chemical Society, vol. 133, No. 13, Apr. 6, 2011, pp. 4965-4974.

International Search Report of the International Searching Authority for International Application No. PCT/US2013/032231; International Filing Date: Mar. 15, 2013; Date of Mailing Jul. 10, 2013; 4 Pages.

Kakuta et al., "Cyclooxygenase-1-Selective Inhibitors Are Attractive Candidates for Analgesics That Do Not Cause Gastric Damage. Design and in Vitro/in Vivo Evaluation of a Benzamide-Type Cyclooxygenase-1 Selective Inhibitor", J. Med. Chem.. (2008), 51, pp. 2400-2411.

Kozic et al., "Synthesis and in vitro Antimycobacterial Activity of 2-Methoxybenzanilides and their Thioxo Analogues", European Journal of Medicinal Chemistry, 56 (2012), pp. 387-395.

Mendel et al., "Anthranilamide Inhibitors of Factor Xa", Bioorganic & Medicinal Chemistry Letters, 17 (2007), pp. 4832-4836.

Ruger et al., "Synthesis of Tetra-Substituted Pyrazoles" Tetrahedron, 68 (2012), pp. 8823-8829.

Wiley et al., "Structure-Based Design of Potent, Amdine-Derived Inhibitors of Factor Xa: Evaluation of Selectivity Anticoagulant Activity, and Antithrombotic Activity", J. Med. Chem., 43, (2000), pp. 883-899.

Written Opinion of the International Searching Authority for International Patent Application No. PCT/US2013/032231; International Filing Date: Mar. 15, 2013; Date of Mailing: Jul. 10, 2013; 8 Pages.

International Preliminary Report on Patentability for International Application No. PCT/US2013/032231; International Filing Date: Mar. 15, 2013; Date of Mailing: Nov. 13, 2014; 8 pages.

Van Der Westhuizen et al.; "Relaxin Receptors—New Drug Targets for Multiple Disease States"; Current Drug Targets, vol. 8, No. 1; 2007; pp. 91-104.

Xiao et al., "Identification and optimization of small-molecule agonists of the human relaxin hormone receptor RXFP1"; Nat. Commun., 4:1953; doi: 10.1038/ncomms2953 (2013).

MODULATORS OF THE RELAXIN RECEPTOR 1

CROSS-REFERENCE TO RELATED APPLICATIONS

This Application is a U.S. National Stage Application of PCT/US2013/032231 filed Mar. 15, 2013 which claims priority to U.S. Provisional Application No. 61/642,986, filed May 4, 2012 both of which are incorporated herewith by reference in their entirety.

STATEMENT OF GOVERNMENT SUPPORT

This invention was made in part with government support from the National Institutes of Health. The government has certain rights in this invention.

BACKGROUND

The peptide hormone relaxin was discovered in 1926 as a hormone of pregnancy, due to its effects to relax pubic ligaments and soften the cervix to facilitate parturition (Hisaw, F. L., *Proc. Soc. Exp. Biol. Med.* 1926, 23(8), 661-663; Fevold. H. L. et al., *J. Am. Chem. Soc.* 1930, 52(8), 3340-3348). Since then, it has been shown that blood concentrations of relaxin rise during the first trimester of pregnancy, promoting cardiovascular and renal adjustments to meet the increased nutritional demands of the growing fetus, and the elevated requirements for renal clearance of metabolic wastes (Baylis. C., *Am. J. Kidney Dis.* 1999, 34, 1142-4). Relaxin induces a 20% increase in cardiac output, 30% decrease in systemic vascular resistance, 30% increase in global arterial compliance, and 45% increase in renal blood flow during pregnancy (Schrier, R. W. et al., *Am. J. Kidney Dis.* 1987, 9, 284-9). Numerous clinical and non-clinical studies using this hormone have now recapitulated these cardiovascular effects in both males and females, demonstrating the pharmacological utility of relaxin in modulating cardiovascular and renal functions in humans.

The X-ray crystal structure of relaxin at 1.5 Å resolution was reported for the physiologically active form of the human hormone in 1991. The physiological effects of relaxin are mediated by its interaction with a G protein-coupled receptor (RXFP1) leading to the modulation of several signal transduction pathways. Activation of RXFP1 by relaxin induces: 1) up-regulation of the endothelin system which leads to vasodilation; 2) extracellular matrix remodeling through regulation of collagen deposition, cell invasiveness, proliferation, and overall tissue homeostasis; 3) a moderation of inflammation by reducing levels of inflammatory cytokines, such as TNF-α and TGF-β; and 4) angiogenesis by activating transcription of VEGF. The understanding of the biological effects of RXFP1 activation by relaxin has led to the evaluation of relaxin as a pharmacologic agent for the treatment of patients with acute heart failure (AHF), pre-eclampsia, and hypertensive disease. In addition, several clinical trials studied the therapeutic role of relaxin in treatment of scleroderma, cervical ripening, fibromyalgia, and orthodontics, given its function as anti-inflammatory and extracellular matrix remodeler.

The latest statistics indicate that 1 of every 2.9 deaths in the United States is due to cardiovascular disease (CVD) (Roger, V. L. et al., *Circulation* 2011, 123(4), 459-463). Each year, ~795,000 people experience a new or recurrent stroke, and 1 in 9 death certificates in the United States mention heart failure. In addition, 33.5% of US adults over 20 years of age have hypertension. These statistics clearly illustrate the limitations of current therapies to address CVD in general and acute heart failure (AHF) in particular. The significant contribution of vascular dysfunction to the pathophysiology of AHF has more recently been recognized. These patients are characterized by preserved or elevated systolic blood pressure and increased vascular stiffness with less fluid overload. They are more likely to be elderly and female. Large-scale registry studies suggest that patients with vascular dysfunction causing AHF represent the majority of patients, and that this may have been underappreciated during previous development of new therapies.

Therapeutically, there is a great medical need for better approaches to treat heart failure. Currently, there are two major methodologies: a) surgery and medical devices: coronary bypass surgery, heart valve repair or replacement, implantable cardioverter-defibrillators (ICDs), heart pumps (left ventricular assist devices, or LVADs), or heart transplant; b) medications: angiotensin-converting enzyme (ACE) inhibitors, angiotensin II receptor blockers (ARBs), digoxin (lanoxin), beta blockers and aldosterone antagonists. Importantly, none of these approaches are able to address the development of scar heart tissue after severe heart failure, or repair it after damage. In that sense the anti-fibrotic and remodeling properties of relaxin, together with its capacity to normalize blood pressure, increase blood and renal flow, while it promotes decongestion and vascular compliance, seem to be ideal for treating these conditions. Clinical data agrees with this theory (Teichman S. L. et al, *Curr. Heart Failure Rep.* 2010, 7, 75-82). Relaxin relieves systemic and renal vasoconstriction and increases vascular compliance, including normalization of high blood pressure, reduction of pulmonary capillary wedge pressure, increase of cardiac output, increase renal blood flow, natriuresis, and decongestion. In addition, animal pharmacology data indicate that relaxin hormone has anti-inflammatory and cardiac protection effects, including reduction of myocardial ischemia, reduction of reperfusion injury, increase of wound healing, and reduction of ventricular fibrosis.

Recombinant relaxin hormone has produced excellent responses in clinical trials for treatment of heart failure and is about to reach commercialization. However, administration of the peptide is difficult in chronic settings. In view of the foregoing, there is an unmet need for new small molecule agonists of the RXFP1 receptor.

SUMMARY

The invention provides a compound of the formula (I):

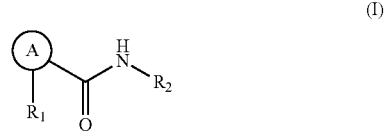

wherein A is 1,2-phenylenyl, 1,2-heteroarylenyl, 1,2-heterocyclyl, or —$CH_2CH_2$—, wherein the 1,2-phenylenyl, 1,2-heteroarylenyl, and 1,2-heterocyclyl are optionally substituted with one or more substituents independently selected from halo, $CF_3$, alkyl, alkyloxy, haloalkyl, haloalkoxy, —$SR^7$, —$SOR^7$, —$SO_2R^7$, —$SCF_3$, and $SO_2CF_3$, $R_1$ is —$NHCOR_3$, $R_4$, —$NHR_5$, or —$OR_6$, $R_2$ is alkyl, cycloalkyl, heteroarylalkyl, orphenyl, which are optionally substituted with one or more substituents independently selected from halo, $CF_3$, $C_1$-$C_{10}$ alkyl, $C_2$-$C_{10}$ alkenyl, $C_1$-$C_{10}$ alkyloxy, trihalo $C_1$-$C_{10}$ alkyl, perhalo $C_1$-$C_{10}$ alkyl, trihalo $C_1$-$C_{10}$ alkyloxy, perhalo $C_1$-$C_{10}$ alkyloxy, aryl, trihaloalkylaryl, perhaloalkylaryl, heterocyclylalkyl, —$SR^7$, —$SOR^7$, —$SO_2R^7$, —$SCF_3$, —$NO_2$, —CN, and —$SO_2CF_3$, $R_3$ is alkyl, cycloalkyl, bicycloalkyl, tricycloalkyl, aryl, heteroaryl, arylalkyl, or phenyl, which are optionally substituted with one or more substituents independently selected from t halo, $CF_3$, $C_1$-$C_{10}$ alkyl, $C_2$-$C_{10}$ alkenyl, $C_1$-$C_{10}$ alkyloxy, $C_1$-$C_{10}$ haloalkyl, $C_1$-$C_{10}$ haloalkoxy, —$SR^7$, —$SOR^7$, —$SO_2R^7$, —$SCF_3$, —$NO_2$, —CN, and —$SO_2CF_3$, $R_4$ is phenyl optionally substituted with alkyloxy, haloalkoxy, arylalkyl, or arylalkyloxy, $R_5$ is hydrogen, alkyl, alkylaryl, aryl, alkylcycloalkyl, or cycloalkylalkyl which are optionally substituted with one or more substituents independently selected from alkyloxy and trifluoromethyl, $R_6$ is alkyl optionally substituted with alkylamino, dialkylamino, alkyloxy, and hetero aryl, and $R_7$ is $C_1$-$C_{10}$ alkyl, $C_1$-$C_{10}$ haloalkyl, $C_1$-$C_{10}$ haloalkyl, $C_1$-$C_{10}$ haloalkoxy.

The disclosure also provides a pharmaceutical composition comprising a compound or salt of the invention and a pharmaceutically acceptable carrier.

The disclosure further provides a method for therapeutic intervention in a facet of mammalian health that is mediated by a mammalian relaxin receptor 1, comprising administering an effective amount of the compound on the disclosure to a mammal afflicted therewith. In some embodiments the mammal is a human and the mammalian relaxin receptor 1 is a human relaxin 1 receptor.

BRIEF DESCRIPTION OF THE SEVERAL VIEWS OF THE DRAWING(S)

FIGS. 1-7 depict synthetic schemes for the preparation of embodiments of the disclosure.

DETAILED DESCRIPTION

Figure 1:
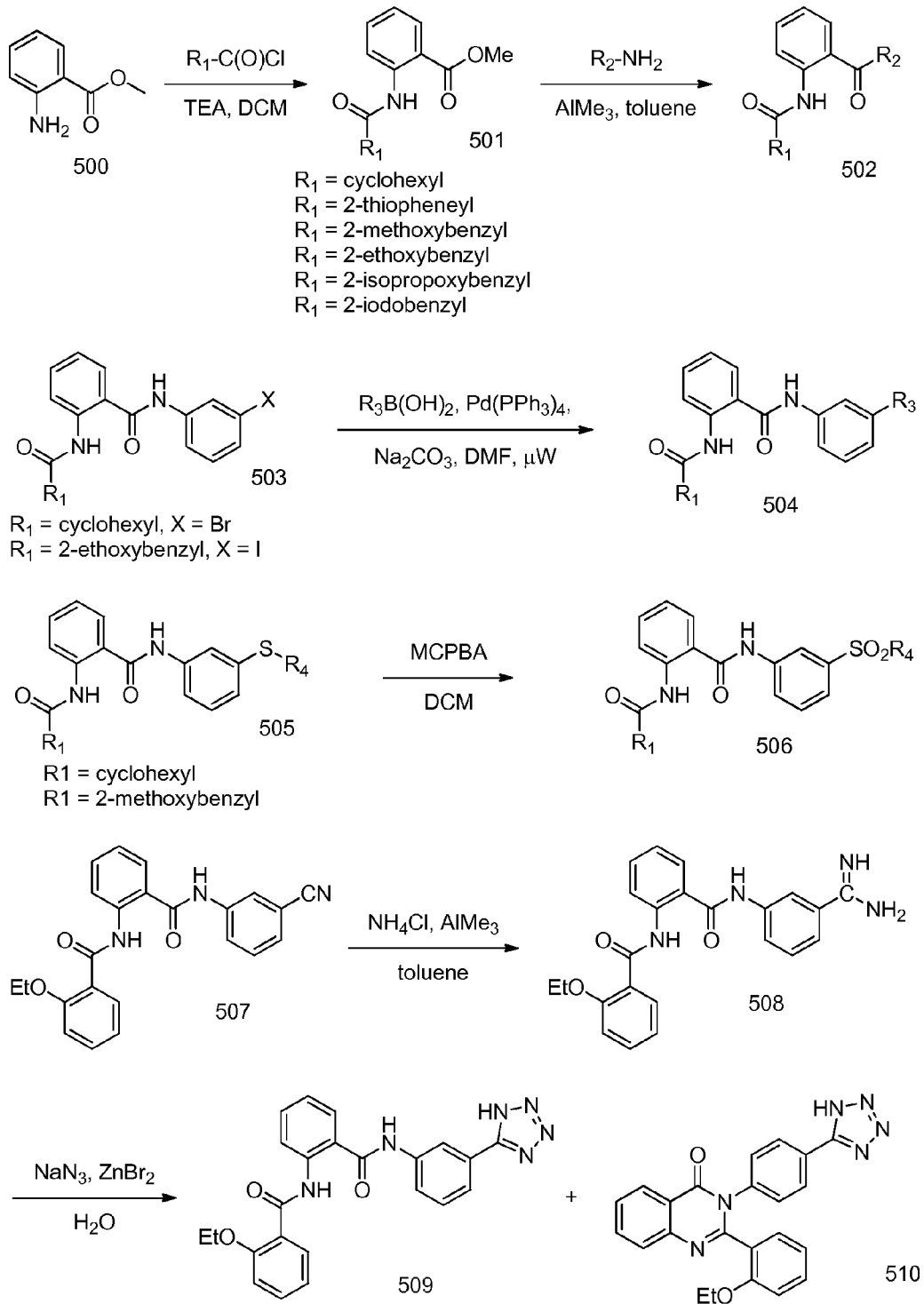
FIG. 1 depicts synthetic schemes for the preparation of compounds in accordance with embodiments of the disclosure.

The disclosure provides a compound of the formula (I):

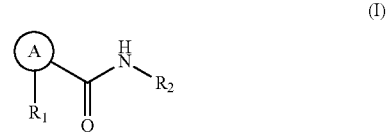

(I)

wherein A is 1,2-phenylenyl, 1,2-heteroarylenyl, 1,2-heterocyclyl, or —$CH_2CH_2$—, wherein the 1,2-phenylenyl, 1,2-heteroarylenyl, and 1,2-heterocyclyl are optionally substituted with one or more substituents independently selected from halo, $CF_3$, alkyl, alkyloxy, haloalkyl, haloalkoxy, —$SR_7$, —$SOR_7$, —$SO_2R_7$, —$SCF_3$, and $SO_2CF_3$, $R_1$ is —$NHCOR_3$, $R_4$, —$NHR_5$, or —$OR_6$, $R_2$ is alkyl, cycloalkyl, heteroarylalkyl, or phenyl, which are optionally substituted with one or more substituents independently selected from halo, $CF_3$, $C_1$-$C_{10}$ alkyl, $C_2$-$C_{10}$ alkenyl, $C_1$-$C_{10}$ alkyloxy, $C_1$-$C_{10}$ haloalkyl, $C_1$-$C_{10}$ haloalkoxy, aryl, haloalkylaryl, heterocyclylalkyl, —$SR_7$, —$SOR_7$, —$SO_2R_7$, —$SCF_3$, —$NO_2$, —CN, and —$SO_2CF_3$, $R_3$ is alkyl, cycloalkyl, bicycloalkyl, tricycloalkyl, aryl, heteroaryl, arylalkyl, or phenyl, each of which are optionally substituted with one or more substituents independently selected from halo, $CF_3$, $C_1$-$C_{10}$ alkyl, $C_2$-$C_{10}$ alkenyl, $C_1$-$C_{10}$ alkyloxy, $C_1$-$C_{10}$ haloalkyl, $C_1$-$C_{10}$ haloalkoxy, —$SR_7$, —$SOR_7$, —$SO_2R_7$, —$SCF_3$, —$NO_2$, —CN, and —$SO_2CF_3$, $R_4$ is phenyl optionally substituted with alkyloxy, haloalkyloxy, arylalkyl, or arylalkyloxy, $R_5$ is hydrogen, alkyl, alkylaryl, aryl, alkylcycloalkyl, or cycloalkylalkyl which are optionally substituted with one or more substituents independently selected from alkyloxy and trifluoromethyl, $R_6$ is alkyl optionally substituted with alkylamino, dialkylamino, alkyloxy, and hetero aryl, and $R_7$ is $C_1$-$C_{10}$ alkyl, $C_1$-$C_{10}$ haloalkyl, $C_1$-$C_{10}$ haloalkyl or $C_1$-$C_{10}$ haloalkoxy, with the provisos that:

(i) when $R_3$ is methyl, chloromethyl, or dichloromethyl, and A is 1,2-phenylenyl, then $R_2$ is not methyl, phenyl, 2-methylphenyl, 2-methoxyphenyl, or 4-methoxyphenyl; and (ii) when $R_3$ is phenyl, and A is 1,2-phenylenyl, then $R_2$ is not halophenyl, methoxyphenyl, 2,6-dimethylphenyl, or 2,4,6-trimethylphenyl; and (iii) when $R_3$ is phenyl substituted with alkyl, and A is 1,2-phenylenyl, then $R_2$ is not methoxyphenyl;

or a pharmaceutically acceptable salt thereof.

In accordance with certain embodiments, $R_2$ is phenyl substituted with a substituent selected from —$SO_2CF_3$, —$SCF_3$, and —CF3.

In accordance with certain embodiments, A is 1,2-phenylene optionally substituted with one or more substituents selected from hydrogen, halo, —$CF_3$, alkyl, alkyloxy, haloalkyl, haloalkoxy, —$SR_7$, —$SOR_7$, —$SO_2R_7$, —$SCF_3$, and —$SO_2CF_3$.

In accordance with certain embodiments, R1 is —NH-COR3, wherein R3 is phenyl substituted with a substituent selected from —CF$_3$, C$_1$-C$_{10}$alkyl, C$_1$-C$_{10}$ alkyloxy, C$_1$-C$_{10}$haloalkyl, C$_1$-C$_{10}$haloalkoxy, alkyloxyalkyloxy, dimethylaminoalkyloxy, —SR$_7$, —SOR$_7$, —SO$_2$R$_7$, —SCF$_3$, and —SO$_2$CF$_3$.

In accordance with certain preferred embodiments, R$_3$ is 2-(C$_1$-C$_{10}$)alkyloxyphenyl.

In accordance with certain preferred embodiments, R2 is phenyl substituted with a substituent selected from —CF$_3$, C$_1$-C$_{10}$ alkyl, C$_1$-C$_{10}$ alkyloxy, C$_1$-C$_{10}$ haloalkyl, C1-C10haloalkoxy, —SR$_7$, —SOR$_7$, —SO$_2$R$_7$, —SCF$_3$, and —SO$_2$CF$_3$.

In certain preferred embodiments, the compound is selected from the group consisting of:

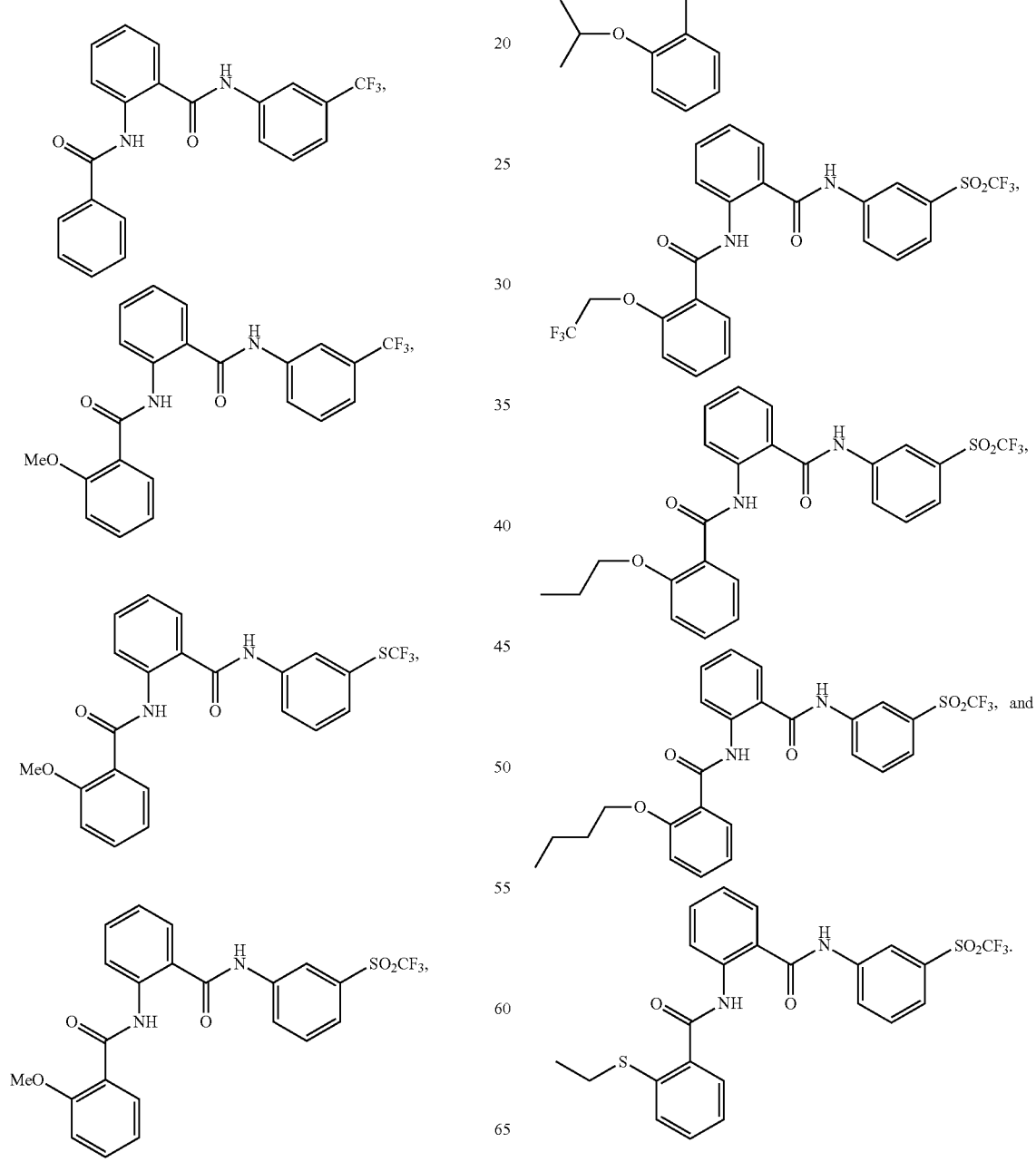

In accordance with certain embodiments, $R_1$ is $R_4$, wherein $R_4$ is 2-($C_1$-$C_{10}$)alkyloxyphenyl or 2-($C_1$-$C_{10}$)haloalkyloxyphenyl.

In accordance with certain preferred embodiments, $R_1$ is —$NHR_5$, wherein $R_5$ is aryl optionally substituted with one or more substituents selected from alkyloxy and trifluoromethyl.

In accordance with certain embodiments, $R_1$ is —$OR_6$, wherein $R_6$ is alkyl optionally substituted with alkylamino, dialkylamino, alkyloxy, and heteroaryl.

In accordance with certain embodiments, A is 1,2-heteroarylenyl optionally substituted with one or more substitutents independently selected from halo, —$CF_3$, alkyl, alkyloxy, haloalkyl, haloalkoxy, —$SR_7$, —$SOR_7$, —$SO_2R_7$, —$SCF_3$, and —$SO_2CF_3$.

In accordance with certain preferred embodiments, A is selected from

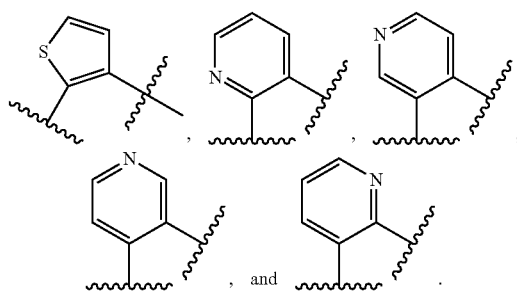

In accordance with certain preferred embodiments, $R_1$ is —$NHCOR_3$, wherein $R_3$ is phenyl substituted with a substituent selected from the group consisting of —$CF_3$, $C_1$-$C_{10}$ alkyl, $C_1$-$C_{10}$ alkyloxy, $C_1$-$C_{10}$haloalkyl, $C_1$-$C_{10}$haloalkoxy, —$SR_7$, —$SOR_7$, —$SO_2R_7$, —$SCF_3$, and —$SO_2CF_3$.

In accordance with certain preferred embodiments, $R_3$ is 2-($C_1$-$C_{10}$)alkyloxyphenyl or 2-($C_1$-$C_{10}$)haloalkyloxyphenyl.

In certain preferred embodiments, wherein the compound is selected from the group consisting of:

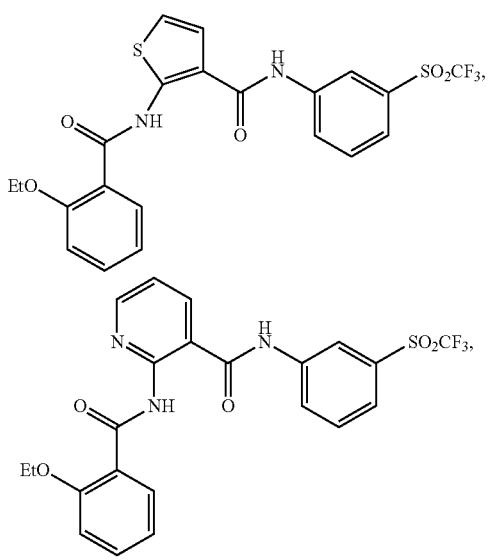

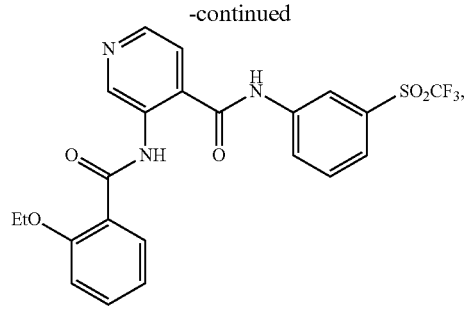

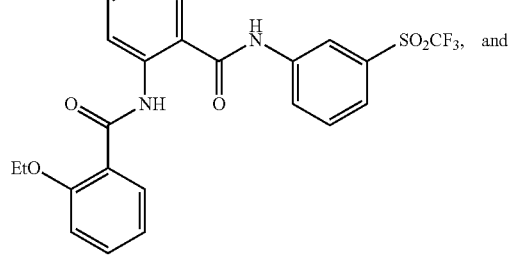

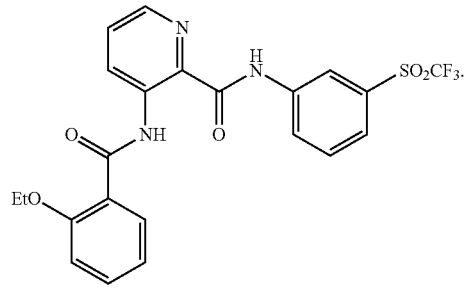

In accordance with certain embodiments, A is □$CH_2CH_2$—.

In accordance with certain embodiments, wherein $R_1$ is —$NHCOR_3$, wherein $R_3$ is phenyl substituted with a substituent independently selected from —$CF_3$, $C_1$-$C_{10}$ alkyl, $C_1$-$C_{10}$ alkyloxy, $C_1$-$C_{10}$haloalkyl, $C_1$-$C_{10}$haloalkoxy, —$SR_7$, —$SOR_7$, —$SO_2R_7$, —$SCF_3$, and —$SO_2CF_3$.

In accordance with certain embodiments, $R_3$ is 2-($C_1$-$C_{10}$)alkyloxyphenyl or 2-($C_1$-$C_{10}$)haloalkyloxyphenyl.

In accordance with a particular embodiment, the compound is:

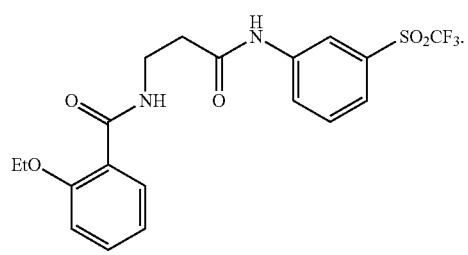

The disclosure provides compounds and pharmaceutically acceptable thereof, having the formula

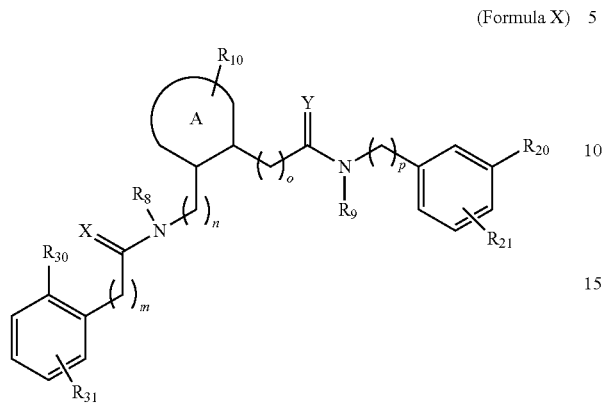

(Formula X)

Where

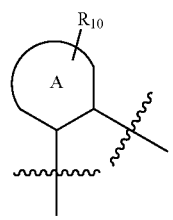

is a 3- to 8-membered carbocyclic ring or a 3- to 8-membered heterocyclic ring containing 1 to 3 heteroatoms independently chosen from N, O, and S, each of which A ring is optionally fused to a 3- to 8-membered carbocyclic ring or a 3- to 8-membered heterocyclic ring containing 1 to 3 heteroatoms independently chosen from N, O, and S, to form a bicyclic ring system; and the A ring and 3 to 8-membered carbocyclic or heterocyclic ring to which A is optionally fused are each substituted with $R_{10}$;

m, n, o, and p are integers independently chosen from 0, 1, and 2 and each of

is unsubstituted or substituted with one or more substituents independently chosen from halogen, hydroxyl, $C_1$-$C_2$alkyl, and $C_1$-$C_2$alkoxy;

X and Y are independently chosen from O and S;

$R_8$ and $R_9$ are independently chosen from hydrogen and $C_1$-$C_4$alkyl;

$R_{10}$, $R_{21}$, and $R_{31}$ are each 0 to 3 substitutents independently chosen from hydroxyl, halogen, nitro, cyano, amino, $C_1$-$C_4$alkyl, $C_1$-$C_4$alkoxy, mono- and di-($C_1$-$C_2$alkyl)amino-, $C_1$-$C_2$haloalkyl, and $C_1$-$C_2$haloalkoxy;

$R_{20}$ is $NO_2$, CN, $C_1$-$C_{10}$haloalkyl, $C_1$-$C_{10}$haloalkoxy, —$SR_7$, —$SOR_7$, or —$SO_2R_7$, where $R_7$ is $C_1$-$C_{10}$carbyhdryl or $C_1$-$C_{10}$haloalkyl;

$R_{30}$ is hydrogen or $R_{30}$ is $C_1$-$C_8$carbhydryloxy or $C_1$-$C_8$carbhydrylthio- each or which is substituted with 0 to 3 substituents independently chosen from hydroxyl, halogen, nitro, cyano, $C_1$-$C_4$alkyl, $C_1$-$C_4$alkoxy, $C_1$-$C_2$haloalkyl, and $C_1$-$C_2$haloalkoxy.

In another embodiment the disclosure includes a compound or salt of Formula X where

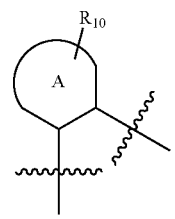

is a phenyl or 5- or 6-membered heteroaryl group containing 1 to 3 heteroatoms independently chosen from N, O, and S, each of which A ring is optionally fused to 5- or 6-membered carbocyclic or heterocyclic ring to form a bicyclic ring system; and the A ring and 5- or 6-membered carbocyclic or heterocyclic ring to which A is optionally fused are each substituted with $R_{10}$.

The disclosure includes compounds or salts for Formula X where

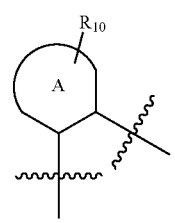

is a group of formula

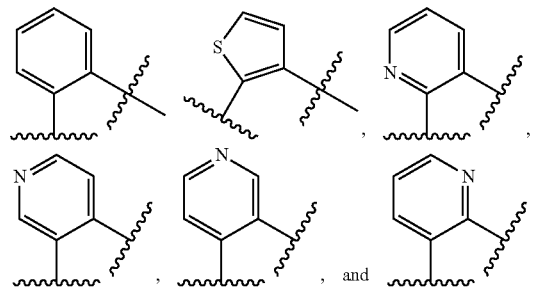

each of which is substituted with $R_{10}$.

The disclosure includes compounds or salts for Formula X, wherein m, n, o, and p are all 0 and X and Y are both O.

The disclosure includes compounds or pharmaceutically salts for Formula XI

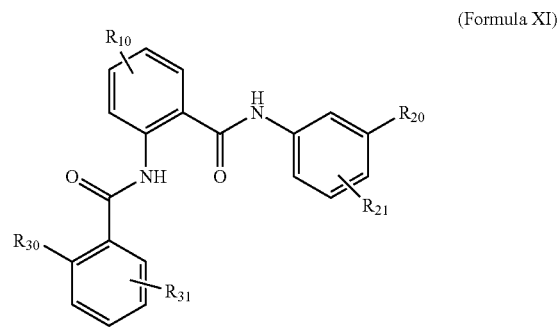

(Formula XI)

where:

$R_{10}$, $R_{21}$, and $R_{31}$ are each 0 to 3 substitutents independently chosen from hydroxyl, halogen, nitro, cyano, amino, $C_1$-$C_4$alkyl, $C_1$-$C_4$alkoxy, mono- and di-($C_1$-$C_2$alkyl)amino-, $C_1$-$C_2$haloalkyl, and $C_1$-$C_2$haloalkoxy;

$R_{20}$ is $NO_2$, CN, $C_1$-$C_{10}$haloalkyl, $C_1$-$C_{10}$haloalkoxy, —$SR_7$, —$SOR_7$, or —$SO_2R_7$, where $R_7$ is $C_1$-$C_{10}$alkyl or $C_1$-$C_{10}$haloalkyl;

$R_{30}$ is hydrogen or $R_{30}$ is $C_1$-$C_8$alkoxy or $C_1$-$C_5$alkylthio- each or which is substituted with 0 to 3 substituents independently chosen from hydroxyl, halogen, nitro, cyano, $C_1$-$C_4$alkyl, $C_1$-$C_4$alkoxy, $C_1$-$C_2$haloalkyl, and $C_1$-$C_2$haloalkoxy.

The disclosure includes compounds and salts of Formula XI, wherein $R_{20}$ is $C_1$-$C_6$haloalkyl, —$S(C_1$-$C_6$haloalkyl), or □$SO_2(C_1$-$C_6$haloalkyl).

The disclosure includes compounds and salts of Formula XI, wherein $R_{10}$, $R_{21}$, and $R_{31}$ are each 0 substituents.

The disclosure includes compounds and salts of Formula XI, wherein $R_{10}$, $R_{21}$, and $R_{31}$ are each 0 substituents; $R_{20}$ is $CF_3$, $SCF_3$, or $SO_2CF_3$, and $R_{30}$ is $C_2$-$C_6$alkoxy or $C_2$-$C_6$alkylthio-, each of which is substituted with 0 to 2 substituents independently chosen from halogen and □$CF_3$.

The disclosure includes compounds and salts of Formula XI, wherein $R_{20}$ is $SO_2CF_3$.

The disclosure includes compounds and salts of Formula XII

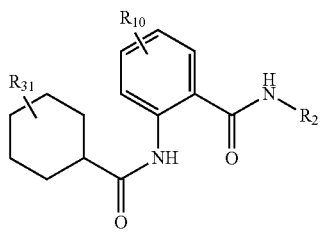

(Formula XII)

where:

$R_{10}$ and $R_{31}$ are each 0 to 3 substitutents independently chosen from hydroxyl, halogen, nitro, cyano, amino, $C_1$-$C_4$alkyl, $C_1$-$C_4$alkoxy, mono- and di-($C_1$-$C_2$alkyl)amino-, $C_1$-$C_2$haloalkyl, and $C_1$-$C_2$haloalkoxy; and $R_2$ is (phenyl)$C_0$-$C_2$alkyl- or (5- or 6-membered heteroaryl)$C_0$-$C_2$alkyl, each of which is substituted with 0 or 1 or more substituents independently chosen from hydroxyl, halogen, nitro, cyano, amino, $C_1$-$C_6$alkyl, $C_2$-$C_6$alkenyl, $C_2$-$C_6$alkynyl, ($C_3$-$C_7$cycloalkyl)$C_0$-$C_2$alkyl, 5- and 6-membered heterocycloalkyl, thienyl, phenyl, phenyl substituted with $CF_3$, mono- and di-$C_1$-$C_6$alkylamino, $C_1$-$C_6$alkylthio, $C_1$-$C_6$alkylsulfonyl, $C_1$-$C_4$alkoxy, $C_1$-$C_2$haloalkyl, and $C_1$-$C_2$haloalkoxy, —$SR_7$, —$SOR_7$, and —$SO_2R_7$, where $R_7$ is $C_1$-$C_{10}$carbhydryl or $C_1$-$C_{10}$haloalkyl; or $R_2$ is dihydroindenyl, benzo[d][1,3]dioxolyl, or indolyl, each of which is substituted with 0 to 3 substitutents independently chosen from hydroxyl, halogen, nitro, cyano, amino, $C_1$-$C_4$alkyl, $C_1$-$C_4$alkoxy, mono- or di-($C_1$-$C_2$alkyl)amino-, $C_1$-$C_2$haloalkyl, and $C_1$-$C_2$haloalkoxy.

The disclosure includes compounds and salts of Formula XII, wherein $R_{10}$ and $R_{31}$ are both 0 substituents.

The disclosure includes compounds and salts of Formula XII, wherein $R_2$ is phenyl substituted with one or two substituents independently chosen from hydroxyl, halogen, nitro, $SCF_3$, $SO_2CF_3$, $C_1$-$C_6$alkyl, $C_2$-$C_6$alkenyl, $C_2$-$C_6$alkynyl, 5- and 6-membered heterocycloalkyl, thienyl, phenyl, phenyl substituted with $CF_3$, mono- and di-$C_1$-$C_6$alkylamino, $C_1$-$C_6$alkylthio, $C_1$-$C_6$alkylsulfonyl, $C_1$-$C_4$alkoxy, $C_1$-$C_2$haloalkyl, and $C_1$-$C_2$haloalkoxy.

The disclosure includes compounds and salts of Formula XII, wherein $R_2$ is phenyl substituted in the meta position with $CF_3$, $SCF_3$, or $SO_2CF_3$.

The disclosure includes compounds and salts of Formula XII, wherein $R_2$ is 2,3-dihydro-1H-indenyl, benzo[d][1,3]dioxolyl, or indolyl, each of which is unsubstituted.

The disclosure includes compounds and pharmaceutically acceptable salts of Formula XIII

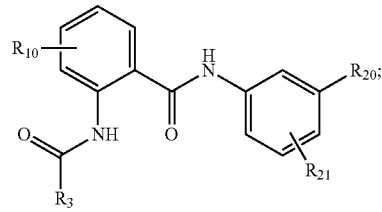

(Formula XIII)

where:

$R_{10}$ and $R_{21}$ are each 0 to 3 substitutents independently chosen from hydroxyl, halogen, nitro, cyano, amino, $C_1$-$C_4$alkyl, $C_1$-$C_4$alkoxy, mono- and di-($C_1$-$C_2$alkyl)amino-, $C_1$-$C_2$haloalkyl, and $C_1$-$C_2$haloalkoxy;

$R_{20}$ is $NO_2$, CN, $C_1$-$C_{10}$haloalkyl, $C_1$-$C_{10}$haloalkoxy, —$SR_7$, —$SOR_7$, or —$SO_2R_7$, where $R_7$ is $C_1$-$C_{10}$carbhydryl or $C_1$-$C_{10}$haloalkyl; and $R_3$ is cyclohexyl; or $R_3$ is phenyl substituted with one or more substituents independently chosen from hydroxyl, halogen, nitro, cyano, amino, $SCF_3$, $SO_2CF_3$, $C_1$-$C_6$alkyl, $C_2$-$C_6$alkenyl, $C_2$-$C_6$alkynyl, phenyl mono- and di-$C_1$-$C_6$alkylamino, $C_1$-$C_6$alkylthio, $C_1$-$C_6$alkylsulfonyl, $C_1$-$C_4$alkoxy, $C_1$-$C_2$haloalkyl, and $C_1$-$C_2$haloalkoxy.

The disclosure includes compounds and salts of Formula XIII, wherein $R_{10}$ and $R_{21}$ are both 0 substituents and $R_3$ is phenyl substituted with one meta-position substituent.

The disclosure includes compounds and salts of Formula XIII, wherein $R_{10}$ and $R_{21}$ are both 0 substituents and $R_{20}$ is $CF_3$, $SCF_3$, or $SO_2CF_3$.

The disclosure includes compounds and salts of Formula XIII, wherein $R_{20}$ is $CF_3$; and $R_3$ is phenyl substituted with one or more substituents independently chosen from hydroxyl, halogen, nitro, cyano, amino, $SCF_3$, $SO_2CF_3$, $C_1$-$C_6$alkyl, $C_2$-$C_6$alkenyl, $C_2$-$C_6$ alkynyl, phenyl mono- and di-$C_1$-$C_6$alkylamino, $C_1$-$C_6$alkylthio, $C_1$-$C_6$alkylsulfonyl, $C_1$-$C_4$alkoxy, $C_1$-$C_2$haloalkyl, and $C_1$-$C_2$haloalkoxy.

The disclosure includes compounds and salts of Formula XIII, wherein $R_{20}$ is $SO_2CF_3$; and $R_3$ is phenyl substituted with one or more substituents independently chosen from hydroxyl, halogen, nitro, cyano, amino, $SCF_3$, $SO_2CF_3$, $C_1$-$C_6$alkyl, $C_2$-$C_6$alkenyl, $C_2$-$C_6$ alkynyl, phenyl mono- and di-$C_1$-$C_6$alkylamino, $C_1$-$C_6$alkylthio, $C_1$-$C_6$alkylsulfonyl, $C_1$-$C_4$alkoxy, $C_1$-$C_2$haloalkyl, and $C_1$-$C_2$haloalkoxy.

The disclosure includes compounds and salts of Formula X, wherein

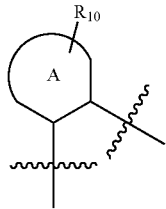

is a group of formula

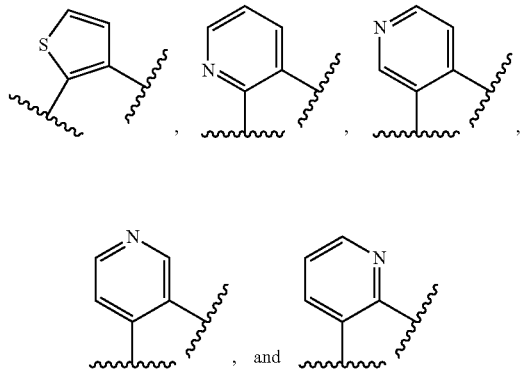

each of which is substituted with $R_{10}$.

Additionally in certain embodiments where the A-ring is a thienyl or pyridyl $R_{10}$, $R_{21}$, and $R_{31}$ are each 0 substituents.

The disclosure also includes compounds and salts where the A ring is a thienyl or pyridyl, wherein each of m, n, o, and p are 0 and X and Y are both 0.

The disclosure also includes compounds and salts where the A ring is a thienyl or pyridyl $R_{20}$ is $NO_2$, CN, $C_1$-$C_{10}$haloalkyl, $C_1$-$C_{10}$haloalkoxy, —$SR_7$, —$SOR_7$, or —$SO_2R_7$, where $R_7$ is $C_1$-$C_{10}$alkyl or $C_1$-$C_{10}$haloalkyl; and $R_{30}$ is hydrogen or $R_{30}$ is $C_1$-$C_8$alkoxy or $C_1$-$C_8$alkylthio- each or which is substituted with 0 to 3 substituents independently chosen from hydroxyl, halogen, nitro, cyano, $C_1$-$C_4$alkyl, $C_1$-$C_4$alkoxy, $C_1$-$C_2$haloalkyl, and $C_1$-$C_2$haloalkoxy.

The disclosure also includes compounds and salts where the A ring is a thienyl or pyridyl, wherein $R_{20}$ is $C_1$-$C_6$haloalkyl, —S($C_1$-$C_6$haloalkyl), or □$SO_2$($C_1$-$C_6$haloalkyl).

The disclosure also includes compounds and salts where the A ring is a thienyl or pyridyl, wherein $R_{10}$, $R_{21}$, and $R_{31}$ are each 0 substituents; $R_{20}$ is $CF_3$, $SCF_3$, or $SO_2CF_3$, and $R_{30}$ is $C_2$-$C_6$alkoxy or $C_2$-$C_6$alkylthio-, each of which is substituted with 0 to 2 substituents independently chosen from halogen and □$CF_3$.

The disclosure also includes compounds and salts where the A ring is a thienyl or pyridyl, wherein $R_{20}$ is $SO_2CF_3$.

The disclosure further includes compounds and salts of Formula XIV

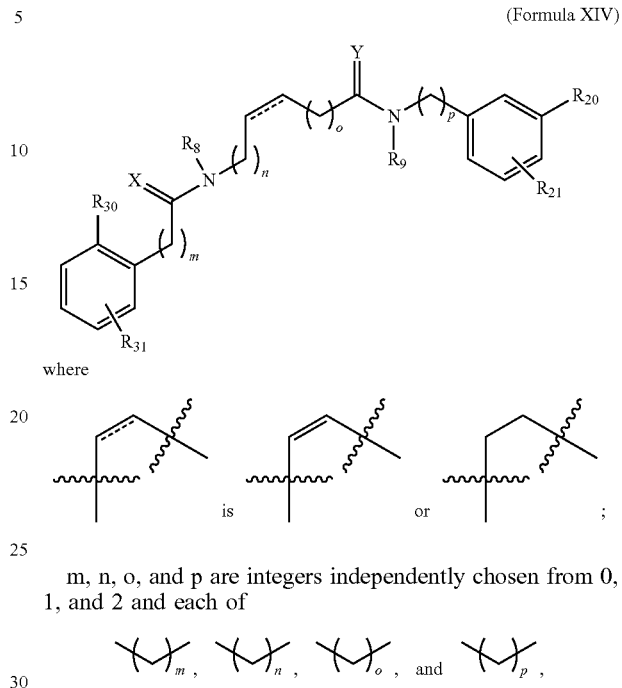

(Formula XIV)

where m, n, o, and p are integers independently chosen from 0, 1, and 2 and each of is unsubstituted or substituted with one or more substituents independently chosen from halogen, hydroxyl, $C_1$-$C_2$alkyl, and $C_1$-$C_2$alkoxy;

X and Y are independently chosen from O and S;

$R_8$ and $R_9$ are independently chosen from hydrogen and $C_1$-$C_4$alkyl;

$R_{10}$, $R_{21}$, and $R_{31}$ are each 0 to 3 substitutents independently chosen from hydroxyl, halogen, nitro, cyano, amino, $C_1$-$C_4$alkyl, $C_1$-$C_4$alkoxy, mono- and di-($C_1$-$C_2$alkyl) amino-, $C_1$-$C_2$haloalkyl, and $C_1$-$C_2$haloalkoxy;

$R_{20}$ is $NO_2$, CN, $C_1$-$C_{10}$haloalkyl, $C_1$-$C_{10}$haloalkoxy, —$SR_7$, —$SOR_7$, or —$SO_2R_7$, where $R_7$ is $C_1$-$C_{10}$carbhydryl or $C_1$-$C_{10}$haloalkyl;

$R_{30}$ is hydrogen or $R_{30}$ is $C_1$-$C_8$carbhydryloxy or $C_1$-$C_8$carbhydrylthio- each or which is substituted with 0 to 3 substituents independently chosen from hydroxyl, halogen, nitro, cyano, $C_1$-$C_4$alkyl, $C_1$-$C_4$alkoxy, $C_1$-$C_2$haloalkyl, and $C_1$-$C_2$haloalkoxy.

The disclosure includes compounds and salts of Formula XIV, wherein m, n, o, and p are all 0 and X and Y are both O.

The disclosure includes compounds and salts of Formula XV

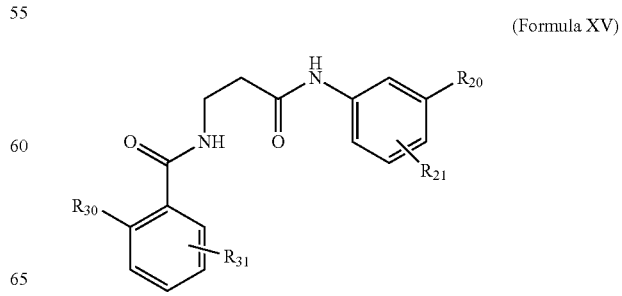

(Formula XV)

where:

$R_{10}$, $R_{21}$, and $R_{31}$ are each 0 to 3 substitutents independently chosen from hydroxyl, halogen, nitro, cyano, amino, $C_1$-$C_4$alkyl, $C_1$-$C_4$alkoxy, mono- and di-($C_1$-$C_2$alkyl)amino-, $C_1$-$C_2$haloalkyl, and $C_1$-$C_2$haloalkoxy;

$R_{20}$ is $NO_2$, CN, $C_1$-$C_{10}$haloalkyl, $C_1$-$C_{10}$haloalkoxy, —$SR_7$, —$SOR_7$, or —$SO_2R_7$, where $R_7$ is $C_1$-$C_{10}$alkyl or $C_1$-$C_{10}$haloalkyl;

$R_{30}$ is hydrogen or $R_{30}$ is $C_1$-$C_8$alkoxy or $C_1$-$C_8$alkylthio- each or which is substituted with 0 to 3 substituents independently chosen from hydroxyl, halogen, nitro, cyano, $C_1$-$C_4$alkyl, $C_1$-$C_4$alkoxy, $C_1$-$C_2$haloalkyl, and $C_1$-$C_2$haloalkoxy.

The disclosure includes compounds and salts of Formula XVI

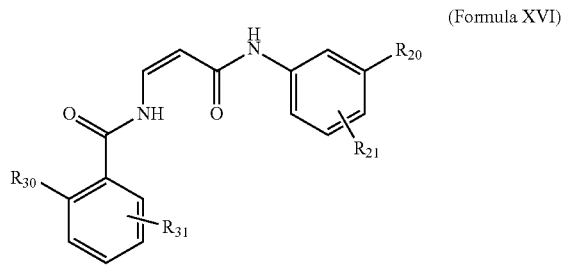

(Formula XVI)

where:

$R_{10}$, $R_{21}$, and $R_{31}$ are each 0 to 3 substitutents independently chosen from hydroxyl, halogen, nitro, cyano, amino, $C_1$-$C_4$alkyl, $C_1$-$C_4$alkoxy, mono- and di-($C_1$-$C_2$alkyl)amino-, $C_1$-$C_2$haloalkyl, and $C_1$-$C_2$haloalkoxy;

$R_{20}$ is $NO_2$, CN, $C_1$-$C_{10}$haloalkyl, $C_1$-$C_{10}$haloalkoxy, —$SR_7$, —$SOR_7$, or —$SO_2R_7$, where $R_7$ is $C_1$-$C_{10}$alkyl or $C_1$-$C_{10}$haloalkyl;

$R_{30}$ is hydrogen or $R_{30}$ is $C_1$-$C_8$alkoxy or $C_1$-$C_8$alkylthio- each or which is substituted with 0 to 3 substituents independently chosen from hydroxyl, halogen, nitro, cyano, $C_1$-$C_4$alkyl, $C_1$-$C_4$alkoxy, $C_1$-$C_2$haloalkyl, and $C_1$-$C_2$haloalkoxy.

The disclosure includes compounds of Formula XV and XVI, wherein $R_{20}$ is $C_1$-$C_6$haloalkyl, —$S(C_1$-$C_6$haloalkyl), or □$SO_2(C_1$-$C_6$haloalkyl).

The disclosure includes compounds of Formula XV and XVI, wherein $R_{21}$, and $R_{31}$ are both 0 substituents.

The disclosure includes compounds of Formula XV and XVI, wherein $R_{21}$ and $R_{31}$ are both 0 substituents; $R_{20}$ is $CF_3$, $SCF_3$, or $SO_2CF_3$, and $R_{30}$ is $C_2$-$C_6$alkoxy or $C_2$-$C_6$alkylthio-, each of which is substituted with 0 to 2 substituents independently chosen from halogen and □$CF_3$.

The disclosure includes compounds of Formula XV and XVI, wherein $R_{20}$ is $SO_2CF_3$.

Any of the variable definitions set forth herein (e.g. $R_{10}$, $R_{20}$, $R_{21}$, $R_{30}$, $R_{31}$, $R_8$, $R_9$, X, Y, m, n, o, and p) may be combined so long as a stable compound results, and all such combinations which result in a stable compound are included as compounds within the scope of the disclosure.

Any of the genuses, subgenuses, and compounds in the scope of the disclosure, including compounds and salts of Formula X to Formula XVI, can be used for treating any of the conditions, disorders, diseases, or other facets of mammalian health listed in this application.

Any of the genuses, subgenuses, and compounds of the disclosure, including compounds and salts of Formula X to XI can be used for the manufacture of a medicament for any of the conditions, disorders, diseases, or other facets of mammalian health listed in this application.

Referring now to terminology used generically herein, the term □akyl□ means a straight-chain or branched alkyl substituent containing from, for example, 1 to about 10 carbon atoms, preferably from 1 to about 4 carbon atoms, more preferably from 1 to 2 carbon atoms. Examples of such substituents include methyl, ethyl, propyl, isopropyl, n-butyl, sec-butyl, isobutyl, tert-butyl, pentyl, isoamyl, hexyl, and the like.

The term □alkenyl,□ as used herein, means a linear or branched alkenyl substituent containing at least one carbon-carbon double bond and from, for example, linear alkenyl of about 2 to about 10 carbon atoms (branched alkenyls are about 3 to about 6 carbons atoms), preferably from about 2 to about 5 carbon atoms (branched alkenyls are preferably from about 3 to about 5 carbon atoms), more preferably linear alkenyl of about 3 to about 4 carbon atoms. Examples of such substituents include vinyl, propenyl, isopropenyl, n-butenyl, sec-butenyl, isobutenyl, tert-butenyl, pentenyl, isopentenyl, hexenyl, and the like.

The term □alkynyl,□ as used herein, means a linear or branched alkynyl substituent containing at least one carbon-carbon triple bond and from, for example, linear alkynyl of 2 to about 10 carbon atoms (branched alkynyls are about 3 to about 6 carbons atoms), preferably from 2 to about 5 carbon atoms (branched alkynyls are preferably from about 3 to about 5 carbon atoms), more preferably linear alkynyl of about 3 to about 4 carbon atoms. Examples of such substituents include ethynyl, propynyl, isopropynyl, n-butynyl, sec-butynyl, isobutynyl, tert-butyryl, pentynyl, isopentynyl, hexynyl, and the like.

□Carbhydryl□ is a hydrocarbon group that is straight, branched or cyclic (including (cycloalkyl)alkyl) and contains any combination of single, double, and triple covalent bonds. For example a carbhydryl group may be an alkyl, alkenyl, or alkynyl group. When the term carbhydryl is used in conjuction with □oxy□carbhydryl is a group as defined covalently bound to the group it substitutes through an oxygen, —O—, bridge. Similarly, carbhydrylthio is a carbhydryl group as defined covalently bound to the group it substitutes through a sulfur, —S—, bridge.

The term □cycloalkyl,□ as used herein, means a cyclic alkyl substituent containing from, for example, about 3 to about 8 carbon atoms, preferably from about 4 to about 7 carbon atoms, and more preferably from about 4 to about 6 carbon atoms. Examples of such substituents include cyclopropyl, cyclobutyl, cyclopentyl, cyclohexyl, cycloheptyl, cyclooctyl, and the like. The cyclic alkyl groups may be unsubstituted or further substituted with alkyl groups such as methyl groups, ethyl groups, and the like.

The term □bicycloalkyl,□ as used herein, means a bicyclic alkyl substituent containing from, for example, about 4 to about 12 carbon atoms, preferably from about 4 to about 7 carbon atoms, and more preferably from about 6 to about 10 carbon atoms. Examples of such substituents include bicyclo[3.2.0]heptyl, bicyclo[3.3.0]octyl, bicyclo[4.3.0]nonyl, bicyclo[4.4.0]decyl, and the like. The bicyclic alkyl groups may be unsubstituted or further substituted with alkyl groups such as methyl groups, ethyl groups, and the like.

The term tricycloalkyl,□ as used herein, means a tricyclic alkyl substituent containing from, for example, about 6 to about 18 carbon atoms, preferably from about 8 to about 16 carbon atoms. Examples of such substituents include adamantyl and the like. The tricyclic alkyl groups may be unsubstituted or further substituted with alkyl groups such as methyl groups, ethyl groups, and the like.

"Haloalkyl" indicates both branched and straight-chain alkyl groups having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined herein attached through an oxygen bridge (oxygen of an alcohol radical). The term "heterocyclyl," or "heterocyclic" as used herein, refers to a monocyclic or bicyclic 3- to 8-membered ring system containing one or more heteroatoms selected from O, N, S, and combinations thereof. The heterocyclyl group can be any suitable heterocyclyl group and can be an aliphatic heterocyclyl group, an aromatic heterocyclyl group, or a combination thereof. The heterocyclyl group can be a monocyclic heterocyclyl group or a bicyclic heterocyclyl group. Suitable bicyclic heterocyclyl groups include monocyclic heterocyclyl rings fused to a $C_6$-$C_{10}$ aryl ring. When the heterocyclyl group is a bicyclic heterocyclyl group, both ring systems can be aliphatic or aromatic, or one ring system can be aromatic and the other ring system can be aliphatic as in, for example, dihydrobenzofuran. Preferably, the heterocyclyl group is an aromatic heterocyclyl group. Non-limiting examples of suitable heterocyclyl groups include furanyl, thiophenyl, pyrrolyl, pyrazolyl, imidazolyl, 1,2,3-triazolyl, 1,2,4-triazolyl, isoxazolyl, oxazolyl, isothiazolyl, thiazolyl, 1,3,4-oxadiazol-2-yl, 1,2,4-oxadiazol-2-yl, 5-methyl-1,3,4-oxadiazole, 3-methyl-1,2,4-oxadiazole, pyridinyl, pyrimidinyl, pyrazinyl, triazinyl, benzofuranyl, benzothiophenyl, indolyl, quinolinyl, isoquinolinyl, benzimidazolyl, benzoxazolinyl, benzothiazolinyl, and quinazolinyl. The heterocyclyl group is optionally substituted with 1, 2, 3, 4, or 5 substituents as recited herein such as with alkyl groups such as methyl groups, ethyl groups, and the like, or with aryl groups such as phenyl groups, naphthyl groups and the like, wherein the aryl groups can be further substituted with, for example halo, dihaloalkyl, trihaloalkyl, nitro, hydroxy, alkoxy, aryloxy, amino, substituted amino, alkylcarbonyl, alkoxycarbonyl, arylcarbonyl, aryloxycarbonyl, thio, alkylthio, arylthio, and the like, wherein the optional substituent can be present at any open position on the heterocyclyl group.

The term "heteroaryl," as used herein, refers to a monocyclic or bicyclic 5- or 6-membered ring system containing one or more heteroatoms selected from O, N, S, and combinations thereof. The heteroaryl group can be any suitable heteroaryl. The heteroaryl group can be a monocyclic heteroaryl group or a bicyclic heteroaryl group. Suitable bicyclic heteroaryl groups include monocyclic heteroaryl rings fused to a $C_6$-$C_{10}$ aryl ring. When the heteroaryl group is a bicyclic heteroaryl group, both ring systems are preferably aryl. Non-limiting examples of suitable heteroaryl groups include furanyl, thiophenyl, pyrrolyl, pyrazolyl, imidazolyl, 1,2,3-triazolyl, 1,2,4-triazolyl, isoxazolyl, oxazolyl, isothiazolyl, thiazolyl, pyridinyl, pyrimidinyl, pyrazinyl, triazinyl, benzofuranyl, benzothiophenyl, indolyl, quinolinyl, isoquinolinyl, benzimidazolyl, benzoxazolinyl, benzothiazolinyl, and quinazolinyl. The heteroaryl group is optionally substituted with 1, 2, 3, 4, or 5 substituents as recited herein, wherein the optional substituent can be present at any open position on the heteroaryl group.

The terms "heteroarylalkyl" and "heterocyclylalkyl," as used herein, refers to a heteroaryl or heterocyclyl group as defined herein having an alkyl linker group attached thereto, wherein the heteroarylalkyl and heterocyclylalkyl groups are attached to the rest of the molecule via the alkyl linker group.

The terms "1,2-phenylenyl" and "1,2-heteroarylenyl," as used herein, refer to a phenyl group or a heteroaryl group having attached to the ring two groups positioned at adjacent positions on the phenyl or heteroaryl group, i.e., forming an ortho substitution on the phenyl or heteroaryl group.

The term "arylalkyl," as used herein, refers to an alkyl group linked to a $C_6$-$C_{10}$ aryl ring and further linked to a molecule via the alkyl group. The term "alkylaryl," as used herein, refers to a $C_6$-$C_{10}$ aryl ring linked to an alkyl group and further linked to a molecule via the aryl group.

The term "alkylcarbonyl," as used herein, refers to an alkyl group linked to a carbonyl group and further linked to a molecule via the carbonyl group, e.g., alkyl-C(=O)—. The term "alkoxycarbonyl," as used herein, refers to an alkoxy group linked to a carbonyl group and further linked to a molecule via the carbonyl group, e.g., alkyl-O—C(=O)—.

Whenever a range of the number of atoms in a structure is indicated (e.g., a $C_1$-$C_{12}$, $C_1$-$C_8$, $C_1$-$C_6$, $C_1$-$C_4$, or $C_2$-$C_{12}$, $C_2$-$C_8$, $C_2$-$C_6$, $C_2$-$C_4$ alkyl, alkenyl, alkynyl, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate). Similarly, the recitation of a range of 6-10 carbon atoms (e.g., $C_6$-$C_{10}$) as used with respect to any chemical group (e.g., aryl) referenced herein encompasses and specifically describes 6, 7, 8, 9, and/or 10 carbon atoms, as appropriate, as well as any sub-range thereof (e.g., 6-10 carbon atoms, 6-9 carbon atoms, 6-8 carbon atoms, 6-7 carbon atoms, 7-10 carbon atoms, 7-9 carbon atoms, 7-8 carbon atoms, 8-10 carbon atoms, and/or 8-9 carbon atoms, etc., as appropriate).

The term "halo" or "halogen," as used herein, means a substituent selected from Group VIIA, such as, for example, fluorine, bromine, chlorine, and iodine.

The term "aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise 4n+2π electrons, according to Hückel's Rule. The term "carbocyclic" refers to an aliphatic or aromatic ring containing only carbon ring atoms.

The phrase "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, nonaqueous media such as ether, ethyl acetate, ethanol, isopropanol, or acetonitrile are preferred. Lists of suitable salts are found in Remington□s Pharmaceutical Sciences, 18th ed., Mack Publishing Company, Easton, Pa., 1990, p. 1445, and Journal of Pharmaceutical Science, 66, 2-19 (1977).

Suitable bases include inorganic bases such as alkali and alkaline earth metal bases, e.g., those containing metallic cations such as sodium, potassium, magnesium, calcium and the like. Non-limiting examples of suitable bases include sodium hydroxide, potassium hydroxide, sodium carbonate, and potassium carbonate. Suitable acids include inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, maleic acid, tartaric acid, fatty acids, long chain fatty acids, and the like. Preferred pharmaceutically acceptable salts of inventive compounds having an acidic moiety include sodium and potassium salts. Preferred pharmaceutically acceptable salts of inventive compounds having a basic moiety (e.g., a dimethylaminoalkyl group) include hydrochloride and hydrobromide salts. The compounds of the present disclosure containing an acidic or basic moiety are useful in the form of the free base or acid or in the form of a pharmaceutically acceptable salt thereof.

It should be recognized that the particular counterion forming a part of any salt of this disclosure is usually not of a critical nature, so long as the salt as a whole is pharmacologically acceptable and as long as the counterion does not contribute undesired qualities to the salt as a whole.

It is further understood that the above compounds and salts may form solvates, or exist in a substantially uncomplexed form, such as the anhydrous form. As used herein, the term "solvate" refers to a molecular complex wherein the solvent molecule, such as the crystallizing solvent, is incorporated into the crystal lattice. When the solvent incorporated in the solvate is water, the molecular complex is called a hydrate. Pharmaceutically acceptable solvates include hydrates, alcoholates such as methanolates and ethanolates, acetonitrilates and the like. These compounds can also exist in polymorphic forms.

The compounds of the disclosure can be synthesized using any suitable synthetic route. Referring to FIG. 1, methyl 2-aminobenzoate 500 can be reacted with an acid chloride in the presence of a base such as triethylamine in a solvent such as dichloromethane to provide amide 501. Amide 501 can be reacted with an amine in the presence of a catalyst such as trimethylaluminum in a solvent such as toluene to provide bis-amide 502. Compound 503 can be reacted with a boronic acid in the presence of a catalyst such as $Pd(PPh_3)_4$, a base such as sodium carbonate, in a solvent such as dimethylformamide under microwave irradiation to give the coupled product 504. Arylthiol compound 505 can be oxidized with an agent such as m-chloroperoxybenzoic acid in a solvent such as dichloromethane to give sulfone 506. The cyano compound 507 can be reacted with ammonium chloride in the presence of a catalyst such as trimethylaluminum in a solvent such as toluene to give amidine 508. Reaction of amidine 508 with an azide such as sodium azide in the presence of a catalyst such as zinc bromide in a solvent such as water gives tetrazole 510.

Figure 2:
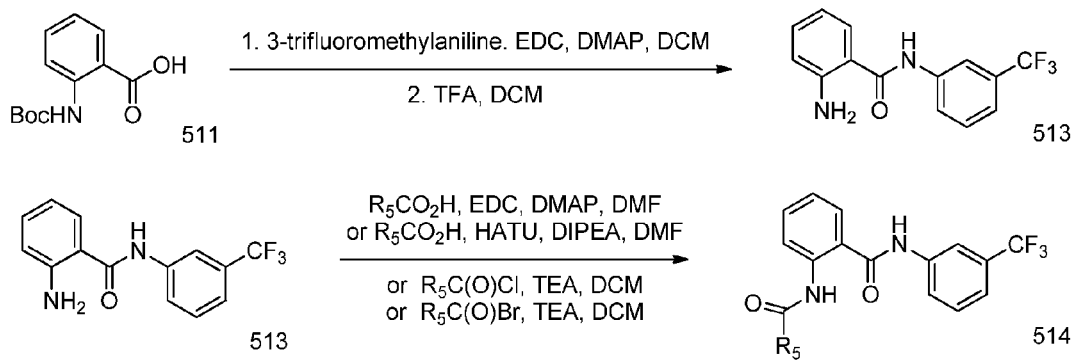
FIG. 2 depicts synthetic schemes for the preparation of compounds in accordance with embodiments of the disclosure.

Referring to FIG. 2, carboxylic acid 511 can be reacted with an amine such as 1,3-trifluoromethylaniline in the presence of a coupling agent such as EDC and a basic catalyst such as dimethylaminopyridine in a solvent such as dichloromethane, followed by deprotection with an agent such as trifluoroacetic acid in a solvent such as dichloromethane to give free amine 513. Reaction of amine 513 with a carboxylic acid in the presence of coupling agentssuch as EDC or HATU in the presence of a basic catalyst such as dimethylaminopyridine in a solvent such as dimethylformamide gives amide 514. Alternatively, reaction of amine 513 with an acid chloride or an acid bromide in the presence of a base such as triethylamine in a solvent such as dichloromethane provides amide 514.

Figure 3:
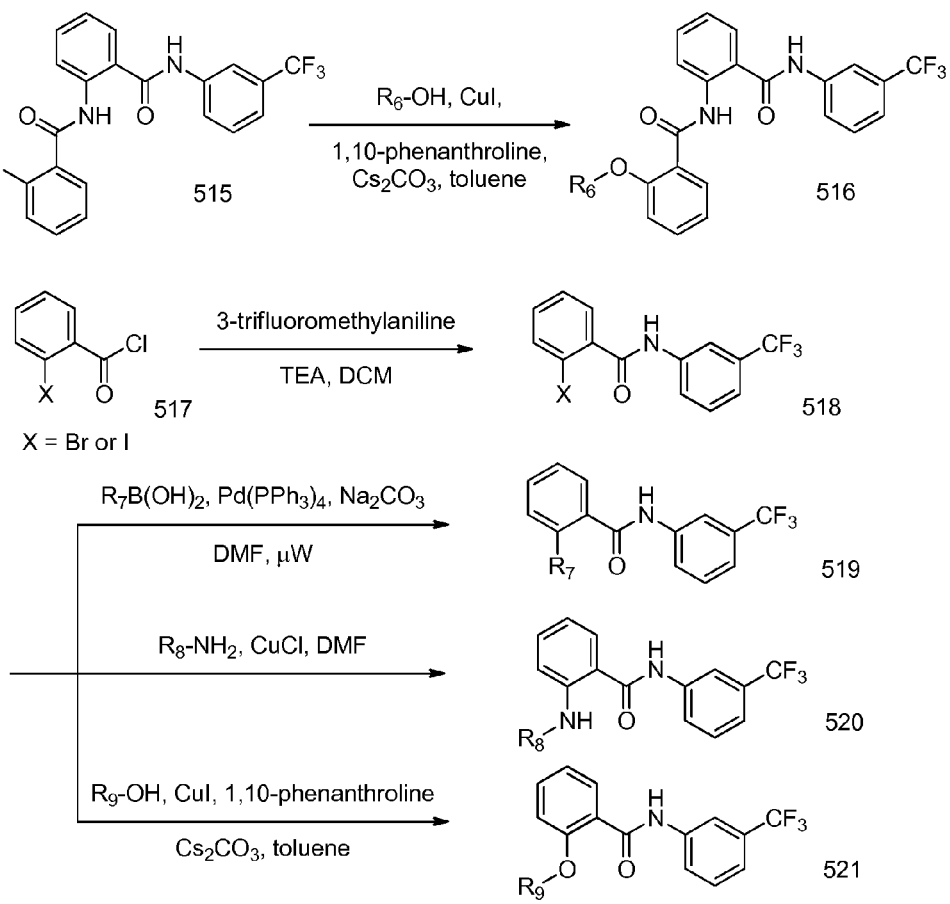
FIG. 3 depicts synthetic schemes for the preparation of compounds in accordance with embodiments of the disclosure.

Referring to FIG. 3, reaction of aryl iodide 515 with an alcohol in the presence of a catalyst such as 1,10-phenanthroline and a base such as cesium carbonate in a solvent such as toluene gives aryl ether 516. Reaction of 2-bromobenzoyl chloride or 2-iodobenzoyl chloride 517 with 3-trifluoromethylaniline in the presence of a base such as triethylamine in a solvent such as dichloromethane provides amide 518. Amide 518 reacts with a boronic acid in the presence of a catalyst such as $Pd(PPh_3)_4$, a base such as sodium carbonate, in a solvent such as dimethylformamide under microwave irradiation gives alkylated/arylated compound 519. Reaction of compound 518 with a primary amine in the presence of a catalyst such as cuprous chloride in a solvent such as dimethylformamide provides arylamine 520. Reaction of 518 with an alcohol in the presence of catalysts such as copper (I) iodide and 1,10-phenanthroline in the presence of a base such as cesium carbonate in a solvent such as toluene gives aryl ether 521.

Figure 4:
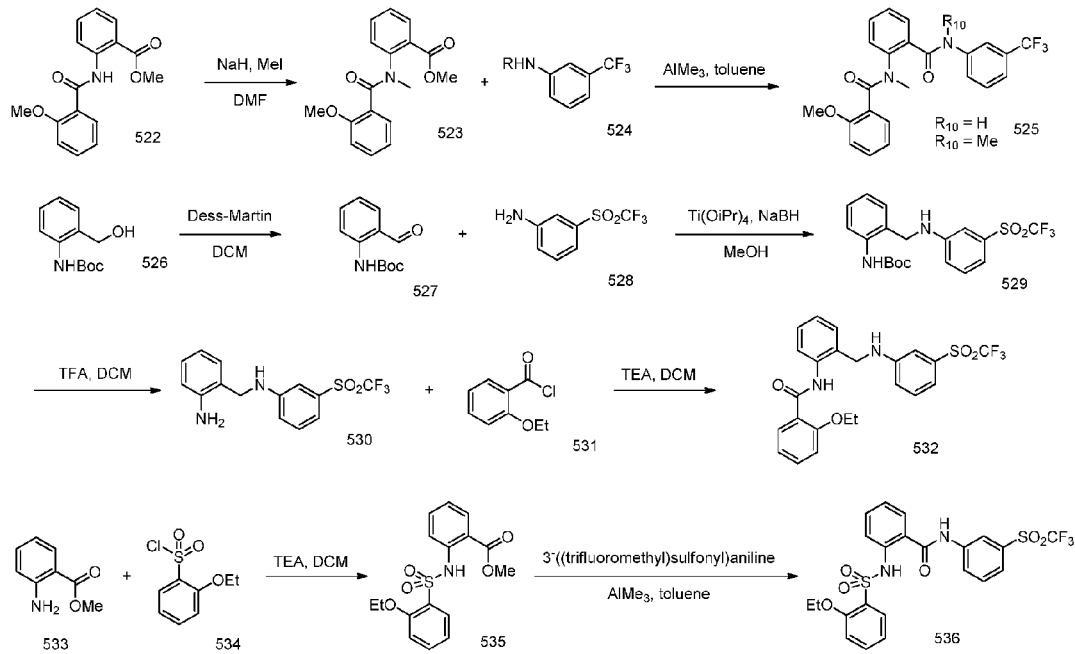
FIG. 4 depicts synthetic schemes for the preparation of compounds in accordance with embodiments of the disclosure.

Referring to FIG. 4, reaction of amide 522 with an alkylating agent such as iodomethane in the presence of a base such as NaH in a solvent such as dimethylformamide gives N-methylamide 523. Compound 523 reacts with an arylamine such as compound 524 in the presence of a catalyst such as trimethylaluminum in a solvent such as toluene to give bis-amide 525. Oxidation of alcohol 526 with an oxidant such as Dess-Martin periodinane in a solvent such as dichloromethane gives aldehyde 527. Reductive amination of aldehyde 527 with an amine such as 528 in the presence of a catalyst such as $Ti(OiPr)_4$ and a reductant such as sodium borohydride gives amine 529. Deprotection of Boc compound 529 with an agent such as trifluoroacetic acid in a solvent such as dichloromethane gives arylamine 530. Coupling of arylamine 530 with an acyl chloride such as 531 in the presence of a base such as triethylamine in a solvent such as dichloromethane gives amine-amide 532. Sulfonamides can be prepared by reaction of methyl 2-aminobenzoate 533 with sulfonyl chloride 534 in the presence of a base such as triethylamine in a solvent such as dichloromethane to give sulfonamide 535. Reaction of 535 with 3-trifluoromethylsulfonylaniline in the presence of a catalyst such as trimethylaluminum in a solvent such as toluene gives compound 536.

Figure 5:
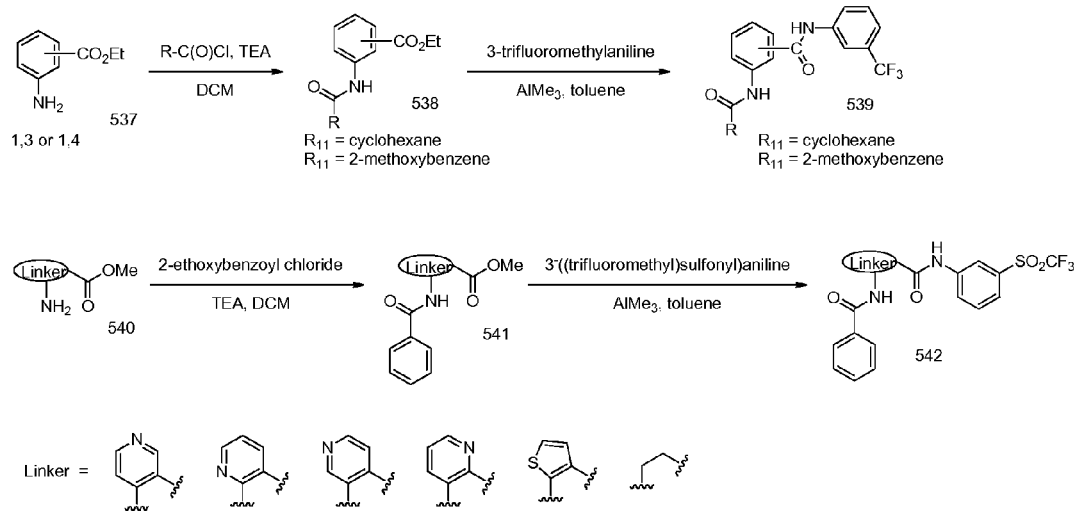
FIG. 5 depicts synthetic schemes for the preparation of compounds in accordance with embodiments of the disclosure.

Referring to FIG. 5, aniline derivative 537 can be reacted with an acyl chloride in the presence of a base such as triethylamine in a solvent such as dichloromethane to provide amide 538. Reaction of 538 with 3-trifluoromethylaniline in the presence of a catalyst such as trimethylaluminum in a solvent such as toluene gives bis-amide 539. The same chemistry can be performed substituting heterocyclic/heteroaryl analogs of compound 537.

Figure 6:
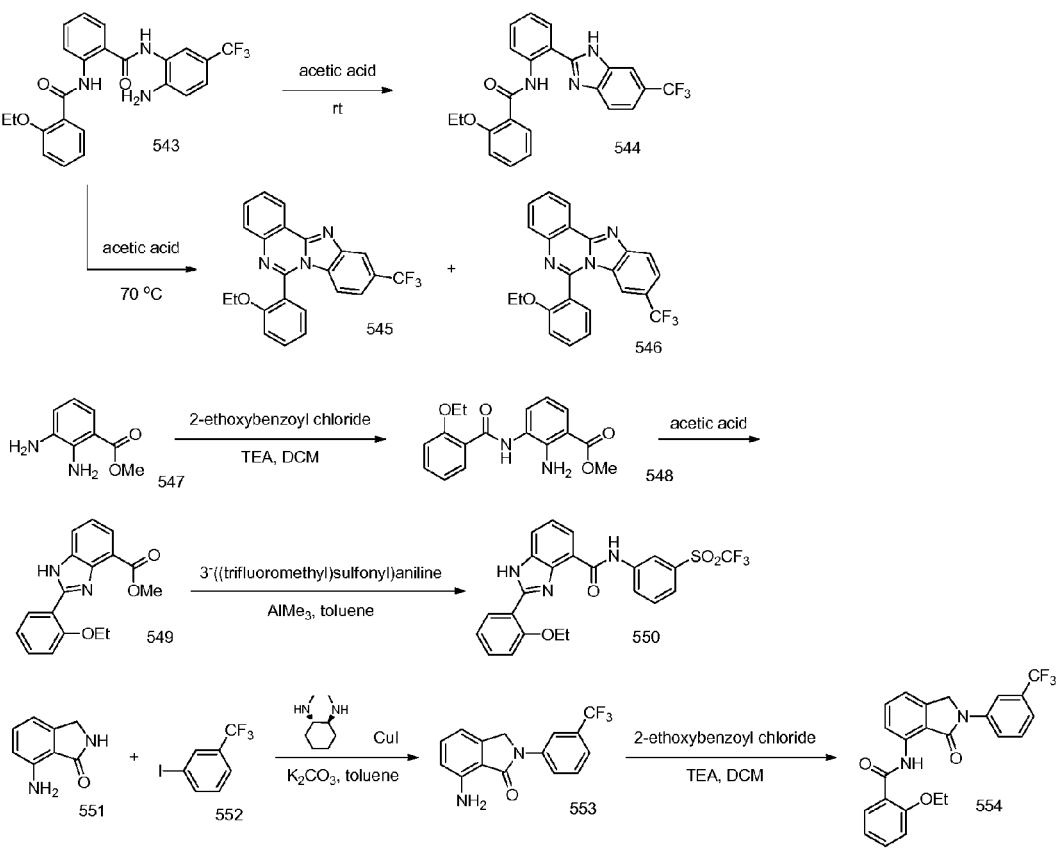
FIG. 6 depicts synthetic schemes for the preparation of compounds in accordance with embodiments of the disclosure.

Referring to FIG. 6, cyclization of amino amide 543 in a solvent such as acetic acid at room temperature provides benzimidazole 544. Cyclization at 70° C. gives a mixture of isomeric tetracyclic compounds 545 and 546. Reaction of bis-amine compound 547 with an acid chloride such as 2-ethoxybenzoyl chloride in the presence of a base such as triethylamine in a solvent such as dichloromethane gives amino amide 548. Cyclization of 548 in a solvent such as acetic acid gives benzimidazole 549. Amidation of 549 with 3-trifluoromethylsulfonylaniline in the presence of a catalyst such as trimethylaluminum in a solvent such as toluene gives compound 550. Reaction of amine 551 with 3-iodotrifluorobenzene in the presence of a catalyst such as 1,2-methylaminocyclohexane in the presence of a catalyst such as copper (I) iodide and a base such as potassium carbonate in a solvent such as toluene gives the coupled product 553. Reaction of 553 with 2-ethoxybenzoyl chloride in the presence of a base such as triethylamine in a solvent such as dichloromethane gives amide 554.

Figure 7:
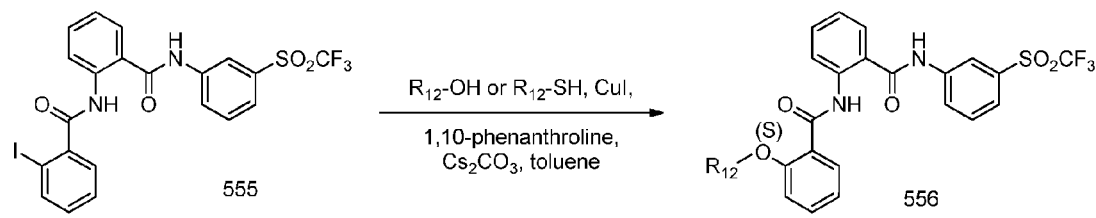
FIG. 7 depicts synthetic schemes for the preparation of compounds in accordance with embodiments of the disclosure.
Figure 8A:
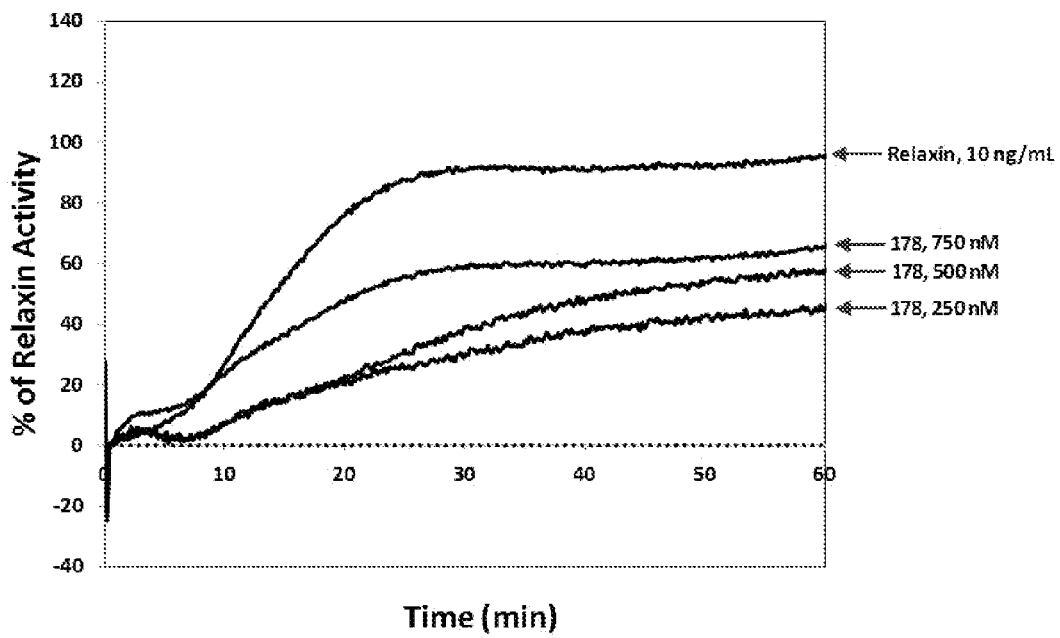
FIG. 8 depicts the cell impedence observed for representative embodiments of the disclosure.
Figure 8B:
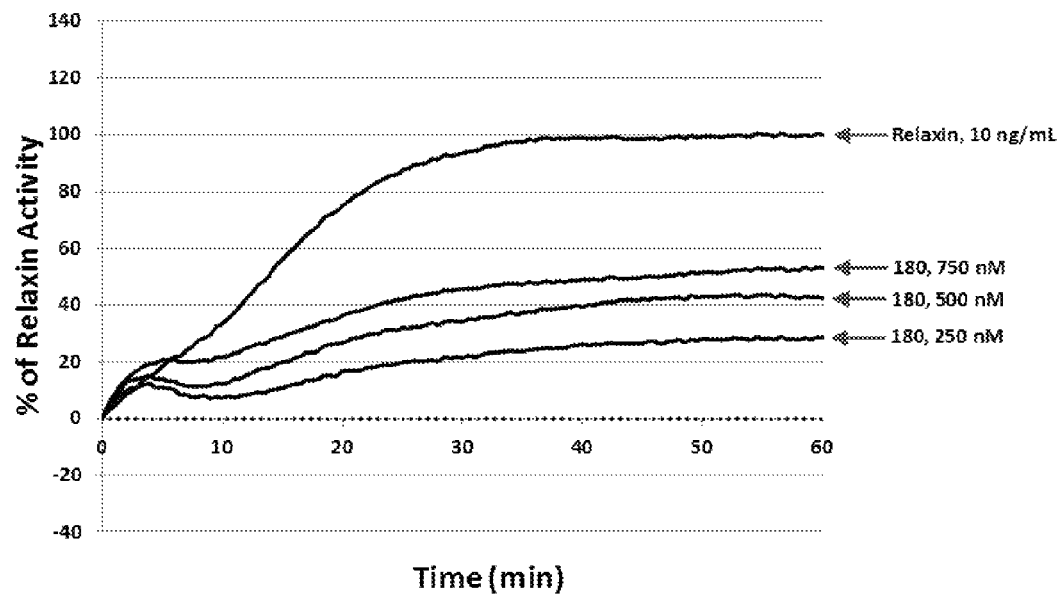
Figure 8C:
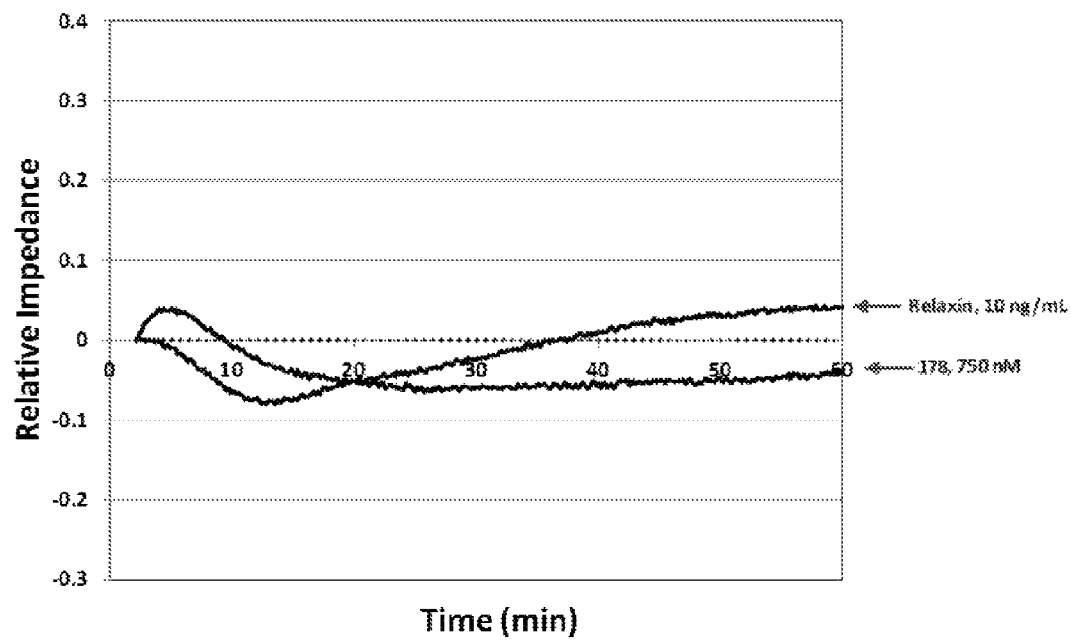
Figure 8D:
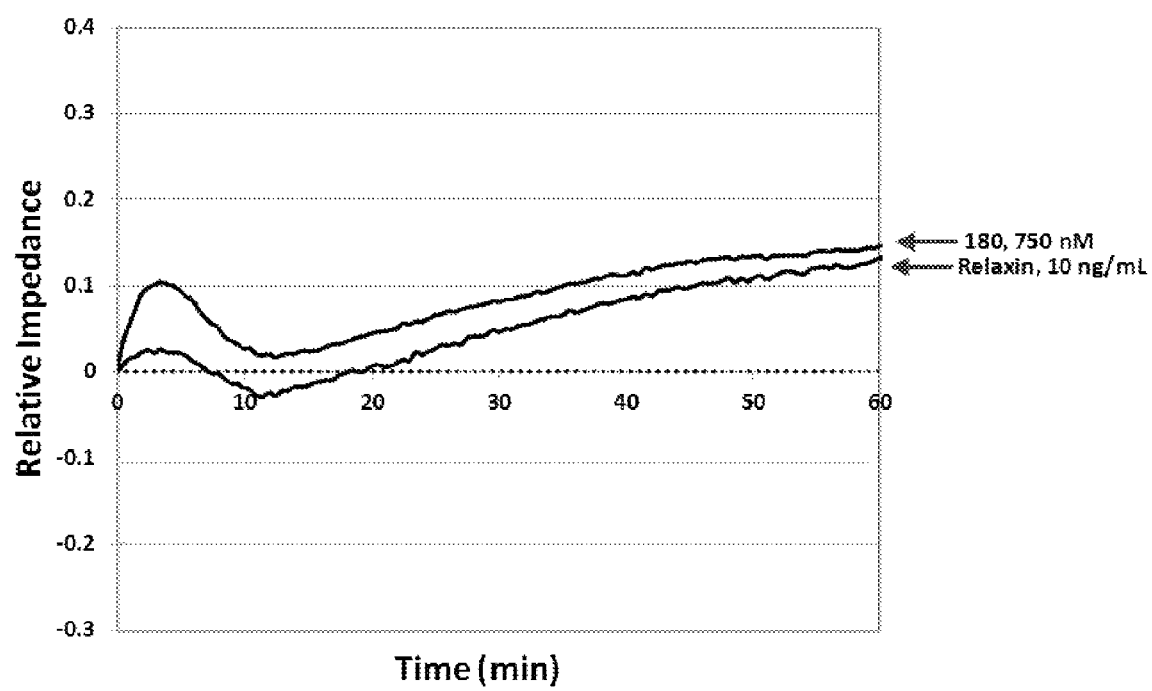
Figure 9:
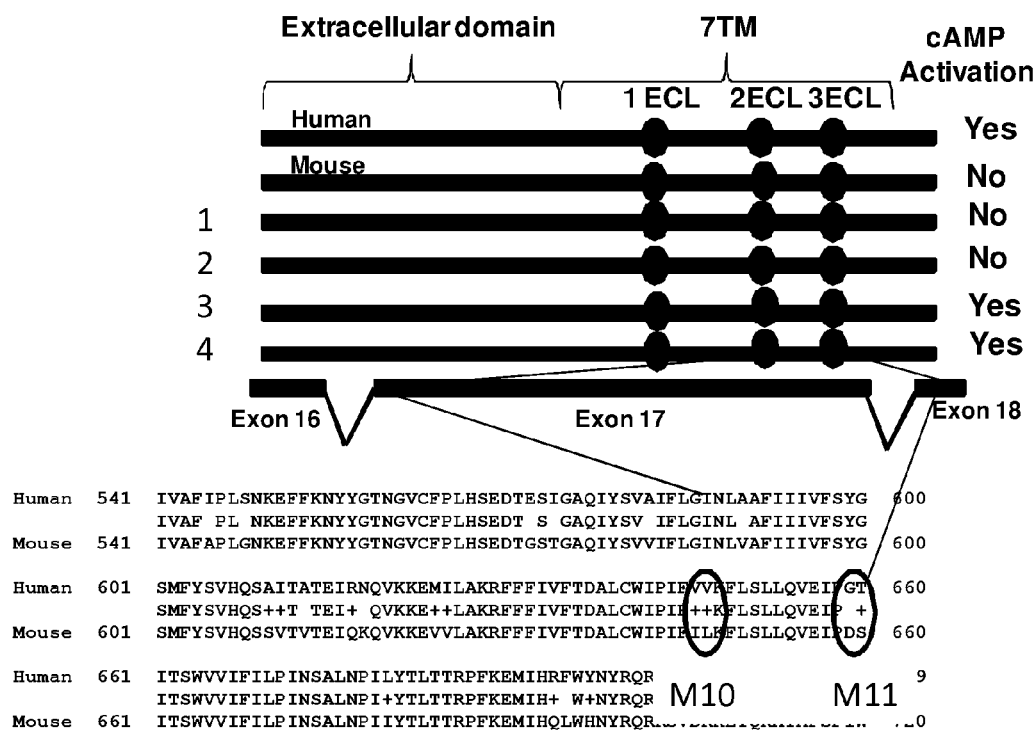
FIG. 9 depicts the results of substitution of mouse sequence with human sequence on activation of cAMP in accordance with an embodiment of the disclosure.
Figure 10:
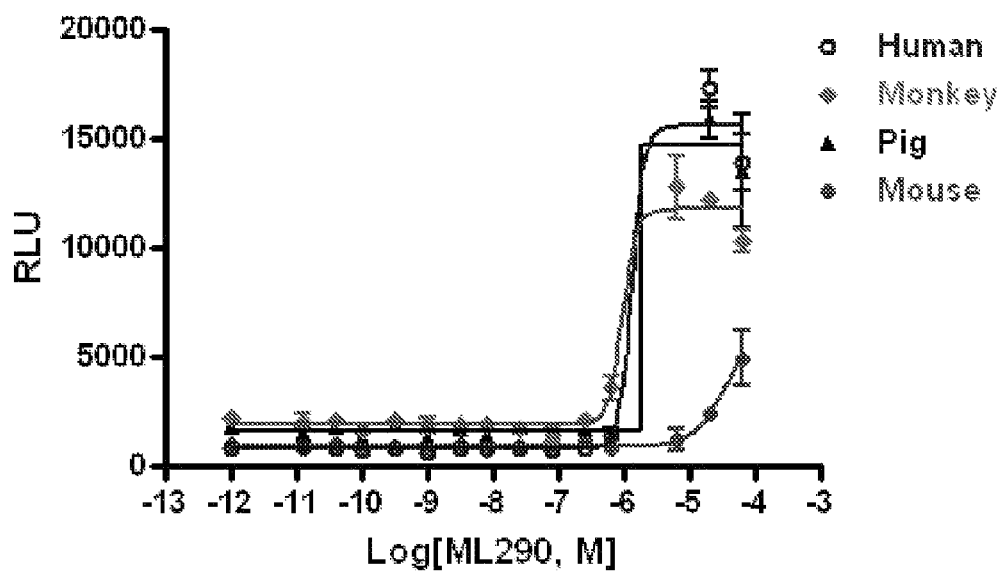
FIG. 10 depicts the activiation of relaxin receptors from human, monkey, pig, and mouse by compound 178.

Referring to FIG. 7, reaction of aryl iodide 555 with an alcohol or a thiol in the presence of catalyst such as copper (I) iodide chloride and 1,10-phenanthroline in the presence of base such as cesium carbonate in a solvent such as toluene gives aryl ether 556.

The present disclosure is further directed to a pharmaceutical composition comprising a pharmaceutically acceptable carrier and at least one compound or salt described herein.

It is preferred that the pharmaceutically acceptable carrier be one that is chemically inert to the active compounds and one that has no detrimental side effects or toxicity under the conditions of use.

The choice of carrier will be determined in part by the particular compound of the present disclosure chosen, as well as by the particular method used to administer the composition. Accordingly, there is a wide variety of suitable formulations of the pharmaceutical composition of the present disclosure. The following formulations for oral, aerosol, nasal, pulmonary, parenteral, subcutaneous, intravenous, intramuscular, intraperitoneal, intrathecal, intratumoral, topical, rectal, and vaginal administration are merely exemplary and are in no way limiting.

The pharmaceutical composition can be administered parenterally, e.g., intravenously, subcutaneously, intradermally, or intramuscularly. Thus, the disclosure provides compositions for parenteral administration that comprise a solution or suspension of the inventive compound or salt dissolved or suspended in an acceptable carrier suitable for parenteral administration, including aqueous and non-aqueous isotonic sterile injection solutions.

Overall, the requirements for effective pharmaceutical carriers for parenteral compositions are well known to those of ordinary skill in the art. See, e.g., Banker and Chalmers, eds., *Pharmaceutics and Pharmacy Practice*, J. B. Lippincott Company, Philadelphia, pp. 238-250 (1982), and Toissel, *ASHP Handbook on Injectable Drugs*, 4th ed., pp. 622-630 (1986). Such solutions can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound or salt of the present disclosure may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-beta-aminopropionates, and 2-alkyl-imidazoline quaternary ammonium salts, and (e) mixtures thereof.

The parenteral formulations can contain preservatives and buffers. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Topical formulations, including those that are useful for transdermal drug release, are well-known to those of skill in the art and are suitable in the context of the disclosure for application to skin. Topically applied compositions are generally in the form of liquids, creams, pastes, lotions and gels. Topical administration includes application to the oral mucosa, which includes the oral cavity, oral epithelium, palate, gingival, and the nasal mucosa. In some embodiments, the composition contains at least one active component and a suitable vehicle or carrier. It may also contain other components, such as an anti-irritant. The carrier can be a liquid, solid or semi-solid. In embodiments, the composition is an aqueous solution. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the disclosure, the vehicle for topical application to the skin can include water, buffered solutions, various alcohols, glycols such as glycerin, lipid materials such as fatty acids, mineral oils, phosphoglycerides, collagen, gelatin and silicone based materials.

Formulations suitable for oral administration can consist of (a) liquid solutions, such as a therapeutically effective amount of the inventive compound dissolved in diluents, such as water, saline, or orange juice, (b) capsules, sachets, tablets, lozenges, and troches, each containing a predetermined amount of the active ingredient, as solids or granules, (c) powders, (d) suspensions in an appropriate liquid, and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compound or salt of the present disclosure, alone or in combination with other suitable components, can be made into aerosol formulations to be administered via inhalation. The compounds are preferably supplied in finely divided form along with a surfactant and propellant. Typical percentages of active compound are 0.01%-20% by weight, preferably 1%-10%. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25%-5%. The balance of the composition is ordinarily propellant. A carrier can also be included as desired, e.g., lecithin for intranasal delivery. These aerosol formulations can be placed into acceptable pressurized propellants, such as dichlorodifluoromethane, propane, nitrogen, and the like. They also may be formulated as pharmaceuticals for non-pressured preparations, such as in a nebulizer or an atomizer. Such spray formulations may be used to spray mucosa.

Additionally, the compound or salt of the present disclosure may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

It will be appreciated by one of ordinary skill in the art that, in addition to the aforedescribed pharmaceutical compositions, the compound or salt of the present disclosure may be formulated as inclusion complexes, such as cyclodextrin inclusion complexes, or liposomes. Liposomes serve to target the compounds to a particular tissue, such as lymphoid tissue or cancerous hepatic cells. Liposomes can also be used to increase the half-life of the inventive compound. Liposomes useful in the present disclosure include emulsions, foams, micelles, insoluble monolayers, liquid crystals, phospholipid dispersions, lamellar layers and the like. In these preparations, the active agent to be delivered is incorporated as part of a liposome, alone or in conjunction with a suitable chemotherapeutic agent. Thus, liposomes filled with a desired inventive compound or salt thereof, can be directed to the site of a specific tissue type, hepatic cells, for example, where the liposomes then deliver the selected compositions. Liposomes for use in the disclosure are formed from standard vesicle-forming lipids, which generally include neutral and negatively charged phospholipids and a sterol, such as cholesterol. The selection of lipids is generally guided by consideration of, for example, liposome size and stability of the liposomes in the blood stream. A variety of methods are available for preparing liposomes, as described in, for example, Szoka et al., *Ann. Rev. Biophys. Bioeng.*, 9, 467 (1980), and U.S. Pat. Nos. 4,235,871, 4,501,728, 4,837,028, and 5,019,369. For targeting to the cells of a particular tissue type, a ligand to be incorporated into the liposome can include, for example, antibodies or fragments thereof specific for cell surface determinants of the targeted tissue type. A liposome suspension containing a compound or salt of the present disclosure may be administered intravenously, locally, topically, etc. in a dose that varies according to the mode of administration, the agent being delivered, and the stage of disease being treated.

The disclosure further provides a method for therapeutic intervention in a facet of mammalian health that is mediated by a mammalian relaxin receptor 1 comprising administering to a mammal in need thereof a therapeutically effective amount of a compound or salt thereof represented by Formula (I):

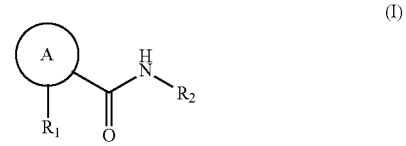

(I)

wherein A is 1,2-phenylenyl, 1,2-heteroarylenyl, 1,2-heterocyclyl, or —CH$_2$CH$_2$—, wherein the 1,2-phenylenyl, 1,2-heteroarylenyl, or 1,2-heterocyclyl are optionally substituted with one or more substituents independently selected from halo, CF$_3$, alkyl, alkyloxy, haloalkyl, haloalkoxy —SR$_7$, —SOR$_7$, —SO$_2$R$_7$, —SCF$_3$, and SO$_2$CF$_3$, R$_1$ is —NHCOR$_3$, R$_4$, —NHR$_5$, or —OR$_6$, R$_2$ is alkyl, cycloalkyl, heteroarylalkyl, or phenyl, which are optionally substituted with one or more substituents independently selected from halo, CF$_3$, C$_1$-C$_{10}$ alkyl, C$_2$-C$_{10}$ alkenyl, C$_1$-C$_{10}$ alkyloxy, C$_1$-C$_{10}$ haloalkyl, C$_1$-C$_{10}$ haloalkoxy aryl, haloalkylaryl, heterocyclylalkyl, —SR$_7$, —SOR$_7$, —SO$_2$R$_7$, —SCF$_3$, —NO$_2$, —CN, and —SO$_2$CF$_3$, R$_3$ is alkyl, cycloalkyl, bicycloalkyl, tricycloalkyl, aryl, heteroaryl, arylalkyl, or phenyl, which are optionally substituted with one or more substituents selected from halo, CF$_3$, C$_1$-C$_{10}$ alkyl, C$_2$-C$_{10}$ alkenyl, C$_1$-C$_{10}$ alkyloxy, C$_1$-C$_{10}$haloalkyl, C$_1$-C$_{10}$haloalkoxy, —SR$_7$, —SOR$_7$, —SO$_2$R$_7$, —SCF$_3$, —NO$_2$, —CN, and —SO$_2$CF$_3$, R$_4$ is phenyl optionally substituted with alkyloxy, haloalkyloxy, arylalkyl, or arylalkyloxy, R$_5$ is hydrogen, alkyl, alkylaryl, aryl, alkylcycloalkyl, or cycloalkylalkyl which are optionally substituted with one or more substituents independently selected from alkyloxy and trifluoromethyl, R$_6$ is alkyl optionally substituted with alkylamino, dialkylamino, alkyloxy, and hetero aryl, and R$_7$ is C$_1$-C$_{10}$ alkyl, C$_1$-C$_{10}$ haloalkyl, C$_1$-C$_{10}$haloalkyl, or C$_1$-C$_{10}$haloalkoxy.

In accordance with certain embodiments, R$_2$ is phenyl substituted with —SO$_2$CF$_3$, —SCF$_3$, or —CF$_3$.

In accordance with certain embodiments, A is 1,2-phenylene optionally substituted with one or more substituents independently selected from halo, —CF$_3$, alkyl, alkyloxy, haloalkyl, haloalkoxy, —SR$_7$, —SOR$_7$, —SO$_2$R$_7$, —SCF$_3$, and —SO$_2$CF$_3$.

In accordance with certain embodiments, R$_1$ is —NH-COR$_3$, wherein R$_3$ is phenyl substituted with a substituent selected from —CF$_3$, C$_1$-C$_{10}$ alkyl, C$_1$-C$_{10}$ alkyloxy, C$_1$-C$_{10}$haloalkyl, C$_1$-C$_{10}$haloalkoxy, alkyloxyalkyloxy, dimethylaminoalkyloxy, —SR$_7$, —SOR$_7$, —SO$_2$R$_7$, —SCF$_3$, and —SO$_2$CF$_3$.

In accordance with certain preferred embodiments, R$_3$ is 2-(C$_1$-C$_{10}$)alkyloxyphenyl.

In accordance with certain preferred embodiments, R$_2$ is phenyl substituted with a substituent selected from —CF$_3$, C$_1$-C$_{10}$ alkyl, C$_1$-C$_{10}$ alkyloxy, C$_1$-C$_{10}$haloalkyl, C$_1$-C$_{10}$haloalkoxy —SR$_7$, —SOR$_7$, —SO$_2$R$_7$, —SCF$_3$, and —SO$_2$CF$_3$.

In certain preferred embodiments, the compound is selected from the group consisting of:

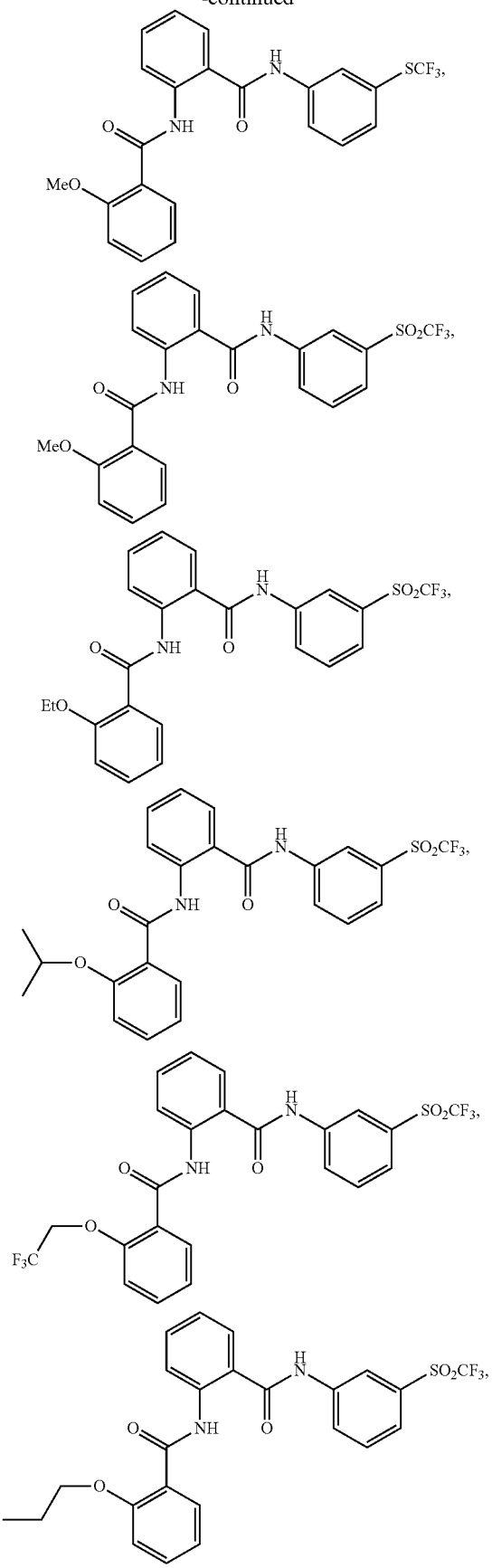

-continued

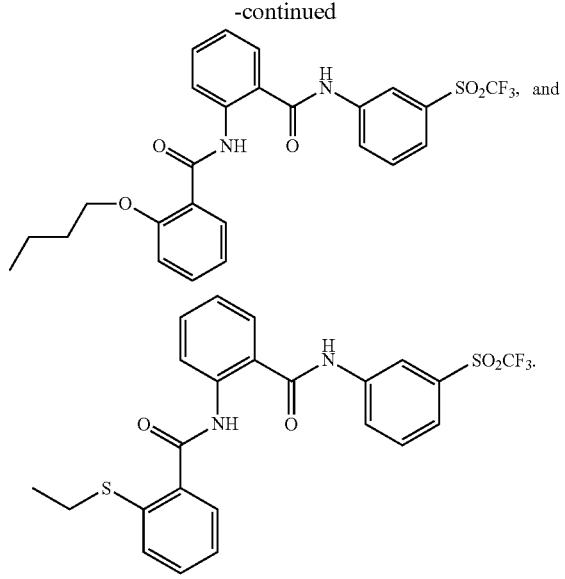

In accordance with certain embodiments, $R_1$ is $R_4$, wherein $R_4$ is 2-($C_1$-$C_{10}$)alkyloxyphenyl or 2-($C_1$-$C_{10}$)haloalkyloxyphenyl.

In accordance with certain preferred embodiments, $R_1$ is —$NHR_5$, wherein $R_5$ is aryl optionally substituted with one or more substituents independently selected from alkyloxy and trifluoromethyl.

In accordance with certain embodiments, $R_1$ is —$OR_6$, wherein $R_6$ is alkyl optionally substituted with alkylamino, dialkylamino, alkyloxy, and heteroaryl.

In accordance with certain embodiments, A is 1,2-heteroarylenyl optionally substituted with one or more substitutents independently selected from halo, —$CF_3$, alkyl, alkyloxy, haloalkyl, haloalkoxy —$SR_7$, —$SOR_7$, —$SO_2R_7$, —$SCF_3$, and —$SO_2CF_3$.

In accordance with certain preferred embodiments, A is selected from

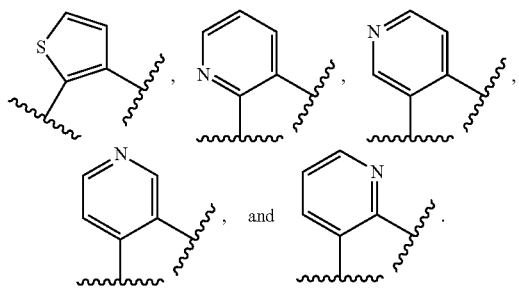

In accordance with certain preferred embodiments, $R_1$ is —$NHCOR_3$, wherein $R_3$ is phenyl substituted with a substituent selected from independently —$CF3$, $C_1$-$C_{10}$ alkyl, $C_1$-$C_{10}$ alkyloxy, $C_1$-$C_{10}$haloalkyl, C1-$C_{10}$haloalkoxy, —$SR_7$, —$SOR_7$, —$SO_2R_7$, —$SCF_3$, and —$SO_2CF_3$.

In accordance with certain preferred embodiments, R3 is 2-($C_1$-$C_{10}$)alkyloxyphenyl or 2-($C_1$-$C_{10}$)haloalkyloxyphenyl.

In certain preferred embodiments, wherein the compound is selected from the group consisting of:

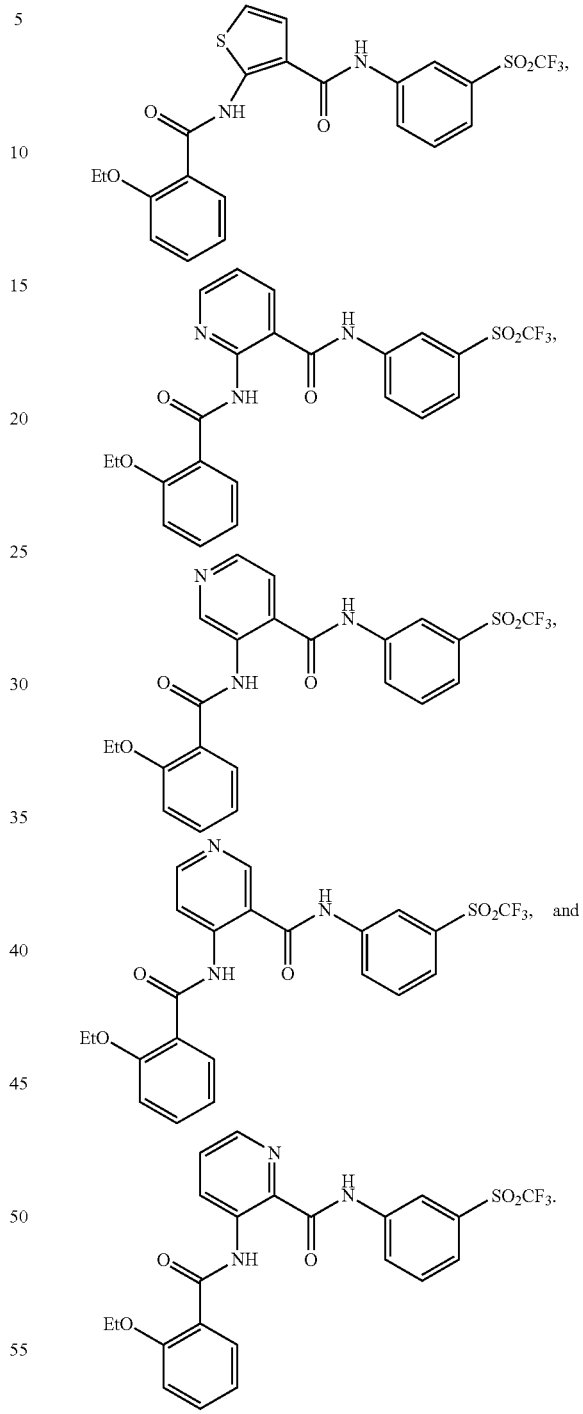

In accordance with certain embodiments, A is —$CH_2CH_2$—.

In accordance with certain embodiments, wherein $R_1$ is —$NHCOR_3$, wherein $R_3$ is phenyl substituted with a substituent selected from —$CF_3$, $C_1$-$C_{10}$ alkyl, $C_1$-$C_{10}$ alkyloxy, $C_1$-$C_{10}$haloalkyl, $C_1$-$C_{10}$haloalkoxy, —$SR_7$, —$SOR_7$, —$SO_2R_7$, —$SCF_3$, and —$SO_2CF_3$.

In accordance with certain embodiments, R3 is 2-($C_1$-$C_{10}$)alkyloxyphenyl or 2-($C_1$-$C_{10}$)haloalkyloxyphenyl.

In accordance with a particular embodiment, the compound is:

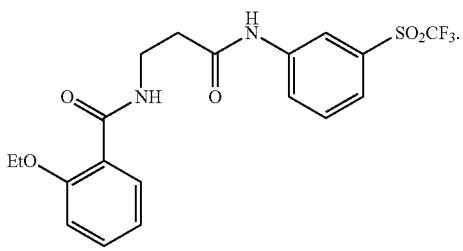

The facet of mammalian health can be any disease, disorder, or aspect of mammalian health that is mediated by a mammalian relaxin receptor 1. Examples of facets of mammalian health, wherein the mammal is a human, that are mediated by a mammalian relaxin receptor 1, wherein the mammalian relaxin receptor 1 is a human relaxin receptor 1, are disclosed in, e.g., E. T. Van Der Westhuizen et al., Current Drug Targets 2007, 8, 91-104; U.S. Pat. No. 8,053,411; and U.S. Patent Application Publication 2011/0177998, the discloses of which are incorporated herein.

The mammal can be any suitable mammal. Examples of suitable mammals include, but are not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simioids (monkeys) or of the order Anthropoids (humans and apes). An especially preferred mammal is the human. Furthermore, the subject can be the unborn offspring of any of the forgoing hosts, especially mammals (e.g., humans), in which case any screening of the subject or cells of the subject, or administration of compounds to the subject or cells of the subject, can be performed in utero.

The mammalian relaxin receptor 1 can be any suitable mammalian relaxin receptor 1. Typically, the mammalian relaxin receptor 1 is a relaxin receptor 1 that exists in the particular mammal being treated.

In some embodiments, the facet of mammalian health is a facet of human health. In these embodiments, the mammalian relaxin receptor 1 is a human relaxin receptor 1.

In an embodiment, the facet of mammalian health is cardiovascular disease. Non-limiting examples of cardiovascular disease include acute heart failure, myocardial ischemia-reperfusion injury, cardiac fibrosis, acute congestive heart failure, cerebrovascular disease and stroke, post-infarction heart, cardiac anaphylaxis, cerebral ischemia (stroke), intestinal ischemia-reperfusion injury, systemic and pulmonary hypertension, vascular inflammation, hypertension, high blood pressure; left ventricular hypertrophy (LVH); vasodilation; renal hypertension; diuresis; nephritis; natriuresis; scleroderma renal crisis; angina pectoris (stable and unstable); myocardial infarction; heart attack; coronary artery disease; coronary heart disease; cardiac arrhythmias; atrial fibrillation; portal hypertension; raised intraocular pressure; vascular restenosis; chronic hypertension; valvular disease; myocardial ischemia; acute pulmonary edema; acute coronary syndrome; hypertensive retinopathy; hypertensive pregnancy sickness; Raynaud's phenomenon; erectile dysfunction, glaucoma, and preeclampsia.

In an embodiment, the facet of mammalian health is dyspnea associated with acute heart failure in a human subject, wherein said subject has dyspnea associated with acute heart failure and is in a hypertensive or normotensive state at the onset of said administering.

In an embodiment, the facet of mammalian health is acute decompensated heart failure, wherein the method is effective to reduce in-hospital worsening of said acute decompensated heart failure in said subject. In a preferred embodiment, the in-hospital worsening of said acute decompensated heart failure comprises one or more of worsening dyspnea, need for additional therapy to treat said heart failure, need for mechanical support of breathing, and need for mechanical support of blood pressure. In another preferred embodiment, the method further comprises a reduction in the risk of death or rehospitalization of said subject.

In an embodiment, the facet of mammalian health is fibrotic disease. In selected embodiments, the fibrotic disease is selected from the group of but not limited to pulmonary fibrosis, renal tubulointerstitial fibrosis, mesangial proliferative nephritis, hepatic fibrosis (cirrhosis) alcohol and non-alcohol related (including viral infection such as HAV, HBV and HCV); fibromatosis; granulomatous lung disease; glomerulonephritis, myocardial scarring following infarction; endometrial fibrosis and endometriosis, polycystic kidney disease, scleroderma and systemic sclerosis, keloids, arthritis, autoimmune disorder, inflammatory condition associated with infection, skeletal muscle injuries, conditions involving tissue remodeling following inflammation or ischemia-reperfusion injury and is selected from endomyocardial and cardiac fibrosis; mediastinal fibrosis; retroperitoneal fibrosis; fibrosis of the spleen; fibrosis of the pancreas; wound healing whether by injury or surgical procedures, diabetes related wound fibrosis.

In an embodiment, the facet of mammalian health is respiratory disease selected from asthma, bronchial disease, lung diseases, chronic obstructive pulmonary disease (COPD), Acute Respiratory Distress Syndrome (ARDS), severe acute respiratory syndrome (SARS), Fibrosis related Asthma, and cystic fibrosis.

In an embodiment, the facet of mammalian health is skin disease selected from dermal repair, wound healing; burns, erythemas, lesions, wound healing following surgical procedures; skin or tissue lesions including lesions induced by Psoriasis, Lupus and Kaposhi Sarcoma; Scleroderma, and collagenous diseases of the skin and skin tumors.

In an embodiment, the facet of mammalian health is female reproduction. In selected embodiments, the facet of female reproduction is selected from in vitro fertilization, abnormal implantation, pre-term birth and induction of labor, mammary functions and lactation disorders; plasma osmolarity during pregnancy, uterine fibroids, abnormal endometrial angiogenesis; placental development defects; cervical ripening (softening); nipple development and disfunction; pregnancy related remodeling of the uterine tissue; endometriosis; preeclampsia; estrogenic and non-estrogenic related hormonal disorders; pre-term labor; post term labor; and labor complications.

In an embodiment, the facet of mammalian health is male reproduction. In particular embodiments, the facet of male reproduction is selected from sperm functions and fertilization.

In an embodiment, the facet of mammalian health is surgical transplantation of a liver.

In an embodiment, the facet of mammalian health is a cancer selected from colon cancer, lung cancer, breast cancer, prostate cancer, brain cancer, pancreatic cancer, ovarian cancer, kidney cancer, testicular cancer, bone cancer, osteosarcoma, liver cancer, melanoma, glioma, sarcoma, leukemia, or lymphoma, and wherein the cancer is invasive or metastatic.

In an embodiment, the facet of mammalian health is enhancement of drug delivery in the treatment of a solid cancer, in combination with a chemotherapeutic treatment or radiation treatment of the cancer.

In an embodiment, the facet of mammalian health is orthodontic tooth movement.

In an embodiment, the facet of mammalian health is bone joint disease.

In an embodiment, the facet of mammalian health is selected from osteoporosis; osteoarthritis; osteopetrosis; bone inconsistency; osteosarcoma; and cancer metastasis to the bone.

In an embodiment, the facet of mammalian health is diabetes mellitus.

In an embodiment, the facet of mammalian health is ischemia-reperfusion injury associated with ischemic and post-ischemic events in organs and tissues and in a group of patients with thrombotic stroke; myocardial infarction; angina pectoris; embolic vascular occlusions; peripheral vascular insufficiency; splanchnic artery occlusion; arterial occlusion by thrombi or embolisms, arterial occlusion by non-occlusive processes such as following low mesenteric flow or sepsis; mesenteric arterial occlusion; mesenteric vein occlusion; ischemia-reperfusion injury to the mesenteric microcirculation; ischemic acute renal failure; ischemia-reperfusion injury to the cerebral tissue; intestinal intussusception; hemodynamic shock; tissue dysfunction; organ failure; restenosis; atherosclerosis; thrombosis; platelet aggregation, ischemia-reperfusion injury following cardiac surgery; organ surgery; organ transplantation; angiography; cardiopulmonary and cerebral resuscitation.

In an embodiment, the facet of mammalian health is an inflammatory condition associated with an infection, wherein the infection is selected from a viral infection caused by human immunodeficiency virus I (HIV-1) or HIV-2, acquired immune deficiency (AIDS), West Nile encephalitis virus, coronavirus, rhinovirus, influenza virus, dengue virus, HCV, HBV, HAV, hemorrhagic fever; an otological infection; severe acute respiratory syndrome (SARS), sepsis and sinusitis.

In an embodiment, the facet of mammalian health is kidney diseases selected from diabetic nephropathy; glomerulosclerosis; nephropathies; renal impairment; scleroderma renal crisis and chronic renal failure.

In an embodiment, the facet of mammalian health is an angiogenesis related condition selected from retinal angiogenesis in a number of mammalian ocular diseases such as diabetes mellitus, retinopathy of prematury, and age-related macular degeneration, or cancer associated angiogenesis in primary or metastatic cancer, including but not limited to cancer of the prostate, brain, breast, colorectal, lung, ovarian, pancreatic, renal, cervical, melanoma, soft tissue sarcomas, lymphomas, head-and-neck, and glioblastomas.

In an embodiment, the facet of mammalian health is an inflammatory disorder selected from gastritis, gout, gouty arthritis, arthritis, rheumatoid arthritis, inflammatory bowel disease, Crohn's disease, ulcerative colitis, ulcers, chronic bronchitis, asthma, allergy, acute lung injury, pulmonary inflammation, airway hyper-responsiveness, vasculitis, septic shock and inflammatory skin disorders, including but not limited to psoriasis, atopic dermatitis, eczema.

In an embodiment, the facet of mammalian health is an autoimmune disorder is selected from multiple sclerosis, psoriasis, rheumatoid arthritis, systemic lupus erythematosus, ulcerative colitis, Crohn's disease, transplant rejection, immune disorders associated with graft transplantation rejection, benign lymphocytic angiitis, lupus erythematosus, Hashimoto's thyroiditis, primary myxedema, Graves' disease, pernicious anemia, autoimmune atrophic gastritis, Addison's disease, insulin dependent diabetes mellitus, Good pasture's syndrome, myasthenia gravis, pemphigus, sympathetic ophthalmia, autoimmune uveitis, autoimmune hemolytic anemia, idiopathic thrombocytopenia, primary biliary cirrhosis, chronic action hepatitis, ulceratis colitis, Sjogren's syndrome, rheumatic disease, polymyositis, scleroderma, mixed connective tissue disease, inflammatory rheumatism, degenerative rheumatism, extra-articular rheumatism, collagen diseases, chronic polyarthritis, psoriasis arthropathica, ankylosing spondylitis, juvenile rheumatoid arthritis, periarthritis humeroscapularis, panarteriitis nodosa, progressive systemic scleroderma, arthritis uratica, dermatomyositis, muscular rheumatism, myositis, myogelosis, and chondrocalcinosis.

In an embodiment, the facet of mammalian health is an behavioral abnormality or disease.

☐Therapeutic intervention in a facet of mammalian health that is mediated by a mammalian relaxin receptor 1☐ refers to a therapeutic intervention that ameliorates a sign or symptom of a disease or pathological condition after it has begun to develop. As used herein, the term ☐ameliorating,☐ with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. Treatment of cardiovascular disease can be evidenced, for example, by reduction of blood pressure, an enhancement of vascular compliance, a reduction in clinical symptoms resulting from the cardiovascular disease, or other parameters well known in the art that are specific to the cardiovascular disease. The phrase ☐treating a disease☐ refers to inhibiting the full development of a disease or condition, for example, in a subject who is at risk for a disease such as cardiovascular disease.

In other embodiments, the therapeutic intervention provides an enhancement in a desirable facet of mammalian health. In certain embodiments the therapeutic intervention provides an enhancement in a desirable facet of human health. For example, the therapeutic intervention can lead to improved outcomes in organ transplantation, in improvements in female fertility such as increased success in in vitro fertilization, and the like.

One skilled in the art will appreciate that suitable methods of utilizing a compound and administering it to a mammal for the treatment or prevention of disease states which would be useful in the method of the present disclosure, are available. Although more than one route can be used to administer a particular compound, a particular route can provide a more immediate and more effective reaction than another route. Accordingly, the described methods are merely exemplary and are in no way limiting.

The dose administered to a mammal, particularly, a human, in accordance with the present disclosure should be sufficient to effect the desired response. Such responses include reversal or prevention of the bad effects of the disease for which treatment is desired or to elicit the desired benefit. One skilled in the art will recognize that dosage will depend upon a variety of factors, including the age, condition, and body weight of the mammal, as well as the source, particular type of the disease, and extent of the disease in the human. The size of the dose will also be determined by the route, timing and frequency of administration as well as the existence, nature, and extent of any adverse side-effects that might accompany the administration of a particular compound and the desired physiological effect. It will be appreciated by one of skill in the art that various conditions or disease states may require prolonged treatment involving multiple administrations.

Suitable doses and dosage regimens can be determined by conventional range-finding techniques known to those of ordinary skill in the art. Generally, treatment is initiated with smaller dosages that are less than the optimum dose of the compound. Thereafter, the dosage is increased by small increments until the optimum effect under the circumstances is reached. The present inventive method typically will involve the administration of about 0.1 to about 300 mg of one or more of the compounds described above per kg body weight of the mammal.

The therapeutically effective amount of the compound or compounds administered can vary depending upon the desired effects and the factors noted above. Typically, dosages will be between 0.01 mg/kg and 250 mg/kg of the subject's body weight, and more typically between about 0.05 mg/kg and 100 mg/kg, such as from about 0.2 to about 80 mg/kg, from about 5 to about 40 mg/kg or from about 10 to about 30 mg/kg of the subject's body weight. Thus, unit dosage forms can be formulated based upon the suitable ranges recited above and the subject's body weight. The term "unit dosage form" as used herein refers to a physically discrete unit of therapeutic agent appropriate for the subject to be treated.

Alternatively, dosages are calculated based on body surface area and from about 1 mg/m$^2$ to about 200 mg/m$^2$, such as from about 5 mg/m$^2$ to about 100 mg/m$^2$ will be administered to the subject per day. In particular embodiments, administration of the therapeutically effective amount of the compound or compounds involves administering to the subject from about 5 mg/m$^2$ to about 50 mg/m$^2$, such as from about 10 mg/m$^2$ to about 40 mg/m$^2$ per day. It is currently believed that a single dosage of the compound or compounds is suitable, however a therapeutically effective dosage can be supplied over an extended period of time or in multiple doses per day. Thus, unit dosage forms also can be calculated using a subject's body surface area based on the suitable ranges recited above and the desired dosing schedule.

The disclosure further provides a use of a compound or salt of the disclosure in the manufacture of a medicament for therapeutic intervention in a facet of mammalian health that is mediated by a mammalian relaxin receptor 1. The medicament typically is a pharmaceutical composition as described herein.

The following examples further illustrate the disclosure but, of course, should not be construed as in any way limiting its scope.

General Methods for Chemistry. All air or moisture sensitive reactions were performed under positive pressure of nitrogen with oven-dried glassware Anhydrous solvents such as dichloromethane, N,N-dimethylformamide (DMF), acetonitrile, methanol and triethylamine were purchased from Sigma-Aldrich (St. Louis, Mo.). Preparative purification was performed on a Waters semi-preparative HPLC system (Waters Corp., Milford, Mass.). The column used was a Phenomenex Luna $C_{18}$ (5 micron, 30×75 mm; Phenomenex, Inc., Torrance, Calif.) at a flow rate of 45.0 mL/min. The mobile phase consisted of acetonitrile and water (each containing 0.1% trifluoroacetic acid). A gradient of 10% to 50% acetonitrile over 8 minutes was used during the purification. Fraction collection was triggered by UV detection at 220 nM. Analytical analysis was performed on an Agilent LC/MS (Agilent Technologies, Santa Clara, Calif.). Method 1 ($t_1$): A 7-minute gradient of 4% to 100% acetonitrile (containing 0.025% trifluoroacetic acid) in water (containing 0.05% trifluoroacetic acid) was used with an 8-minute run time at a flow rate of 1.0 mL/min. Method 2 ($t_2$): A 3-minute gradient of 4% to 100% acetonitrile (containing 0.025% trifluoroacetic acid) in water (containing 0.05% trifluoroacetic acid) was used with a 4.5-minute run time at a flow rate of 1.0 mL/min. A Phenomenex Luna $C_{18}$ column (3 micron, 3×75 mm) was used at a temperature of 50° C. Purity determination was performed using an Agilent diode array detector for both Method 1 and Method 2. Mass determination was performed using an Agilent 6130 mass spectrometer with electrospray ionization in the positive mode. $^1$H NMR spectra were recorded on Varian 400 MHz spectrometers (Agilent Technologies, Santa Clara, Calif.). Chemical shifts are reported in ppm with undeuterated solvent (DMSO-$d_6$ at 2.49 ppm) as internal standard for DMSO-$d_6$ solutions. All of the analogs tested in the biological assays have a purity of greater than 95% based on both analytical methods. High resolution mass spectrometry was recorded on Agilent 6210 Time-of-Flight (TOF) LC/MS system. Confirmation of molecular formula was accomplished using electrospray ionization in the positive mode with the Agilent Masshunter software (Version B.02).

General Protocol A. A solution of methyl or ethyl benzoate (0.191 mmol) and amine (0.383 mmol) in toluene (2.00 mL) was treated at room temperature with AlMe$_3$ (0.192 mL, 2.0 M in toluene, 0.384 mmol). The reaction mixture was stirred overnight at 100° C. and then quenched with 100 µL of water. The mixture was concentrated, re-dissolved in 2.00 mL of DMSO, filtered and purified via $C_{18}$ reverse phase HPLC to give the final product.

General Protocol B. A solution of carboxylic acid (0.178 mmol) in DMF (2.00 mL) was treated at room temperature with 2-amino-N-(3-(trifluoromethyl)phenyl)benzamide (25.0 mg, 0.089 mmol) followed by EDC (17.1 mg, 0.089 mmol) and DMAP (10.9 mg, 0.089 mmol). The reaction mixture was stirred overnight at room temperature. The mixture was purified via $C_{18}$ reverse phase HPLC to give the final product.

General Protocol C. A solution of 2-amino-N-(3-(trifluoromethyl)phenyl)benzamide (50.0 mg, 0.178 mmol) in dichloromethane (2.00 mL) and TEA (0.075 mL, 0.535 mmol) was treated at room temperature with carbonyl chloride (0.357 mmol). The reaction mixture was stirred at room temperature for 2 h. The mixture was concentrated, re-dissolved in 2.00 mL of DMSO, filtered and purified via $C_{18}$ reverse phase HPLC to give the final product.

General Protocol D. A solution of carboxylic acid (0.357 mmol) in DMF (2.00 mL) was added DIPEA (0.093 mL, 0.535 mmol) and HATU (136 mg, 0.357 mmol). The reaction mixture was stirred at room temperature for 5 min, followed by 2-amino-N-(3-(trifluoromethyl)phenyl)benzamide (50.0 mg, 0.178 mmol). The reaction mixture was stirred overnight at room temperature, filtered and purified via $C_{18}$ reverse phase HPLC to give the final product.

General Protocol E. A mixture of 2-bromo-N-(3-(trifluoromethyl)phenyl)benzamide (50.0 mg, 0.145 mmol, 1.0 equiv.) or N-(3-bromophenyl)-2-(cyclohexanecarboxamido)

benzamide (100 mg, 0.249 mmol, 1.0 equiv.), boronic acid or pinacol ester (2.0 equiv.) and Pd(PPh$_3$)$_4$ (0.05 equiv) in DMF (1.50 mL) and 2.0 N Na$_2$CO$_3$ (0.50 mL) aqueous solution was heated in μW at 100° C. for 30 min-1 h. The reaction was cooled to room temperature, added a small portion of Si-THIOL to get rid of Palladium. The reaction mixture was filtered and purified via C$_{18}$ reverse phase HPLC to give the final product.

General Protocol F. 2-Iodo-N-(3-(trifluoromethyl)phenyl) benzamide (100 mg, 0.256 mmol), amine (0.767 mmol), and CuCl (7.59 mg, 0.077 mmol) in DMF (1.00 mL) was stirred at room temperature for 15-30 min. The reaction was treated with a small portion of Si-THIOL to get rid of Palladium, filtered and purified via C$_{18}$ reverse phase HPLC to give the final product.

General Protocol G. A solution of thio-compound (0.255 mmol) in dichloromethane (3.00 mL) was treated at room temperature with MCPBA (220 mg, 1.27 mmol). The reaction mixture was stirred overnight at room temperature. 10% aqueous NaHSO$_3$ solution was added to quench excess MCPBA and the mixture was stirred at room temperature for 15 min. The reaction mixture was worked up with dichloromethane and water. The organic layer was separated, dried, concentrated, and purified via C$_{18}$ reverse phase HPLC to give the final product.

General Protocol H. A tube was charged with CuI (0.1 equiv.), 1,10-phenanthroline (0.2 equiv.), Cs$_2$CO$_3$ (2.0 equiv.), iodo substrate (1.0 equiv.) and alcohol (2.0 equiv.) in toluene (2.00 mL) under N$_2$. The tube was sealed and the reaction mixture was stirred at 110° C. for 24 h. The resulting mixture was cooled to room temperature and treated with a small portion of Si-THIOL to get rid of copper. The mixture was concentrated, re-dissolved in 2.00 mL of DMSO, filtered and purified via C$_{18}$ reverse phase HPLC to give the final product

EXAMPLE 1

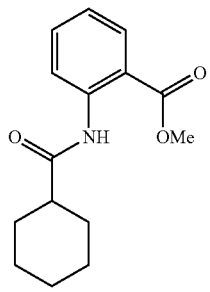 [SMILES: COC(=O)c1ccccc1NC(=O)C1CCCCC1]

This example illustrates a synthesis of Methyl 2-(cyclohexanecarboxamido)benzoate (XJB05-077, NCGC00189490-01). A solution of methyl 2-aminobenzoate (3.00 g, 19.9 mmol) in dichloromethane (100 mL) and triethylamine (8.30 mL, 59.5 mmol) was treated at 0° C. with cyclohexanecarbonyl chloride (2.70 mL, 19.9 mmol). The reaction was stirred at 0° C. for 2 h and room temperature for additional 2 h. The reaction mixture was concentrated and purified via silica gel chromatography using a gradient of 0-40% of EtOAc in hexanes to give 5.00 g (96%) of the title product as a white solid. LC-MS Retention Time: t$_1$ (Method 1)=6.453 min; $^1$H NMR (400 MHz, DMSO-d$_6$) δ ppm 10.65 (s, 1H), 8.31 (dd, J=8.5, 1.1 Hz, 1H), 7.90 (dd, J=7.9, 1.7 Hz, 1H), 7.57 (ddd, J=8.6, 7.2, 1.7 Hz, 1H), 6.87-7.29 (m, 1H), 3.83 (s, 3H), 2.31 (tt, J=11.3, 3.5 Hz, 1H), 1.88 (dd, J=12.9, 2.5 Hz, 2H), 1.73 (ddd, J=12.4, 3.3, 3.1 Hz, 2H), 1.55-1.67 (m, 1H), 1.08-1.47 (m, 5H).

EXAMPLE 2

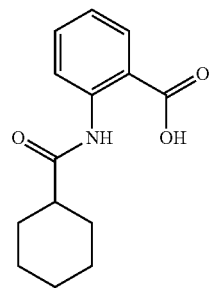 [SMILES: O=C(O)c1ccccc1NC(=O)C1CCCCC1]

This example illustrates a synthesis of 2-(Cyclohexanecarboxamido)benzoic acid (XJB05-087, NCGC00189489-01). A solution of methyl 2-(cyclohexanecarboxamido)benzoate (4.00 g, 15.3 mmol) in MeOH (100 mL) was treated at room temperature with 4.0 N NaOH aqueous solution (40.0 mL, 153 mmol). The reaction mixture was stirred at room temperature for 1 h. MeOH was removed by rotavapor and the mixture was cooled in ice-bath and acidified with 5.0 N HCl until white precipitation was appeared. The white precipitation was filtered and washed with water to give 3.60 g (95%) of the title product as a white solid. LC-MS Retention Time: t$_1$ (Method 1)=5.345 min.

EXAMPLE 3

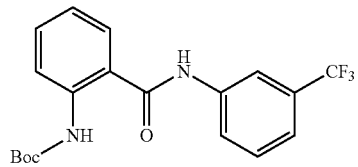 [SMILES: CC(C)(C)OC(=O)Nc1ccccc1C(=O)Nc1cccc(C(F)(F)F)c1]

This example illustrates a synthesis of tert-Butyl 2-(3-(trifluoromethyl)phenylcarbamoyl)phenylcarbamate (XJB05-088, NCGC00189488-01). A solution of 2-(tert-butoxycarbonylamino)benzoic acid (3.00 g, 12.6 mmol) and 3-(trifluoromethyl)aniline (2.36 mL, 19.0 mmol) in dichloromethane (75.0 mL) was treated at room temperature with DMAP (1.55 g, 12.6 mmol) and EDC (4.85 g, 25.3 mmol) and stirred at room temperature for 24 h. The reaction mixture was concentrated and purified via silica gel chromatography using a gradient of 0-100% of dichloromethane in hexanes followed by 10% of EtOAc in dichloromethane to give 2.20 g (46%) of the title product as a white solid. LC-MS Retention Time: t$_1$ (Method 1)=7.042 min; $^1$H NMR (400 MHz, DMSO-d$_6$) δ ppm 10.64 (s, 1H), 9.75 (s, 1H), 8.14 (s, 1H), 7.98 (d, J=7.6 Hz, 1H), 7.94 (d, J=9.2 Hz, 1H), 7.77 (dd, J=7.9, 1.5 Hz, 1H), 7.58 (t, J=8.0 Hz, 1H), 7.51 (ddd, J=8.5, 7.2, 1.5 Hz, 1H), 7.45 (d, J=7.8 Hz, 1H), 7.16 (td, J=7.6, 1.1 Hz, 1H), 1.41 (s, 9H); $^{19}$F NMR (376 MHz, DMSO-d$_6$) δ ppm −61.20 (s, 3F); HRMS (ESI) m/z (M+H)$^+$ calcd. for C$_{19}$H$_{20}$F$_3$N$_2$O$_3$, 381.1421; found 381.1426.

EXAMPLE 4

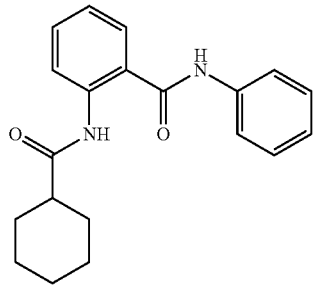 [SMILES: O=C(Nc1ccccc1)c1ccccc1NC(=O)C1CCCCC1]

This example illustrates a synthesis of 2-(Cyclohexanecarboxamido)-N-phenylbenzamide (XJB06-001, NCGC00189487-01). The title compound was prepared according to general protocol A. LC-MS Retention Time: $t_1$ (Method 1)=6.326 min; $^1$H NMR (400 MHz, DMSO-$d_6$) δ ppm 10.54 (s, 1H), 10.37 (s, 1H), 8.23 (dd, J=8.2, 1.0 Hz, 1H), 7.77 (dd, J=7.9, 1.5 Hz, 1H), 7.63-7.71 (m, 2H), 7.49 (ddd, J=8.4, 7.2, 1.6 Hz, 1H), 7.28-7.41 (m, 2H), 7.19 (td, J=7.6, 1.3 Hz, 1H), 7.07-7.14 (m, 1H), 2.17-2.34 (m, 1H), 1.76-1.88 (m, 2H), 1.69 (ddd, J=12.5, 3.4, 3.2 Hz, 2H), 1.59 (d, J=12.1 Hz, 1H), 1.03-1.43 (m, 5H); HRMS (ESI) m/z (M+H)$^+$ calcd. for $C_{20}H_{23}N_2O_0$, 323.1754; found 323.1758.

EXAMPLE 5

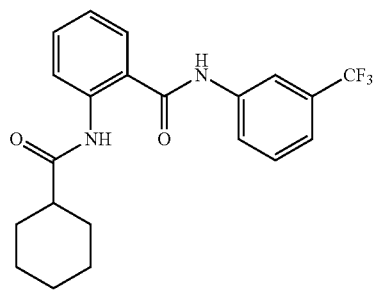 [SMILES: O=C(Nc1cccc(C(F)(F)F)c1)c1ccccc1NC(=O)C1CCCCC1]

This example illustrates a synthesis of 2-(Cyclohexanecarboxamido)-N-(3-(trifluoromethyl)phenyl)benzamide (XJB06-002, NCGC00189486-01). The title compound was prepared according to general protocol A. LC-MS Retention Time: $t_1$ (Method 1)=6.910 min; $^1$H NMR (400 MHz, DMSO-$d_6$) δ ppm 10.61 (s, 1H), 10.27 (s, 1H), 8.12 (s, 1H), 8.07 (dd, J=8.4, 1.0 Hz, 1H), 7.94 (d, J=9.2 Hz, 1H), 7.74 (dd, J=7.7, 1.5 Hz, 1H), 7.58 (t, J=8.0 Hz, 1H), 7.47-7.54 (m, 1H), 7.44 (dt, J=7.7, 0.8 Hz, 1H), 7.21 (td, J=7.5, 1.2 Hz, 1H), 2.22-2.35 (m, 1H), 1.79 (dd, J=13.3, 2.3 Hz, 2H), 1.68 (ddd, J=12.3, 3.1, 2.9 Hz, 2H), 1.58 (ddd, J=11.9, 3.2, 3.0 Hz, 1H), 1.00-1.40 (m, 5H); $^{19}$F NMR (376 MHz, DMSO-$d_6$) δ ppm –61.30 (s, 3F); HRMS (ESI) m/z (M+H)$^+$ calcd. for $C_{21}H_{22}F_3N_2O_2$, 391.1628; found 391.1632.

EXAMPLE 6

This example illustrates a synthesis of N-(3-Bromophenyl)-2-(cyclohexanecarboxamido)benzamide (XJB06-005, NCGC00189485-01). The title compound was prepared according to general protocol A. LC-MS Retention Time: $t_1$ (Method 1)=6.904 min; $^1$H NMR (400 MHz, DMSO-$d_6$) δ ppm 10.47 (s, 1H), 10.31 (s, 1H), 8.11 (dd, J=8.4, 1.0 Hz, 1H), 7.94-8.04 (m, 1H), 7.72 (dd, J=7.8, 1.6 Hz, 1H), 7.64 (ddd, J=6.7, 2.3, 2.2 Hz, 1H), 7.49 (ddd, J=8.4, 7.2, 1.6 Hz, 1H), 7.24-7.35 (m, 2H), 7.19 (td, J=7.6, 1.2 Hz, 1H), 2.21-2.37 (m, 1H), 1.80 (d, J=11.5 Hz, 2H), 1.69 (dt, J=12.2, 3.2 Hz, 2H), 1.59 (d, J=12.5 Hz, 1H), 1.07-1.42 (m, 5H); HRMS (ESI) m/z (M+H)$^+$ calcd. for $C_{20}H_{22}BrN_2O_2$, 401.0859; found 401.0859.

EXAMPLE 7

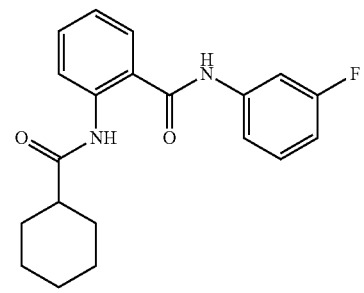 [SMILES: O=C(Nc1cccc(F)c1)c1ccccc1NC(=O)C1CCCCC1]

This example illustrates a synthesis of 2-(Cyclohexanecarboxamido)-N-(3-fluorophenyl)benzamide (XJB06-006, NCGC00189484-01). The title compound was prepared according to general protocol A. LC-MS Retention Time: $t_1$ (Method 1)=6.529 min; $^1$H NMR (400 MHz, DMSO-$d_6$) δ ppm 10.51 (s, 1H), 10.33 (s, 1H), 8.12 (dd, J=8.3, 1.1 Hz, 1H), 7.73 (dd, J=7.7, 1.5 Hz, 1H), 7.64 (dt, J=11.7, 2.3 Hz, 1H), 7.43-7.55 (m, 2H), 7.37 (td, J=8.2, 6.7 Hz, 1H), 7.20 (td, J=7.5, 1.2 Hz, 1H), 6.82-6.98 (m, 1H), 2.21-2.35 (m, 1H), 1.81 (d, J=11.5 Hz, 2H), 1.69 (dt, J=12.4, 3.3 Hz, 2H), 1.59 (d, J=11.7 Hz, 1H), 1.02-1.43 (m, 5H); $^{19}$F NMR (376 MHz, DMSO-$d_6$) δ ppm –112.20--112.29 (m, 1F); HRMS (ESI) m/z (M+H)$^+$ calcd. for $C_{20}H_{22}FN_2O_2$, 341.1660; found 341.1660.

EXAMPLE 8

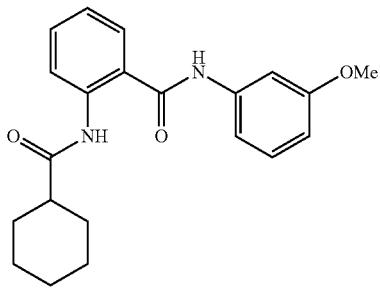 [SMILES: COc1cccc(NC(=O)c2ccccc2NC(=O)C2CCCCC2)c1]

This example illustrates a synthesis of 2-(Cyclohexanecarboxamido)-N-(3-methoxyphenyl)benzamide (XJB06-007, NCGC00189483-01). The title compound was prepared according to general protocol A. LC-MS Retention Time: $t_1$ (Method 1)=6.344 min; $^1$H NMR (400 MHz, DMSO-$d_6$) δ ppm 10.47 (s, 1H), 10.33 (s, 1H), 8.20 (dd, J=8.4, 1.0 Hz, 1H), 7.74 (dd, J=7.8, 1.4 Hz, 1H), 7.49 (ddd, J=8.4, 7.2, 1.6 Hz, 1H), 7.33 (t, J=2.2 Hz, 1H), 7.13-7.30 (m, 3H), 6.69 (ddd, J=7.8, 2.5, 1.4 Hz, 1H), 3.73 (s, 3H), 2.26 (tt, J=11.3, 3.6 Hz, 1H), 1.82 (dd, J=12.5, 2.7 Hz, 2H), 1.69 (ddd, J=12.4, 3.1, 2.8 Hz, 2H), 1.51-1.64 (m, 1H), 1.02-1.41 (m, 5H); HRMS (ESI) m/z (M+H)$^+$ calcd. for $C_{21}H_{25}N_2O_3$, 353.1860; found 353.1856.

EXAMPLE 9

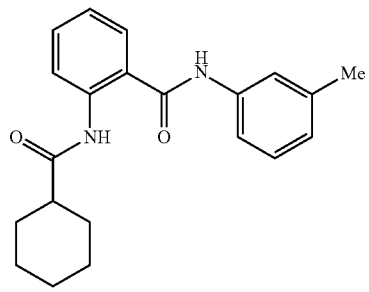 [SMILES: Cc1cccc(NC(=O)c2ccccc2NC(=O)C2CCCCC2)c1]

This example illustrates a synthesis of 2-(Cyclohexanecarboxamido)-N-m-tolylbenzamide (XJB06-008, NCGC00189482-01). The title compound was prepared according to general protocol A. LC-MS Retention Time: $t_1$ (Method 1)=6.632 min; $^1$H NMR (400 MHz, DMSO-$d_6$) δ ppm 10.54 (s, 1H), 10.30 (s, 1H), 8.24 (dd, J=8.3, 1.1 Hz, 1H), 7.76 (dd, J=7.8, 1.4 Hz, 1H), 7.38-7.54 (m, 3H), 7.10-7.31 (m, 2H), 6.93 (dddd, J=7.5, 1.5, 1.1, 0.8 Hz, 1H), 2.29 (s, 3H), 2.19-2.35 (m, 1H), 1.82 (dd, J=12.8, 2.6 Hz, 2H), 1.69 (dt, J=12.4, 3.4 Hz, 2H), 1.59 (d, J=12.3 Hz, 1H), 1.04-1.42 (m, 5H); HRMS (ESI) m/z (M+H)$^+$ calcd. for $C_{21}H_{25}N_2O_2$, 337.1911; found 337.1908.

EXAMPLE 10

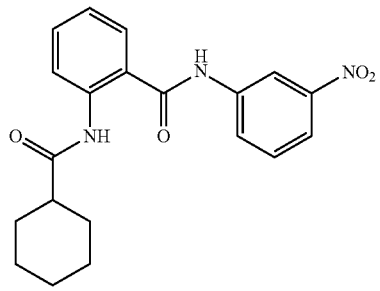 [SMILES: O=C(Nc1cccc([N+](=O)[O-])c1)c1ccccc1NC(=O)C1CCCCC1]

This example illustrates a synthesis of 2-(Cyclohexanecarboxamido)-N-(3-nitrophenyl)benzamide (XJB06-009, NCGC00189481-01). The title compound was prepared according to general protocol A. LC-MS Retention Time: $t_1$ (Method 1)=6.392 min; $^1$H NMR (400 MHz, DMSO-$d_6$) δ ppm 10.76 (s, 1H), 10.26 (s, 1H), 8.69 (t, J=2.2 Hz, 1H), 8.01-8.15 (m, 2H), 7.95 (ddd, J=8.3, 2.3, 1.0 Hz, 1H), 7.75 (dd, J=7.8, 1.6 Hz, 1H), 7.64 (t, J=8.2 Hz, 1H), 7.46-7.56 (m, 1H), 7.22 (td, J=7.6, 1.2 Hz, 1H), 2.19-2.35 (m, 1H), 1.79 (dd, J=12.5, 2.5 Hz, 2H), 1.68 (dt, J=12.3, 3.1 Hz, 2H), 1.58 (d, J=12.5 Hz, 1H), 1.03-1.43 (m, 5H); HRMS (ESI) m/z (M+H)$^+$ calcd. for $C_{20}H_{22}N_3O_4$, 368.1605; found 368.1616.

EXAMPLE 11

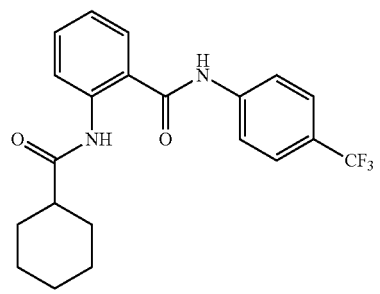 [SMILES: O=C(Nc1ccc(C(F)(F)F)cc1)c1ccccc1NC(=O)C1CCCCC1]

This example illustrates a synthesis of 2-(Cyclohexanecarboxamido)-N-(4-(trifluoromethyl)phenyl)benzamide (XJB06-012, NCGC00189480-01). The title compound was prepared according to general protocol A. LC-MS Retention Time: $t_1$ (Method 1)=6.943 min; $^1$H NMR (400 MHz, DMSO-$d_6$) δ ppm 10.65 (s, 1H), 10.29 (s, 1H), 8.09 (dd, J=8.4, 1.0 Hz, 1H), 7.91 (d, J=8.6 Hz, 2H), 7.74 (dd, J=7.8, 1.4 Hz, 1H), 7.71 (d, J=8.4 Hz, 2H), 7.51 (ddd, J=8.4, 7.3, 1.6 Hz, 1H), 7.21 (td, J=7.6, 1.2 Hz, 1H), 2.18-2.35 (m, 1H), 1.80 (dd, J=12.7, 2.9 Hz, 2H), 1.68 (dt, J=12.2, 3.4 Hz, 2H), 1.59 (d, J=11.9 Hz, 1H), 1.01-1.43 (m, 5H); $^{19}$F NMR (376 MHz, DMSO-$d_6$) δ ppm −60.26 (s, 3F); HRMS (ESI) m/z (M+H)$^+$ calcd. for $C_{21}H_{22}F_3N_2O_2$, 391.1628; found 391.1628.

EXAMPLE 12

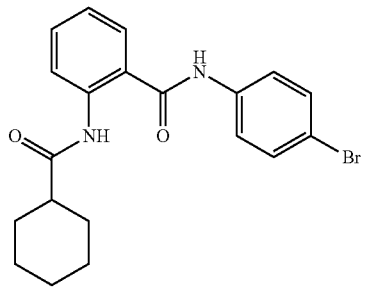 [SMILES: O=C(Nc1ccc(Br)cc1)c1ccccc1NC(=O)C1CCCCC1]

This example illustrates a synthesis of N-(4-Bromophenyl)-2-(cyclohexanecarboxamido)benzamide (XJB06-013, NCGC00189479-01). The title compound was prepared according to general protocol A. LC-MS Retention Time: $t_1$ (Method 1)=6.893 min; $^1$H NMR (400 MHz, DMSO-$d_6$) δ ppm 10.46 (s, 1H), 10.41 (s, 1H), 8.16 (dd, J=8.2, 1.0 Hz, 1H), 7.74 (dd, J=7.8, 1.6 Hz, 1H), 7.60-7.69 (m, 2H), 7.50-7.56 (m, 2H), 7.46-7.50 (m, 1H), 7.19 (td, J=7.5, 1.2 Hz, 1H), 2.18-2.34 (m, 1H), 1.81 (dd, J=12.1, 3.3 Hz, 2H), 1.69 (dt, J=12.3, 3.1 Hz, 2H), 1.59 (d, J=11.9 Hz, 1H), 1.06-1.42 (m, 5H); HRMS (ESI) m/z (M+H)$^+$ calcd. for $C_{20}H_{22}BrN_2O_2$, 401.0859; found 401.0858.

EXAMPLE 13

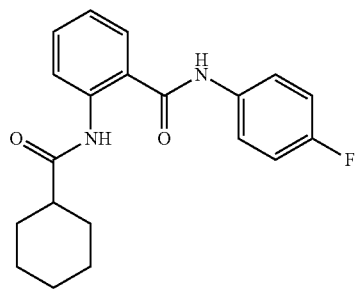 [SMILES: O=C(Nc1ccc(F)cc1)c1ccccc1NC(=O)C1CCCCC1]

This example illustrates a synthesis of 2-(Cyclohexanecarboxamido)-N-(4-fluorophenyl)benzamide (XJB06-014, NCGC00189478-01). The title compound was prepared according to general protocol A. LC-MS Retention Time: $t_1$ (Method 1)=6.413 min; $^1$H NMR (400 MHz, DMSO-$d_6$) δ ppm 10.52 (s, 1H), 10.41 (s, 1H), 8.22 (dd, J=8.3, 0.9 Hz, 1H), 7.76 (dd, J=7.8, 1.4 Hz, 1H), 7.62-7.73 (m, 2H), 7.49 (ddd, J=8.4, 7.2, 1.6 Hz, 1H), 7.10-7.28 (m, 3H), 2.17-2.35 (m, 1H), 1.82 (dd, J=12.9, 2.5 Hz, 2H), 1.69 (dt, J=12.3, 3.3 Hz, 2H), 1.53-1.63 (m, 1H), 0.97-1.43 (m, 5H); $^{19}$F NMR (376 MHz, DMSO-$d_6$) δ ppm −118.31−−118.38 (m, 1F); HRMS (ESI) m/z (M+H)$^+$ calcd. for $C_{20}H_{22}FN_2O_2$, 341.1660; found 341.1659.

EXAMPLE 14

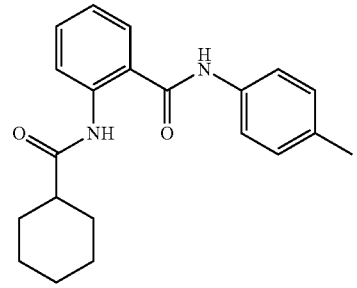 [SMILES: Cc1ccc(NC(=O)c2ccccc2NC(=O)C2CCCCC2)cc1]

This example illustrates a synthesis of 2-(cyclohexanecarboxamido)-N-p-tolylbenzamide (XJB06-015, NCGC00189477-01). The title compound was prepared according to general protocol A. LC-MS Retention Time: $t_1$ (Method 1)=6.636 min; $^1$H NMR (400 MHz, DMSO-$d_6$) δ ppm 10.61 (s, 1H), 10.30 (s, 1H), 8.26 (dd, J=8.2, 0.8 Hz, 1H), 7.77 (dd, J=7.8, 1.4 Hz, 1H), 7.52-7.59 (m, 2H), 7.48 (ddd, J=8.4, 7.2, 1.6 Hz, 1H), 7.18 (dd, J=7.8, 1.2 Hz, 1H), 7.11-7.17 (m, 2H), 2.26 (s, 3H), 2.16-2.36 (m, 1H), 1.82 (dd, J=13.0, 2.1 Hz, 2H), 1.69 (ddd, J=12.2, 3.3, 3.1 Hz, 2H), 1.51-1.64 (m, 1H), 1.02-1.47 (m, 5H); HRMS (ESI) m/z (M+H)$^+$ calcd. for $C_{21}H_{25}N_2O_2$, 337.1911; found 337.1916.

EXAMPLE 15

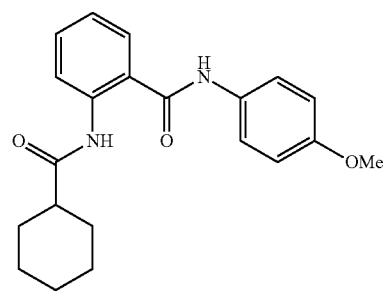 [SMILES: COc1ccc(NC(=O)c2ccccc2NC(=O)C2CCCCC2)cc1]

This example illustrates a synthesis of 2-(Cyclohexanecarboxamido)-N-(4-methoxyphenyl)benzamide (XJB06-016, NCGC00189476-01). The title compound was prepared according to general protocol A. LC-MS Retention Time: $t_1$ (Method 1)=6.243 min; $^1$H NMR (400 MHz, DMSO-$d_6$) δ ppm 10.71 (s, 1H), 10.27 (s, 1H), 8.29 (dd, J=8.3, 0.9 Hz, 1H), 7.78 (dd, J=7.8, 1.4 Hz, 1H), 7.52-7.63 (m, 2H), 7.48 (ddd, J=8.4, 7.3, 1.5 Hz, 1H), 7.17 (td, J=7.5, 1.2 Hz, 1H), 6.83-7.02 (m, 2H), 3.73 (s, 3H), 2.25 (tt, J=11.2, 3.4 Hz, 1H), 1.77-1.93 (m, 2H), 1.70 (ddd, J=12.3, 3.2, 2.9 Hz, 2H), 1.52-1.64 (m, 1H), 1.00-1.47 (m, 5H); HRMS (ESI) m/z (M+H)$^+$ calcd. for $C_{21}H_{25}N_2O_3$, 353.1860; found 353.1857.

EXAMPLE 16

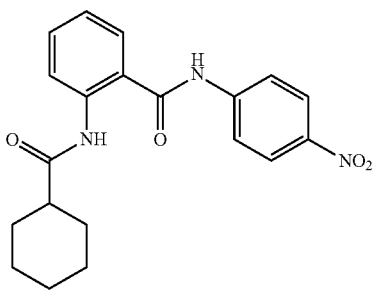 [SMILES: O=C(Nc1ccc([N+](=O)[O-])cc1)c1ccccc1NC(=O)C1CCCCC1]

This example illustrates a synthesis of 2-(Cyclohexanecarboxamido)-N-(4-nitrophenyl)benzamide (XJB06-017, NCGC00189475-01). The title compound was prepared according to general protocol A. LC-MS Retention Time: $t_1$ (Method 1)=6.408 min; $^1$H NMR (400 MHz, DMSO-$d_6$) δ ppm 10.85 (s, 1H), 10.17 (s, 1H), 8.16-8.32 (m, 2H), 7.85-8.06 (m, 3H), 7.72 (dd, J=7.8, 1.4 Hz, 1H), 7.43-7.58 (m, 1H), 7.22 (td, J=7.5, 1.2 Hz, 1H), 2.27 (tt, J=11.2, 3.5 Hz, 1H), 1.72-1.88 (m, 2H), 1.68 (ddd, J=9.0, 6.1, 2.7 Hz, 2H), 1.52-1.63 (m, 1H), 0.99-1.45 (m, 5H); HRMS (ESI) m/z (M+H)$^+$ calcd. for $C_{20}H_{22}N_3O_4$, 368.1605; found 368.1605.

EXAMPLE 17

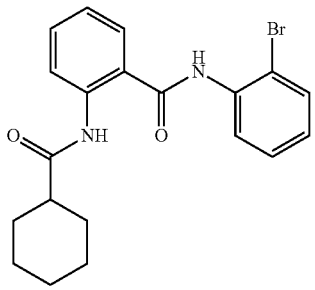 [SMILES: O=C(Nc1ccccc1Br)c1ccccc1NC(=O)C1CCCCC1]

This example illustrates a synthesis of N-(2-Bromophenyl)-2-(cyclohexanecarboxamido)benzamide (XJB06-027, NCGC00189474-01). The title compound was prepared according to general protocol A. LC-MS Retention Time: $t_1$ (Method 1)=6.689 min; $^1$H NMR (400 MHz, DMSO-$d_6$) δ ppm 10.91 (s, 1H), 10.26 (s, 1H), 8.36 (dd, J=8.4, 1.0 Hz, 1H), 7.93 (dd, J=7.8, 1.4 Hz, 1H), 7.71 (dd, J=8.0, 1.4 Hz, 1H), 7.49-7.59 (m, 2H), 7.44 (td, J=7.6, 1.4 Hz, 1H), 7.22-7.27 (m, 1H), 7.20 (td, J=7.6, 1.2 Hz, 1H), 2.24 (tt, J=11.3, 3.5 Hz, 1H), 1.82 (dd, J=12.6, 2.4 Hz, 2H), 1.69 (ddd, J=12.5, 3.2, 2.9 Hz, 2H), 1.51-1.64 (m, 1H), 1.05-1.45 (m, 5H); HRMS (ESI) m/z (M+H)$^+$ calcd. for $C_{20}H_{22}BrN_2O_2$, 401.0859; found 401.0863.

EXAMPLE 18

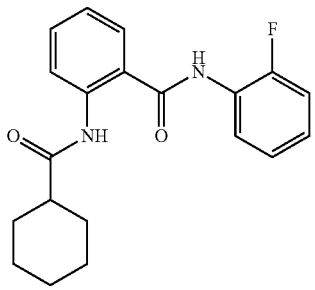 [SMILES: O=C(Nc1ccccc1F)c1ccccc1NC(=O)C1CCCCC1]

This example illustrates a synthesis of 2-(Cyclohexanecarboxamido)-N-(2-fluorophenyl)benzamide (XJB06-028, NCGC00189473-01). The title compound was prepared according to general protocol A. LC-MS Retention Time: $t_1$ (Method 1)=6.305 min; $^1$H NMR (400 MHz, DMSO-$d_6$) δ ppm 10.85 (br. s., 1H), 10.28 (s, 1H), 8.34 (dd, J=8.4, 1.0 Hz, 1H), 7.88 (dd, J=7.8, 1.4 Hz, 1H), 7.42-7.64 (m, 2H), 7.24-7.34 (m, 2H), 7.13-7.24 (m, 2H), 2.24 (tt, J=11.2, 3.5 Hz, 1H), 1.76-1.86 (m, 2H), 1.64-1.75 (m, 2H), 1.52-1.64 (m, 1H), 0.99-1.43 (m, 5H); $^{19}$F NMR (376 MHz, DMSO-$d_6$) δ ppm −120.74--−120.85 (m, 1F); HRMS (ESI) m/z (M+H)$^+$ calcd. for $C_{20}H_{22}FN_2O_2$, 341.1660; found 341.1656.

EXAMPLE 19

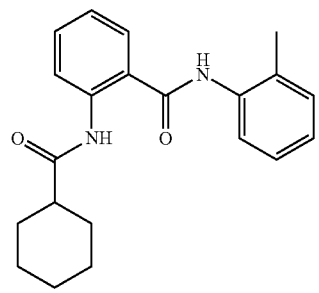 [SMILES: Cc1ccccc1NC(=O)c1ccccc1NC(=O)C1CCCCC1]

This example illustrates a synthesis of 2-(cyclohexanecarboxamido)-N-o-tolylbenzamide (XJB06-029, NCGC00189472-01). The title compound was prepared according to general protocol A. LC-MS Retention Time: $t_1$ (Method 1)=6.401 min; $^1$H NMR (400 MHz, DMSO-$d_6$) δ ppm 11.00 (s, 1H), 10.09 (s, 1H), 8.38 (dd, J=8.4, 1.2 Hz, 1H), 7.91 (d, J=7.8 Hz, 1H), 7.51 (ddd, J=8.6, 7.2, 1.7 Hz, 1H), 7.25-7.35 (m, 2H), 7.10-7.25 (m, 3H), 2.21 (s, 3H), 2.16-2.28 (m, 1H), 1.77-1.91 (m, 2H), 1.69 (dt, J=12.4, 3.5 Hz, 2H), 1.53-1.65 (m, 1H), 0.99-1.44 (m, 5H); HRMS (ESI) m/z (M+H)$^+$ calcd. for $C_{21}H_{25}N_2O_2$, 337.1911; found 337.1912.

EXAMPLE 20

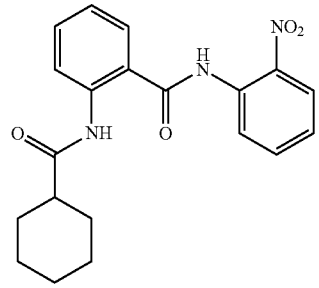 [SMILES: O=C(Nc1ccccc1[N+](=O)[O-])c1ccccc1NC(=O)C1CCCCC1]

This example illustrates a synthesis of 2-(Cyclohexanecarboxamido)-N-(2-nitrophenyl)benzamide (XJB06-031, NCGC00189471-01). The title compound was prepared according to general protocol A. LC-MS Retention Time: $t_1$ (Method 1)=6.550 min; $^1$H NMR (400 MHz, DMSO-$d_6$) δ ppm 10.85 (s, 1H), 10.44 (s, 1H), 8.25 (dd, J=8.4, 1.2 Hz, 1H), 8.01 (dd, J=8.2, 1.6 Hz, 1H), 7.84 (dd, J=7.8, 1.6 Hz, 1H), 7.67-7.80 (m, 2H), 7.54 (ddd, J=8.6, 7.3, 1.6 Hz, 1H), 7.44 (ddd, J=8.4, 6.7, 2.0 Hz, 1H), 7.23 (td, J=7.6, 1.3 Hz, 1H), 2.22 (tt, J=11.4, 3.5 Hz, 1H), 1.80 (d, J=14.7 Hz, 2H), 1.68 (ddd, J=12.3, 3.4, 3.3 Hz, 2H), 1.59 (d, J=11.9 Hz, 1H), 1.05-1.41 (m, 5H); HRMS (ESI) m/z (M+H)$^+$ calcd. for C$_{20}$H$_{22}$N$_3$O$_4$, 368.1605; found 368.1605.

EXAMPLE 21

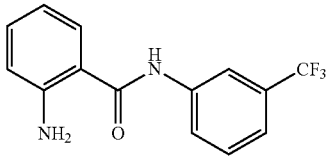 [SMILES: Nc1ccccc1C(=O)Nc1cccc(C(F)(F)F)c1]

This example illustrates a synthesis of 2-Amino-N-(3-(trifluoromethyl)phenyl)benzamide (XJB06-036, NCGC00189470-01). A solution of tert-butyl 2-(3-(trifluoromethyl)phenylcarbamoyl)phenylcarbamate (2.11 g, 5.55 mmol) in dichloromethane (15.0 mL) was treated at 0° C. with TFA (5.34 mL, 69.3 mmol). The reaction mixture was stirred at 0° C. for 1 h and room temperature for additional 2 h. The reaction mixture was concentrated and re-dissolved in dichloromethane and washed with saturated Na$_2$CO$_3$ aqueous solution. The organic layer was separated, dried and concentrated to give 1.45 g (99%) of the title compound as a white solid. LC-MS Retention Time: t$_1$ (Method 1)=5.590 min; $^1$H NMR (400 MHz, DMSO-d$_6$) δ ppm 10.24 (s, 1H), 8.18 (t, J=2.2 Hz, 1H), 7.95 (ddd, J=8.4, 1.2, 1.0 Hz, 1H), 7.63 (dd, J=8.0, 1.6 Hz, 1H), 7.54 (t, J=8.3 Hz, 1H), 7.34-7.43 (m, 1H), 7.19 (ddd, J=8.4, 7.0, 1.6 Hz, 1H), 6.74 (dd, J=8.3, 1.3 Hz, 1H), 6.57 (ddd, J=8.1, 7.0, 1.2 Hz, 1H), 6.34 (br. s., 2H); $^{19}$F NMR (376 MHz, DMSO-d$_6$) δ ppm −61.18 (s, 3F).

EXAMPLE 22

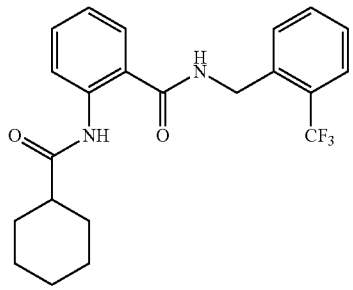 [SMILES: O=C(NCc1ccccc1C(F)(F)F)c1ccccc1NC(=O)C1CCCCC1]

This example illustrates a synthesis of 2-(Cyclohexanecarboxamido)-N-(2-(trifluoromethyl)benzyl)benzamide (XJB06-038, NCGC00189469-01). The title compound was prepared according to general protocol A. LC-MS Retention Time: t$_1$ (Method 1)=6.797 min; $^1$H NMR (400 MHz, DMSO-d$_6$) δ ppm 11.12 (s, 1H), 9.29 (t, J=5.9 Hz, 1H), 8.40 (dd, J=8.4, 1.4 Hz, 1H), 7.82 (dd, J=7.9, 1.7 Hz, 1H), 7.73 (dt, J=7.8, 0.8 Hz, 1H), 7.64 (t, J=7.3 Hz, 1H), 7.42-7.56 (m, 3H), 7.09-7.19 (m, 1H), 4.65 (d, J=6.1 Hz, 2H), 2.21 (tt, J=11.2, 3.5 Hz, 1H), 1.76-1.88 (m, 2H), 1.63-1.73 (m, 2H), 1.51-1.63 (m, 1H), 1.03-1.44 (m, 5H); $^{19}$F NMR (376 MHz, DMSO-d$_6$) δ ppm −58.97 (s, 3F); HRMS (ESI) m/z (M+H) calcd. for C$_{22}$H$_{24}$F$_3$N$_2$O$_2$, 405.1784; found 405.1790.

EXAMPLE 23

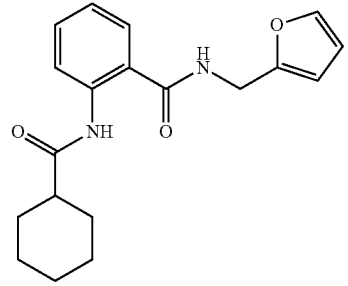

This example illustrates a synthesis of 2-(Cyclohexanecarboxamido)-N-(furan-2-ylmethyl)benzamide (XJB06-039, NCGC00189468-01). The title compound was prepared according to general protocol A. LC-MS Retention Time: t$_1$ (Method 1)=5.946 min; $^1$H NMR (400 MHz, DMSO-d$_6$) δ ppm 11.24 (s, 1H), 9.19 (t, J=5.7 Hz, 1H), 8.40 (dd, J=8.4, 1.4 Hz, 1H), 7.72 (dd, J=7.8, 1.6 Hz, 1H), 7.56 (dd, J=1.9, 0.9 Hz, 1H), 7.45 (ddd, J=8.5, 7.1, 1.6 Hz, 1H), 6.99-7.15 (m, 1H), 6.38 (dd, J=3.2, 1.9 Hz, 1H), 6.22-6.33 (m, 1H), 4.45 (dd, J=5.6, 0.5 Hz, 2H), 2.23 (tt, J=11.2, 3.5 Hz, 1H), 1.79-1.93 (m, 2H), 1.71 (dt, J=12.6, 3.6 Hz, 2H), 1.54-1.67 (m, 1H), 1.03-1.47 (m, 5H); HRMS (ESI) m/z (M+H)$^+$ calcd. for C$_{19}$H$_{23}$N$_2$O$_3$, 327.1703; found 327.1708.

EXAMPLE 24

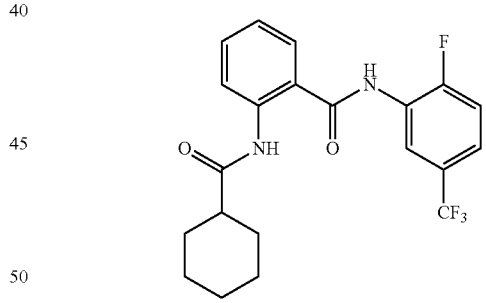

This example illustrates a synthesis of 2-(Cyclohexanecarboxamido)-N-(2-fluoro-5-(trifluoromethyl)phenyl)benzamide (XJB06-040, NCGC00189467-01). The title compound was prepared according to general protocol A. LC-MS Retention Time: t$_1$ (Method 1)=6.825 min; $^1$H NMR (400 MHz, DMSO-d$_6$) δ ppm 10.51 (s, 1H), 10.44 (s, 1H), 8.14 (dd, J=8.3, 1.3 Hz, 1H), 8.07 (dd, J=6.8, 2.3 Hz, 1H), 7.81 (dd, J=7.8, 1.6 Hz, 1H), 7.61-7.73 (m, 1H), 7.46-7.59 (m, 2H), 7.21 (td, J=7.6, 1.3 Hz, 1H), 2.20-2.34 (m, 1H), 1.75-1.88 (m, 2H), 1.68 (ddd, J=12.8, 3.1, 2.9 Hz, 2H), 1.52-1.64 (m, 1H), 1.07-1.42 (m, 5H); $^{19}$F NMR (376 MHz, DMSO-d$_6$) δ ppm −60.47 (s, 3F), −119.15--111.85 (m, 1F); HRMS (ESI) m/z (M+H)$^+$ calcd. for C$_{21}$H$_{21}$F$_4$N$_2$O$_2$, 409.1534; found 409.1534.

EXAMPLE 25

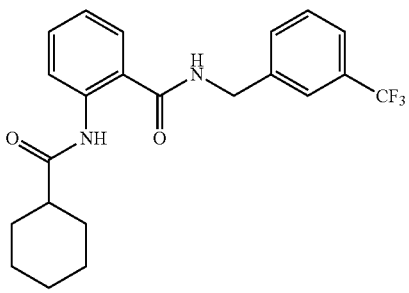 [SMILES: O=C(NCc1cccc(C(F)(F)F)c1)c1ccccc1NC(=O)C1CCCCC1]

This example illustrates a synthesis of 2-(Cyclohexanecarboxamido)-N-(3-(trifluoromethyl)benzyl)benzamide (XJB06-041, NCGC00189466-01). The title compound was prepared according to general protocol A. LC-MS Retention Time: $t_1$ (Method 1)=6.781 min; $^1$H NMR (400 MHz, DMSO-$d_6$) δ ppm 11.13 (s, 1H), 9.34 (t, J=6.1 Hz, 1H), 8.37 (dd, J=8.4, 1.4 Hz, 1H), 7.76 (dd, J=7.9, 1.7 Hz, 1H), 7.66-7.70 (m, 1H), 7.58-7.66 (m, 2H), 7.53-7.58 (m, 1H), 7.47 (ddd, J=8.5, 7.2, 1.7 Hz, 1H), 7.13 (td, J=7.6, 1.3 Hz, 1H), 4.54 (d, J=5.9 Hz, 2H), 2.20 (tt, J=11.2, 3.5 Hz, 1H), 1.75-1.87 (m, 2H), 1.68 (dt, J=12.3, 3.2 Hz, 2H), 1.53-1.64 (m, 1H), 1.02-1.42 (m, 5H); $^{19}$F NMR (376 MHz, DMSO-$d_6$) δ ppm −61.02 (s, 3F); HRMS (ESI) m/z (M+H)$^+$ calcd. for $C_{22}H_{24}F_3N_2O_2$, 405.1784; found 405.1790.

EXAMPLE 26

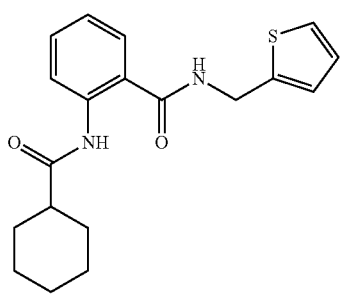 [SMILES: O=C(NCc1cccs1)c1ccccc1NC(=O)C1CCCCC1]

This example illustrates a synthesis of 2-(Cyclohexanecarboxamido)-N-(thiophen-2-ylmethyl)benzamide (XJB06-042, NCGC00189465-01). The title compound was prepared according to general protocol A. LC-MS Retention Time: $t_1$ (Method 1)=6.211 min; $^1$H NMR (400 MHz, DMSO-$d_6$) δ ppm 11.21 (s, 1H), 9.22-9.73 (m, 1H), 8.40 (dd, J=8.4, 1.4 Hz, 1H), 7.70 (dd, J=8.0, 1.6 Hz, 1H), 7.45 (ddd, J=8.5, 7.1, 1.6 Hz, 1H), 7.38 (dd, J=5.1, 1.2 Hz, 1H), 7.10 (td, J=7.6, 1.3 Hz, 1H), 6.99-7.05 (m, 1H), 6.94 (dd, J=5.1, 3.5 Hz, 1H), 4.61 (dd, J=5.9, 1.0 Hz, 2H), 2.23 (tt, J=11.3, 3.4 Hz, 1H), 1.80-1.93 (m, 2H), 1.68-1.79 (m, 2H), 1.56-1.68 (m, J=12.3, 3.4, 1.8, 1.8 Hz, 1H), 1.03-1.47 (m, 5H); HRMS (ESI) m/z (M+H)$^+$ calcd. for $C_{19}H_{23}N_2O_2S$, 343.1475; found 343.1485.

EXAMPLE 27

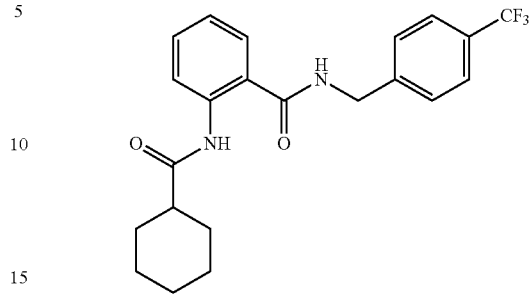

This example illustrates a synthesis of 2-(cyclohexanecarboxamido)-N-(4-(trifluoromethyl)benzyl)benzamide (XJB06-043, NCGC00189464-01). The title compound was prepared according to general protocol A. LC-MS Retention Time: $t_1$ (Method 1)=6.763 min; $^1$H NMR (400 MHz, DMSO-$d_6$) δ ppm 11.15 (s, 1H), 9.36 (t, J=6.0 Hz, 1H), 8.38 (dd, J=8.4, 1.4 Hz, 1H), 7.78 (dd, J=7.8, 1.6 Hz, 1H), 7.68 (d, J=8.0 Hz, 2H), 7.50-7.58 (m, 2H), 7.47 (ddd, J=8.6, 7.3, 1.6 Hz, 1H), 7.08-7.20 (m, 1H), 4.54 (d, J=5.9 Hz, 2H), 2.20 (tt, J=11.2, 3.4 Hz, 1H), 1.73-1.89 (m, 2H), 1.68 (ddd, J=12.5, 3.4, 3.1 Hz, 2H), 1.53-1.63 (m, 1H), 1.02-1.43 (m, 5H); $^{19}$F NMR (376 MHz, DMSO-$d_6$) δ ppm −60.75 (s, 3F); HRMS (ESI) m/z (M+H)$^+$ calcd. for $C_{22}H_{24}F_3N_2O_2$, 405.1784; found 405.1789.

EXAMPLE 28

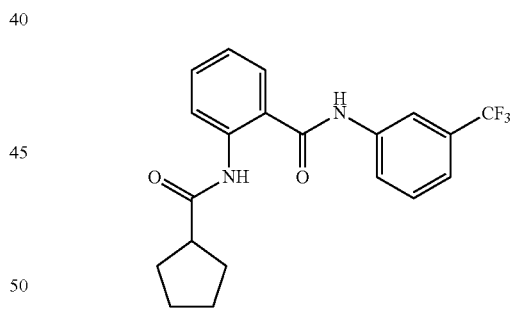

This example illustrates a synthesis of 2-(Cyclopentanecarboxamido)-N-(3-(trifluoromethyl)phenyl)benzamide (XJB06-046, NCGC00189463-01). The title compound was prepared according to general protocol B. LC-MS Retention Time: $t_1$ (Method 1)=6.780 min; $^1$H NMR (400 MHz, DMSO-$d_6$) δ ppm 10.60 (s, 1H), 10.29 (s, 1H), 8.15 (t, J=2.2 Hz, 1H), 8.04 (d, J=7.8 Hz, 1H), 7.93 (d, J=8.4 Hz, 1H), 7.73 (dd, J=7.8, 1.6 Hz, 1H), 7.57 (t, J=7.9 Hz, 1H), 7.50 (ddd, J=8.5, 7.2, 1.6 Hz, 1H), 7.44 (d, J=7.6 Hz, 1H), 7.21 (td, J=7.6, 1.3 Hz, 1H), 2.75 (quin, J=8.0 Hz, 1H), 1.74-1.86 (m, 2H), 1.63-1.74 (m, 2H), 1.41-1.63 (m, 4H); $^{19}$F NMR (376 MHz, DMSO-$d_6$) δ ppm −61.21 (s, 3F); HRMS (ESI) m/z (M+H)$^+$ calcd. for $C_{20}H_{20}F_3N_2O_2$, 377.1471; found 377.1481.

EXAMPLE 29

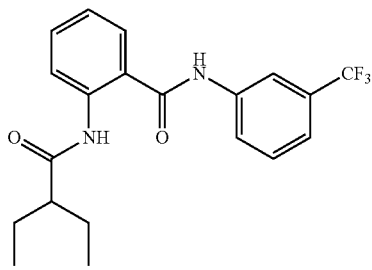 [SMILES: CCC(CC)C(=O)Nc1ccccc1C(=O)Nc1cccc(C(F)(F)F)c1]

This example illustrates a synthesis of 2-(2-Ethylbutanamido)-N-(3-(trifluoromethyl)phenyl)benzamide (XJB06-047, NCGC00189462-01). The title compound was prepared according to general protocol C. LC-MS Retention Time: $t_1$ (Method 1)=6.751 min; $^1$H NMR (400 MHz, DMSO-$d_6$) δ ppm 10.60 (s, 1H), 10.25 (s, 1H), 8.15 (t, J=2.2 Hz, 1H), 7.98 (dd, J=8.2, 1.4 Hz, 1H), 7.93 (ddd, J=8.2, 1.2, 1.0 Hz, 1H), 7.72 (dd, J=7.7, 1.7 Hz, 1H), 7.57 (t, J=7.9 Hz, 1H), 7.50 (ddd, J=8.4, 7.1, 1.7 Hz, 1H), 7.38-7.47 (m, 1H), 7.23 (td, J=7.6, 1.3 Hz, 1H), 2.15 (tt, J=8.8, 5.4 Hz, 1H), 1.30-1.62 (m, 4H), 0.74-0.86 (m, 6H); $^{19}$F NMR (376 MHz, DMSO-$d_6$) δ ppm −61.23 (s, 3F); HRMS (ESI) m/z (M+H)$^+$ calcd. for $C_{20}H_{22}F_3N_2O_2$, 379.1628; found 379.1634.

EXAMPLE 30

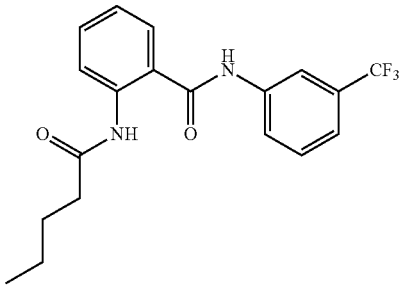 [SMILES: CCCCC(=O)Nc1ccccc1C(=O)Nc1cccc(C(F)(F)F)c1]

This example illustrates a synthesis of 2-Pentanamido-N-(3-(trifluoromethyl)phenyl)benzamide (XJB06-048, NCGC00189461-01). The title compound was prepared according to general protocol C. LC-MS Retention Time: $t_1$ (Method 1)=6.546 min; $^1$H NMR (400 MHz, DMSO-$d_6$) δ ppm 10.61 (s, 1H), 10.19 (s, 1H), 8.17 (t, J=2.2 Hz, 1H), 7.98 (dd, J=8.1, 1.1 Hz, 1H), 7.92 (ddd, J=8.2, 2.0, 0.8 Hz, 1H), 7.71 (dd, J=7.7, 1.7 Hz, 1H), 7.57 (t, J=8.1 Hz, 1H), 7.47-7.54 (m, 1H), 7.39-7.47 (m, 1H), 7.21 (td, J=7.6, 1.3 Hz, 1H), 2.28 (t, J=7.4 Hz, 2H), 1.43-1.60 (m, 2H), 1.18-1.34 (m, 2H), 0.80 (t, J=7.6 Hz, 3H); $^{19}$F NMR (376 MHz, DMSO-$d_6$) δ ppm −61.21 (s, 3F); HRMS (ESI) m/z (M+H)$^+$ calcd. for $C_{19}H_{20}F_3N_2O_2$, 365.1471; found 365.1476.

EXAMPLE 31

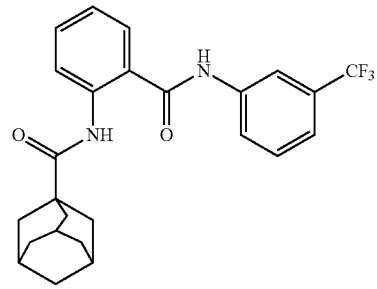 [SMILES: O=C(Nc1cccc(C(F)(F)F)c1)c1ccccc1NC(=O)C12CC3CC(CC(C3)C1)C2]

This example illustrates a synthesis of N-(2-((3-(Trifluoromethyl)phenyl)carbamoyl)phenyl)adamantane-1-carboxamide (XJB06-049, NCGC00189460-01). The title compound was prepared according to general protocol C. LC-MS Retention Time: $t_1$ (Method 1)=7.461 min; $^1$H NMR (400 MHz, DMSO-$d_6$) δ ppm 10.68 (s, 1H), 10.64 (s, 1H), 8.34 (dd, J=8.3, 1.3 Hz, 1H), 8.07 (t, J=2.2 Hz, 1H), 7.95-8.04 (m, 1H), 7.85 (dd, J=7.8, 1.6 Hz, 1H), 7.61 (t, J=8.0 Hz, 1H), 7.53 (ddd, J=8.6, 7.2, 1.7 Hz, 1H), 7.41-7.50 (m, 1H), 7.17-7.26 (m, 1H), 1.90-2.10 (m, 3H), 1.79-1.89 (m, 6H), 1.57-1.75 (m, 6H); $^{19}$F NMR (376 MHz, DMSO-$d_6$) δ ppm −61.22 (s, 3F); HRMS (ESI) m/z (M+H)$^+$ calcd. for $C_{25}H_{26}F_3N_2O_2$, 443.1941; found 443.1939.

EXAMPLE 32

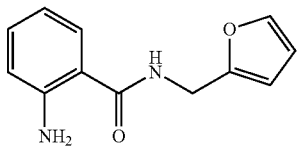 [SMILES: Nc1ccccc1C(=O)NCc1ccco1]

This example illustrates a synthesis of 2-Amino-N-(furan-2-ylmethyl)benzamide (XJB06-052, NCGC00165247-02). A solution of methyl 2-aminobenzoate (0.857 mL, 6.62 mmol) and furan-2-ylmethanamine (1.84 mL, 19.9 mmol) in toluene (20.0 mL) was treated at room temperature with AlMe$_3$ (6.62 mL, 2.0 M in toluene, 13.2 mmol). The reaction mixture was stirred at 100° C. for 5 h and then quenched with water after cooling to room temperature. The reaction mixture was concentrated in vacuo and the crude residue was purified via silica gel chromatography using a gradient of 0-80% of EtOAc in hexanes to give 1.35 g (94%) of the title compound as a white solid. LC-MS Retention Time: $t_1$ (Method 1)=3.644 min.

EXAMPLE 33

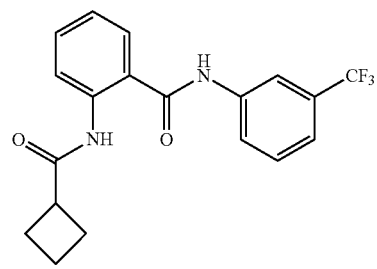 [SMILES: O=C(Nc1cccc(C(F)(F)F)c1)c1ccccc1NC(=O)C1CCC1]

This example illustrates a synthesis of 2-(Cyclobutanecarboxamido)-N-(3-(trifluoromethyl)phenyl)benzamide (XJB06-053, NCGC00189459-01). The title compound was prepared according to general protocol B. LC-MS Retention Time: $t_1$ (Method 1)=6.412 min; $^1$H NMR (400 MHz, DMSO-$d_6$) δ ppm 10.61 (s, 1H), 10.22 (s, 1H), 8.15 (t, J=2.2 Hz, 1H), 8.09 (dt, J=8.1, 0.6 Hz, 1H), 7.93 (ddd, J=8.2, 1.2, 1.0 Hz, 1H), 7.75 (dd, J=7.8, 1.6 Hz, 1H), 7.58 (t, J=7.8 Hz, 1H), 7.51 (ddd, J=8.5, 7.2, 1.6 Hz, 1H), 7.40-7.48 (m, 1H), 7.21 (td, J=7.6, 1.3 Hz, 1H), 3.15-3.26 (m, 1H), 2.01-2.24 (m, 4H), 1.80-1.97 (m, 1H), 1.64-1.80 (m, 1H); $^{19}$F NMR (376 MHz, DMSO-$d_6$) δ ppm −61.18 (s, 3F); HRMS (ESI) m/z (M+H)$^+$ calcd. for $C_{19}H_{18}F_3N_2O_2$, 363.1315; found 363.1317.

EXAMPLE 34

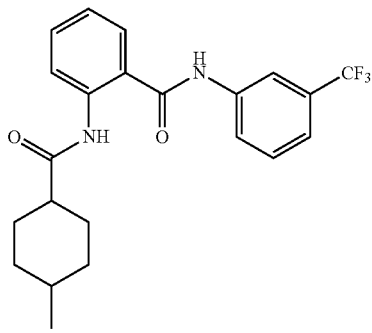 [SMILES: CC1CCC(C(=O)Nc2ccccc2C(=O)Nc2cccc(C(F)(F)F)c2)CC1]

This example illustrates a synthesis of 2-(4-Methylcyclohexanecarboxamido)-N-(3-(trifluoromethyl)phenyl)benzamide (XJB06-054, NCGC00189458-01, mixture of cis- and trans-isomers). The title compound was prepared according to general protocol B. LC-MS Retention Time: $t_1$ (Method 1)=7.150 min; $^1$H NMR (400 MHz, DMSO-$d_6$) δ ppm 10.60 (s, 1H), 10.32 (s, 0.5H), 10.27 (s, 0.5H), 8.09-8.18 (m, 1H), 8.02-8.09 (m, 1H), 7.88-7.97 (m, 1H), 7.68-7.80 (m, 1H), 7.54-7.61 (m, 1H), 7.47-7.54 (m, 1H), 7.40-7.47 (m, 1H), 7.14-7.26 (m, 1H), 2.13-2.26 (m, 1H), 1.73-1.89 (m, 2H), 1.66 (dd, J=13.4, 3.4 Hz, 1H), 1.13-1.60 (m, 5H), 0.85-1.01 (m, 1H), 0.83 (d, J=6.7 Hz, 1.5H), 0.80 (d, J=6.8 Hz, 1.5H); $^{19}$F NMR (376 MHz, DMSO-$d_6$) δ ppm −61.21 (s, 3F); HRMS (ESI) m/z (M+H)$^+$ calcd. for $C_{22}H_{24}F_3N_2O_2$, 405.1784; found 405.1788.

EXAMPLE 35

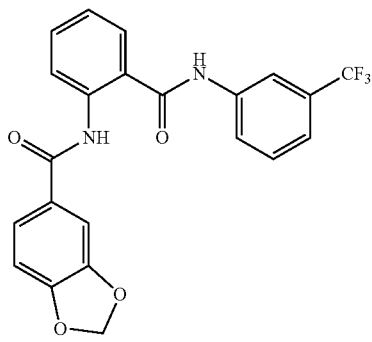 [SMILES: O=C(Nc1ccccc1C(=O)Nc1cccc(C(F)(F)F)c1)c1ccc2c(c1)OCO2]

This example illustrates a synthesis of N-(2-((3-(Trifluoromethyl)phenyl)carbamoyl)phenyl)benzo[d][1,3]dioxole-5-carboxamide (XJB06-055, NCGC00189457-01). The title compound was prepared according to general protocol B. LC-MS Retention Time: $t_1$ (Method 1)=6.524 min; $^1$H NMR (400 MHz, DMSO-$d_6$) δ ppm 11.19 (s, 1H), 10.72 (s, 1H), 8.28 (dd, J=8.3, 1.3 Hz, 1H), 8.08 (t, J=2.2 Hz, 1H), 7.92-8.01 (m, 1H), 7.87 (dd, J=7.8, 1.6 Hz, 1H), 7.53-7.64 (m, 2H), 7.41-7.49 (m, 2H), 7.37 (d, J=1.8 Hz, 1H), 7.27 (td, J=7.6, 1.3 Hz, 1H), 7.05 (d, J=8.2 Hz, 1H), 6.11 (s, 2H); $^{19}$F NMR (376 MHz, DMSO-$d_6$) δ ppm −61.18 (s, 3F); HRMS (ESI) m/z (M+H)$^+$ calcd. for $C_{22}H_{16}F_3N_2O_4$, 429.1057; found 429.1055.

EXAMPLE 36

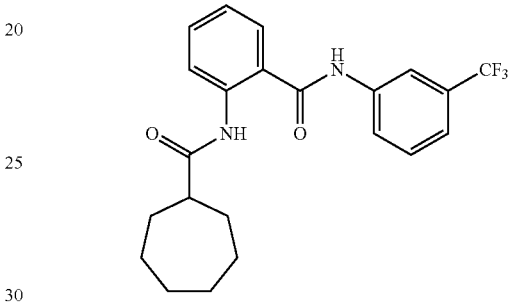

This example illustrates a synthesis of N-(2-((3-(Trifluoromethyl)phenyl)carbamoyl)phenyl)cyclo-heptanecarboxamide (XJB06-056, NCGC00189456-01, CID-56593317). The title compound was prepared according to general protocol B. LC-MS Retention Time: $t_1$ (Method 1)=7.093 min; $^1$H NMR (400 MHz, DMSO-$d_6$) δ ppm 10.58 (s, 1H), 10.18 (s, 1H), 8.13 (s, 1H), 7.98 (dd, J=8.1, 0.9 Hz, 1H), 7.93 (d, J=8.0 Hz, 1H), 7.71 (dd, J=7.8, 1.6 Hz, 1H), 7.57 (t, J=7.8 Hz, 1H), 7.49 (ddd, J=8.4, 7.2, 1.6 Hz, 1H), 7.39-7.46 (m, 1H), 7.21 (td, J=7.6, 1.2 Hz, 1H), 2.40-2.51 (m, 1H), 1.75-1.88 (m, 2H), 1.31-1.71 (m, 10H); $^{19}$F NMR (376 MHz, DMSO-$d_6$) δ ppm −61.20 (s, 3F); HRMS (ESI) m/z (M+H)$^+$ calcd. for $C_{22}H_{24}F_3N_2O_2$, 405.1784; found 405.1794.

EXAMPLE 37

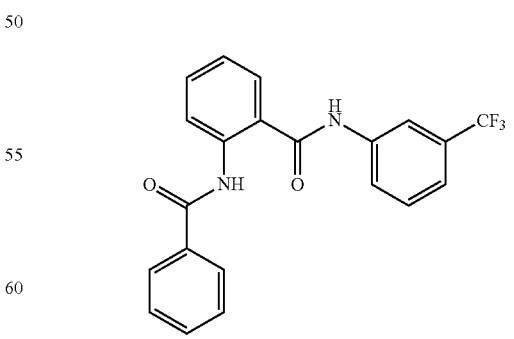

This example illustrates a synthesis of 2-Benzamido-N-(3-(trifluoromethyl)phenyl)benzamide (XJB06-058, NCGC00189455-01). The title compound was prepared according to general protocol C. LC-MS Retention Time: $t_1$ (Method 1)=6.644 min; HRMS (ESI) m/z (M+H)+ calcd. for $C_{21}H_{16}F_3N_2O_2$, 385.1158; found 385.1163.

EXAMPLE 38

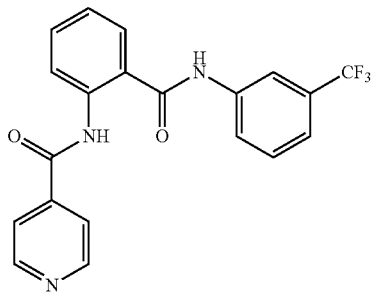 [SMILES: O=C(Nc1ccccc1C(=O)Nc1cccc(C(F)(F)F)c1)c1ccncc1]

This example illustrates a synthesis of N-(2-((3-(Trifluoromethyl)phenyl)carbamoyl)phenyl)isonicotinamide (XJB06-059, NCGC00189454-01). The title compound was prepared according to general protocol C. LC-MS Retention Time: $t_1$ (Method 1)=5.174 min; 1H NMR (400 MHz, DMSO-$d_6$) δ ppm 11.35 (s, 1H), 10.74 (d, J=0.4 Hz, 1H), 8.67-8.99 (m, 2H), 8.13-8.22 (m, 1H), 8.04-8.11 (m, 1H), 7.94-8.02 (m, 1H), 7.87 (dd, J=7.8, 1.6 Hz, 1H), 7.74-7.81 (m, 2H), 7.52-7.67 (m, 2H), 7.44 (dt, J=7.7, 1.0 Hz, 1H), 7.34 (td, J=7.6, 1.3 Hz, 1H); 19F NMR (376 MHz, DMSO-$d_6$) δ ppm −61.18 (s, 3F); HRMS (ESI) m/z (M+H)+ calcd. for $C_{20}H_{15}F_3N_3O_2$, 386.1111; found 386.1123.

EXAMPLE 39

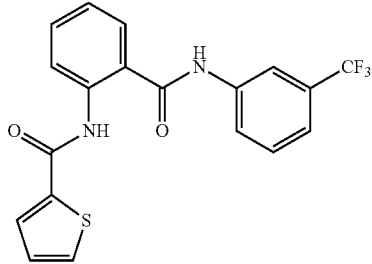 [SMILES: O=C(Nc1ccccc1C(=O)Nc1cccc(C(F)(F)F)c1)c1cccs1]

This example illustrates a synthesis of N-(2-((3-(trifluoromethyl)phenyl)carbamoyl)phenyl)thiophene-2-carboxamide (XJB06-060, NCGC00189453-01). The title compound was prepared according to general protocol C. LC-MS Retention Time: $t_1$ (Method 1)=6.571 min; 1H NMR (400 MHz, DMSO-$d_6$) δ ppm 11.31 (s, 1H), 10.73 (s, 1H), 8.21 (dd, J=8.2, 1.2 Hz, 1H), 8.10 (td, J=1.8, 0.9 Hz, 1H), 7.99 (d, J=8.8 Hz, 1H), 7.81-7.92 (m, 2H), 7.75 (dd, J=3.8, 1.3 Hz, 1H), 7.55-7.63 (m, 2H), 7.43-7.49 (m, 1H), 7.29 (td, J=7.6, 1.2 Hz, 1H), 7.22 (dd, J=5.0, 3.8 Hz, 1H); 19F NMR (376 MHz, DMSO-$d_6$) δ ppm −61.16 (s, 3F); HRMS (ESI) m/z (M+H)+ calcd. for $C_{19}H_{14}F_3N_2O_2S$, 391.0723; found 391.0731.

EXAMPLE 40

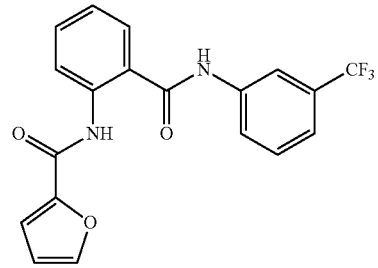 [SMILES: O=C(Nc1ccccc1C(=O)Nc1cccc(C(F)(F)F)c1)c1ccco1]

This example illustrates a synthesis of N-(2-((3-(Trifluoromethyl)phenyl)carbamoyl)phenyl)furan-2-carboxamide (XJB06-061, NCGC00189452-01). The title compound was prepared according to general protocol C. LC-MS Retention Time: $t_1$ (Method 1)=6.221 min; 1H NMR (400 MHz, DMSO-$d_6$) δ ppm 11.42 (s, 1H), 10.77 (s, 1H), 8.41 (dd, J=8.4, 1.4 Hz, 1H), 8.04-8.15 (m, 1H), 7.98-8.04 (m, 1H), 7.96 (dd, J=1.9, 0.9 Hz, 1H), 7.91 (dd, J=8.0, 1.6 Hz, 1H), 7.52-7.65 (m, 2H), 7.44-7.50 (m, 1H), 7.28 (td, J=7.6, 1.2 Hz, 1H), 7.24 (dd, J=3.5, 0.8 Hz, 1H), 6.69 (dd, J=3.5, 1.8 Hz, 1H); 19F NMR (376 MHz, DMSO-$d_6$) δ ppm −61.15 (s, 3F); HRMS (ESI) m/z (M+H)+ calcd. for $C_{19}H_{14}F_3N_2O_3$, 375.0951; found 375.0957.

EXAMPLE 41

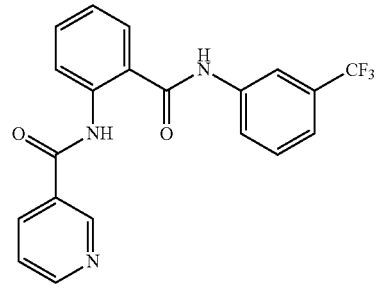 [SMILES: O=C(Nc1ccccc1C(=O)Nc1cccc(C(F)(F)F)c1)c1cccnc1]

This example illustrates a synthesis of N-(2-((3-(Trifluoromethyl)phenyl)carbamoyl)phenyl)nicotinamide (XJB06-062, NCGC00189451-01). The title compound was prepared according to general protocol C. LC-MS Retention Time: $t_1$ (Method 1)=5.342 min; 1H NMR (400 MHz, DMSO-$d_6$) δ ppm 11.27 (s, 1H), 10.74 (s, 1H), 8.95-9.12 (m, 1H), 8.67-8.91 (m, 1H), 8.19-8.29 (m, 1H), 8.17 (dd, J=8.3, 1.3 Hz, 1H), 8.10 (t, J=2.1 Hz, 1H), 7.92-8.02 (m, 1H), 7.86 (dd, J=7.8, 1.6 Hz, 1H), 7.52-7.69 (m, 3H), 7.38-7.48 (m, 1H), 7.33 (td, J=7.6, 1.4 Hz, 1H); 19F NMR (376 MHz, DMSO-$d_6$) δ ppm −61.20 (s, 3F); HRMS (ESI) m/z (M+H)+ calcd. for $C_{20}H_{15}F_3N_3O_2$, 386.1111; found 386.1116.

EXAMPLE 42

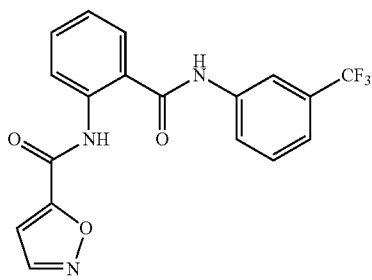 [SMILES: O=C(Nc1ccccc1C(=O)Nc1cccc(C(F)(F)F)c1)c1ccno1]

This example illustrates a synthesis of N-(2-((3-(Trifluoromethyl)phenyl)carbamoyl)phenyl)isoxazole-5-carboxamide (XJB06-063, NCGC00189450-01). The title compound was prepared according to general protocol C. LC-MS Retention Time: $t_1$ (Method 1)=6.043 min; $^1$H NMR (400 MHz, DMSO-$d_6$) δ ppm 11.63 (s, 1H), 10.79 (s, 1H), 8.80 (d, J=2.0 Hz, 1H), 8.23 (dd, J=8.4, 1.2 Hz, 1H), 8.08-8.15 (m, 1H), 7.99 (dd, J=8.3, 1.5 Hz, 1H), 7.91 (dd, J=7.8, 1.6 Hz, 1H), 7.56-7.68 (m, 2H), 7.44-7.51 (m, 1H), 7.36 (td, J=7.6, 1.4 Hz, 1H), 7.19 (d, J=2.0 Hz, 1H); $^{19}$F NMR (376 MHz, DMSO-$d_6$) δ ppm −61.18 (s, 3F); HRMS (ESI) m/z (M+H)$^+$ calcd. for $C_{18}H_{13}F_3N_3O_3$, 376.0904; found 376.0910.

EXAMPLE 43

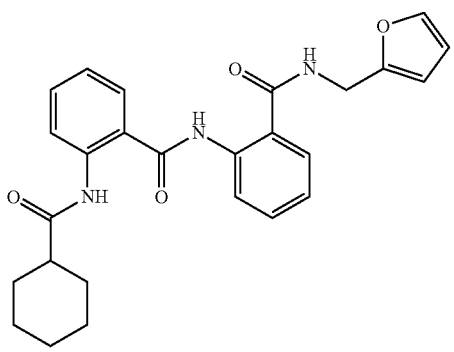 [SMILES: O=C(NCc1ccco1)c1ccccc1NC(=O)c1ccccc1NC(=O)C1CCCCC1]

This example illustrates a synthesis of 2-(Cyclohexanecarboxamido)-N-(2-((furan-2-ylmethyl)carbamoyl)phenyl)benzamide (XJB06-065, NCGC00189449-01). A solution of methyl 2-(cyclohexanecarboxamido)benzoate (50.0 mg, 0.191 mmol) and 2-amino-N-(furan-2-ylmethyl)benzamide (41.4 mg, 0.191 mmol) in toluene (2.00 mL) was treated at room temperature with AlMe$_3$ (0.192 mL, 2.0 M in toluene, 0.384 mmol). The reaction mixture was stirred at 100° C. for overnight and then quenched with 100 μL of water. The mixture was concentrated, re-dissolved in 2.00 mL of DMSO, filtered and purified via C$_{18}$ reverse phase HPLC to give the title compound as a white solid. LC-MS Retention Time: $t_1$ (Method 1)=6.799 min; $^1$H NMR (400 MHz, DMSO-$d_6$) δ ppm 12.07 (s, 1H), 10.69 (s, 1H), 9.29 (t, J=5.8 Hz, 1H), 8.41 (dd, J=8.3, 1.3 Hz, 1H), 8.22 (dd, J=8.3, 1.3 Hz, 1H), 7.80 (dd, J=8.0, 1.6 Hz, 1H), 7.73 (dd, J=7.8, 1.6 Hz, 1H), 7.45-7.64 (m, 3H), 7.13-7.29 (m, J=7.9, 7.7, 7.7, 1.3 Hz, 2H), 6.36 (dd, J=3.2, 1.9 Hz, 1H), 6.22-6.33 (m, 1H), 4.45 (d, J=5.5 Hz, 2H), 2.18-2.36 (m, 1H), 1.76-1.91 (m, 2H), 1.64-1.76 (m, 2H), 1.50-1.64 (m, 1H), 1.05-1.44 (m, 5H); HRMS (ESI) m/z (M+H)$^+$ calcd. for $C_{26}H_{28}N_3O_4$, 446.2074; found 446.2080.

EXAMPLE 44

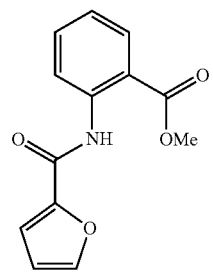 [SMILES: COC(=O)c1ccccc1NC(=O)c1ccco1]

This example illustrates a synthesis of Methyl 2-(furan-2-carboxamido)benzoate (XJB06-066, NCGC00026064-02). A solution of methyl 2-aminobenzoate (1.71 mL, 13.2 mmol) in dichloromethane (50.0 mL) and TEA (5.53 mL, 39.7 mmol) was treated at room temperature with furan-2-carbonyl chloride (2.62 mL, 26.5 mmol). The reaction mixture was stirred at room temperature for 1 h. The reaction mixture was quenched with methanol, concentrated, and purified via silica gel chromatography using a gradient of 0-40% of EtOAc in hexanes to give 3.00 g (92%) of the title compound as a white solid. LC-MS Retention Time: $t_1$ (Method 1)=6.516 min.

EXAMPLE 45

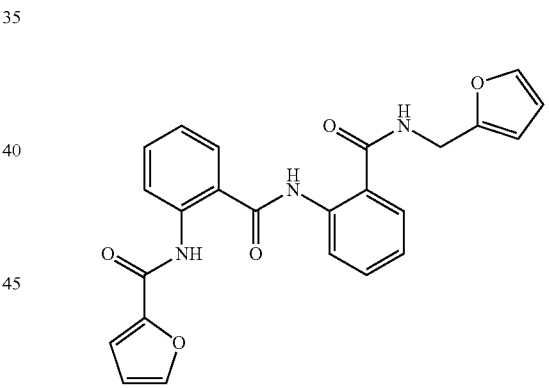

This example illustrates a synthesis of N-(2-((2-((Furan-2-ylmethyl)carbamoyl)phenyl)carbamoyl)phenyl)furan-2-carboxamide (XJB06-067, NCGC00052938-02). A solution of 2-(furan-2-carboxamido)benzoate (50.0 mg, 0.204 mmol) and 2-amino-N-(furan-2-ylmethyl)benzamide (44.1 mg, 0.204 mmol) in toluene (2.00 mL) was treated at room temperature with AlMe$_3$ (0.204 mL, 2.0 M in toluene, 0.408 mmol). The reaction mixture was stirred at 100° C. for overnight and then quenched with 100 μL of water. The mixture was concentrated, re-dissolved in 2.00 mL of DMSO, filtered and purified via C$_{18}$ reverse phase HPLC to give the title compound as a white solid. LC-MS Retention Time: $t_1$ (Method 1)=6.103 min; $^1$H NMR (400 MHz, DMSO-$d_6$) δ ppm 12.33 (s, 1H), 11.87 (s, 1H), 9.32 (t, J=5.3 Hz, 1H), 8.53 (dd, J=8.4, 1.4 Hz, 1H), 8.45 (dd, J=8.3, 1.3 Hz, 1H), 7.97 (dd, J=1.8, 1.0 Hz, 1H), 7.86 (dd, J=8.0, 1.6 Hz, 1H), 7.83 (dd, J=8.0, 1.6 Hz, 1H), 7.55-7.67 (m, 2H), 7.53 (dd, J=2.0, 1.0 Hz, 1H), 7.27-7.35 (m, 1H), 7.18-7.27 (m, 2H), 6.70 (dd, J=3.5, 1.8 Hz, 1H), 6.35 (dd, J=3.2, 1.9 Hz, 1H), 6.28 (dd, J=3.1, 1.0 Hz, 1H), 4.44 (d, J=5.5 Hz, 2H); HRMS (ESI) m/z (M+H)+ calcd. for $C_{24}H_{20}N_3O_5$, 430.1397; found 430.1406.

EXAMPLE 46

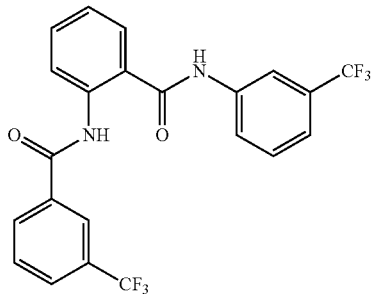 [SMILES: O=C(Nc1ccccc1C(=O)Nc1cccc(C(F)(F)F)c1)c1cccc(C(F)(F)F)c1]

This example illustrates a synthesis of 2-(3-(Trifluoromethyl)benzamido)-N-(3-(trifluoromethyl)phenyl)benzamide (XJB06-070, NCGC00189448-01). The title compound was prepared according to general protocol D. LC-MS Retention Time: $t_1$ (Method 1)=7.060 min; $^1$H NMR (400 MHz, DMSO-$d_6$) δ ppm 11.28 (s, 1H), 10.72 (s, 1H), 8.13-8.32 (m, 3H), 8.11 (dd, J=8.2, 1.2 Hz, 1H), 7.88-8.00 (m, 2H), 7.84 (dd, J=7.8, 1.6 Hz, 1H), 7.78 (t, J=7.7 Hz, 1H), 7.49-7.66 (m, 2H), 7.39-7.45 (m, 1H), 7.33 (td, J=7.6, 1.4 Hz, 1H); $^{19}$F NMR (376 MHz, DMSO-$d_6$) δ ppm −61.32 (s, 6F); HRMS (ESI) m/z (M+H)+ calcd. for $C_{22}H_{15}F_6N_2O_2$, 453.1032; found 453.1033.

EXAMPLE 47

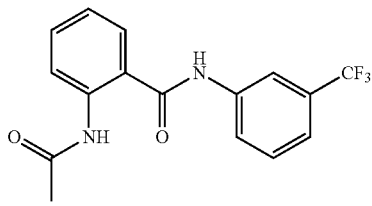 [SMILES: CC(=O)Nc1ccccc1C(=O)Nc1cccc(C(F)(F)F)c1]

This example illustrates a synthesis of 2-Acetamido-N-(3-(trifluoromethyl)phenyl)benzamide (XJB06-071, NCGC00189447-01). The title compound was prepared according to general protocol C. LC-MS Retention Time: $t_1$ (Method 1)=5.593 min; $^1$H NMR (400 MHz, DMSO-$d_6$) δ ppm 10.64 (s, 1H), 10.18 (br. s., 1H), 8.18 (t, J=2.2 Hz, 1H), 7.97-8.04 (m, 1H), 7.92 (dt, J=8.0, 1.2 Hz, 1H), 7.71 (dd, J=7.7, 1.7 Hz, 1H), 7.57 (t, J=8.0 Hz, 1H), 7.50 (ddd, J=8.4, 7.1, 1.7 Hz, 1H), 7.41-7.47 (m, 1H), 7.21 (td, J=7.6, 1.3 Hz, 1H), 2.02 (s, 3H); $^{19}$F NMR (376 MHz, DMSO-$d_6$) δ ppm −61.18 (s, 3F); HRMS (ESI) m/z (M+H)+ calcd. for $C_{16}H_{14}F_3N_2O_2$, 323.1002; found 323.1010.

EXAMPLE 48

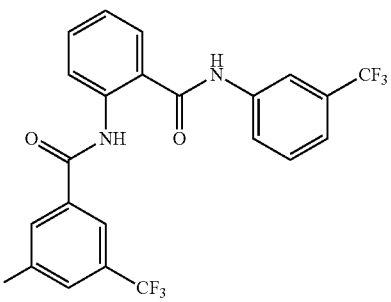

This example illustrates a synthesis of 2-Acetamido-N-(3-(trifluoromethyl)phenyl)benzamide (XJB06-072, NCGC00189446-01). The title compound was prepared according to general protocol D. LC-MS Retention Time: $t_1$ (Method 1)=7.415 min; $^1$H NMR (400 MHz, DMSO-$d_6$) δ ppm 11.25 (s, 1H), 10.71 (s, 1H), 8.39-8.57 (m, 2H), 8.35 (s, 1H), 8.19 (s, 1H), 7.92-8.00 (m, 1H), 7.84-7.92 (m, 1H), 7.81 (dd, J=7.7, 1.7 Hz, 1H), 7.58-7.68 (m, 1H), 7.53 (t, J=7.9 Hz, 1H), 7.22-7.47 (m, 2H); $^{19}$F NMR (376 MHz, DMSO-$d_6$) δ ppm −61.42 (s, 3F); HRMS (ESI) m/z (M+H)+ calcd. for $C_{23}H_{14}F_9N_2O_2$, 521.0906; found 521.0905.

EXAMPLE 49

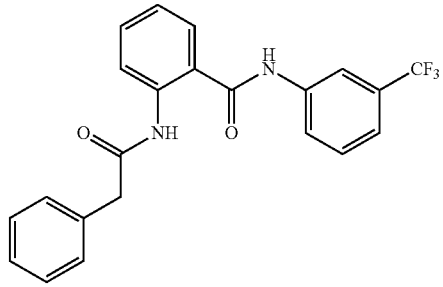 [SMILES: O=C(Cc1ccccc1)Nc1ccccc1C(=O)Nc1cccc(C(F)(F)F)c1]

This example illustrates a synthesis of 2-(2-Phenylacetamido)-N-(3-(trifluoromethyl)phenyl)benzamide (XJB06-074, NCGC00189445-01). The title compound was prepared according to general protocol C. LC-MS Retention Time: $t_1$ (Method 1)=6.443 min; $^1$H NMR (400 MHz, DMSO-$d_6$) δ ppm 10.61 (s, 1H), 10.30 (s, 1H), 8.17 (t, J=2.1 Hz, 1H), 8.00-8.07 (m, 1H), 7.83-7.91 (m, 1H), 7.71 (dd, J=7.8, 1.6 Hz, 1H), 7.57 (t, J=7.9 Hz, 1H), 7.50 (ddd, J=8.5, 7.2, 1.6 Hz, 1H), 7.41-7.47 (m, 1H), 7.11-7.34 (m, 6H), 3.66 (s, 2H); $^{19}$F NMR (376 MHz, DMSO-$d_6$) δ ppm −61.15 (s, 3F); HRMS (ESI) m/z (M+H)+ calcd. for $C_{22}H_{18}F_3N_2O_2$, 399.1315; found 399.1312.

EXAMPLE 50

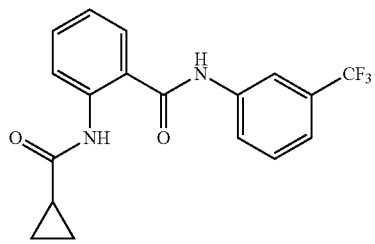 [SMILES: O=C(Nc1cccc(C(F)(F)F)c1)c1ccccc1NC(=O)C1CC1]

This example illustrates a synthesis of 2-(Cyclopropanecarboxamido)-N-(3-(trifluoromethyl)phenyl)benzamide (XJB06-081, NCGC00189444-01). The title compound was prepared according to general protocol B. LC-MS Retention Time: $t_1$ (Method 1)=6.131 min; $^1$H NMR (400 MHz, DMSO-$d_6$) δ ppm 10.61 (s, 1H), 10.46 (s, 1H), 8.17 (s, 1H), 7.95-8.08 (m, 1H), 7.91 (dd, J=7.9, 1.3 Hz, 1H), 7.71 (dd, J=7.9, 1.5 Hz, 1H), 7.57 (t, J=7.9 Hz, 1H), 7.46-7.53 (m, 1H), 7.40-7.46 (m, 1H), 7.20 (tt, J=7.6, 0.8 Hz, 1H), 1.61-1.81 (m, 1H), 0.65-0.79 (m, 4H); $^{19}$F NMR (376 MHz, DMSO-$d_6$) δ ppm −61.28 (s, 3F); HRMS (ESI) m/z (M+H)$^+$ calcd. for $C_{18}H_{16}F_3N_2O_2$, 349.1158; found 349.1160.

EXAMPLE 51

This example illustrates a synthesis of N-(3-(tert-Butyl)phenyl)-2-(cyclohexanecarboxamido)benzamide (XJB07-026, NCGC00238733-01). The title compound was prepared according to general protocol A. LC-MS Retention Time: $t_1$ (Method 1)=7.324 min; HRMS (ESI) m/z (M+H)$^+$ calcd. for $C_{24}H_{31}N_2O_2$, 379.2380; found 379.2387.

EXAMPLE 52

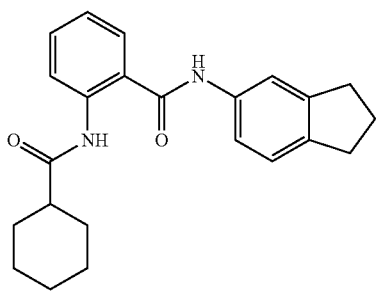 [SMILES: O=C(Nc1ccc2c(c1)CCC2)c1ccccc1NC(=O)C1CCCCC1]

This example illustrates a synthesis of 2-(Cyclohexanecarboxamido)-N-(2,3-dihydro-1H-inden-5-yl)benzamide (XJB07-028, NCGC00238732-01). The title compound was prepared according to general protocol A. LC-MS Retention Time: $t_1$ (Method 1)=7.053 min; $^1$H NMR (400 MHz, DMSO-$d_6$) δ ppm 10.62 (s, 1H), 10.27 (s, 1H), 8.26 (d, J=8.2 Hz, 1H), 7.75 (d, J=7.8 Hz, 1H), 7.55 (s, 1H), 7.42-7.51 (m, 1H), 7.31-7.41 (m, 1H), 7.08-7.23 (m, 2H), 2.74-2.90 (m, 4H), 2.17-2.32 (m, 1H), 1.92-2.08 (m, J=7.8, 7.5, 7.4, 7.4 Hz, 2H), 1.76-1.89 (m, 2H), 1.63-1.76 (m, 2H), 1.52-1.62 (m, 1H), 1.05-1.46 (m, 5H); HRMS (ESI) m/z (M+H)$^+$ calcd. for $C_{23}H_{27}N_2O_2$, 363.2067; found 363.2075.

EXAMPLE 53

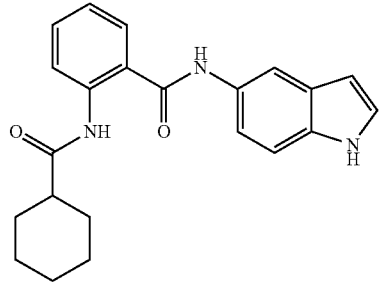 [SMILES: O=C(Nc1ccc2[nH]ccc2c1)c1ccccc1NC(=O)C1CCCCC1]

This example illustrates a synthesis of 2-(Cyclohexanecarboxamido)-N-(1H-indol-5-yl)benzamide (XJB07-031, NCGC00238734-01). The title compound was prepared according to general protocol A. LC-MS Retention Time: $t_1$ (Method 1)=5.982 min; $^1$H NMR (400 MHz, DMSO-$d_6$) δ ppm 11.04 (br. s., 1H), 10.87 (s, 1H), 10.26 (s, 1H), 8.34 (d, J=8.4 Hz, 1H), 7.65-8.00 (m, 2H), 7.44-7.53 (m, 1H), 7.24-7.41 (m, 3H), 7.16 (t, J=7.6 Hz, 1H), 6.31-6.45 (m, 1H), 2.17-2.31 (m, 1H), 1.77-1.92 (m, 2H), 1.68 (ddd, J=12.5, 3.4, 3.2 Hz, 2H), 1.51-1.62 (m, 1H), 1.01-1.44 (m, 5H); HRMS (ESI) m/z (M+H)$^+$ calcd. for $C_{22}H_{24}N_3O_2$, 362.1863; found 362.1867.

EXAMPLE 54

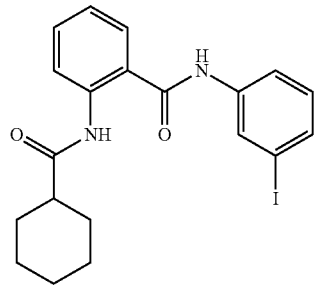 [SMILES: O=C(Nc1cccc(I)c1)c1ccccc1NC(=O)C1CCCCC1]

This example illustrates a synthesis of 2-(Cyclohexanecarboxamido)-N-(3-iodophenyl)benzamide (XJB07-032, NCGC00238735-01). The title compound was prepared according to general protocol A. LC-MS Retention Time: $t_1$ (Method 1)=7.076 min; $^1$H NMR (400 MHz, DMSO-$d_6$) δ ppm 10.39 (s, 1H), 10.32 (s, 1H), 8.05-8.20 (m, 2H), 7.68-7.76 (m, 1H), 7.66 (ddd, J=8.2, 1.1, 0.9 Hz, 1H), 7.39-7.55 (m, 2H), 7.06-7.27 (m, 2H), 2.11-2.33 (m, 1H), 1.79 (dd, J=12.7, 2.2 Hz, 2H), 1.63-1.73 (m, 2H), 1.49-1.63 (m, 1H), 1.05-1.44 (m, 5H); HRMS (ESI) m/z (M+H)$^+$ calcd. for $C_{20}H_{22}IN_2O_2$, 449.0720; found 449.0720.

EXAMPLE 55

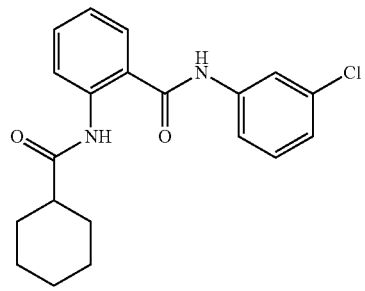 [SMILES: O=C(Nc1cccc(Cl)c1)c1ccccc1NC(=O)C1CCCCC1]

This example illustrates a synthesis of N-(3-Chlorophenyl)-2-(cyclohexanecarboxamido)benzamide (XJB07-033, NCGC00238736-01, CID-56593336). The title compound was prepared according to general protocol A. LC-MS Retention Time: $t_1$ (Method 1)=6.898 min; $^1$H NMR (400 MHz, DMSO-$d_6$) δ ppm 10.48 (s, 1H), 10.31 (s, 1H), 8.11 (d, J=7.8 Hz, 1H), 7.85 (t, J=2.0 Hz, 1H), 7.71 (dd, J=7.7, 1.3 Hz, 1H), 7.59 (dd, J=8.0, 1.8 Hz, 1H), 7.43-7.54 (m, 1H), 7.35 (t, J=8.1 Hz, 1H), 7.06-7.24 (m, 2H), 2.26 (tt J=11.3, 3.6 Hz, 1H), 1.79 (d, J=14.1 Hz, 2H), 1.68 (ddd, J=12.7, 3.0, 2.7 Hz, 2H), 1.52-1.62 (m, 1H), 1.03-1.41 (m, 5H); HRMS (ESI) m/z (M+H)$^+$ calcd. for $C_{20}H_{22}ClN_2O_2$, 357.1364; found 357.1366.

EXAMPLE 56

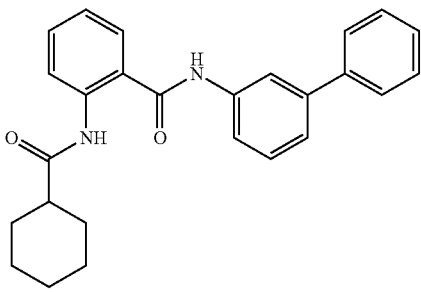 [SMILES: O=C(Nc1cccc(-c2ccccc2)c1)c1ccccc1NC(=O)C1CCCCC1]

This example illustrates a synthesis of N-([1,1'-Biphenyl]-3-yl)-2-(cyclohexanecarboxamido)benzamide (XJB07-034, NCGC00238737-01). The title compound was prepared according to general protocol A. LC-MS Retention Time: $t_1$ (Method 1)=7.181 min; $^1$H NMR (400 MHz, DMSO-$d_6$) δ ppm 10.49 (s, 1H), 10.44 (s, 1H), 8.19 (ddd, J=8.2, 0.8, 0.6 Hz, 1H), 7.96 (t, J=2.0 Hz, 1H), 7.78 (dd, J=7.8, 1.6 Hz, 1H), 7.70 (dt, J=7.6, 1.9 Hz, 1H), 7.56-7.66 (m, 2H), 7.31-7.55 (m, 6H), 7.15-7.23 (m, 1H), 2.19-2.32 (m, 1H), 1.76-1.87 (m, 2H), 1.62-1.74 (m, 2H), 1.52-1.62 (m, 1H), 1.04-1.45 (m, 5H); HRMS (ESI) m/z (M+H)$^+$ calcd. for $C_{26}H_{27}N_2O_2$, 399.2067; found 399.2071.

EXAMPLE 57

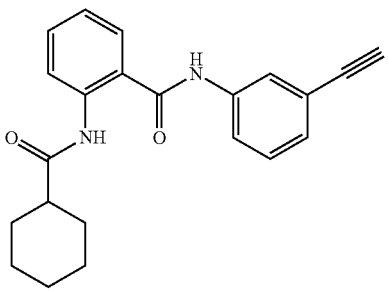 [SMILES: C#Cc1cccc(NC(=O)c2ccccc2NC(=O)C2CCCCC2)c1]

This example illustrates a synthesis of 2-(Cyclohexanecarboxamido)-N-(3-ethynylphenyl)benzamide (XJB07-035, NCGC00238738-01). The title compound was prepared according to general protocol A. LC-MS Retention Time: $t_1$ (Method 1)=6.586 min; $^1$H NMR (400 MHz, DMSO-$d_6$) δ ppm 10.42 (s, 1H), 10.38 (s, 1H), 8.15 (d, J=8.2 Hz, 1H), 7.84 (s, 1H), 7.71-7.78 (m, 1H), 7.62-7.71 (m, 1H), 7.44-7.53 (m, 1H), 7.34 (t, J=8.0 Hz, 1H), 7.14-7.24 (m, 2H), 4.17 (s, 1H), 2.08-2.35 (m, 1H), 1.74-1.89 (m, 2H), 1.62-1.74 (m, 2H), 1.53-1.62 (m, 1H), 1.00-1.43 (m, 5H); HRMS (ESI) m/z (M+H)$^+$ calcd. for $C_{22}H_{23}N_2O_2$, 347.1754; found 347.1757.

EXAMPLE 58

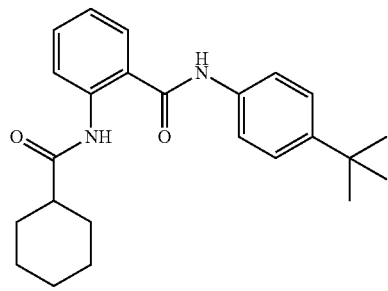 [SMILES: CC(C)(C)c1ccc(NC(=O)c2ccccc2NC(=O)C2CCCCC2)cc1]

This example illustrates a synthesis of N-(4-(tert-Butyl)phenyl)-2-(cyclohexanecarboxamido)benzamide (XJB07-037, NCGC00238739-01). The title compound was prepared according to general protocol A. LC-MS Retention Time: $t_1$ (Method 1)=7.389 min; $^1$H NMR (400 MHz, DMSO-$d_6$) δ ppm 10.63 (s, 1H), 10.33 (s, 1H), 8.26 (d, J=8.2 Hz, 1H), 7.76 (dt, J=7.9, 1.0 Hz, 1H), 7.52-7.61 (m, 2H), 7.43-7.52 (m, 1H), 7.29-7.42 (m, 2H), 7.17 (tt, J=7.6, 1.0 Hz, 1H), 2.16-2.29 (m, 1H), 1.77-1.89 (m, 2H), 1.64-1.77 (m, 2H), 1.49-1.64 (m, 1H), 1.25 (s, 9H), 1.01-1.44 (m, 5H); HRMS (ESI) m/z (M+H)$^+$ calcd. for $C_{24}H_{31}N_2O_2$, 379.2380; found 379.2391.

EXAMPLE 59

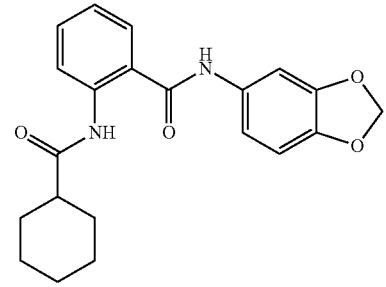 [SMILES: O=C(Nc1ccc2c(c1)OCO2)c1ccccc1NC(=O)C1CCCCC1]

This example illustrates a synthesis of N-(Benzo[d][1,3]dioxol-5-yl)-2-(cyclohexanecarboxamido)benzamide (XJB07-039, NCGC00238740-01). The title compound was prepared according to general protocol A. LC-MS Retention Time: $t_1$ (Method 1)=6.279 min; $^1$H NMR (400 MHz, DMSO-$d_6$) δ ppm 10.57 (s, 1H), 10.28 (s, 1H), 8.23 (d, J=8.6 Hz, 1H), 7.73 (dd, J=7.9, 1.7 Hz, 1H), 7.44-7.62 (m, 1H), 7.26-7.35 (m, 1H), 7.13-7.21 (m, 1H), 7.08 (dd, J=8.4, 2.0 Hz, 1H), 6.88 (d, J=8.4 Hz, 1H), 5.98 (s, 2H), 2.25 (tt, J=11.3, 3.6 Hz, 1H), 1.75-1.90 (m, 2H), 1.64-1.75 (m, 2H), 1.50-1.64 (m, 1H), 1.01-1.43 (m, 5H); HRMS (ESI) m/z (M+H)$^+$ calcd. for $C_{21}H_{23}N_2O_4$, 367.1652; found 367.1657.

EXAMPLE 60

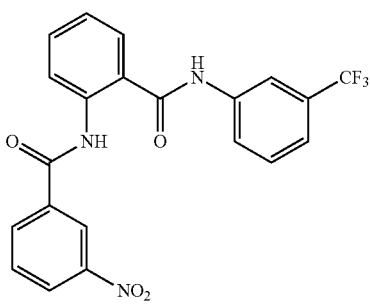

This example illustrates a synthesis of 2-(3-Nitrobenzamido)-N-(3-(trifluoromethyl)phenyl)benzamide (XJB07-047, NCGC00238741-01). The title compound was prepared according to general protocol C. LC-MS Retention Time: $t_1$ (Method 1)=6.687 min; $^1$H NMR (400 MHz, DMSO-$d_6$) δ ppm 11.32 (s, 1H), 10.73 (s, 1H), 8.68 (t, J=2.1 Hz, 1H), 8.36-8.48 (m, 1H), 8.29 (dt, J=7.8, 1.5 Hz, 1H), 8.12 (s, 1H), 7.99-8.10 (m, 1H), 7.95 (d, J=8.2 Hz, 1H), 7.76-7.88 (m, 2H), 7.58-7.66 (m, J=7.6, 7.6, 1.2, 0.8 Hz, 1H), 7.50-7.58 (m, 1H), 7.38-7.45 (m, 1H), 7.29-7.38 (m, 1H); $^{19}$F NMR (376 MHz, DMSO-$d_6$) δ ppm −61.34 (s, 3F); HRMS (ESI) m/z (M+H)$^+$ calcd. for $C_{21}H_{15}F_3N_3O_4$, 430.1009; found 430.1012.

EXAMPLE 61

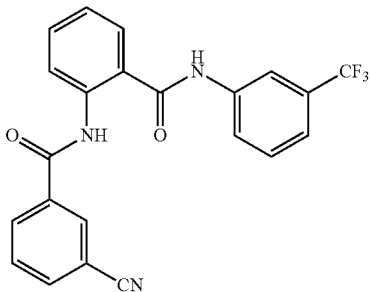 [SMILES: N#Cc1cccc(C(=O)Nc2ccccc2C(=O)Nc2cccc(C(F)(F)F)c2)c1]

This example illustrates a synthesis of 2-(3-Cyanobenzamido)-N-(3-(trifluoromethyl)phenyl)benzamide (XJB07-048, NCGC00238743-01). The title compound was prepared according to general protocol C. LC-MS Retention Time: $t_1$ (Method 1)=6.508 min; $^1$H NMR (400 MHz, DMSO-$d_6$) δ ppm 11.16 (s, 1H), 10.71 (s, 1H), 8.27 (t, J=1.8 Hz, 1H), 8.15 (dt, J=7.9, 1.6 Hz, 1H), 8.01-8.12 (m, 3H), 7.88-7.96 (m, 1H), 7.79-7.87 (m, 1H), 7.73 (t, J=7.8 Hz, 1H), 7.51-7.65 (m, 2H), 7.42 (d, J=7.6 Hz, 1H), 7.32 (td, J=7.7, 0.8 Hz, 1H); $^{19}$F NMR (376 MHz, DMSO-$d_6$) δ ppm −61.33 (s, 3F); HRMS (ESI) m/z (M+H)$^+$ calcd. for $C_{22}H_{15}F_3N_3O_2$, 410.1111; found 410.1120.

EXAMPLE 62

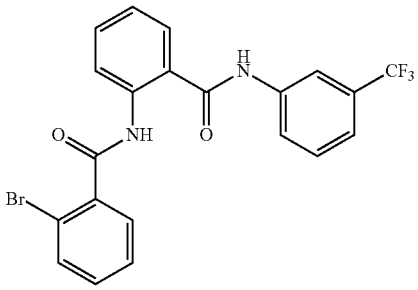 [SMILES: O=C(Nc1ccccc1C(=O)Nc1cccc(C(F)(F)F)c1)c1ccccc1Br]

This example illustrates a synthesis of 2-Bromo-N-(2-((3-(trifluoromethyl)phenyl)carbamoyl)phenyl)benzamide (XJB07-050, NCGC00238742-01). The title compound was prepared according to general protocol C. LC-MS Retention Time: $t_1$ (Method 1)=6.641 min; HRMS (ESI) m/z (M+H)$^+$ calcd. for $C_{21}H_{15}BrF_3N_2O_2$, 463.0264; found 463.0264.

EXAMPLE 63

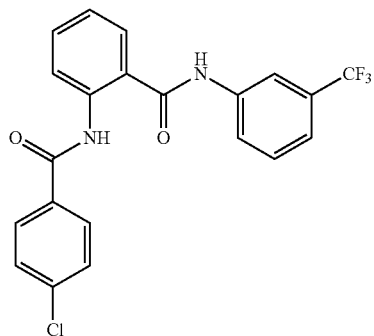 [SMILES: O=C(Nc1ccccc1C(=O)Nc1cccc(C(F)(F)F)c1)c1ccc(Cl)cc1]

This example illustrates a synthesis of 2-(4-Chlorobenzamido)-N-(3-(trifluoromethyl)phenyl)benzamide (XJB07-051, NCGC00238744-01). The title compound was prepared according to general protocol C. LC-MS Retention Time: $t_1$ (Method 1)=7.132 min; $^1$H NMR (400 MHz, DMSO-$d_6$) δ ppm 11.26 (s, 1H), 10.72 (s, 1H), 8.21 (d, J=8.2 Hz, 1H), 8.06 (s, 1H), 7.96 (d, J=8.4 Hz, 1H), 7.82-7.93 (m, 3H), 7.52-7.66 (m, 4H), 7.44 (d, J=7.8 Hz, 1H), 7.30 (t, J=7.4 Hz, 1H); $^{19}$F NMR (376 MHz, DMSO-$d_6$) δ ppm −61.28 (s, 3F); HRMS (ESI) m/z (M+H)$^+$ calcd. for $C_{21}H_{15}ClF_3N_2O_2$, 419.0769; found 419.0775.

EXAMPLE 64

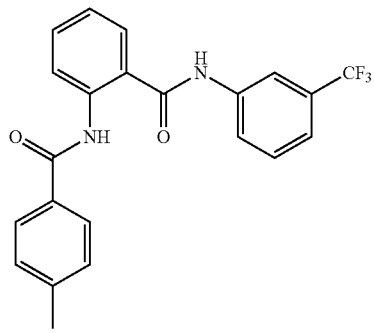 [SMILES: Cc1ccc(C(=O)Nc2ccccc2C(=O)Nc2cccc(C(F)(F)F)c2)cc1]

This example illustrates a synthesis of 2-(4-Methylbenzamido)-N-(3-(trifluoromethyl)phenyl)benzamide (XJB07-052, NCGC00238745-01). The title compound was prepared according to general protocol C. LC-MS Retention Time: $t_1$ (Method 1)=6.967 min; $^1$H NMR (400 MHz, DMSO-$d_6$) δ ppm 11.31 (s, 1H), 10.73 (s, 1H), 8.33 (d, J=8.4 Hz, 1H), 8.08 (s, 1H), 7.98 (d, J=8.4 Hz, 1H), 7.88 (dd, J=7.6, 1.6 Hz, 1H), 7.78 (d, J=8.2 Hz, 2H), 7.53-7.64 (m, 2H), 7.45 (ddd, J=7.7, 1.8, 0.9 Hz, 1H), 7.33 (d, J=8.6 Hz, 2H), 7.27 (td, J=7.6, 1.2 Hz, 1H), 2.34 (s, 3H); $^{19}$F NMR (376 MHz, DMSO-$d_6$) δ ppm −61.28 (s, 3F); HRMS (ESI) m/z (M+H)$^+$ calcd. for $C_{22}H_{18}F_3N_2O_2$, 399.1315; found 399.1321.

EXAMPLE 65

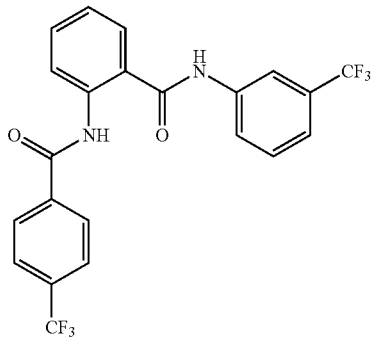

This example illustrates a synthesis of 2-(4-(Trifluoromethyl)benzamido)-N-(3-(trifluoromethyl)phenyl)benzamide (XJB07-054, NCGC00238746-01). The title compound was prepared according to general protocol C. LC-MS Retention Time: $t_1$ (Method 1)=7.128 min; $^1$H NMR (400 MHz, DMSO-$d_6$) δ ppm 11.33 (d, J=0.4 Hz, 1H), 10.73 (s, 1H), 8.19 (d, J=8.2 Hz, 1H), 8.01-8.11 (m, 3H), 7.97 (d, J=8.4 Hz, 1H), 7.90 (d, J=8.6 Hz, 2H), 7.82-7.88 (m, 1H), 7.51-7.64 (m, 2H), 7.40-7.45 (m, 1H), 7.32 (t, J=7.4 Hz, 1H); $^{19}$F NMR (376 MHz, DMSO-$d_6$) δ ppm −61.30 (s, 3F), −61.45 (s, 3F); HRMS (ESI) m/z (M+H)$^+$ calcd. for $C_{22}H_{15}F_6N_2O_2$, 453.1032; found 453.1034.

EXAMPLE 66

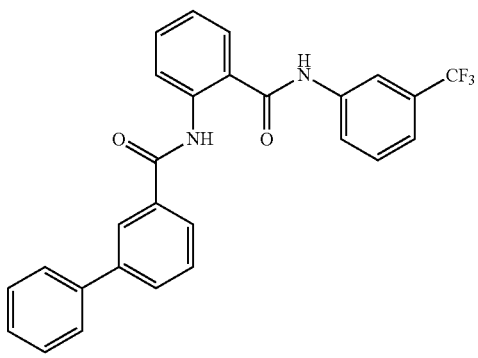 [SMILES: O=C(Nc1ccccc1C(=O)Nc1cccc(C(F)(F)F)c1)c1cccc(-c2ccccc2)c1]

This example illustrates a synthesis of N-(2-((3-(Trifluoromethyl)phenyl)carbamoyl)phenyl)-[1,1'-biphenyl]-3-carboxamide (XJB07-055, NCGC00238747-01). The title compound was prepared according to general protocol C. LC-MS Retention Time: $t_1$ (Method 1)=7.398 min; $^1$H NMR (400 MHz, DMSO-$d_6$) δ ppm 11.40 (s, 1H), 10.76 (s, 1H), 8.25-8.35 (m, 1H), 8.10-8.22 (m, 2H), 7.99 (d, J=8.2 Hz, 1H), 7.81-7.94 (m, 3H), 7.67-7.75 (m, 2H), 7.54-7.66 (m, 3H), 7.43-7.51 (m, 3H), 7.37-7.43 (m, 1H), 7.32 (td, J=7.6, 1.3 Hz, 1H); $^{19}$F NMR (376 MHz, DMSO-$d_6$) δ ppm −61.28 (s, 3F); HRMS (ESI) m/z (M+H)$^+$ calcd. for $C_{27}H_{20}F_3N_2O_2$, 461.1471; found 461.1478.

EXAMPLE 67

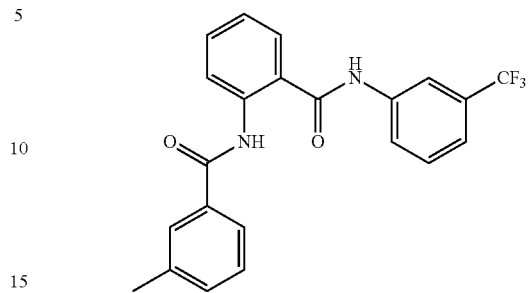

This example illustrates a synthesis of 2-(3-Methylbenzamido)-N-(3-(trifluoromethyl)phenyl)benzamide (XJB07-056, NCGC00238759-02). The title compound was prepared according to general protocol C. LC-MS Retention Time: $t_1$ (Method 1)=6.975 min; $^1$H NMR (400 MHz, DMSO-$d_6$) δ ppm 11.27 (s, 1H), 10.75 (s, 1H), 8.30 (dd, J=8.3, 1.3 Hz, 1H), 8.14 (s, 1H), 7.98 (d, J=8.4 Hz, 1H), 7.88 (dd, J=7.8, 1.6 Hz, 1H), 7.71 (t, J=1.7 Hz, 1H), 7.64-7.69 (m, 1H), 7.54-7.64 (m, 2H), 7.43-7.48 (m, 1H), 7.37-7.43 (m, 2H), 7.30 (td, J=7.6, 1.3 Hz, 1H), 2.36 (s, 3H); $^{19}$F NMR (376 MHz, DMSO-$d_6$) δ ppm −61.31 (s, 3F); HRMS (ESI) m/z (M+H)$^+$ calcd. for $C_{22}H_{18}F_3N_2O_2$, 399.1315; found 399.1323.

EXAMPLE 68

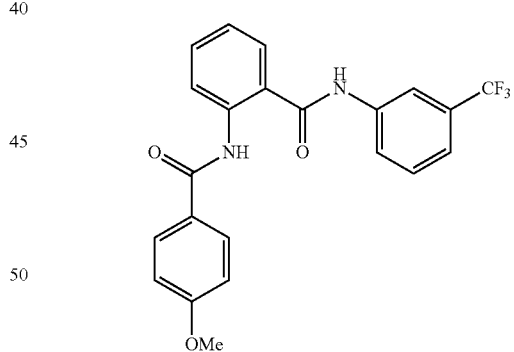

This example illustrates a synthesis of 2-(4-Methoxybenzamido)-N-(3-(trifluoromethyl)phenyl)benzamide (XJB07-057, NCGC00238760-01). The title compound was prepared according to general protocol C. LC-MS Retention Time: $t_1$ (Method 1)=6.679 min; $^1$H NMR (400 MHz, DMSO-$d_6$) δ ppm 11.31 (s, 1H), 10.75 (s, 1H), 8.36 (dd, J=8.3, 1.3 Hz, 1H), 8.08 (t, J=2.2 Hz, 1H), 8.01 (ddd, J=8.2, 1.2, 1.0 Hz, 1H), 7.78-7.92 (m, 3H), 7.54-7.64 (m, 2H), 7.42-7.49 (m, 1H), 7.27 (td, J=7.6, 1.2 Hz, 1H), 7.00-7.12 (m, 2H), 3.81 (s, 3H); $^{19}$F NMR (376 MHz, DMSO-$d_6$) δ ppm −61.25 (s, 3F); HRMS (ESI) m/z (M+H)$^+$ calcd. for $C_{22}H_{18}F_3N_2O_3$, 415.1264; found 415.1272.

EXAMPLE 69

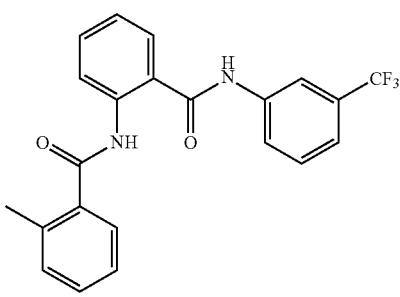 [SMILES: Cc1ccccc1C(=O)Nc1ccccc1C(=O)Nc1cccc(C(F)(F)F)c1]

This example illustrates a synthesis of 2-Methyl-N-(2-((3-(trifluoromethyl)phenyl)carbamoyl)phenyl)benzamide (XJB07-058, NCGC00238761-01). The title compound was prepared according to general protocol C. LC-MS Retention Time: $t_1$ (Method 1)=6.769 min; $^1$H NMR (400 MHz, DMSO-$d_6$) δ ppm 10.74 (s, 1H), 10.70 (s, 1H), 8.08-8.19 (m, 2H), 7.95 (dt, J=8.2, 1.2 Hz, 1H), 7.79 (dd, J=7.8, 1.8 Hz, 1H), 7.48-7.65 (m, 3H), 7.33-7.47 (m, 2H), 7.22-7.33 (m, 3H), 2.37 (s, 3H); $^{19}$F NMR (376 MHz, DMSO-$d_6$) δ ppm −61.30 (s, 3F); HRMS (ESI) m/z (M+H)$^+$ calcd. for $C_{22}H_{18}F_3N_2O_2$, 399.1315; found 399.1324.

EXAMPLE 70

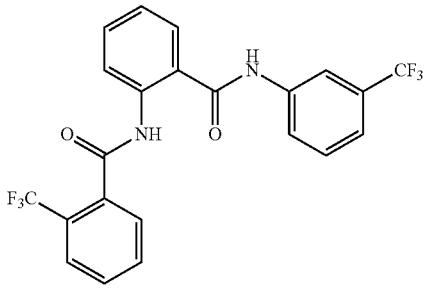 [SMILES: O=C(Nc1cccc(C(F)(F)F)c1)c1ccccc1NC(=O)c1ccccc1C(F)(F)F]

This example illustrates a synthesis of 2-(Trifluoromethyl)-N-(2-((3-(trifluoromethyl)phenyl)carbamoyl)phenyl)benzamide (XJB07-059, NCGC00238762-01). The title compound was prepared according to general protocol C. LC-MS Retention Time: $t_1$ (Method 1)=6.708 min; $^1$H NMR (400 MHz, DMSO-$d_6$) δ ppm 10.83 (s, 1H), 10.71 (s, 1H), 8.13 (s, 1H), 8.00 (d, J=8.2 Hz, 1H), 7.94 (d, J=8.2 Hz, 1H), 7.64-7.87 (m, 5H), 7.49-7.63 (m, 2H), 7.42 (dt, J=7.8, 1.0 Hz, 1H), 7.33 (td, J=7.6, 1.4 Hz, 1H); $^{19}$F NMR (376 MHz, DMSO-$d_6$) δ ppm −57.86 (s, 3F), −61.31 (s, 3F); HRMS (ESI) m/z (M+H)$^+$ calcd. for $C_{22}H_{15}F_6N_2O_2$, 453.1032; found 453.1027.

EXAMPLE 71

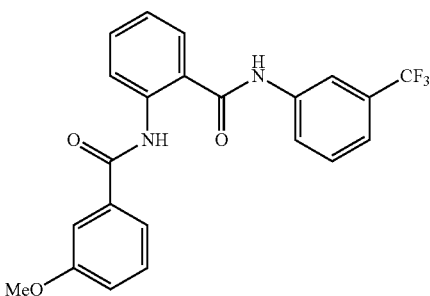 [SMILES: COc1cccc(C(=O)Nc2ccccc2C(=O)Nc2cccc(C(F)(F)F)c2)c1]

This example illustrates a synthesis of 2-(3-Methoxybenzamido)-N-(3-(trifluoromethyl)phenyl)benzamide (XJB07-060, NCGC00238763-01). The title compound was prepared according to general protocol C. LC-MS Retention Time: $t_1$ (Method 1)=6.778 min; $^1$H NMR (400 MHz, DMSO-$d_6$) δ ppm 11.33 (s, 1H), 10.75 (s, 1H), 8.32 (dd, J=8.3, 1.3 Hz, 1H), 8.14 (t, J=2.1 Hz, 1H), 7.98 (dt, J=8.1, 1.2 Hz, 1H), 7.89 (dd, J=7.9, 1.7 Hz, 1H), 7.52-7.66 (m, 2H), 7.39-7.52 (m, 4H), 7.30 (td, J=7.6, 1.4 Hz, 1H), 7.13-7.25 (m, 1H), 3.80 (s, 3H); $^{19}$F NMR (376 MHz, DMSO-$d_6$) δ ppm −61.31 (s, 3F); HRMS (ESI) m/z (M+H)$^+$ calcd. for $C_{22}H_{18}F_3N_2O_3$, 415.1264; found 415.1270.

EXAMPLE 72

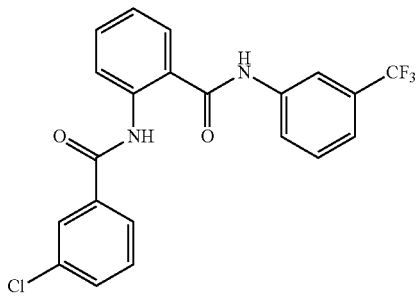 [SMILES: O=C(Nc1ccccc1C(=O)Nc1cccc(C(F)(F)F)c1)c1cccc(Cl)c1]

This example illustrates a synthesis of 2-(3-Chlorobenzamido)-N-(3-(trifluoromethyl)phenyl)benzamide (XJB07-062, NCGC00238764-01). The title compound was prepared according to general protocol C. LC-MS Retention Time: $t_1$ (Method 1)=7.105 min; $^1$H NMR (400 MHz, DMSO-$d_6$) δ ppm 11.20 (s, 1H), 10.73 (s, 1H), 8.15 (dd, J=8.2, 1.4 Hz, 1H), 8.13 (t, J=2.1 Hz, 1H), 7.92-7.99 (m, 1H), 7.90 (t, J=2.0 Hz, 1H), 7.76-7.89 (m, 2H), 7.64-7.69 (m, 1H), 7.53-7.64 (m, 3H), 7.40-7.47 (m, 1H), 7.33 (td, J=7.6, 1.2 Hz, 1H); $^{19}$F NMR (376 MHz, DMSO-$d_6$) δ ppm −61.30 (s, 3F); HRMS (ESI) m/z (M+H)$^+$ calcd. for $C_{21}H_{15}ClF_3N_2O_2$, 419.0769; found 419.0772.

EXAMPLE 73

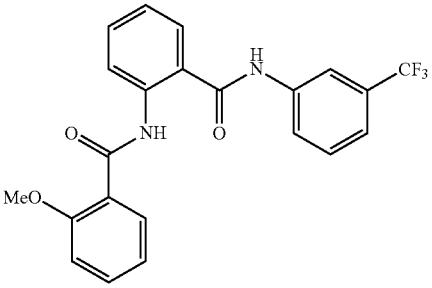 [SMILES: COc1ccccc1C(=O)Nc1ccccc1C(=O)Nc1cccc(C(F)(F)F)c1]

This example illustrates a synthesis of 2-Methoxy-N-(2-((3-(trifluoromethyl)phenyl)carbamoyl)phenyl)benzamide (XJB07-063, NCGC00238748-01). The title compound was prepared according to general protocol C. LC-MS Retention Time: $t_1$ (Method 1)=6.734 min; $^1$H NMR (400 MHz, DMSO-$d_6$) δ ppm 11.54 (s, 1H), 10.84 (s, 1H), 8.52-8.63 (m, 1H), 8.32 (t, J=2.2 Hz, 1H), 7.94-8.06 (m, 2H), 7.79 (dd, J=7.7, 1.7 Hz, 1H), 7.51-7.68 (m, 3H), 7.43-7.51 (m, 1H), 7.24-7.30 (m, 1H), 7.17-7.23 (m, 1H), 6.99-7.13 (m, 1H), 3.97 (s, 3H); $^{19}$F NMR (376 MHz, DMSO-d$_6$) δ ppm −61.40 (s, 3F); HRMS (ESI) m/z (M+H)$^+$ calcd. for C$_{22}$H$_{18}$F$_3$N$_2$O$_3$, 415.1264; found 415.1266.

EXAMPLE 74

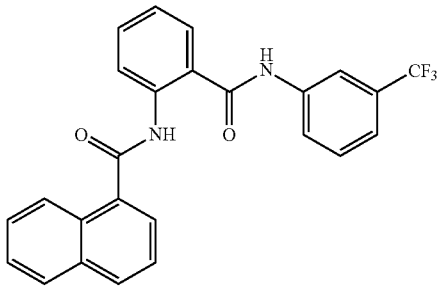 [SMILES: O=C(Nc1cccc(C(F)(F)F)c1)c1ccccc1NC(=O)c1cccc2ccccc12]

This example illustrates a synthesis of N-(2-((3-(Trifluoromethyl)phenyl)carbamoyl)phenyl)-1-naphthamide (XJB07-064, NCGC00238749-01). The title compound was prepared according to general protocol C. LC-MS Retention Time: t$_1$ (Method 1)=6.952 min; $^1$H NMR (400 MHz, DMSO-d$_6$) δ ppm 10.94 (s, 1H), 10.74 (s, 1H), 8.26-8.32 (m, 1H), 8.16 (t, J=2.2 Hz, 1H), 8.02-8.11 (m, 2H), 7.91-8.01 (m, 2H), 7.81 (dd, J=3.2, 1.5 Hz, 1H), 7.79 (dd, J=3.9, 1.6 Hz, 1H), 7.44-7.67 (m, 5H), 7.38-7.43 (m, 1H), 7.34 (td, J=7.6, 1.3 Hz, 1H); $^{19}$F NMR (376 MHz, DMSO-d$_6$) δ ppm −61.28 (s, 3F); HRMS (ESI) m/z (M+H)$^+$ calcd. for C$_{25}$H$_{18}$F$_3$N$_2$O$_2$, 435.1315; found 435.1318.

EXAMPLE 75

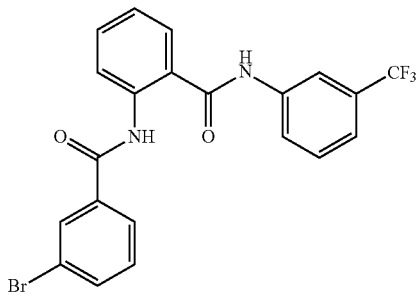

This example illustrates a synthesis of 2-(3-Bromobenzamido)-N-(3-(trifluoromethyl)phenyl)benzamide (XJB07-065, NCGC00238750-01). The title compound was prepared according to general protocol C. LC-MS Retention Time: t$_1$ (Method 1)=7.174 min; $^1$H NMR (400 MHz, DMSO-d$_6$) δ ppm 11.19 (s, 1H), 10.73 (s, 1H), 8.09-8.24 (m, 2H), 8.04 (t, J=1.8 Hz, 1H), 7.96 (dt, J=8.2, 1.2 Hz, 1H), 7.82-7.91 (m, 2H), 7.79 (ddd, J=8.0, 2.1, 1.1 Hz, 1H), 7.54-7.65 (m, 2H), 7.50 (t, J=7.8 Hz, 1H), 7.44 (dt, J=7.8, 0.9 Hz, 1H), 7.32 (td, J=7.6, 1.3 Hz, 1H); $^{19}$F NMR (376 MHz, DMSO-d$_6$) δ ppm −61.29 (s, 3F); HRMS (ESI) m/z (M+H)$^+$ calcd. for C$_{21}$H$_{15}$BrF$_3$N$_2$O$_2$, 463.0264; found 463.0271.

EXAMPLE 76

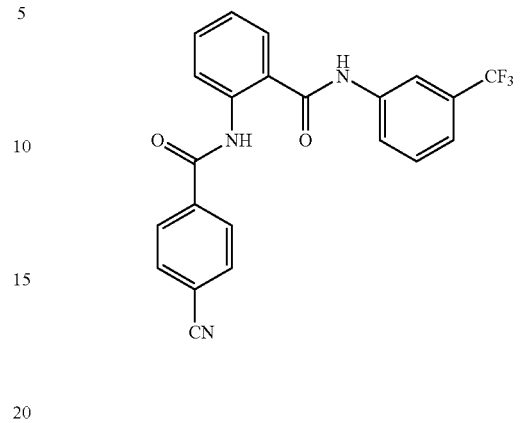

This example illustrates a synthesis of 2-(4-Cyanobenzamido)-N-(3-(trifluoromethyl)phenyl)benzamide (XJB07-066, NCGC00238751-01). The title compound was prepared according to general protocol C. LC-MS Retention Time: t$_1$ (Method 1)=6.522 min; $^1$H NMR (400 MHz, DMSO-d$_6$) δ ppm 11.32 (s, 1H), 10.74 (s, 1H), 8.18 (dd, J=8.2, 1.2 Hz, 1H), 8.08 (t, J=2.2 Hz, 1H), 8.00-8.06 (m, 4H), 7.94-7.99 (m, 1H), 7.87 (dd, J=7.8, 1.6 Hz, 1H), 7.54-7.66 (m, 2H), 7.40-7.50 (m, 1H), 7.34 (td, J=7.6, 1.4 Hz, 1H); $^{19}$F NMR (376 MHz, DMSO-d$_6$) δ ppm −61.27 (s, 3F); HRMS (ESI) m/z (M+H)$^+$ calcd. for C$_{22}$H$_{15}$F$_3$N$_3$O$_2$, 410.1111; found 410.1119.

EXAMPLE 77

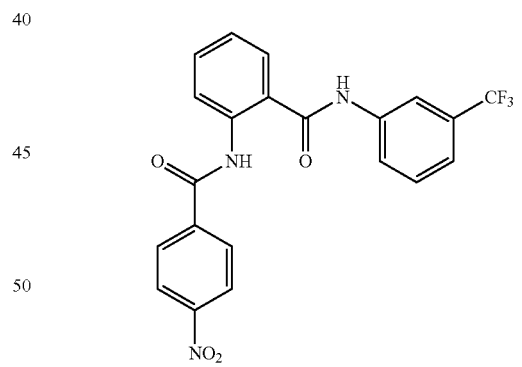

This example illustrates a synthesis of 2-(4-Nitrobenzamido)-N-(3-(trifluoromethyl)phenyl)benzamide (XJB07-067, NCGC00238752-01). The title compound was prepared according to general protocol C. LC-MS Retention Time: t$_1$ (Method 1)=6.711 min; $^1$H NMR (400 MHz, DMSO-d$_6$) δ ppm 11.36 (s, 1H), 10.75 (s, 1H), 8.33-8.41 (m, 2H), 8.16 (dd, J=8.2, 1.2 Hz, 1H), 8.05-8.14 (m, 3H), 7.93-8.01 (m, 1H), 7.83-7.92 (m, 1H), 7.63 (ddd, J=8.4, 7.3, 1.6 Hz, 1H), 7.58 (t, J=8.0 Hz, 1H), 7.45 (dt, J=7.8, 0.9 Hz, 1H), 7.35 (td, J=7.6, 1.2 Hz, 1H); $^{19}$F NMR (376 MHz, DMSO-d$_6$) δ ppm −61.27 (s, 3F); HRMS (ESI) m/z (M+H)$^+$ calcd. for C$_{21}$H$_{15}$F$_3$N$_3$O$_4$, 430.1009; found 430.1008.

EXAMPLE 78

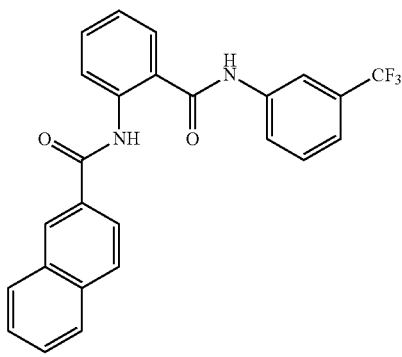 [SMILES: O=C(Nc1ccccc1C(=O)Nc1cccc(C(F)(F)F)c1)c1ccc2ccccc2c1]

This example illustrates a synthesis of N-(2-((3-(Trifluoromethyl)phenyl)carbamoyl)phenyl)-2-naphthamide (XJB07-069, NCGC00238753-01). The title compound was prepared according to general protocol C. LC-MS Retention Time: $t_1$ (Method 1)=7.197 min; HRMS (ESI) m/z (M+H)$^+$ calcd. for $C_{25}H_{18}F_3N_2O_2$, 435.1315; found 435.1314.

EXAMPLE 79

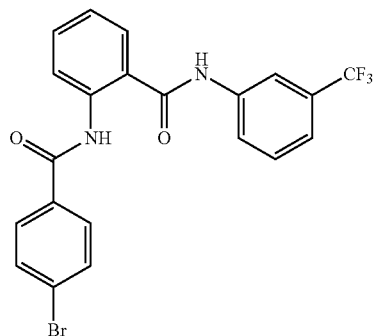 [SMILES: O=C(Nc1ccccc1C(=O)Nc1cccc(C(F)(F)F)c1)c1ccc(Br)cc1]

This example illustrates a synthesis of 2-(4-Bromobenzamido)-N-(3-(trifluoromethyl)phenyl)benzamide (XJB07-073, NCGC00238754-01). A solution of 2-amino-N-(3-(trifluoromethyl)phenyl)benzamide (50.0 mg, 0.178 mmol) in dichloromethane (2.00 mL) and TEA (0.075 mL, 0.535 mmol) was treated at room temperature with 4-bromobenzoyl bromide (70.6 mg, 0.268 mmol). The reaction mixture was stirred at room temperature for overnight. The mixture was concentrated, re-dissolved in 2.00 mL of DMSO, filtered and purified via C$_{18}$ reverse phase HPLC to give the final product. LC-MS Retention Time: $t_1$ (Method 1)=7.158 min; $^1$H NMR (400 MHz, DMSO-d$_6$) δ ppm 11.28 (s, 1H), 10.74 (s, 1H), 8.23 (dd, J=8.2, 1.2 Hz, 1H), 8.08 (t, J=2.2 Hz, 1H), 7.92-8.02 (m, 1H), 7.87 (dd, J=7.8, 1.8 Hz, 1H), 7.79-7.85 (m, 2H), 7.72-7.78 (m, 2H), 7.55-7.64 (m, 2H), 7.42-7.50 (m, 1H), 7.27-7.36 (m, 1H); $^{19}$F NMR (376 MHz, DMSO-d$_6$) δ ppm −61.26 (s, 3F); HRMS (ESI) m/z (M+H)$^+$ calcd. for $C_{21}H_{15}BrF_3N_2O_2$, 463.0264; found 463.0268.

EXAMPLE 80

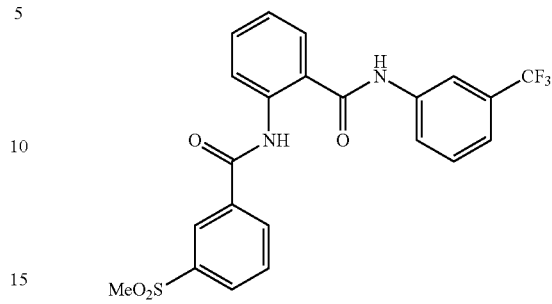

This example illustrates a synthesis of 2-(3-(Methylsulfonyl)benzamido)-N-(3-(trifluoromethyl)phenyl)benzamide (XJB07-075, NCGC00238755-01). The title compound was prepared according to general protocol D. LC-MS Retention Time: $t_1$ (Method 1)=6.025 min; $^1$H NMR (400 MHz, DMSO-d$_6$) δ ppm 11.30 (s, 1H), 10.74 (s, 1H), 8.42 (t, J=1.9 Hz, 1H), 8.20 (ddd, J=7.9, 1.5, 1.4 Hz, 1H), 8.08-8.17 (m, 3H), 7.97 (d, J=8.2 Hz, 1H), 7.77-7.89 (m, 2H), 7.62 (ddd, J=8.4, 7.2, 1.6 Hz, 1H), 7.57 (t, J=8.0 Hz, 1H), 7.44 (dd, J=6.8, 1.2 Hz, 1H), 7.35 (td, J=7.6, 1.2 Hz, 1H), 3.25 (s, 3H); $^{19}$F NMR (376 MHz, DMSO-d$_6$) δ ppm −61.28 (s, 3F); HRMS (ESI) m/z (M+H)$^+$ calcd. for $C_{22}H_{18}F_3N_2O_4S$, 463.0934; found 463.0939.

EXAMPLE 81

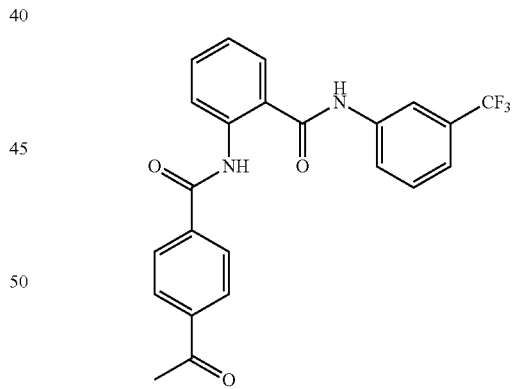

This example illustrates a synthesis of 2-(4-Acetylbenzamido)-N-(3-(trifluoromethyl)phenyl)benzamide (XJB07-076, NCGC00238756-01). The title compound was prepared according to general protocol D. LC-MS Retention Time: $t_1$ (Method 1)=6.474 min; $^1$H NMR (400 MHz, DMSO-d$_6$) δ ppm 11.38 (s, 1H), 10.76 (s, 1H), 8.21-8.30 (m, 1H), 8.04-8.12 (m, 3H), 7.94-8.03 (m, 3H), 7.89 (dd, J=7.8, 1.6 Hz, 1H), 7.54-7.68 (m, 2H), 7.41-7.52 (m, 1H), 7.33 (td, J=7.6, 1.2 Hz, 1H), 2.62 (s, 3H); $^{19}$F NMR (376 MHz, DMSO-d$_6$) δ ppm −61.26 (s, 3F); HRMS (ESI) m/z (M+H)$^+$ calcd. for $C_{23}H_{18}F_3N_2O_3$, 427.1264; found 427.1267.

EXAMPLE 82

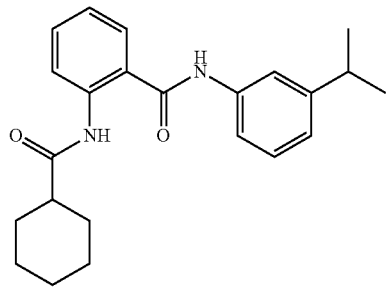 [SMILES: CC(C)c1cccc(NC(=O)c2ccccc2NC(=O)C2CCCCC2)c1]

This example illustrates a synthesis of 2-(Cyclohexanecarboxamido)-N-(3-isopropylphenyl)benzamide (XJB07-080, NCGC00238757-01). The title compound was prepared according to general protocol A. LC-MS Retention Time: $t_1$ (Method 1)=7.166 min; $^1$H NMR (400 MHz, DMSO-$d_6$) δ ppm 10.52 (s, 1H), 10.30 (s, 1H), 8.21 (dd, J=8.4, 1.4 Hz, 1H), 7.77 (dd, J=7.8, 1.6 Hz, 1H), 7.44–7.58 (m, 3H), 7.26 (t, J=7.8 Hz, 1H), 7.19 (td, J=7.6, 1.2 Hz, 1H), 7.00 (dt, J=7.7, 1.5 Hz, 1H), 2.86 (quin, J=6.8 Hz, 1H), 2.20–2.36 (m, 1H), 1.76–1.90 (m, 2H), 1.65–1.76 (m, 2H), 1.55–1.65 (m, 1H), 1.20 (d, J=4.0 Hz, 6H), 1.08–1.44 (m, 5H); HRMS (ESI) m/z (M+H)$^+$ calcd. for $C_{23}H_{29}N_2O_2$, 365.2239; found 365.2239.

EXAMPLE 83

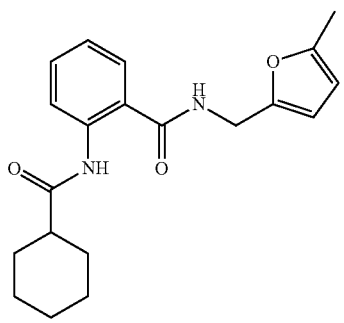 [SMILES: Cc1ccc(CNC(=O)c2ccccc2NC(=O)C2CCCCC2)o1]

This example illustrates a synthesis of 2-(Cyclohexanecarboxamido)-N-((5-methylfuran-2-yl)methyl)benzamide (XJB07-081, NCGC00238758-01). The title compound was prepared according to general protocol A. LC-MS Retention Time: $t_1$ (Method 1)=6.284 min; $^1$H NMR (400 MHz, DMSO-$d_6$) δ ppm 11.26 (s, 1H), 9.16 (t, J=5.5 Hz, 1H), 8.40 (dd, J=8.4, 1.2 Hz, 1H), 7.72 (dd, J=7.8, 1.6 Hz, 1H), 7.42–7.48 (m, 1H), 7.10 (ddd, J=8.0, 7.2, 1.2 Hz, 1H), 6.15 (d, J=2.9 Hz, 1H), 5.96–6.00 (m, 1H), 4.39 (d, J=5.7 Hz, 2H), 2.21 (d, J=0.8 Hz, 3H), 2.18–2.28 (m, 1H), 1.78–1.94 (m, 2H), 1.66–1.78 (m, 2H), 1.55–1.66 (m, 1H), 1.07–1.47 (m, 5H); HRMS (ESI) m/z (M+H)$^+$ calcd. for $C_{20}H_{25}N_2O_3$, 341.1860; found 341.1869.

EXAMPLE 84

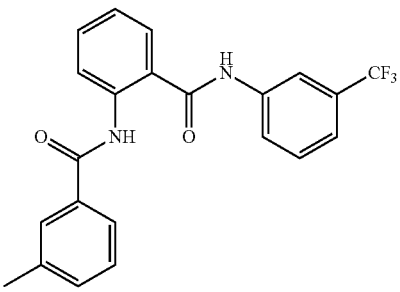 [SMILES: Cc1cccc(C(=O)Nc2ccccc2C(=O)Nc2cccc(C(F)(F)F)c2)c1]

This example illustrates a synthesis of 2-(3-Methylbenzamido)-N-(3-(trifluoromethyl)phenyl)benzamide (XJB07-093, NCGC00238759-01). The title compound was prepared according to general protocol C. LC-MS Retention Time: $t_1$ (Method 1)=6.938 min; $^1$H NMR (400 MHz, DMSO-$d_6$) δ ppm 11.26 (s, 1H), 10.74 (s, 1H), 8.29 (dd, J=8.3, 0.9 Hz, 1H), 8.13 (s, 1H), 7.94-7.99 (m, 1H), 7.87 (ddd, J=7.8, 1.1, 0.9 Hz, 1H), 7.70 (s, 1H), 7.63-7.69 (m, 1H), 7.54-7.63 (m, 2H), 7.36-7.49 (m, 3H), 7.20-7.32 (m, 1H), 2.35 (s, 3H); $^{19}$F NMR (376 MHz, DMSO-$d_6$) δ ppm −61.31 (s, 3F); HRMS (ESI) m/z (M+H)$^+$ calcd. for $C_{22}H_{18}F_3N_2O_2$, 399.1315; found 399.1319.

EXAMPLE 85

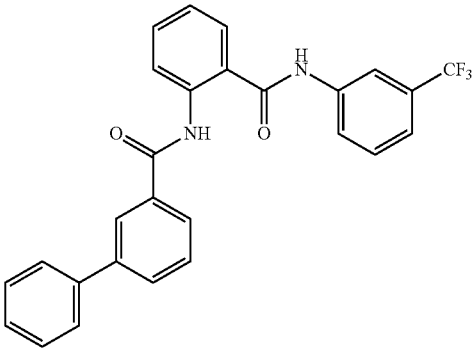 [SMILES: O=C(Nc1ccccc1C(=O)Nc1cccc(C(F)(F)F)c1)c1cccc(-c2ccccc2)c1]

This example illustrates a synthesis of N-(2-((3-(Trifluoromethyl)phenyl)carbamoyl)phenyl)-[1,1′-biphenyl]-3-carboxamide (XJB07-094, NCGC00238747-02). The title compound was prepared according to general protocol C. LC-MS Retention Time: $t_1$ (Method 1)=7.389 min; $^1$H NMR (400 MHz, DMSO-$d_6$) δ ppm 11.39 (s, 1H), 10.75 (s, 1H), 8.28 (dt, J=8.3, 0.7 Hz, 1H), 8.13–8.19 (m, 2H), 7.97–8.01 (m, 1H), 7.82–7.92 (m, 3H), 7.67–7.79 (m, 2H), 7.53–7.66 (m, 3H), 7.36–7.53 (m, 4H), 7.31 (tt, J=7.7, 0.7 Hz, 1H); $^{19}$F NMR (376 MHz, DMSO-$d_6$) δ ppm −61.29 (s, 3F); HRMS (ESI) m/z (M+H)$^+$ calcd. for $C_{27}H_{20}F_3N_2O_2$, 461.1471; found 461.1476.

EXAMPLE 86

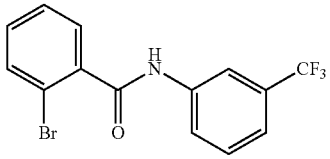 [SMILES: O=C(Nc1cccc(C(F)(F)F)c1)c1ccccc1Br]

This example illustrates a synthesis of 2-Bromo-N-(3-(trifluoromethyl)phenyl)benzamide (XJB09-014). A solution of 3-(trifluoromethyl)aniline (0.850 mL, 6.83 mmol) in dichloromethane (15.0 mL) and triethylamine (2.86 mL, 20.5 mmol) was treated at 0° C. with 2-bromobenzoyl chloride (0.893 mL, 6.83 mmol) and stirred at room temperature for 3 h. The reaction mixture was diluted with dichloromethane and washed with $Na_2CO_3$ solution. The organic layer was separated, dried, and concentrated to give 2.30 g (98%) of the title compound as a white foam which was used directly for the next reaction without further purification.

EXAMPLE 87

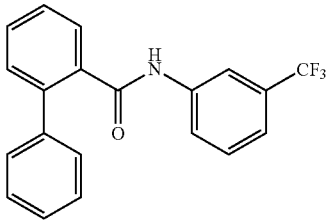 [SMILES: O=C(Nc1cccc(C(F)(F)F)c1)c1ccccc1-c1ccccc1]

This example illustrates a synthesis of N-(3-(Trifluoromethyl)phenyl)-[1,1□-biphenyl]-2-carboxamide (XJB09-016, NCGC00244471-01). The title compound was prepared according to general protocol E. LC-MS Retention Time: $t_1$ (Method 1)=6.365 min; $^1H$ NMR (400 MHz, DMSO-$d_6$) δ ppm 10.54 (s, 1H), 7.97 (t, J=2.1 Hz, 1H), 7.64□7.73 (m, 1H), 7.55□7.64 (m, 2H), 7.44□7.54 (m, 3H), 7.32□7.44 (m, 5H), 7.25□7.32 (m, 1H); $^{19}F$ NMR (376 MHz, DMSO-$d_6$) δ ppm −61.34 (s, 3F); HRMS (ESI) m/z (M+H)$^+$ calcd. for $C_{20}H_{15}F_3NO$, 342.1100; found 342.1110.

EXAMPLE 88

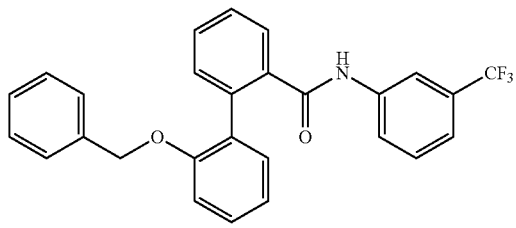 [SMILES: O=C(Nc1cccc(C(F)(F)F)c1)c1ccccc1-c1ccccc1OCc1ccccc1]

This example illustrates a synthesis of 2□-(Benzyloxy)-N-(3-(trifluoromethyl)phenyl)-[1,1□-biphenyl]-2-carboxamide (XJB09-019, NCGC00244472-01). The title compound was prepared according to general protocol E. LC-MS Retention Time: $t_1$ (Method 1)=6.997 min; HRMS (ESI) m/z (M+H)$^+$ calcd. for $C_{27}H_{21}F_3NO_2$, 448.1519; found 448.1524.

EXAMPLE 89

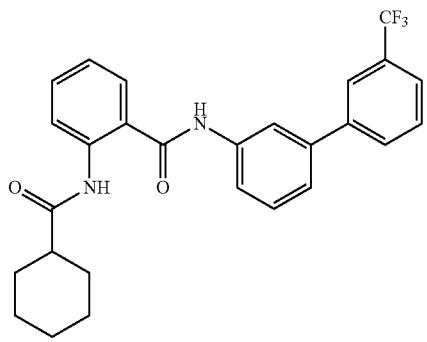 [SMILES: O=C(Nc1cccc(-c2cccc(C(F)(F)F)c2)c1)c1ccccc1NC(=O)C1CCCCC1]

This example illustrates a synthesis of 2-(Cyclohexanecarboxamido)-N-(3□-(trifluoromethyl)-[1,1□-biphenyl]-3-yl)benzamide (XJB09-023, NCGC00244469-01). A mixture of N-(3-bromophenyl)-2-(cyclohexanecarboxamido) benzamide (50.0 mg, 0.125 mmol), 3-(trifluoromethyl)phenylboronic acid (35.5 mg, 0.187 mmol) and Pd(PPh$_3$)$_4$ (7.2 mg, 6.23 μmol) in DMF (1.50 mL) and 2.0 N Na$_2$CO$_3$ (0.50 mL) aqueous solution was heated in μW at 100° C. for 30 min. The reaction was cooled to room temperature, added a small portion of Si-THIOL to get rid of Palladium. The mixture was filtered and purified via C$_{18}$ reverse phase HPLC to give the final product. LC-MS Retention Time: $t_1$ (Method 1)=7.438 min; $^1H$ NMR (400 MHz, DMSO-$d_6$) δ ppm 10.50 (br. s., 1H), 10.49 (s, 1H), 8.14□8.24 (m, 1H), 8.01□8.08 (m, 1H), 7.94□8.01 (m, 1H), 7.91 (s, 1H), 7.78□7.84 (m, 2H), 7.70 □7.77 (m, 2H), 7.41□7.56 (m, 3H), 7.22 (td, J=7.6, 1.3 Hz, 1H), 2.21□2.35 (m, 1H), 1.83 (d, J=15.8 Hz, 2H), 1.64□1.74 (m, 2H), 1.52□1.63 (m, 1H), 1.08□1.46 (m, 5H); $^{19}F$ NMR (376 MHz, DMSO-$d_6$) δ ppm −61.11 (s, 3F); HRMS (ESI) m/z (M+H)$^+$ calcd. for $C_{27}H_{26}F_3N_2O_2$, 467.1941; found 467.1943.

EXAMPLE 90

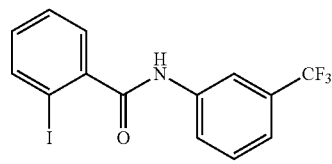 [SMILES: O=C(Nc1cccc(C(F)(F)F)c1)c1ccccc1I]

This example illustrates a synthesis of 2-Iodo-N-(3-(trifluoromethyl)phenyl)benzamide (XJB09-026). A solution of 3-(trifluoromethyl)aniline (0.467 mL, 3.75 mmol) in dichloromethane (15.0 mL) and triethylamine (1.57 mL, 11.3 mmol) was treated at 0° C. with 2-iodobenzoyl chloride (1.00 g, 3.75 mmol) and stirred at room temperature for 3 h. The reaction mixture was diluted with dichloromethane and washed with Na$_2$CO$_3$ solution. The organic layer was separated, dried, and concentrated to give 1.40 g (95%) of the title compound as a white foam which was used directly for the next reaction without further purification.

EXAMPLE 91

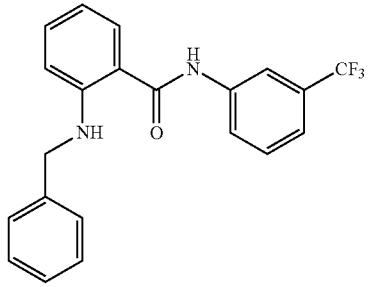 [SMILES: O=C(Nc1cccc(C(F)(F)F)c1)c1ccccc1NCc1ccccc1]

This example illustrates a synthesis of 2-(Benzylamino)-N-(3-(trifluoromethyl)phenyl)benzamide (XJB09-027, NCGC00244464-01). The title compound was prepared according to general protocol F. LC-MS Retention Time: $t_1$ (Method 1)=7.001 min; HRMS (ESI) m/z (M+H)$^+$ calcd. for $C_{21}H_{18}F_3NO_2$, 371.1366; found 371.1374.

EXAMPLE 92

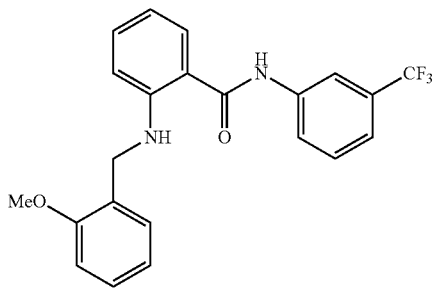 [SMILES: COc1ccccc1CNc1ccccc1C(=O)Nc1cccc(C(F)(F)F)c1]

This example illustrates a synthesis of 2-((2-Methoxybenzyl)amino)-N-(3-(trifluoromethyl)phenyl)benzamide (XJB09-028, NCGC00244511-01). The title compound was prepared according to general protocol F. LC-MS Retention Time: $t_1$ (Method 1)=6.914 min; $^1$H NMR (400 MHz, DMSO-$d_6$) δ ppm 10.36 (s, 1H), 8.18 (t, J=2.1 Hz, 1H), 7.87☐8.01 (m, 1H), 7.65☐7.80 (m, 2H), 7.49☐7.61 (m, 1H), 7.38☐7.45 (m, 1H), 7.16☐7.31 (m, 3H), 6.95☐7.03 (m, 1H), 6.83☐6.90 (m, 1H), 6.57☐6.67 (m, 2H), 4.35 (d, J=5.9 Hz, 2H), 3.81 (s, 3H); $^{19}$F NMR (376 MHz, DMSO-$d_6$) δ ppm −61.25 (s, 3F).

EXAMPLE 93

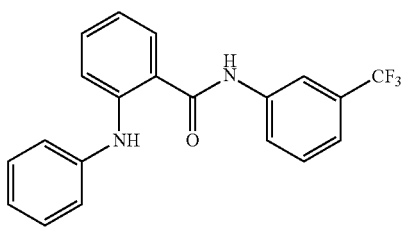 [SMILES: O=C(Nc1cccc(C(F)(F)F)c1)c1ccccc1Nc1ccccc1]

This example illustrates a synthesis of 2-(Phenylamino)-N-(3-(trifluoromethyl)phenyl)benzamide (XJB09-029, NCGC00244510-01). The title compound was prepared according to general protocol F. LC-MS Retention Time: $t_1$ (Method 1)=6.999 min; $^1$H NMR (400 MHz, DMSO-$d_6$) δ ppm 10.59 (s, 1H), 8.99 (s, 1H), 8.18 (t, J=2.2 Hz, 1H), 7.89☐7.99 (m, 1H), 7.76 (dd, J=7.8, 1.6 Hz, 1H), 7.57 (t, J=7.9 Hz, 1H), 7.34☐7.47 (m, 2H), 7.20☐7.33 (m, 3H), 7.11☐7.20 (m, 2H), 6.82☐7.02 (m, 2H); $^{19}$F NMR (376 MHz, DMSO-$d_6$) δ ppm −61.26 (s, 3F); HRMS (ESI) m/z (M+H)$^+$ calcd. for $C_{20}H_{16}F_3N_2O$, 357.1209; found 357.1216.

EXAMPLE 94

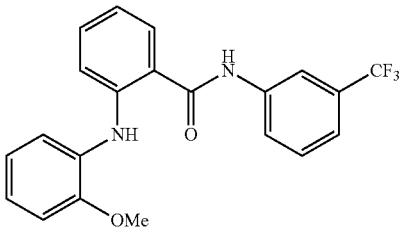 [SMILES: COc1ccccc1Nc1ccccc1C(=O)Nc1cccc(C(F)(F)F)c1]

This example illustrates a synthesis of 2-((2-Methoxyphenyl)amino)-N-(3-(trifluoromethyl)phenyl)benzamide (XJB09-030, NCGC00244488-01). The title compound was prepared according to general protocol F. LC-MS Retention Time: $t_1$ (Method 1)=6.918 min; $^1$H NMR (400 MHz, DMSO-$d_6$) δ ppm 10.59 (s, 1H), 9.02 (s, 1H), 8.13 (t, J=2.2 Hz, 1H), 7.94☐8.03 (m, 1H), 7.78 (dd, J=7.8, 1.6 Hz, 1H), 7.53☐7.65 (m, 1H), 7.42☐7.49 (m, 1H), 7.35☐7.42 (m, 1H), 7.24☐7.34 (m, 2H), 7.01☐7.08 (m, 1H), 6.82☐7.01 (m, 3H), 3.82 (s, 3H); $^{19}$F NMR (376 MHz, DMSO-$d_6$) δ ppm −61.23 (s, 3F); HRMS (ESI) m/z (M+H)$^+$ calcd. for $C_{21}H_{18}F_3N_2O_2$, 387.1315; found 387.1322.

EXAMPLE 95

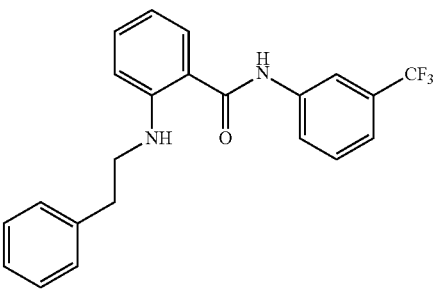 [SMILES: O=C(Nc1cccc(C(F)(F)F)c1)c1ccccc1NCCc1ccccc1]

This example illustrates a synthesis of 2-(Phenethylamino)-N-(3-(trifluoromethyl)phenyl)benzamide (XJB09-031, NCGC00244489-01). The title compound was prepared according to general protocol F. LC-MS Retention Time: $t_1$ (Method 1)=7.119 min; $^1$H NMR (400 MHz, DMSO-$d_6$) δ ppm 10.32 (s, 1H), 8.16 (t, J=2.2 Hz, 1H), 7.85-7.98 (m, 1H), 7.70 (dd, J=7.9, 1.7 Hz, 1H), 7.56 (t, J=8.0 Hz, 1H), 7.47 (t, J=5.5 Hz, 1H), 7.39-7.44 (m, 1H), 7.35 (ddd, J=8.5, 7.0, 1.6 Hz, 1H), 7.23-7.31 (m, 4H), 7.12-7.22 (m, 1H), 6.76-6.87 (m, 1H), 6.64 (ddd, J=7.9, 7.0, 1.1 Hz, 1H), 3.33-3.46 (m, 2H), 2.87 (t, J=7.3 Hz, 2H); $^{19}$F NMR (376 MHz, DMSO-$d_6$) δ ppm −61.25 (s, 3F); HRMS (ESI) m/z (M+H)$^+$ calcd. for $C_{22}H_{20}F_3N_2O$, 385.1522; found 385.1533.

EXAMPLE 96

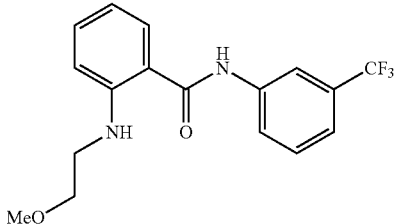 [SMILES: COCCNc1ccccc1C(=O)Nc1cccc(C(F)(F)F)c1]

This example illustrates a synthesis of 2-((2-Methoxyethyl)amino)-N-(3-(trifluoromethyl)phenyl)benzamide (XJB09-032, NCGC00244512-01). The title compound was prepared according to general protocol F. LC-MS Retention Time: $t_1$ (Method 1)=6.254 min; $^1$H NMR (400 MHz, DMSO-$d_6$) δ ppm 10.33 (s, 1H), 8.14 (t, J=2.2 Hz, 1H), 7.88–8.05 (m, 1H), 7.70 (dd, J=7.8, 1.6 Hz, 1H), 7.54–7.63 (m, 1H), 7.44–7.52 (m, 1H), 7.37–7.44 (m, 1H), 7.34 (ddd, J=8.6, 7.0, 1.7 Hz, 1H), 6.72–6.84 (m, 1H), 6.65 (ddd, J=8.0, 7.1, 1.2 Hz, 1H), 3.53 (t, J=5.5 Hz, 2H), 3.28 (s, 3H), 3.24–3.33 (m, 2H); $^{19}$F NMR (376 MHz, DMSO-$d_6$) δ ppm −61.23 (s, 3F); HRMS (ESI) m/z (M+H)$^+$ calcd. for $C_{17}H_{18}F_3N_2O_2$, 339.1315; found 339.1326.

EXAMPLE 97

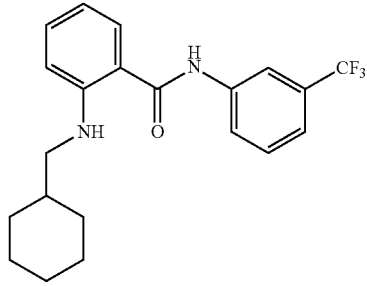 [SMILES: O=C(Nc1cccc(C(F)(F)F)c1)c1ccccc1NCC1CCCCC1]

This example illustrates a synthesis of 2-((Cyclohexylmethyl)amino)-N-(3-(trifluoromethyl)phenyl)benzamide (XJB09-033, NCGC00244473-01). The title compound was prepared according to general protocol F. LC-MS Retention Time: $t_1$ (Method 1)=7.597 min; $^1$H NMR (400 MHz, DMSO-$d_6$) δ ppm 10.31 (s, 1H), 8.11 (t, J=2.2 Hz, 1H), 7.92–8.00 (m, 1H), 7.70 (dd, J=8.0, 1.6 Hz, 1H), 7.49–7.61 (m, 2H), 7.39–7.45 (m, 1H), 7.32 (ddd, J=8.6, 7.0, 1.6 Hz, 1H), 6.69–6.76 (m, 1H), 6.61 (ddd, J=8.0, 7.1, 1.2 Hz, 1H), 2.92–3.06 (m, 2H), 1.72–1.83 (m, 2H), 1.65–1.72 (m, 2H), 1.49–1.65 (m, 2H), 1.04–1.30 (m, 3H), 0.88–1.05 (m, 2H); $^{19}$F NMR (376 MHz, DMSO-$d_6$) δ ppm −61.21 (s, 3F); HRMS (ESI) m/z (M+H)$^+$ calcd. for $C_{21}H_{24}F_3N_2O$, 377.1835; found 377.1843.

EXAMPLE 98

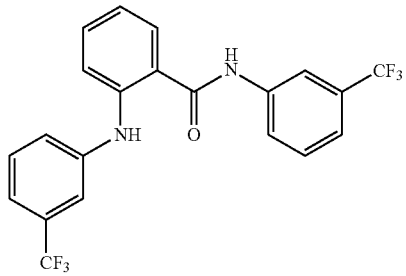 [SMILES: O=C(Nc1cccc(C(F)(F)F)c1)c1ccccc1Nc1cccc(C(F)(F)F)c1]

This example illustrates a synthesis of N-(3-(Trifluoromethyl)phenyl)-2-((3-(trifluoromethyl)phenyl)amino)benzamide (XJB09-034, NCGC00244513-01). The title compound was prepared according to general protocol F. LC-MS Retention Time: $t_1$ (Method 1)=7.252 min; HRMS (ESI) m/z (M+H)$^+$ calcd. for $C_{21}H_{15}F_6N_2O$, 425.1083; found 425.1092.

EXAMPLE 99

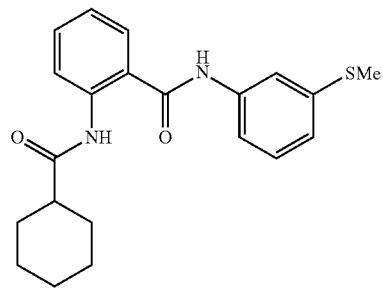 [SMILES: CSc1cccc(NC(=O)c2ccccc2NC(=O)C2CCCCC2)c1]

This example illustrates a synthesis of 2-(Cyclohexanecarboxamido)-N-(3-(methylthio)phenyl)benzamide (XJB09-035, NCGC00244465-02). The title compound was prepared according to general protocol A. LC-MS Retention Time: $t_1$ (Method 1)=6.687 min; $^1$H NMR (400 MHz, DMSO-$d_6$) δ ppm 10.44 (s, 1H), 10.37 (s, 1H), 8.18 (d, J=8.2 Hz, 1H), 7.75 (dd, J=7.8, 1.6 Hz, 1H), 7.63 (t, J=2.1 Hz, 1H), 7.44-7.55 (m, 2H), 7.29 (t, J=7.9 Hz, 1H), 7.20 (td, J=7.6, 1.3 Hz, 1H), 7.01 (ddd, J=7.8, 2.0, 1.0 Hz, 1H), 2.46 (s, 3H), 2.19-2.35 (m, 1H), 1.76-1.90 (m, 2H), 1.65-1.76 (m, 2H), 1.52-1.65 (m, 1H), 1.03-1.47 (m, 5H); HRMS (ESI) m/z (M+H)$^+$ calcd. for $C_{21}H_{25}N_2O_2S$, 369.1631; found 369.1625.

EXAMPLE 100

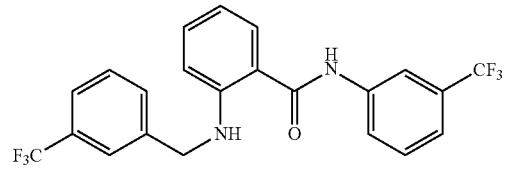 [SMILES: O=C(Nc1cccc(C(F)(F)F)c1)c1ccccc1NCc1cccc(C(F)(F)F)c1]

This example illustrates a synthesis of 2-((3-(Trifluoromethyl)benzyl)amino)-N-(3-(trifluoromethyl)phenyl)benzamide (XJB09-037, NCGC00244514-01). The title compound was prepared according to general protocol F. LC-MS Retention Time: $t_1$ (Method 1)=7.370 min; HRMS (ESI) m/z (M+H)+ calcd. for $C_{22}H_{17}F_6N_2O$, 439.1240; found 439.1247.

EXAMPLE 101

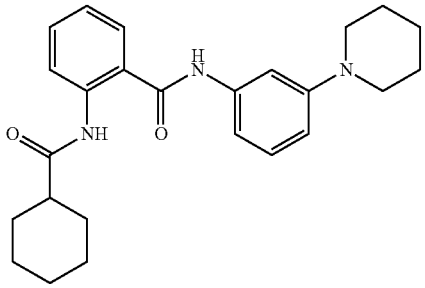 [SMILES: O=C(Nc1cccc(N2CCCCC2)c1)c1ccccc1NC(=O)C1CCCCC1]

This example illustrates a synthesis of 2-(Cyclohexanecarboxamido)-N-(3-(piperidin-1-yl)phenyl)benzamide (XJB09-040, NCGC00244515-01). The title compound was prepared according to general protocol A. LC-MS Retention Time: $t_1$ (Method 1)=4.605 min; HRMS (ESI) m/z (M+H)+ calcd. for $C_{25}H_{32}N_3O_2$, 406.2489; found 406.2501.

EXAMPLE 102

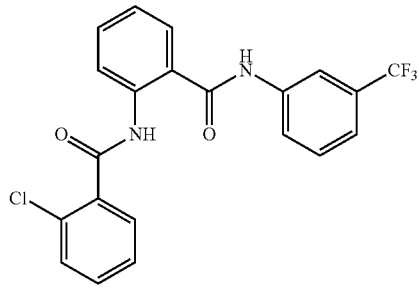 [SMILES: O=C(Nc1ccccc1C(=O)Nc1cccc(C(F)(F)F)c1)c1ccccc1Cl]

This example illustrates a synthesis of 2-Chloro-N-(2-((3-(trifluoromethyl)phenyl)carbamoyl)phenyl)benzamide (XJB09-047, NCGC00244490-01). The title compound was prepared according to general protocol C. LC-MS Retention Time: $t_1$ (Method 1)=6.765 min; $^1$H NMR (400 MHz, DMSO-$d_6$) δ ppm 10.83 (s, 1H), 10.70 (s, 1H), 8.01☐8.22 (m, 2H), 7.89☐8.00 (m, 1H), 7.69☐7.85 (m, 1H), 7.38☐7.67 (m, 7H), 7.33 (td, J=7.6, 1.4 Hz, 1H); $^{19}$F NMR (376 MHz, DMSO-$d_6$) δ ppm −61.28 (s, 3F); HRMS (ESI) m/z (M+H)+ calcd. for $C_{21}H_{15}ClF_3N_2O_2$, 419.0769; found 419.0769.

EXAMPLE 103

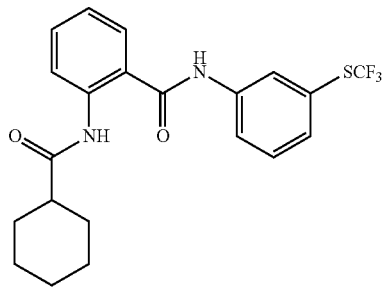

This example illustrates a synthesis of 2-(Cyclohexanecarboxamido)-N-(3-((trifluoromethyl)thio)phenyl)benzamide (XJB09-048, NCGC00244491-01). The title compound was prepared according to general protocol A. LC-MS Retention Time: $t_1$ (Method 1)=7.349 min; HRMS (ESI) m/z (M+H)+ calcd. for $C_{21}H_{22}F_3N_2O_2S$, 423.1349; found 423.1360.

EXAMPLE 104

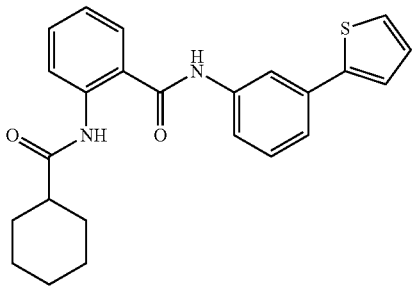 [SMILES: O=C(Nc1cccc(-c2cccs2)c1)c1ccccc1NC(=O)C1CCCCC1]

This example illustrates a synthesis of 2-(Cyclohexanecarboxamido)-N-(3-(thiophen-2-yl)phenyl)benzamide (XJB09-050, NCGC00244466-01). The title compound was prepared according to general protocol A. LC-MS Retention Time: t, (Method 1)=7.234 min; $^1$H NMR (400 MHz, DMSO-$d_6$) δ ppm 10.46 (br. s., 1H), 10.45 (br. s., 1H), 8.11☐8.25 (m, 1H), 7.92☐8.02 (m, 1H), 7.75☐7.83 (m, 1H), 7.62☐7.71 (m, 1H), 7.55 (dd, J=5.1, 1.2 Hz, 1H), 7.48☐7.54 (m, 1H), 7.34☐7.48 (m, 3H), 7.17☐7.26 (m, 1H), 7.14 (dd, J=5.0, 3.6 Hz, 1H), 2.19☐2.31 (m, 1H), 1.78☐1.89 (m, 2H), 1.65☐1.76 (m, 2H), 1.53☐1.64 (m, 1H), 1.08☐1.47 (m, 5H); HRMS (ESI) m/z (M+H)+ calcd. for $C_{24}H_{25}N_2O_2S$, 405.1631; found 405.1637.

EXAMPLE 105

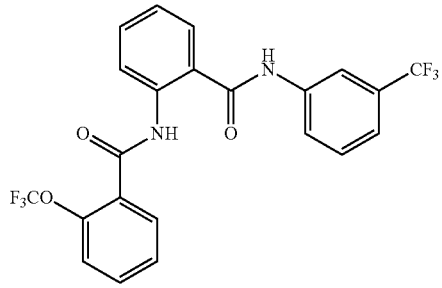 [SMILES: O=C(Nc1cccc(C(F)(F)F)c1)c1ccccc1NC(=O)c1ccccc1OC(F)(F)F]

This example illustrates a synthesis of 2-(Trifluoromethoxy)-N-(2-((3-(trifluoromethyl)phenyl)carbamoyl)phenyl)benzamide (XJB09-052, NCGC00244470-01). The title compound was prepared according to general protocol C. LC-MS Retention Time: $t_1$ (Method 1)=6.983 min; $^1$H NMR (400 MHz, DMSO-$d_6$) δ ppm 10.97 (s, 1H), 10.74 (s, 1H), 8.09-8.26 (m, 2H), 7.91-8.03 (m, 1H), 7.83 (dd, J=7.8, 1.6 Hz, 1H), 7.77 (dd, J=7.6, 2.0 Hz, 1H), 7.39-7.70 (m, 6H), 7.33 (td, J=7.6, 1.3 Hz, 1H); $^{19}$F NMR (376 MHz, DMSO-$d_6$) δ ppm −56.63 (s, 3F), −61.33 (s, 3F); HRMS (ESI) m/z (M+H)+ calcd. for $C_{22}H_{15}F_6N_2O_3$, 468.0981; found 468.0982.

EXAMPLE 106

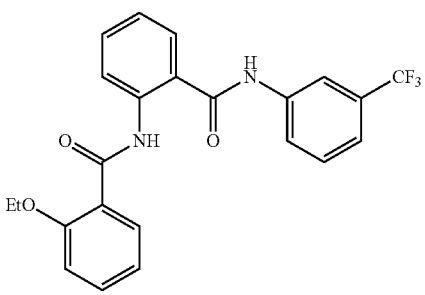 [SMILES: CCOc1ccccc1C(=O)Nc1ccccc1C(=O)Nc1cccc(C(F)(F)F)c1]

This example illustrates a synthesis of 2-Ethoxy-N-(2-((3-(trifluoromethyl)phenyl)carbamoyl)phenyl)benzamide (XJB09-053, NCGC00244467-01, compound 99). The title compound was prepared according to general protocol C. LC-MS Retention Time: $t_1$ (Method 1)=6.998 min; $^1$H NMR (400 MHz, DMSO-$d_6$) δ 11.33 (s, 1H), 10.82 (s, 1H), 8.51 (dd, J=8.4, 1.2 Hz, 1H), 8.28 (t, J=2.1 Hz, 1H), 7.89-8.07 (m, 2H), 7.80 (dd, J=7.8, 1.6 Hz, 1H), 7.55-7.65 (m, 2H), 7.38-7.55 (m, 2H), 7.27 (td, J=7.6, 1.3 Hz, 1H), 7.19 (dd, J=8.4, 1.0 Hz, 1H), 7.01-7.12 (m, 1H), 4.30 (q, J=6.9 Hz, 2H), 1.30 (t, J=6.9 Hz, 3H); $^{19}$F NMR (376 MHz, DMSO-$d_6$) δ ppm −61.40 (s, 3F); HRMS (ESI) m/z (M+H)$^+$ calcd. for $C_{23}H_{20}F_3N_2O_3$, 429.1421; found 429.1425.

EXAMPLE 107

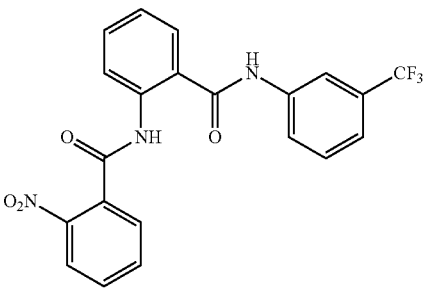 [SMILES: O=C(Nc1cccc(C(F)(F)F)c1)c1ccccc1NC(=O)c1ccccc1[N+](=O)[O-]]

This example illustrates a synthesis of 2-Nitro-N-(2-((3-(trifluoromethyl)phenyl)carbamoyl)phenyl)benzamide (XJB09-055, NCGC00244468-01). The title compound was prepared according to general protocol C. LC-MS Retention Time: $t_1$ (Method 1)=6.695 min; HRMS (ESI) m/z (M+H)$^+$ calcd. for $C_{21}H_{15}F_3N_3O_4$, 430.1009; found 430.1009.

EXAMPLE 108

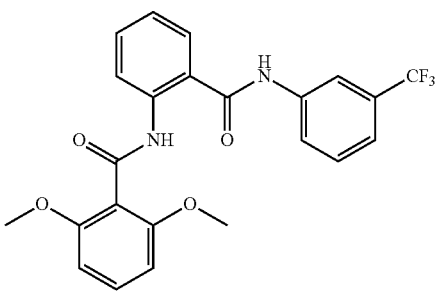 [SMILES: COc1cccc(OC)c1C(=O)Nc1ccccc1C(=O)Nc1cccc(C(F)(F)F)c1]

This example illustrates a synthesis of 2,6-Dimethoxy-N-(2-((3-(trifluoromethyl)phenyl)carbamoyl)phenyl)benzamide (XJB09-056, NCGC00244474-01, CID-56593296). The title compound was prepared according to general protocol C. LC-MS Retention Time: $t_1$ (Method 1)=6.400 min; $^1$H NMR (400 MHz, DMSO-$d_6$) δ ppm 10.68 (s, 1H), 10.62 (s, 1H), 8.43 (d, J=8.2 Hz, 1H), 8.08 (s, 1H), 7.93 (d, J=8.4 Hz, 1H), 7.85 (dd, J=7.7, 1.1 Hz, 1H), 7.52-7.64 (m, 2H), 7.45 (d, J=7.6 Hz, 1H), 7.34 (t, J=8.4 Hz, 1H), 7.27 (td, J=7.6, 1.1 Hz, 1H), 6.71 (d, J=8.4 Hz, 2H), 3.69 (s, 6H); $^{19}$F NMR (376 MHz, DMSO-$d_6$) δ ppm −61.29 (s, 3F); HRMS (ESI) m/z (M+H)$^+$ calcd. for $C_{23}H_{20}F_3N_2O_4$, 445.1370; found 445.1380.

EXAMPLE 109

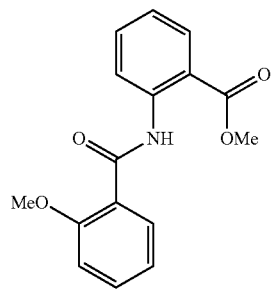 [SMILES: COC(=O)c1ccccc1NC(=O)c1ccccc1OC]

This example illustrates a synthesis of Methyl 2-(2-methoxybenzamido)benzoate (XJB09-051). A solution of 2-aminobenzoate (2.57 mL, 19.9 mmol) in dichloromethane (50.0 mL) and TEA (8.30 mL, 59.5 mmol) was treated at 0° C. with 2-methoxybenzoyl chloride (2.67 mL, 19.9 mmol). The reaction mixture was stirred at 0° C. for 2 h and at room temperature for 2 h. The reaction mixture was concentrated and purified via silica gel chromatography using a gradient of 0-50% of EtOAc in hexanes to give 5.50 g (97%) of the title product as a white solid. LC-MS Retention Time: t2 (Method 2)=3.761 min; m/z (M+H)$^+$ 286.0.

EXAMPLE 110

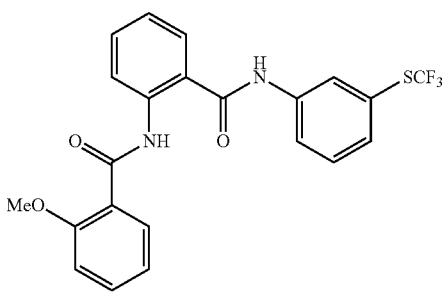

This example illustrates a synthesis of 2-Methoxy-N-(2-((3-((trifluoromethyl)thio)phenyl)carbamoyl)phenyl)benzamide (XJB09-058, NCGC00244475-01, compound 158). The title compound was prepared according to general protocol A. LC-MS Retention Time: $t_1$ (Method 1)=7.128 min; $^1$H NMR (400 MHz, DMSO-$d_6$) δ ppm 11.53 (s, 1H), 10.79 (s, 1H), 8.56 (dd, J=8.4, 1.2 Hz, 1H), 8.22-8.39 (m, 1H), 8.02 (dd, J=7.8, 1.8 Hz, 1H), 7.91 (ddd, J=8.2, 2.2, 1.2 Hz, 1H), 7.78 (dd, J=7.8, 1.6 Hz, 1H), 7.50-7.64 (m, 3H), 7.43-7.49 (m, 1H), 7.26 (td, J=7.5, 1.2 Hz, 1H), 7.20 (dd, J=8.5, 1.1 Hz, 1H), 7.09 (ddd, J=7.9, 7.2, 1.2 Hz, 1H), 3.97 (s, 3H); $^{19}$F NMR (376 MHz, DMSO-d$_6$) δ ppm −41.91 (s, 3F); HRMS (ESI) m/z (M+H)$^+$ calcd. for C$_{22}$H$_{18}$F$_3$N$_2$O$_3$S, 447.0985; found 447.0984.

EXAMPLE 111

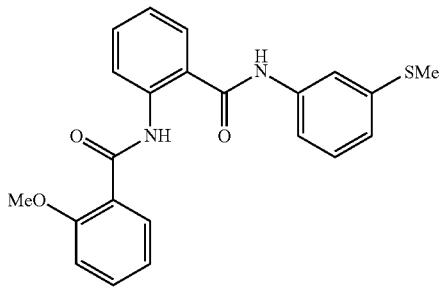

This example illustrates a synthesis of 2-Methoxy-N-(2-((3-(methylthio)phenyl)carbamoyl)phenyl)benzamide (XJB09-059, NCGC00244476-01). The title compound was prepared according to general protocol A. LC-MS Retention Time: t$_1$ (Method 1)=6.575 min; $^1$H NMR (400 MHz, DMSO-d$_6$) δ ppm 11.55 (s, 1H), 10.54 (s, 1H), 8.56 (dd, J=8.4, 1.2 Hz, 1H), 8.02 (dd, J=7.8, 1.8 Hz, 1H), 7.67-7.86 (m, 2H), 7.46-7.65 (m, 3H), 7.30 (t, J=7.9 Hz, 1H), 7.24 (td, J=7.6, 1.3 Hz, 1H), 7.19 (dd, J=8.5, 1.1 Hz, 1H), 7.05-7.12 (m, 1H), 7.01 (ddd, J=7.8, 2.0, 1.0 Hz, 1H), 3.98 (s, 3H), 2.46 (s, 3H); HRMS (ESI) m/z (M+H)$^+$ calcd. for C$_{22}$H$_{21}$N$_2$O$_3$S, 393.1267; found 393.1268.

EXAMPLE 112

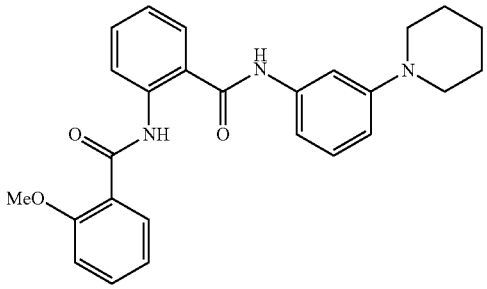 [SMILES: COc1ccccc1C(=O)Nc1ccccc1C(=O)Nc1cccc(N2CCCCC2)c1]

This example illustrates a synthesis of 2-Methoxy-N-(2-((3-(piperidin-1-yl)phenyl)carbamoyl)phenyl)benzamide (XJB09-061, NCGC00244492-01). The title compound was prepared according to general protocol A. LC-MS Retention Time: t$_1$ (Method 1)=4.511 min; $^1$H NMR (400 MHz, DMSO-d$_6$) δ ppm 11.56 (br. s., 1H), 10.43 (br. s., 1H), 8.56 (dd, J=8.4, 1.2 Hz, 1H), 8.01 (dd, J=7.8, 1.8 Hz, 1H), 7.62-7.80 (m, 1H), 7.50-7.61 (m, 4H), 7.15-7.31 (m, 4H), 7.09 (ddd, J=7.9, 7.2, 1.2 Hz, 1H), 3.98 (s, 3H), 3.10-3.33 (m, 4H), 1.60-1.78 (m, 4H), 1.50-1.61 (m, 2H); HRMS (ESI) m/z (M+H)$^+$ calcd. for C$_{26}$H$_{28}$N$_3$O$_3$, 430.2125; found 430.2135.

EXAMPLE 113

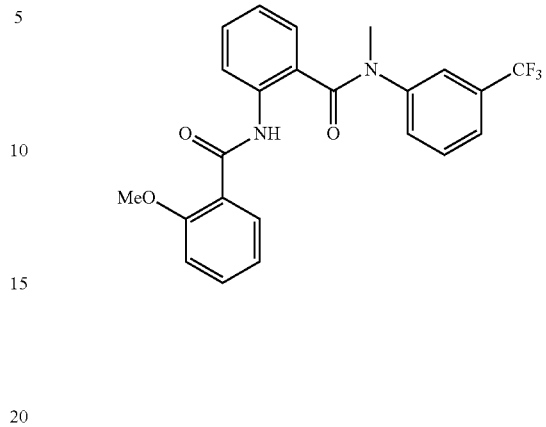

This example illustrates a synthesis of 2-(2-Methoxybenzamido)-N-methyl-N-(3-(trifluoromethyl)phenyl)benzamide (XJB09-062, NCGC00244493-01). The title compound was prepared according to general protocol A. LC-MS Retention Time: t$_1$ (Method 1)=6.442 min; $^1$H NMR (400 MHz, DMSO-d$_6$) δ ppm 10.65 (d, J=0.8 Hz, 1H), 8.21 (dt, J=8.4, 0.6 Hz, 1H), 8.03 (dd, J=7.8, 1.8 Hz, 1H), 7.54-7.66 (m, 2H), 7.37-7.54 (m, 3H), 7.20-7.33 (m, 2H), 7.13 (ddd, J=7.9, 7.2, 1.0 Hz, 1H), 7.04-7.11 (m, 1H), 6.86-6.96 (m, 1H), 4.02 (s, 3H), 3.44 (s, 3H); HRMS (ESI) m/z (M+H)$^+$ calcd. for C$_{23}$H$_{20}$F$_3$N$_2$O$_3$, 429.1241; found 429.1418.

EXAMPLE 114

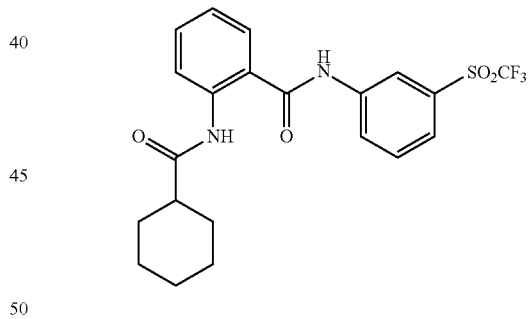

This example illustrates a synthesis of 2-(Cyclohexanecarboxamido)-N-(3-((trifluoromethyl)sulfonyl)phenyl)benzamide (XJB09-067, NCGC00244477-01). The title compound was prepared according to general protocol G. LC-MS Retention Time: t$_1$ (Method 1)=6.964 min; $^1$H NMR (400 MHz, DMSO-d$_6$) δ ppm 10.83 (s, 1H), 10.16 (s, 1H), 8.57 (t, J=1.6 Hz, 1H), 8.26 (ddd, J=5.7, 3.7, 2.2 Hz, 1H), 7.93 (dd, J=8.3, 1.3 Hz, 1H), 7.76-7.86 (m, 2H), 7.72 (dd, J=7.8, 1.6 Hz, 1H), 7.52 (ddd, J=8.5, 7.2, 1.6 Hz, 1H), 7.23 (td, J=7.6, 1.2 Hz, 1H), 2.16-2.36 (m, 1H), 1.73-1.87 (m, 2H), 1.62-1.73 (m, 2H), 1.50-1.62 (m, 1H), 0.82-1.46 (m, 5H); $^{19}$F NMR (376 MHz, DMSO-d$_6$) δ ppm −78.42 (s, 3F); HRMS (ESI) m/z (M+H)$^+$ calcd. for C$_{21}$H$_{22}$F$_3$N$_2$O$_4$S, 455.1247; found 455.1253.

EXAMPLE 115

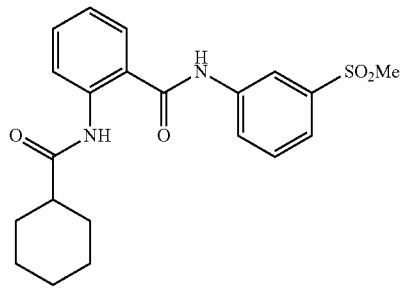 [SMILES: CS(=O)(=O)c1cccc(NC(=O)c2ccccc2NC(=O)C2CCCCC2)c1]

This example illustrates a synthesis of 2-(Cyclohexanecarboxamido)-N-(3-(methylsulfonyl)phenyl)benzamide (XJB09-068, NCGC00244478-01). The title compound was prepared according to general protocol G. LC-MS Retention Time: $t_1$ (Method 1)=5.745 min; $^1$H NMR (400 MHz, DMSO-$d_6$) δ ppm 10.69 (s, 1H), 10.34 (s, 1H), 8.30-8.40 (m, 1H), 8.11 (dd, J=8.3, 1.3 Hz, 1H), 8.00 (dt, J=7.2, 2.1 Hz, 1H), 7.76 (dd, J=7.8, 1.6 Hz, 1H), 7.59-7.71 (m, 2H), 7.52 (ddd, J=8.5, 7.1, 1.6 Hz, 1H), 7.22 (td, J=7.6, 1.3 Hz, 1H), 3.20 (s, 3H), 2.20-2.37 (m, 1H), 1.75-1.91 (m, 2H), 1.65-1.75 (m, 2H), 1.52-1.64 (m, 1H), 0.95-1.45 (m, 5H); HRMS (ESI) m/z (M+H)$^+$ calcd. for $C_{21}H_{25}N_2O_4S$, 401.1530; found 401.1524.

EXAMPLE 116

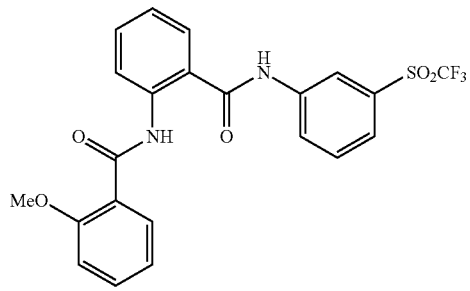

This example illustrates a synthesis of 2-Methoxy-N-(2-((3-(((trifluoromethyl)sulfonyl)phenyl)carbamoyl)phenyl) benzamide (XJB09-069, NCGC00244479-01, compound 159). The title compound was prepared according to general protocol G. LC-MS Retention Time: $t_1$ (Method 1)=6.810 min; $^1$H NMR (400 MHz, DMSO-$d_6$) δ ppm 11.58 (s, 1H), 11.09 (s, 1H), 8.82 (t, J=2.1 Hz, 1H), 8.58 (dd, J=8.5, 1.3 Hz, 1H), 8.23 (dt, J=7.0, 2.2 Hz, 1H), 8.02 (dd, J=7.7, 1.9 Hz, 1H), 7.76-7.99 (m, 3H), 7.51-7.63 (m, 2H), 7.27 (td, J=7.5, 1.2 Hz, 1H), 7.22 (dd, J=8.4, 1.2 Hz, 1H), 7.09 (ddd, J=7.9, 7.2, 1.2 Hz, 1H), 3.99 (s, 3H); $^{19}$F NMR (376 MHz, DMSO-$d_6$) δ ppm −78.39 (s, 3F); HRMS (ESI) m/z (M+H)$^+$ calcd. for $C_{22}H_{18}F_3N_2O_5S$, 479.0883; found 479.0886.

EXAMPLE 117

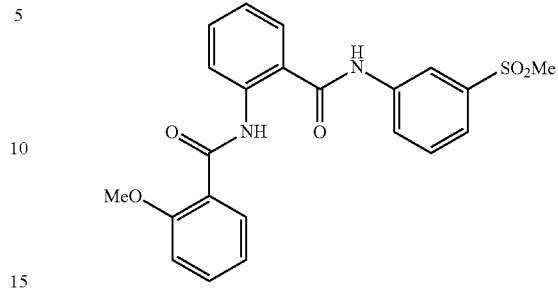

This example illustrates a synthesis of 2-Methoxy-N-(2-((3-(methylsulfonyl)phenyl)carbamoyl)phenyl)benzamide (XJB09-070, NCGC00244501-01). The title compound was prepared according to general protocol G. LC-MS Retention Time: $t_1$ (Method 1)=5.590 min; $^1$H NMR (400 MHz, DMSO-$d_6$) δ ppm 11.60 (s, 1H), 10.90 (s, 1H), 8.47-8.71 (m, 2H), 7.93-8.16 (m, 2H), 7.81 (dd, J=7.8, 1.6 Hz, 1H), 7.62-7.72 (m, 2H), 7.47-7.62 (m, 2H), 7.26 (td, J=7.6, 1.3 Hz, 1H), 7.21 (dd, J=8.5, 1.1 Hz, 1H), 7.09 (ddd, J=7.9, 7.2, 1.0 Hz, 1H), 4.00 (s, 3H), 3.20 (s, 3H); HRMS (ESI) m/z (M+H)$^+$ calcd. for $C_{22}H_{21}N_2O_5S$, 425.1166; found 425.1169.

EXAMPLE 118

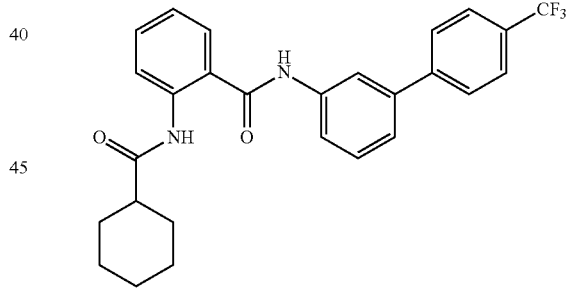

This example illustrates a synthesis of 2-(Cyclohexanecarboxamido)-N-(4'-(trifluoromethyl)-[1,1'-biphenyl]-3-yl)benzamide (XJB09-073, NCGC00244494-01). The title compound was prepared according to general protocol E. LC-MS Retention Time: $t_1$ (Method 1)=7.588 min; $^1$H NMR (400 MHz, DMSO-$d_6$) δ ppm 10.51 (d, J=0.4 Hz, 1H), 10.48 (d, J=0.4 Hz, 1H), 8.20 (dd, J=8.4, 1.2 Hz, 1H), 7.99-8.09 (m, 1H), 7.85 (s, 4H), 7.75-7.82 (m, 2H), 7.46-7.59 (m, 3H), 7.22 (td, J=7.6, 1.3 Hz, 1H), 2.18-2.35 (m, 1H), 1.77-1.89 (m, 2H), 1.64-1.75 (m, 2H), 1.51-1.64 (m, 1H), 1.08-1.45 (m, 5H); $^{19}$F NMR (376 MHz, DMSO-$d_6$) δ ppm −60.89 (s, 3F); HRMS (ESI) m/z (M+H)$^+$ calcd. for $C_{27}H_{26}F_3N_2O_2$, 467.1941; found 467.1942.

EXAMPLE 119

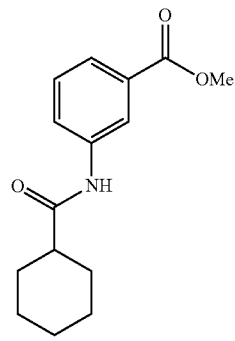 [SMILES: COC(=O)c1cccc(NC(=O)C2CCCCC2)c1]

This example illustrates a synthesis of Methyl 3-(cyclohexanecarboxamido)benzoate (XJB09-080). A solution of methyl 3-aminobenzoate (0.903 mL, 6.62 mmol) in dichloromethane (10.0 mL) and triethylamine (2.77 mL, 19.9 mmol) was treated at 0° C. with cyclohexanecarbonyl chloride (0.970 g, 6.62 mmol). The reaction mixture was stirred at 0° C. for 2 h and at room temperature for 2 h. The reaction mixture was concentrated and purified via silica gel chromatography using a gradient of 0-50% of EtOAc in hexanes to give 1.61 g (94%) of the title product as a white solid which was used directly in the next reaction without further purification. LC-MS Retention Time: $t_2$ (Method 2)=3.676 min; m/z (M+H)$^+$ 276.1.

EXAMPLE 120

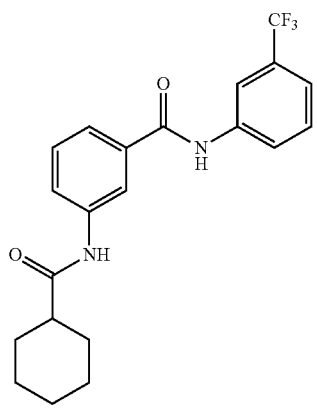 [SMILES: O=C(Nc1cccc(C(F)(F)F)c1)c1cccc(NC(=O)C2CCCCC2)c1]

This example illustrates a synthesis of 3-(Cyclohexanecarboxamido)-N-(3-(trifluoromethyl)phenyl)benzamide (XJB09-097, NCGC00244495-01). The title compound was prepared according to general protocol A. LC-MS Retention Time: $t_1$ (Method 1)=6.516 min; $^1$H NMR (400 MHz, DMSO-d$_6$) δ ppm 10.53 (s, 1H), 10.00 (s, 1H), 8.21 (t, J=2.1 Hz, 1H), 8.14 (t, J=2.0 Hz, 1H), 8.03 (ddd, J=8.2, 1.2, 1.0 Hz, 1H), 7.81 (ddd, J=8.1, 2.2, 1.1 Hz, 1H), 7.55-7.64 (m, 2H), 7.37-7.49 (m, 2H), 2.24-2.41 (m, 1H), 1.69-1.92 (m, 4H), 1.57-1.69 (m, 1H), 1.08-1.50 (m, 5H); $^{19}$F NMR (376 MHz, DMSO-d$_6$) δ ppm −61.29 (s, 3F); HRMS (ESI) m/z (M+H)$^+$ calcd. for $C_{21}H_{22}F_3N_2O_2$, 391.1628; found 391.1637.

EXAMPLE 121

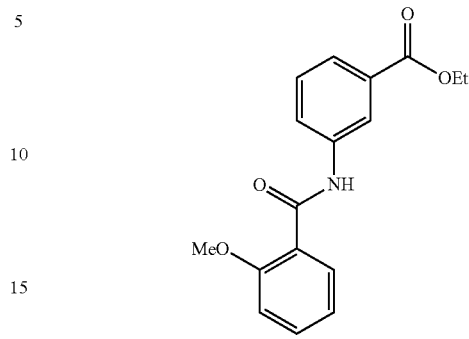

This example illustrates a synthesis of Ethyl 3-(cyclohexanecarboxamido)benzoate (XJB09-079). A solution of ethyl 3-aminobenzoate (1.00 g, 6.05 mmol) in dichloromethane (10.0 mL) and triethylamine (2.53 mL, 18.2 mmol) was treated at 0° C. with 2-methoxybenzoyl chloride (0.814 mL, 6.05 mmol). The reaction mixture was stirred at 0° C. for 2 h and at room temperature for 2 h. The reaction mixture was concentrated and purified via silica gel chromatography using a gradient of 0-50% of EtOAc in hexanes to give 1.11 g (61%) of the title product as a white solid which was used directly in the next reaction without further purification. LC-MS Retention Time: $t_2$ (Method 2)=3.664 min; m/z (M+H)$^+$ 300.1.

EXAMPLE 122

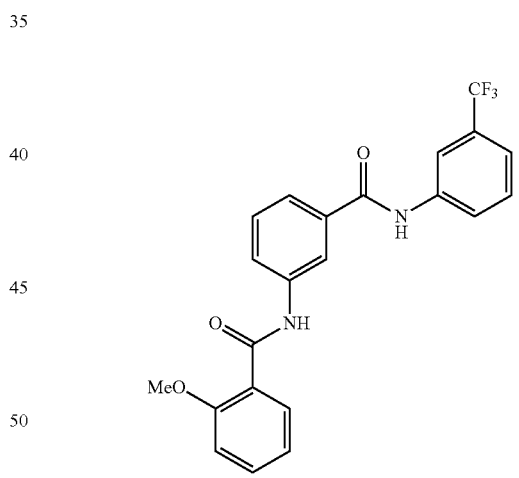

2-Methoxy-N-(3-((3-(trifluoromethyl)phenyl)carbamoyl)phenyl)benzamide (XJB09-098, NCGC00244496-01)

The title compound was prepared according to general protocol A. LC-MS Retention Time: $t_1$ (Method 1)=6.471 min; $^1$H NMR (400 MHz, DMSO-d$_6$) δ ppm 10.58 (s, 1H), 10.30 (s, 1H), 8.27-8.35 (m, 1H), 8.23 (t, J=2.1 Hz, 1H), 8.04 (dt, J=8.2, 1.1 Hz, 1H), 7.88-7.99 (m, 1H), 7.67 (ddd, J=8.0, 1.4, 1.2 Hz, 1H), 7.63 (dd, J=7.6, 1.8 Hz, 1H), 7.56-7.62 (m, 1H), 7.47-7.56 (m, 2H), 7.41-7.47 (m, 1H), 7.14-7.23 (m, 1H), 7.06 (td, J=7.4, 1.0 Hz, 1H), 3.90 (s, 3H);

$^{19}$F NMR (376 MHz, DMSO-d$_6$) δ ppm −61.28 (s, 3F); HRMS (ESI) m/z (M+H)$^+$ calcd. for C$_{22}$H$_{18}$F$_3$N$_2$O$_3$, 415.1264; found 415.1275.

EXAMPLE 123

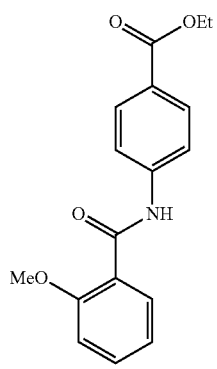 [SMILES: CCOC(=O)c1ccc(NC(=O)c2ccccc2OC)cc1]

This example illustrates a synthesis of Ethyl 4-(2-methoxybenzamido)benzoate (XJB09-077). A solution of ethyl 3-aminobenzoate (1.00 g, 6.05 mmol) in dichloromethane (10.0 mL) and triethylamine (2.53 mL, 18.2 mmol) was treated at 0° C. with 2-methoxybenzoyl chloride (0.814 mL, 6.05 mmol). The reaction mixture was stirred at 0° C. for 2 h and at room temperature for 2 h. The reaction mixture was concentrated and purified via silica gel chromatography using a gradient of 0-50% of EtOAc in hexanes to give 1.77 g (98%) of the title product as a white solid which was used directly in the next reaction without further purification. LC-MS Retention Time: t$_2$ (Method 2)=3.683 min; m/z (M+H)$^+$ 300.1.

EXAMPLE 124

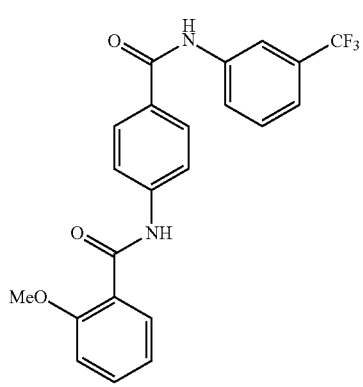 [SMILES: COc1ccccc1C(=O)Nc1ccc(C(=O)Nc2cccc(C(F)(F)F)c2)cc1]

This example illustrates a synthesis of 2-Methoxy-N-(4-((3-(trifluoromethyl)phenyl)carbamoyl)phenyl)benzamide (XJB10-001, NCGC00244497-01). The title compound was prepared according to general protocol A. LC-MS Retention Time: t$_1$ (Method 1)=6.452 min; $^1$H NMR (400 MHz, DMSO-d$_6$) δ ppm 10.43 (s, 1H), 10.39 (s, 1H), 8.24 (t, J=2.2 Hz, 1H), 8.02-8.10 (m, 1H), 7.95-8.02 (m, 2H), 7.80-7.94 (m, 2H), 7.63 (dd, J=7.6, 1.8 Hz, 1H), 7.55-7.62 (m, 1H), 7.47-7.55 (m, 1H), 7.43 (ddd, J=7.8, 1.9, 0.9 Hz, 1H), 7.19 (dd, J=8.5, 1.1 Hz, 1H), 7.07 (td, J=7.5, 1.1 Hz, 1H), 3.90 (s, 3H); $^{19}$F NMR (376 MHz, DMSO-d$_6$) δ ppm −61.27 (s, 3F); HRMS (ESI) m/z (M+H)$^+$ calcd. for C$_{22}$H$_{18}$F$_3$N$_2$O$_3$, 415.1264; found 415.1269.

EXAMPLE 125

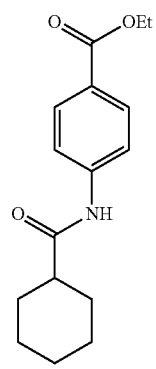 [SMILES: CCOC(=O)c1ccc(NC(=O)C2CCCCC2)cc1]

This example illustrates a synthesis of Ethyl 4-(cyclohexanecarboxamido)benzoate (XJB09-078). A solution of ethyl 4-aminobenzoate (1.00 g, 6.05 mmol) in dichloromethane (10.0 mL) and triethylamine (2.53 mL, 18.2 mmol) was treated at 0° C. with cyclohexanecarbonyl chloride (0.888 g, 6.05 mmol). The reaction mixture was stirred at 0° C. for 2 h and at room temperature for 2 h. The reaction mixture was concentrated and purified via silica gel chromatography using a gradient of 0-50% of EtOAc in hexanes to give 1.58 g (95%) of the title product as a white solid which was used directly in the next reaction without further purification. LC-MS Retention Time: t$_2$ (Method 2)=3.687 min; m/z (M+H)$^+$ 276.1.

EXAMPLE 126

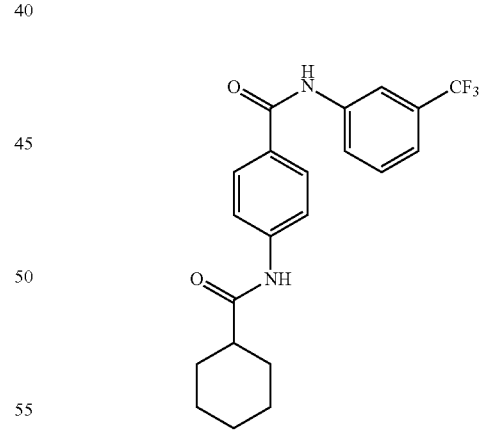

This example illustrates a synthesis of 4-(Cyclohexanecarboxamido)-N-(3-(trifluoromethyl)phenyl)benzamide (XJB10-015, NCGC00244480-01). The title compound was prepared according to general protocol A. LC-MS Retention Time: t$_1$ (Method 1)=6.473 min; $^1$H NMR (400 MHz, DMSO-d$_6$) δ ppm 10.37 (s, 1H), 10.09 (s, 1H), 8.23 (t, J=2.1 Hz, 1H), 8.03 (dd, J=8.4, 1.0 Hz, 1H), 7.85-7.97 (m, 2H), 7.68-7.79 (m, 2H), 7.52-7.64 (m, 1H), 7.36-7.47 (m, 1H), 2.27-2.43 (m, 1H), 1.69-1.94 (m, 4H), 1.58-1.69 (m, 1H), 1.10-1.51 (m, 5H); $^{19}$F NMR (376 MHz, DMSO-d$_6$) δ ppm −61.28 (s, 3F); HRMS (ESI) m/z (M+H)$^+$ calcd. for C$_{21}$H$_{22}$F$_3$N$_2$O$_2$, 391.1628; found 391.1631.

EXAMPLE 127

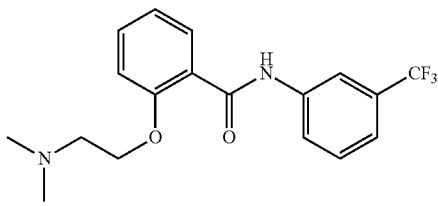 [SMILES: CN(C)CCOc1ccccc1C(=O)Nc1cccc(C(F)(F)F)c1]

This example illustrates a synthesis of 2-(2-(Dimethylamino)ethoxy)-N-(3-(trifluoromethyl)phenyl)benzamide (XJB10-024, NCGC00244498-01). The title compound was prepared according to general protocol H. LC-MS Retention Time: t$_1$ (Method 1)=4.204 min; $^1$H NMR (400 MHz, DMSO-d$_6$) δ ppm 10.49 (s, 1H), 8.11-8.39 (m, 1H), 7.76-7.99 (m, 1H), 7.48-7.68 (m, 3H), 7.39-7.47 (m, 1H), 7.23 (dd, J=8.4, 0.8 Hz, 1H), 7.13 (td, J=7.5, 1.0 Hz, 1H), 4.41 (dd, J=5.5, 4.5 Hz, 2H), 3.41-3.57 (m, 2H), 2.80 (s, 6H); HRMS (ESI) m/z (M+H)$^+$ calcd. for C$_{18}$H$_{20}$F$_3$N$_2$O$_2$, 353.1471; found 353.1474.

EXAMPLE 128

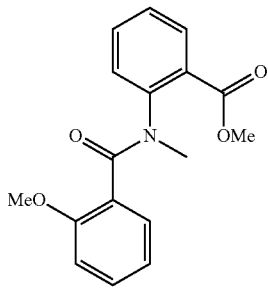 [SMILES: COC(=O)c1ccccc1N(C)C(=O)c1ccccc1OC]

This example illustrates a synthesis of Methyl 2-(2-methoxy-N-methylbenzamido)benzoate (XJB10-022). A solution of methyl 2-(2-methoxybenzamido)benzoate (1.16 g, 4.07 mmol) in DMF (10.0 mL) and was treated at 0° C. with NaH (0.813 g, 60%, 20.3 mmol). The reaction mixture was warmed to room temperature and stirred at room temperature for 1 h. Then a solution of MeI (1.27 mL, 20.3 mmol) in DMF (4.00 mL) was added drop wise. The reaction mixture was stirred at room temperature for 1.5 h. The mixture was carefully quenched with water and extracted with EtOAc. The organic layer was separated, dried, concentrated to give the final product which was used directly in the next reaction. LC-MS Retention Time: t$_2$ (Method 2)=3.293 min; m/z (M+H)$^+$ 300.1.

EXAMPLE 129

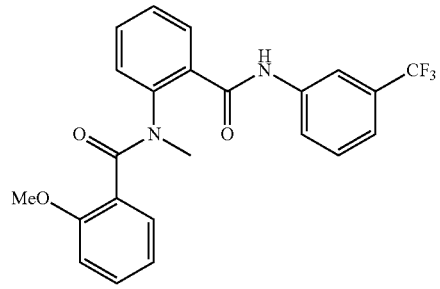 [SMILES: COc1ccccc1C(=O)N(C)c1ccccc1C(=O)Nc1cccc(C(F)(F)F)c1]

This example illustrates a synthesis of 2-Methoxy-N-methyl-N-(2-((3-(trifluoromethyl)phenyl)carbamoyl)phenyl)benzamide (XJB10-025, NCGC00244499-01). The title compound was prepared according to general protocol A. LC-MS Retention Time: t$_1$ (Method 1)=6.046 min; HRMS (ESI) m/z (M+H)$^+$ calcd. for C$_{23}$H$_{20}$F$_3$N$_2$O$_3$, 429.1421; found 429.1438.

EXAMPLE 130

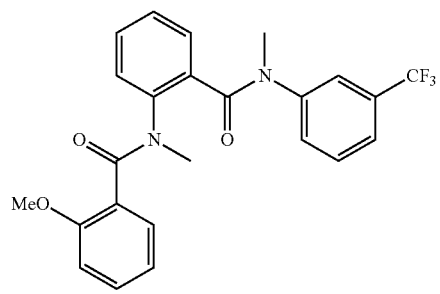 [SMILES: COc1ccccc1C(=O)N(C)c1ccccc1C(=O)N(C)c1cccc(C(F)(F)F)c1]

This example illustrates a synthesis of 2-Methoxy-N-methyl-N-(2-(methyl(3-(trifluoromethyl)phenyl)carbamoyl)phenyl)benzamide (XJB10-026, NCGC00244500-01). The title compound was prepared according to general protocol A. LC-MS Retention Time: t$_1$ (Method 1)=5.994 min; HRMS (ESI) m/z (M+H)$^+$ calcd. for C$_{24}$H$_{22}$F$_3$N$_2$O$_3$, 443.1577; found 443.1579.

EXAMPLE 131

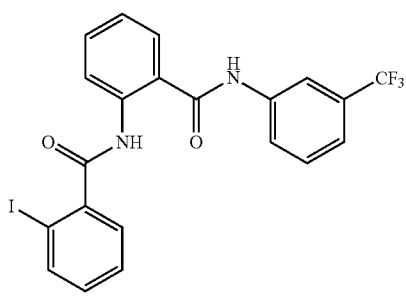 [SMILES: O=C(Nc1ccccc1C(=O)Nc1cccc(C(F)(F)F)c1)c1ccccc1I]

This example illustrates a synthesis of 2-Iodo-N-(2-((3-(trifluoromethyl)phenyl)carbamoyl)phenyl)benzamide (XJB10-027, NCGC00244482-01). The title compound was prepared according to general protocol C. LC-MS Retention Time: $t_1$ (Method 1)=6.879 min; HRMS (ESI) m/z (M+H)$^+$ calcd. for $C_{21}H_{15}F_3IN_2O_2$, 511.0125; found 511.0122.

EXAMPLE 132

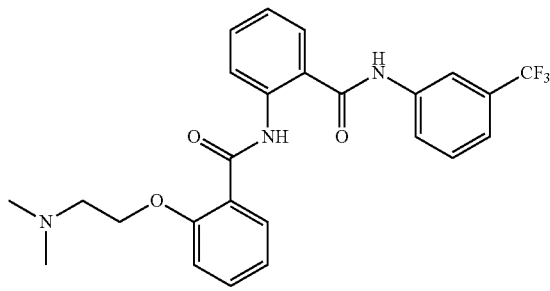 [SMILES: CN(C)CCOc1ccccc1C(=O)Nc1ccccc1C(=O)Nc1cccc(C(F)(F)F)c1]

This example illustrates a synthesis of 2-(2-(Dimethylamino)ethoxy)-N-(2-((3-(trifluoromethyl)phenyl)carbamoyl)phenyl)benzamide (XJB10-028, NCGC00244483-01). The title compound was prepared according to general protocol H. LC-MS Retention Time: $t_1$ (Method 1)=4.705 min; $^1$H NMR (400 MHz, DMSO-$d_6$) δ ppm 11.11 (s, 1H), 10.84 (s, 1H), 8.41 (dd, J=8.5, 1.3 Hz, 1H), 8.07-8.20 (m, 1H), 7.96 (dd, J=8.0, 1.2 Hz, 1H), 7.87 (dd, J=7.7, 1.9 Hz, 1H), 7.84 (dd, J=7.8, 1.8 Hz, 1H), 7.57-7.65 (m, 2H), 7.52-7.57 (m, 1H), 7.45-7.52 (m, 1H), 7.24-7.33 (m, 2H), 7.13 (td, J=7.5, 1.0 Hz, 1H), 4.55 (t, J=5.1 Hz, 2H), 3.49-3.74 (m, 2H), 2.78 (s, 6H); HRMS (ESI) m/z (M+H)$^+$ calcd. for $C_{25}H_{25}F_3N_3O_3$, 472.1843; found 472.1851.

EXAMPLE 133

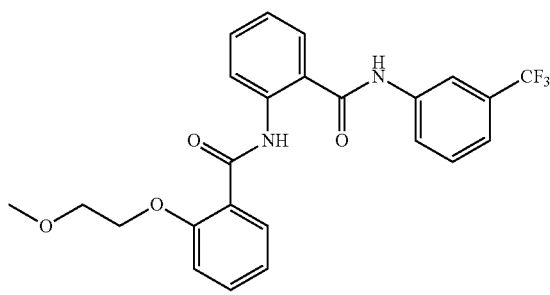 [SMILES: COCCOc1ccccc1C(=O)Nc1ccccc1C(=O)Nc1cccc(C(F)(F)F)c1]

This example illustrates a synthesis of 2-(2-Methoxyethoxy)-N-(2-((3-(trifluoromethyl)phenyl)carbamoyl)phenyl)benzamide (XJB10-029, NCGC00244484-01). The title compound was prepared according to general protocol H. LC-MS Retention Time: $t_1$ (Method 1)=6.625 min; $^1$H NMR (400 MHz, DMSO-$d_6$) δ ppm 1H NMR (400 MHz, DMSO-$d_6$) δ ppm 11.22 (s, 1H), 10.80 (s, 1H), 8.44 (dd, J=8.3, 1.3 Hz, 1H), 8.21 (t, J=2.2 Hz, 1H), 7.93-7.99 (m, 1H), 7.91 (dd, J=7.8, 1.8 Hz, 1H), 7.80 (dd, J=7.7, 1.7 Hz, 1H), 7.55-7.64 (m, 2H), 7.48-7.55 (m, 1H), 7.42-7.48 (m, 1H), 7.27 (td, J=7.6, 1.3 Hz, 1H), 7.23 (dd, J=8.5, 1.1 Hz, 1H), 7.03-7.13 (m, 1H), 4.26-4.37 (m, 2H), 3.61-3.72 (m, 2H), 3.11 (s, 3H); $^{19}$F NMR (376 MHz, DMSO-$d_6$) δ ppm −61.36 (s, 3F); HRMS (ESI) m/z (M+H)$^+$ calcd. for $C_{24}H_{22}F_3N_2O_4$, 459.1526; found 459.1527.

EXAMPLE 134

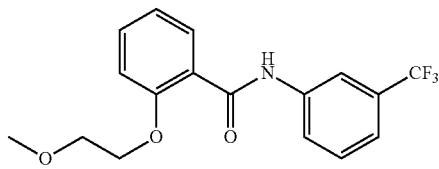 [SMILES: COCCOc1ccccc1C(=O)Nc1cccc(C(F)(F)F)c1]

This example illustrates a synthesis of 2-(2-Methoxyethoxy)-N-(3-(trifluoromethyl)phenyl)benzamide (XJB10-030, NCGC00244485-01). The title compound was prepared according to general protocol H. LC-MS Retention Time: $t_1$ (Method 1)=6.644 min; $^1$H NMR (400 MHz, DMSO-$d_6$) δ ppm 10.45 (s, 1H), 8.08-8.29 (m, 1H), 7.93 (d, J=8.2 Hz, 1H), 7.83 (dt, J=7.7, 1.8 Hz, 1H), 7.57-7.66 (m, 1H), 7.49-7.57 (m, 1H), 7.40-7.49 (m, 1H), 7.20-7.28 (m, 1H), 7.05-7.18 (m, 1H), 4.31 (td, J=4.5, 1.9 Hz, 2H), 3.70-3.83 (m, 2H), 3.29 (s, 3H); $^{19}$F NMR (376 MHz, DMSO-$d_6$) δ ppm −61.26 (s, 3F); HRMS (ESI) m/z (M+H)$^+$ calcd. for $C_{17}H_{17}F_3NO_3$, 340.1155; found 340.1162.

EXAMPLE 135

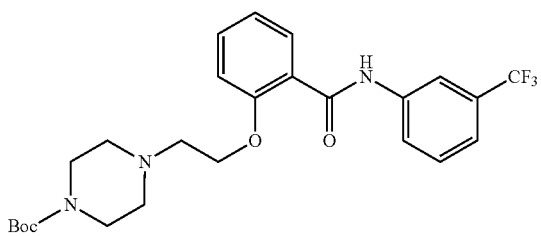 [SMILES: CC(C)(C)OC(=O)N1CCN(CCOc2ccccc2C(=O)Nc2cccc(C(F)(F)F)c2)CC1]

This example illustrates a synthesis of tert-Butyl 4-(2-(2-((3-(trifluoromethyl)phenyl)carbamoyl)phenoxy)ethyl)piperazine-1-carboxylate (XJB10-031, NCGC00244486-01). The title compound was prepared according to general protocol H. LC-MS Retention Time: $t_1$ (Method 1)=4.945 min; HRMS (ESI) m/z (M+H)$^+$ calcd. for $C_{25}H_{31}F_3N_3O_4$, 494.2261; found 494.2270.

EXAMPLE 136

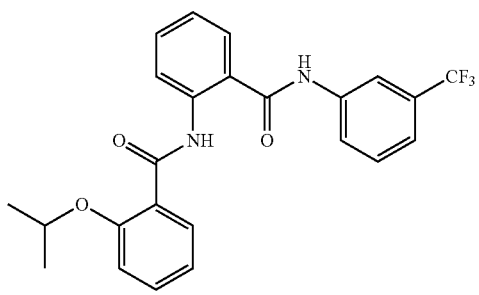 [SMILES: CC(C)Oc1ccccc1C(=O)Nc1ccccc1C(=O)Nc1cccc(C(F)(F)F)c1]

This example illustrates a synthesis of 2-Isopropoxy-N-(2-((3-(trifluoromethyl)phenyl)carbamoyl)phenyl)benzamide (XJB10-036, NCGC00244516-01). The title compound was prepared according to general protocol H.

LC-MS Retention Time: $t_1$ (Method 1)=7.126 min; HRMS (ESI) m/z (M+H)$^+$ calcd. For $C_{24}H_{22}F_3N_2O_3$, 443.1577; found 443.1599.

EXAMPLE 137

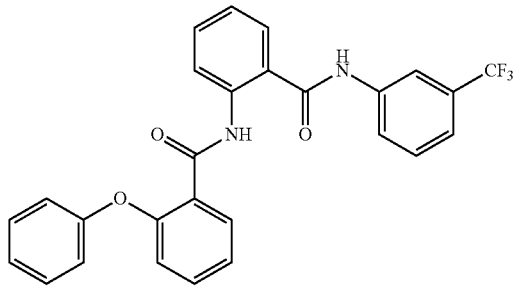 [SMILES: O=C(Nc1cccc(C(F)(F)F)c1)c1ccccc1NC(=O)c1ccccc1Oc1ccccc1]

This example illustrates a synthesis of 2-Phenoxy-N-(2-((3-(trifluoromethyl)phenyl)carbamoyl)phenyl)benzamide (XJB10-037, NCGC00244517-01). The title compound was prepared according to general protocol H. LC-MS Retention Time: $t_1$ (Method 1)=7.314 min; $^1$H NMR (400 MHz, DMSO-$d_6$) δ ppm 11.45 (s, 1H), 10.73 (s, 1H), 8.41-8.58 (m, 1H), 8.11 (t, J=2.1 Hz, 1H), 7.97 (dd, J=7.8, 2.0 Hz, 1H), 7.85 (ddd, J=8.3, 2.2, 1.3 Hz, 1H), 7.80 (dd, J=7.8, 1.6 Hz, 1H), 7.42-7.65 (m, 4H), 7.21-7.37 (m, 4H), 7.15 (tt, J=7.4, 1.2 Hz, 1H), 7.01-7.12 (m, 2H), 6.84 (dd, J=8.2, 1.2 Hz, 1H); $^{19}$F NMR (376 MHz, DMSO-$d_6$) δ ppm −61.27 (s, 3F); HRMS (ESI) m/z (M+H)$^+$ calcd. for $C_{27}H_{20}F_3N_2O_3$, 477.1421; found 477.1425.

EXAMPLE 138

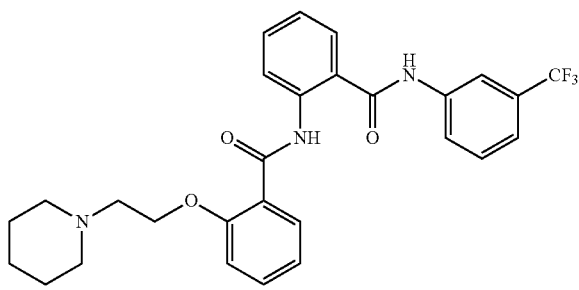 [SMILES: O=C(Nc1cccc(C(F)(F)F)c1)c1ccccc1NC(=O)c1ccccc1OCCN1CCCCC1]

This example illustrates a synthesis of 2-(2-(Piperidin-1-yl)ethoxy)-N-(2-((3-(trifluoromethyl)phenyl)carbamoyl)phenyl)benzamide (XJB10-038, NCGC00244518-01). The title compound was prepared according to general protocol H. LC-MS Retention Time: $t_1$ (Method 1)=4.945 min; HRMS (ESI) m/z (M+H)$^+$ calcd. for $C_{28}H_{29}F_3N_3O_3$, 512.2156; found 512.2172.

EXAMPLE 139

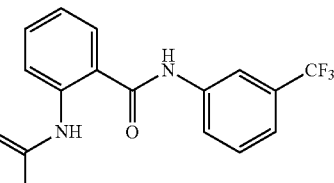

This example illustrates a synthesis of 2-(2-Morpholinoethoxy)-N-(2-((3-(trifluoromethyl)phenyl)carbamoyl)phenyl)benzamide (XJB10-039, NCGC00244519-01). The title compound was prepared according to general protocol H. LC-MS Retention Time: $t_1$ (Method 1)=4.752 min; HRMS (ESI) m/z (M+H)$^+$ calcd. for $C_{27}H_{27}F_3N_3O_4$, 514.1948; found 514.1972.

EXAMPLE 140

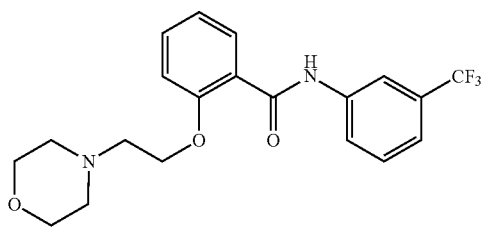 [SMILES: O=C(Nc1cccc(C(F)(F)F)c1)c1ccccc1OCCN1CCOCC1]

This example illustrates a synthesis of 2-(2-(Piperidin-1-yl)ethoxy)-N-(3-(trifluoromethyl)phenyl)benzamide (XJB10-040, NCGC00244519-01). The title compound was prepared according to general protocol H. LC-MS Retention Time: $t_1$ (Method 1)=4.527 min; $^1$H NMR (400 MHz, DMSO-$d_6$) δ ppm 10.57 (s, 1H), 8.23 (br. s., 1H), 7.89 (d, J=8.8 Hz, 1H), 7.49-7.66 (m, 3H), 7.45 (d, J=8.0 Hz, 1H), 7.23 (d, J=8.4 Hz, 1H), 7.13 (t, J=7.4 Hz, 1H), 4.24-4.54 (m, 2H), 3.40-3.61 (m, 4H), 2.84-3.05 (m, 2H), 1.44-1.80 (m, 5H), 1.21-1.35 (m, 1H); HRMS (ESI) m/z (M+H)$^+$ calcd. for $C_{27}H_{27}F_3N_3O_4$, 514.1948; found 514.1972.

EXAMPLE 141

This example illustrates a synthesis of 2-(2-Morpholinoethoxy)-N-(3-(trifluoromethyl)phenyl)benzamide (XJB10-041, NCGC00244502-01). The title compound was prepared according to general protocol H. LC-MS Retention Time: $t_1$ (Method 1)=4.280 min; HRMS (ESI) m/z $(M+H)^+$ calcd. for $C_{20}H_{22}F_3N_2O_3$, 395.1577; found 395.1585.

EXAMPLE 142

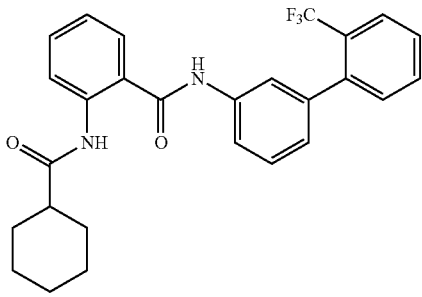 [SMILES: O=C(Nc1cccc(-c2ccccc2C(F)(F)F)c1)c1ccccc1NC(=O)C1CCCCC1]

This example illustrates a synthesis of 2-(Cyclohexanecarboxamido)-N-(2'-(trifluoromethyl)-[1,1'-biphenyl]-3-yl)benzamide (XJB10-042, NCGC00244503-01). The title compound was prepared according to general protocol E. LC-MS Retention Time: $t_1$ (Method 1)=7.417 min; $^1$H NMR (400 MHz, DMSO-$d_6$) δ ppm 10.46 (s, 1H), 10.40 (s, 1H), 8.15 (dd, J=8.3, 1.3 Hz, 1H), 7.83 (dt, J=7.7, 0.8 Hz, 1H), 7.66-7.79 (m, 4H), 7.57-7.65 (m, 1H), 7.45-7.57 (m, 1H), 7.33-7.45 (m, 2H), 7.20 (td, J=7.6, 1.3 Hz, 1H), 7.05 (dd, J=7.6, 1.0 Hz, 1H), 2.18-2.36 (m, 1H), 1.73-1.88 (m, 2H), 1.63-1.74 (m, 2H), 1.50-1.63 (m, 1H), 0.99-1.42 (m, 5H); $^{19}$F NMR (376 MHz, DMSO-$d_6$) δ ppm −55.34 (s, 3F); HRMS (ESI) m/z $(M+H)^+$ calcd. for $C_{27}H_{26}F_3N_2O_2$, 467.1941; found 467.1931.

EXAMPLE 143

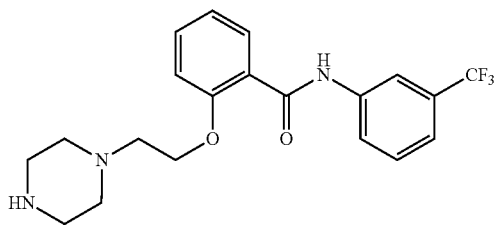 [SMILES: O=C(Nc1cccc(C(F)(F)F)c1)c1ccccc1OCCN1CCNCC1]

This example illustrates a synthesis of 2-(2-(Piperazin-1-yl)ethoxy)-N-(3-(trifluoromethyl)phenyl)benzamide (XJB10-043, NCGC00244504-01). A solution of tert-butyl 4-(2-(2-(3-(trifluoromethyl)phenylcarbamoyl)phenoxy) ethyl)piperazine-1-carboxylate (0.099 g, 0.200 mmol) in dichloromethane (2.00 mL) was treated at 0° C. with TFA (1.00 mL). The reaction mixture was stirred at 0° C. for 1 h. The mixture was concentrated, re-dissolved in 2.00 mL of DMSO, filtered and purified via $C_{18}$ reverse phase HPLC to give the final product. LC-MS Retention Time: $t_1$ (Method 1)=3.872 min; HRMS (ESI) m/z $(M+H)^+$ calcd. for $C_{20}H_{23}F_3N_3O_2$, 394.1737; found 394.1745.

EXAMPLE 144

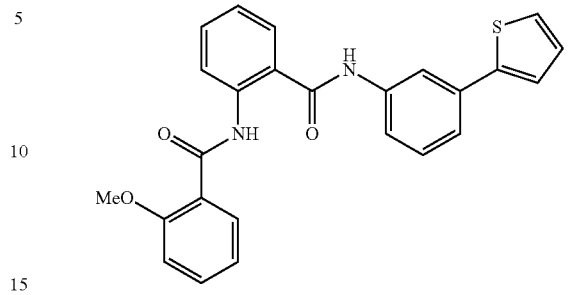

This example illustrates a synthesis of 2-Methoxy-N-(2-((3-(thiophen-2-yl)phenyl)carbamoyl)phenyl)benzamide (XJB10-044, NCGC00244505-01). The title compound was prepared according to general protocol A. LC-MS Retention Time: $t_1$ (Method 1)=6.455 min; HRMS (ESI) m/z $(M+H)^+$ calcd. for $C_{25}H_{21}N_2O_3S$, 429.1267; found 429.1285.

EXAMPLE 145

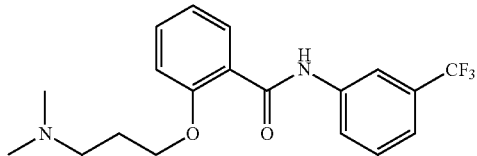 [SMILES: CN(C)CCCOc1ccccc1C(=O)Nc1cccc(C(F)(F)F)c1]

This example illustrates a synthesis of 2-(3-(Dimethylamino)propoxy)-N-(3-(trifluoromethyl)phenyl)benzamide (XJB10-045, NCGC00244506-01). The title compound was prepared according to general protocol H. LC-MS Retention Time: $t_1$ (Method 1)=4.371 min; $^1$H NMR (400 MHz, DMSO-$d_6$) δ ppm 10.27-10.74 (m, 1H), 8.25 (s, 1H), 7.92 (d, J=7.4 Hz, 1H), 7.55-7.65 (m, 2H), 7.48-7.54 (m, 1H), 7.44 (d, J=7.8 Hz, 1H), 7.17 (d, J=8.4 Hz, 1H), 7.09 (t, J=7.5 Hz, 1H), 4.16 (t, J=5.5 Hz, 2H), 3.04-3.21 (m, 2H), 2.68 (s, 6H), 1.97-2.18 (m, 2H); HRMS (ESI) m/z $(M+H)^+$ calcd. for $C_{19}H_{22}F_3N_2O_2$, 367.1628; found 367.1628.

EXAMPLE 146

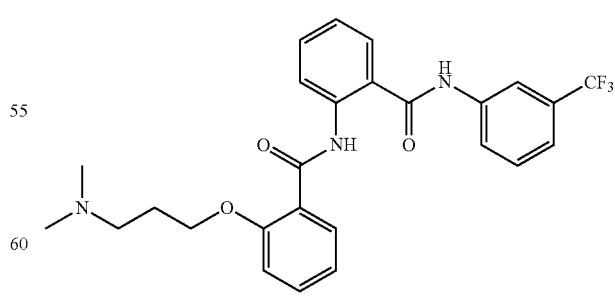

This example illustrates a synthesis of 2-(3-(Dimethylamino)propoxy)-N-(2-((3-(trifluoromethyl)phenyl)carbamoyl)phenyl)benzamide (XJB10-046, NCGC00244507-01). The title compound was prepared according to general protocol H. LC-MS Retention Time: $t_1$ (Method 1)=4.868 min; HRMS (ESI) m/z (M+H)+ calcd. for $C_{26}H_{27}F_3N_3O_3$, 486.1999; found 486.2002.

EXAMPLE 147

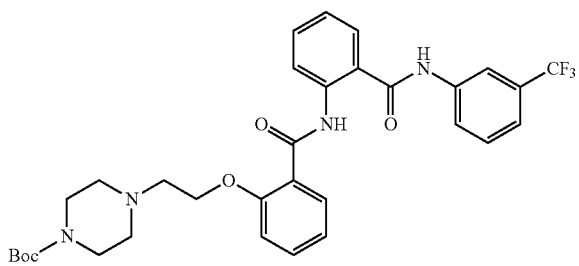 [SMILES: CC(C)(C)OC(=O)N1CCN(CCOc2ccccc2C(=O)Nc2ccccc2C(=O)Nc2cccc(C(F)(F)F)c2)CC1]

This example illustrates a synthesis of tert-Butyl 4-(2-(2-((2-((3-(trifluoromethyl)phenyl)carbamoyl)phenyl)carbamoyl)phenoxy)ethyl)piperazine-1-carboxylate (XJB10-047, NCGC00244481-01). The title compound was prepared according to general protocol H. LC-MS Retention Time: $t_1$ (Method 1)=5.211 min; HRMS (ESI) m/z (M+H)+ calcd. for $C_{32}H_{36}F_3N_4O_5$, 613.2632; found 613.2642.

EXAMPLE 148

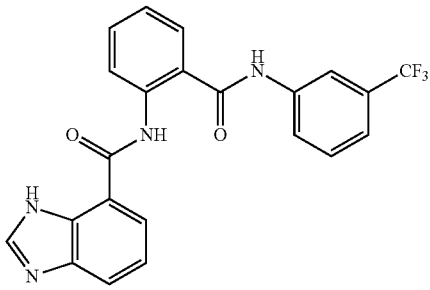 [SMILES: O=C(Nc1cccc(C(F)(F)F)c1)c1ccccc1NC(=O)c1cccc2nc[nH]c12]

This example illustrates a synthesis of N-(2-((3-(Trifluoromethyl)phenyl)carbamoyl)phenyl)-1H-benzo[d]imidazole-7-carboxamide (XJB10-049, NCGC00244508-01). The title compound was prepared according to general protocol H. LC-MS Retention Time: $t_1$ (Method 1)=4.777 min; HRMS (ESI) m/z (M+H)+ calcd. for $C_{22}H_{16}F_3N_4O_2$, 425.1220; found 425.1227.

EXAMPLE 149

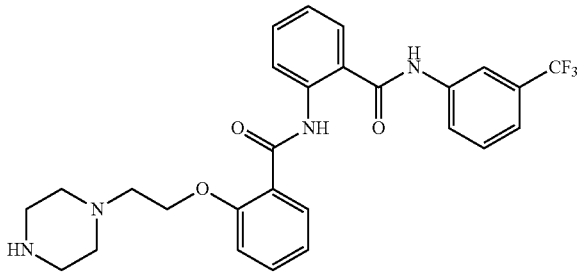 [SMILES: O=C(Nc1cccc(C(F)(F)F)c1)c1ccccc1NC(=O)c1ccccc1OCCN1CCNCC1]

This example illustrates a synthesis of 2-(2-(Piperazin-1-yl)ethoxy)-N-(2-((3-(trifluoromethyl)phenyl)carbamoyl)phenyl)benzamide (XJB10-050, NCGC00244509-01). A solution of tert-butyl 4-(2-(2-(2-(3-(trifluoromethyl)phenylcarbamoyl)phenylcarbamoyl)phenoxy)ethyl)piperazine-1-carboxylate (50.0 mg, 0.082 mmol) in dichloromethane (2.00 mL) was treated at 0° C. with TFA (1.00 mL). The reaction mixture was stirred at 0° C. for 1 h. The mixture was concentrated, re-dissolved in 2.00 mL of DMSO, filtered and purified via $C_{18}$ reverse phase HPLC to give the final product. LC-MS Retention Time: $t_1$ (Method 1)=4.303 min; HRMS (ESI) m/z (M+H)+ calcd. for $C_{27}H_{28}F_3N_4O_3$, 513.2108; found 513.2128.

EXAMPLE 150

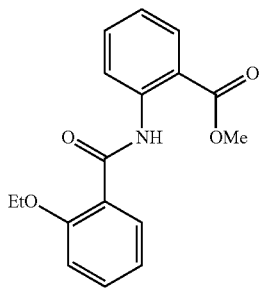

This example illustrates a synthesis of Methyl 2-(2-ethoxybenzamido)benzoate (XJB11-036). A solution of ethyl methyl 2-aminobenzoate (1.29 mL, 9.92 mmol) in dichloromethane (25.0 mL) and triethylamine (4.15 mL, 29.8 mmol) was treated at 0° C. with 2-ethoxybenzoyl chloride (1.83 g, 9.92 mmol). The reaction mixture was stirred at 0° C. for 2 h and at room temperature for 2 h. The reaction mixture was concentrated and purified via silica gel chromatography using a gradient of 0-50% of EtOAc in hexanes to give 2.70 g (91%) of the title product as a white solid which was used directly in the next reaction without further purification. LC-MS Retention Time: $t_2$ (Method 2)=3.908 min; m/z (M+H)+ 300.1.

EXAMPLE 151

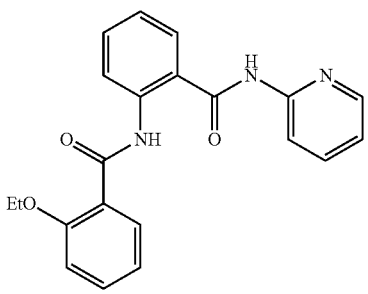 [SMILES: CCOc1ccccc1C(=O)Nc1ccccc1C(=O)Nc1ccccn1]

This example illustrates a synthesis of 2-Ethoxy-N-(2-(pyridin-2-ylcarbamoyl)phenyl)benzamide (XJB11-037, NCGC00250128-01). The title compound was prepared according to general protocol A. LC-MS Retention Time: $t_1$ (Method 1)=5.072 min; 1H NMR (400 MHz, DMSO-$d_6$) δ ppm 11.30 (s, 1H), 11.01 (s, 1H), 8.46 (d, J=8.2 Hz, 1H), 8.37 (dd, J=5.1, 2.3 Hz, 1H), 8.13 (d, J=8.2 Hz, 1H), 7.92 (dd, J=7.6, 2.2 Hz, 1H), 7.82-7.89 (m, 1H), 7.79 (dd, J=7.8, 2.0 Hz, 1H), 7.44-7.61 (m, 2H), 7.13-7.25 (m, 3H), 7.02-7.10 (m, 1H), 4.28 (q, J=6.9 Hz, 2H), 1.29 (t, J=7.0 Hz, 3H); HRMS (ESI) m/z (M+H)+ calcd. for $C_{21}H_{20}N_3O_3$, 362.1499; found 362.1505.

EXAMPLE 152

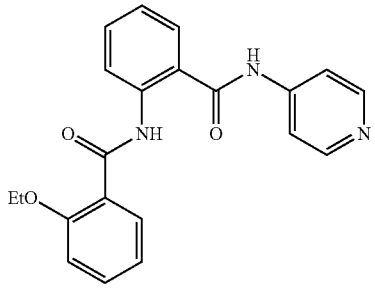 [SMILES: CCOc1ccccc1C(=O)Nc1ccccc1C(=O)Nc1ccncc1]

This example illustrates a synthesis of 2-Ethoxy-N-(2-(pyridin-4-ylcarbamoyl)phenyl)benzamide (XJB11-039, NCGC00250119-02). The title compound was prepared according to general protocol A. LC-MS Retention Time: $t_1$ (Method 1)=4.341 min; $^1$H NMR (400 MHz, DMSO-$d_6$) δ ppm 11.01 (s, 1H), 10.65 (s, 1H), 8.17-8.36 (m, 3H), 7.72 (dd, J=7.8, 2.0 Hz, 1H), 7.57 (dd, J=7.6, 1.8 Hz, 1H), 7.51 (dd, J=4.9, 1.8 Hz, 2H), 7.38 (td, J=7.9, 1.8 Hz, 1H), 7.31 (ddd, J=8.5, 7.1, 2.0 Hz, 1H), 7.03-7.10 (m, 1H), 6.99 (d, J=8.6 Hz, 1H), 6.68-6.91 (m, 1H), 4.09 (q, J=6.8 Hz, 2H), 1.11 (t, J=6.8 Hz, 3H); HRMS (ESI) m/z (M+H)+ calcd. for $C_{21}H_{20}N_3O_3$, 362.1499; found 362.1499.

EXAMPLE 153

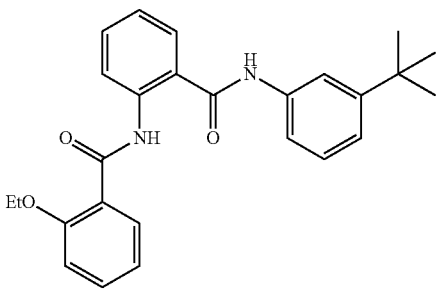 [SMILES: CCOc1ccccc1C(=O)Nc1ccccc1C(=O)Nc1cccc(C(C)(C)C)c1]

This example illustrates a synthesis of N-(3-(tert-Butyl)phenyl)-2-(2-ethoxybenzamido)benzamide (XJB11-040, NCGC00250129-01). The title compound was prepared according to general protocol A. LC-MS Retention Time: $t_1$ (Method 1)=7.379 min; HRMS (ESI) m/z (M+H)+ calcd. for $C_{26}H_{29}N_2O_3$, 417.2173; found 417.2175.

EXAMPLE 154

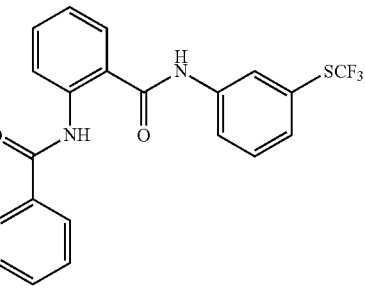

This example illustrates a synthesis of 2-Ethoxy-N-(2-(pyridin-4-ylcarbamoyl)phenyl)benzamide (XJB11-041, NCGC00250107-01). The title compound was prepared according to general protocol A. LC-MS Retention Time: $t_1$ (Method 1)=7.305 min; HRMS (ESI) m/z (M+H)+ calcd. for $C_{23}H_{20}F_3N_2O_3S$, 461.1141; found 461.1146.

EXAMPLE 155

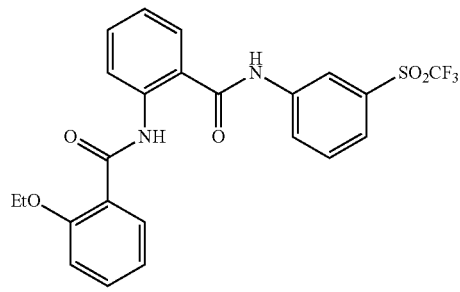

This example illustrates a synthesis of 2-Ethoxy-N-(2-((3-((trifluoromethyl)sulfonyl)phenyl)carbamoyl)phenyl)benzamide (XJB11-043, NCGC00250130-01, compound 174). The title compound was prepared according to general protocol A. LC-MS Retention Time: $t_1$ (Method 1)=6.963 min; HRMS (ESI) m/z (M+H)+ calcd. for $C_{23}H_{20}F_3N_2O_5S$, 493.1040; found 493.1044.

EXAMPLE 156

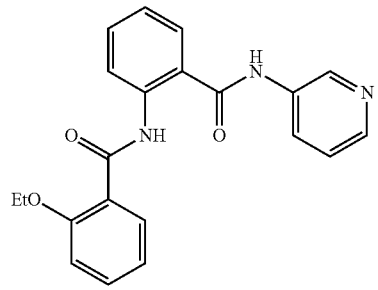 [SMILES: CCOc1ccccc1C(=O)Nc1ccccc1C(=O)Nc1cccnc1]

This example illustrates a synthesis of 2-Ethoxy-N-(2-(pyridin-3-ylcarbamoyl)phenyl)benzamide (XJB11-047, NCGC00250104-01). The title compound was prepared according to general protocol A. LC-MS Retention Time: $t_1$ (Method 1)=4.330 min; $^1$H NMR (400 MHz, DMSO-$d_6$) δ ppm 11.32 (s, 1H), 10.71 (s, 1H), 8.89 (d, J=2.3 Hz, 1H), 8.51 (d, J=8.2 Hz, 1H), 8.31 (dd, J=4.7, 1.6 Hz, 1H), 8.13 (ddd, J=8.7, 2.4, 1.4 Hz, 1H), 7.92 (dd, J=7.8, 2.0 Hz, 1H), 7.80 (dd, J=7.8, 2.0 Hz, 1H), 7.54-7.63 (m, 1H), 7.51 (td, J=7.8, 2.0 Hz, 1H), 7.39 (dd, J=8.2, 4.7 Hz, 1H), 7.22-7.32 (m, 1H), 7.18 (d, J=8.2 Hz, 1H), 7.06 (t, J=7.4 Hz, 1H), 4.27 (q, J=7.0 Hz, 2H), 1.29 (t, J=7.0 Hz, 3H); HRMS (ESI) m/z (M+H)$^+$ calcd. for $C_{21}H_{20}N_3O_3$, 362.1499; found 362.1507.

EXAMPLE 157

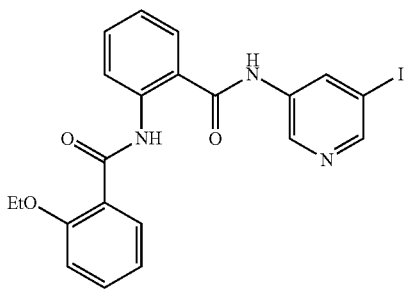 [SMILES: CCOc1ccccc1C(=O)Nc1ccccc1C(=O)Nc1cncc(I)c1]

This example illustrates a synthesis of 2-Ethoxy-N-(2-((5-iodopyridin-3-yl)carbamoyl)phenyl)benzamide (XJB11-048, NCGC00250103-01). The title compound was prepared according to general protocol A. LC-MS Retention Time: $t_1$ (Method 1)=6.305 min; $^1$H NMR (400 MHz, DMSO-$d_6$) δ ppm 11.31 (s, 1H), 10.78 (s, 1H), 8.85 (d, J=2.3 Hz, 1H), 8.63 (t, J=2.3 Hz, 1H), 8.54 (d, J=2.3 Hz, 1H), 8.49 (d, J=8.2 Hz, 1H), 7.93 (dd, J=7.8, 2.0 Hz, 1H), 7.80 (dd, J=7.8, 2.0 Hz, 1H), 7.59 (td, J=7.9, 1.8 Hz, 1H), 7.52 (ddd, J=8.6, 7.0, 2.0 Hz, 1H), 7.23-7.31 (m, 1H), 7.20 (d, J=8.2 Hz, 1H), 7.07 (t, J=7.4 Hz, 1H), 4.31 (q, J=6.8 Hz, 2H), 1.33 (t, J=7.0 Hz, 3H); HRMS (ESI) m/z (M+H)$^+$ calcd. for $C_{21}H_{19}IN_3O_3$, 488.0466; found 488.0475.

EXAMPLE 158

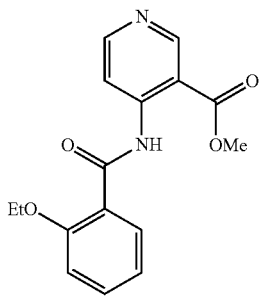 [SMILES: CCOc1ccccc1C(=O)Nc1ccncc1C(=O)OC]

This example illustrates a synthesis of Methyl 4-(2-ethoxybenzamido)nicotinate (XJB11-044). A solution of 4-aminonicotinate (500 mg, 3.29 mmol) in dichloromethane (25.0 mL) and triethylamine (1.37 mL, 9.86 mmol) was treated at 0° C. with 2-ethoxybenzoyl chloride (607 mg, 3.29 mmol). The reaction mixture was stirred at 0° C. for 2 h and at room temperature for 2 h. The reaction mixture was concentrated and purified via silica gel chromatography using a gradient of 0-100% of EtOAc in hexanes to give 924 mg (94%) of the title product as a white solid which was used directly in the next reaction without further purification. LC-MS Retention Time: $t_2$ (Method 2)=3.045 min; m/z (M+H)$^+$ 301.1.

EXAMPLE 159

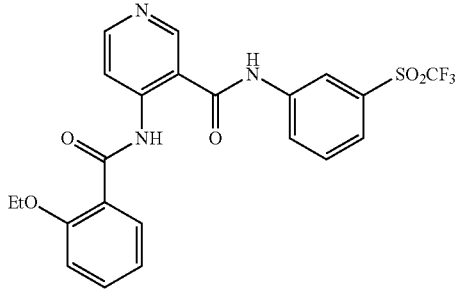

This example illustrates a synthesis of 4-(2-Ethoxybenzamido)-N-(3-((trifluoromethyl)sulfonyl)phenyl)nicotinamide (XJB11-049, NCGC00250117-01). The title compound was prepared according to general protocol A. LC-MS Retention Time: $t_1$ (Method 1)=5.507 min; $^1$H NMR (400 MHz, DMSO-$d_6$) δ ppm 11.71 (s, 1H), 11.25 (s, 1H), 9.00 (s, 1H), 8.77 (t, J=2.2 Hz, 1H), 8.65-8.71 (m, 1H), 8.54-8.64 (m, 1H), 8.15-8.26 (m, 1H), 7.96 (dd, J=7.8, 2.3 Hz, 1H), 7.78-7.93 (m, 2H), 7.56 (ddd, J=8.6, 7.0, 2.0 Hz, 1H), 7.24 (d, J=8.6 Hz, 1H), 7.09 (t, J=7.4 Hz, 1H), 4.35 (q, J=6.9 Hz, 2H), 1.29 (t, J=6.8 Hz, 3H); $^{19}$F NMR (376 MHz, DMSO-$d_6$) δ ppm −78.37 (s, 3F); HRMS (ESI) m/z (M+H)$^+$ calcd. for $C_{22}H_{19}F_3N_3O_5S$, 494.0992; found 494.1004.

EXAMPLE 160

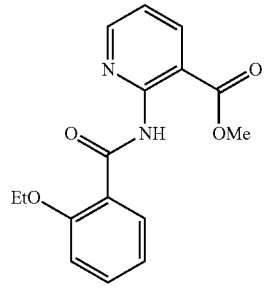 [SMILES: CCOc1ccccc1C(=O)Nc1ncccc1C(=O)OC]

This example illustrates a synthesis of Methyl 2-(2-ethoxybenzamido)nicotinate (XJB11-045). A solution of 4-aminonicotinate (500 mg, 3.29 mmol) in dichloromethane (25.0 mL) and triethylamine (1.37 mL, 9.86 mmol) was treated at 0° C. with 2-ethoxybenzoyl chloride (607 mg, 3.29 mmol). The reaction mixture was stirred at 0° C. for 2 h and at room temperature for 2 h. The reaction mixture was concentrated and purified via silica gel chromatography using a gradient of 0-100% of EtOAc in hexanes to give 840 mg (85%) of the title product as a white solid which was used directly in the next reaction without further purification. LC-MS Retention Time: $t_2$ (Method 2)=2.975 min; m/z (M+H)$^+$ 301.1.

EXAMPLE 161

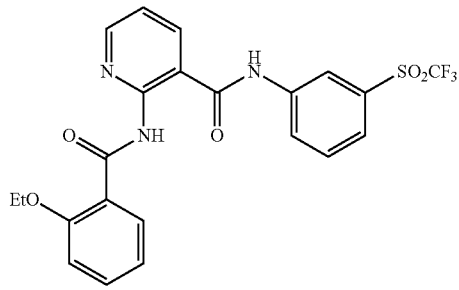

This example illustrates a synthesis of 2-(2-Ethoxybenzamido)-N-(3-((trifluoromethyl)sulfonyl)phenyl)nicotinamide (XJB11-050, NCGC00250118-01). The title compound was prepared according to general protocol A. LC-MS Retention Time: $t_1$ (Method 1)=5.472 min; $^1$H NMR (400 MHz, DMSO-$d_6$) δ ppm 10.98 (s, 1H), 10.81 (s, 1H), 8.47-8.66 (m, 2H), 8.05-8.24 (m, 2H), 7.75-7.87 (m, 2H), 7.72 (dd, J=7.8, 2.0 Hz, 1H), 7.51 (ddd, J=8.5, 7.1, 2.0 Hz, 1H), 7.39 (dd, J=7.6, 4.9 Hz, 1H), 7.20 (d, J=8.2 Hz, 1H), 7.00 (t, J=7.4 Hz, 1H), 4.27 (q, J=7.0 Hz, 2H), 1.42 (t, J=7.0 Hz, 3H); $^{19}$F NMR (376 MHz, DMSO-$d_6$) δ ppm −78.44 (s, 3F); HRMS (ESI) m/z (M+H)$^+$ calcd. for $C_{22}H_{19}F_3N_3O_5S$, 494.0992; found 494.1004.

EXAMPLE 162

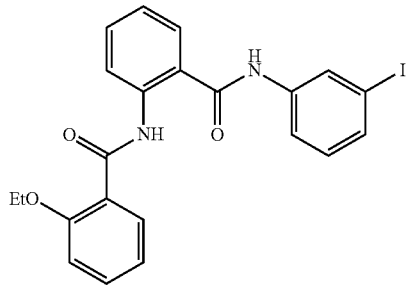 [SMILES: CCOc1ccccc1C(=O)Nc1ccccc1C(=O)Nc1cccc(I)c1]

This example illustrates a synthesis of 2-Ethoxy-N-(2-((3-iodophenyl)carbamoyl)phenyl)benzamide (XJB11-053, NCGC00250105-01). The title compound was prepared according to general protocol A. LC-MS Retention Time: $t_1$ (Method 1)=7.114 min; $^1$H NMR (400 MHz, DMSO-$d_6$) δ ppm 11.31 (s, 1H), 10.59 (s, 1H), 8.50 (d, J=8.2 Hz, 1H), 8.27 (t, J=2.0 Hz, 1H), 7.94 (dd, J=7.8, 2.0 Hz, 1H), 7.75 (dd, J=7.6, 1.8 Hz, 1H), 7.69 (dd, J=8.2, 2.3 Hz, 1H), 7.41-7.60 (m, 3H), 7.10-7.29 (m, 3H), 7.00-7.11 (m, 1H), 4.31 (q, J=7.0 Hz, 2H), 1.33 (t, J=7.0 Hz, 3H); HRMS (ESI) m/z (M+H)$^+$ calcd. for $C_{22}H_{20}IN_2O_3$, 487.0513; found 487.0514.

EXAMPLE 163

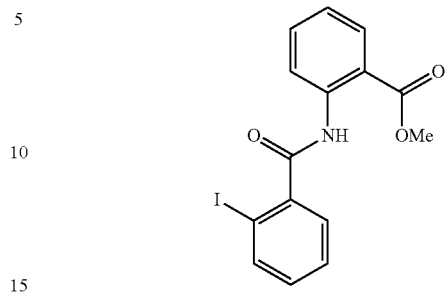

This example illustrates a synthesis of Methyl 2-(2-iodobenzamido)benzoate (XJB11-035). A solution of methyl 2-aminobenzoate (1.29 mL, 9.92 mmol) in dichloromethane (25.0 mL) and triethylamine (4.15 mL, 29.8 mmol) was treated at 0° C. with 2-iodobenzoyl chloride (2.64 g, 9.92 mmol).$^{22}$ The reaction mixture was stirred at 0° C. for 2 hours and at room temperature for another 2 hours. The reaction mixture was concentrated in vacuo and the crude residue was purified via silica gel chromatography using a gradient of 0-50% of EtOAc in hexanes to give 3.40 g (90%) of the title compound as a white solid. LC-MS Retention Time: $t_1$ (Method 1)=6.308 min; $t_2$ (Method 2)=3.744 min; $^1$H NMR (400 MHz, DMSO-$d_6$) δ ppm 10.97 (s, 1H), 8.33 (d, J=8.2 Hz, 1H), 7.87-8.01 (m, 2H), 7.63-7.73 (m, 1H), 7.46-7.62 (m, 2H), 7.13-7.33 (m, 2H), 3.82 (s, 3H); HRMS (ESI) m/z (M+H)$^+$ calcd. for $C_{15}H_{13}INO_3$, 381.9935; found 381.9943.

EXAMPLE 164

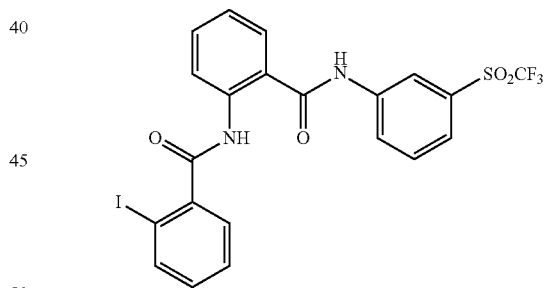

This example illustrates a synthesis of 2-Iodo-N-(2-(3-(trifluoromethylsulfonyl)phenylcarbamoyl)phenyl)benzamide (XJB11-054, NCGC00250120-01). A solution of methyl 2-(2-iodobenzamido)benzoate (500 mg, 1.31 mmol) in toluene (15.0 mL) was treated at room temperature with 3-(trifluoromethylsulfonyl)aniline (443 mg, 1.97 mmol) followed by trimethylaluminum (1.31 mL, 2.0 M in toluene, 2.62 mmol). The reaction mixture was stirred at 100° C. overnight. After cooling, the reaction mixture was concentrated in vacuo; and the crude residue was purified via silica gel chromatography using a gradient of 0-50% of EtOAc in hexanes to give 677 mg (90%) of the title compound as a white solid. LC-MS Retention Time: $t_1$ (Method 1)=6.816 min; $t_2$ (Method 2)=3.857 min; $^1$H NMR (400 MHz, DMSO-$d_6$) δ ppm 10.96 (s, 1H), 10.69 (s, 1H), 8.57 (s, 1H), 8.17-8.36 (m, 1H), 8.02 (d, J=7.8 Hz, 1H), 7.91 (d, J=7.8 Hz, 1H), 7.70-7.86 (m, 3H), 7.61 (t, J=7.4 Hz, 1H), 7.41-7.56 (m, 2H), 7.34 (t, J=7.6 Hz, 1H), 7.11-7.27 (m, 1H); $^{19}$F NMR (376 MHz, DMSO-d$_6$) δ ppm −78.38 (s, 3F); HRMS (ESI) m/z (M+H)$^+$ calcd. for $C_{21}H_{15}F_3IN_2O_4S$, 574.9744; found 574.9752.

EXAMPLE 165

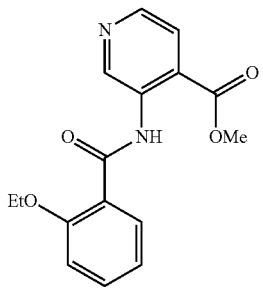 [SMILES: CCOc1ccccc1C(=O)Nc1cnccc1C(=O)OC]

This example illustrates a synthesis of Methyl 3-(2-ethoxybenzamido)isonicotinate (XJB11-046). A solution of methyl 3-aminoisonicotinate (200 mg, 1.31 mmol) in dichloromethane (25.0 mL) and triethylamine (0.550 mL, 3.94 mmol) was treated at 0° C. with 2-ethoxybenzoyl chloride (243 mg, 1.31 mmol). The reaction mixture was stirred at 0° C. for 2 h and at room temperature for 2 h. The reaction mixture was concentrated and purified via silica gel chromatography using a gradient of 0-100% of EtOAc in hexanes to give 45 mg (11%) of the title product as a white solid which was used directly in the next reaction without further purification.

EXAMPLE 166

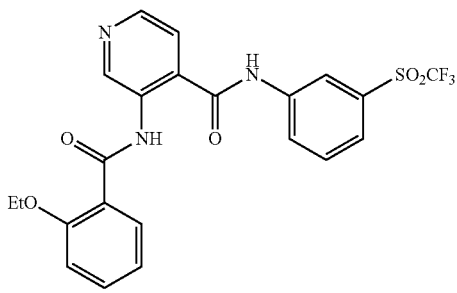

This example illustrates a synthesis of 3-(2-Ethoxybenzamido)-N-(3-((trifluoromethyl)sulfonyl)phenyl)isonicotinamide (XJB11-055, NCGC00250121-01). The title compound was prepared according to general protocol A. LC-MS Retention Time: t$_1$ (Method 1)=5.766 min; HRMS (ESI) m/z (M+H)$^+$ calcd. for $C_{22}H_{19}F_3N_3O_5S$, 494.0992; found 494.1000.

EXAMPLE 167

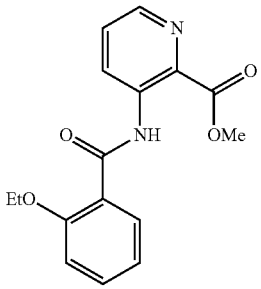 [SMILES: CCOc1ccccc1C(=O)Nc1cccnc1C(=O)OC]

This example illustrates a synthesis of Methyl 3-(2-ethoxybenzamido)picolinate (XJB11-056). A solution of methyl 3-aminopicolinate (500 mg, 3.29 mmol) in dichloromethane (25.0 mL) and triethylamine (1.37 mL, 9.86 mmol) was treated at 0° C. with 2-ethoxybenzoyl chloride (607 mg, 3.29 mmol). The reaction mixture was stirred at 0° C. for 2 h and at room temperature for 2 h. The reaction mixture was concentrated and purified via silica gel chromatography using a gradient of 0-100% of EtOAc in hexanes to give 741 mg (75%) of the title product as a white solid which was used directly in the next reaction without further purification. LC-MS Retention Time: t$_2$ (Method 2)=3.519 min; m/z (M+H)$^+$ 301.1.

EXAMPLE 168

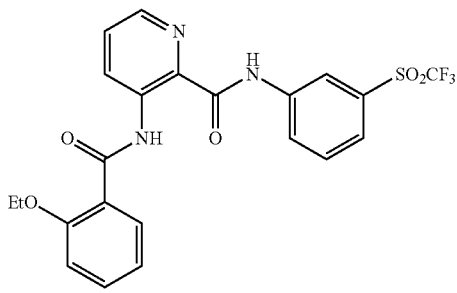

This example illustrates a synthesis of 2-(2-Ethoxybenzamido)-N-(3-((trifluoromethyl)sulfonyl)phenyl)nicotinamide (XJB11-058, NCGC00250122-01). The title compound was prepared according to general protocol A. LC-MS Retention Time: t$_1$ (Method 1)=7.402 min; HRMS (ESI) m/z (M+Na)$^+$ calcd. for $C_{22}H_{18}F_3N_3NaO_5S$, 516.0811; found 516.0837.

EXAMPLE 169

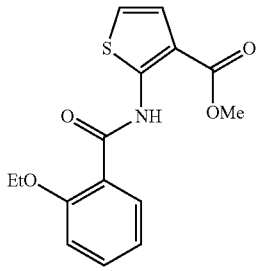 [SMILES: CCOc1ccccc1C(=O)Nc1sccc1C(=O)OC]

This example illustrates a synthesis of Methyl 2-(2-ethoxybenzamido)thiophene-3-carboxylate (XJB11-057). A solution of 2-aminothiophene-3-carboxylate (500 mg, 3.18 mmol) in dichloromethane (25.0 mL) and triethylamine (1.33 mL, 9.54 mmol) was treated at 0° C. with 2-ethoxybenzoyl chloride (587 mg, 3.18 mmol). The reaction mixture was stirred at 0° C. for 2 h and at room temperature for 2 h. The reaction mixture was concentrated and purified via silica gel chromatography using a gradient of 0-100% of EtOAc in hexanes to give 798 mg (82%) of the title product as a white solid which was used directly in the next reaction without further purification.

EXAMPLE 170

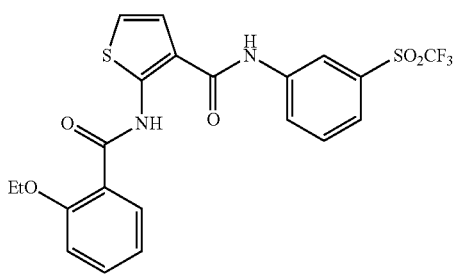

This example illustrates a synthesis of 2-(2-Ethoxybenzamido)-N-(3-((trifluoromethyl)sulfonyl)phenyl)thiophene-3-carboxamide (XJB11-059, NCGC00250123-01). The title compound was prepared according to general protocol A. LC-MS Retention Time: $t_1$ (Method 1)=7.341 min; HRMS (ESI) m/z (M+H)$^+$ calcd. for $C_{21}H_{18}F_3N_2O_5S_2$, 499.0604; found 499.0608.

EXAMPLE 171

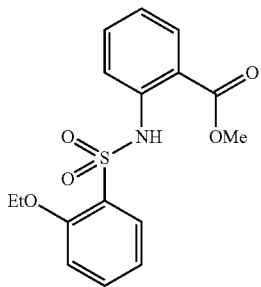 [SMILES: CCOc1ccccc1S(=O)(=O)Nc1ccccc1C(=O)OC]

This example illustrates a synthesis of Methyl 2-(2-ethoxyphenylsulfonamido)benzoate (XJB11-060). A solution of methyl 2-aminobenzoate (206 mg, 1.359 mmol) in dichloromethane (5.00 mL) and triethylamine (0.568 mL, 4.08 mmol) was treated at 0° C. with 2-ethoxybenzene-1-sulfonyl chloride (300 mg, 1.359 mmol). The reaction mixture was stirred at 0° C. for 2 h and at room temperature for 2 h. The reaction mixture was concentrated and purified via silica gel chromatography using a gradient of 0-100% of EtOAc in hexanes to give 274 mg (60%) of the title product as a white solid which was used directly in the next reaction without further purification. LC-MS Retention Time: $t_2$ (Method 2)=3.698 min; m/z (M+H)$^+$ 336.1.

EXAMPLE 172

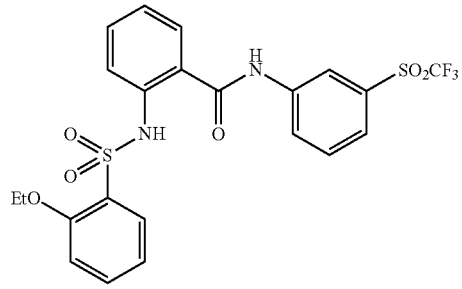

This example illustrates a synthesis of 2-(2-Ethoxyphenylsulfonamido)-N-(3-((trifluoromethyl)sulfonyl)phenyl)benzamide (XJB11-062, NCGC00250124-01). The title compound was prepared according to general protocol A. LC-MS Retention Time: $t_1$ (Method 1)=6.631 min; HRMS (ESI) m/z (M+H)$^+$ calcd. for $C_{22}H_{20}F_3N_2O_6S_2$, 529.0709; found 529.0716.

EXAMPLE 173

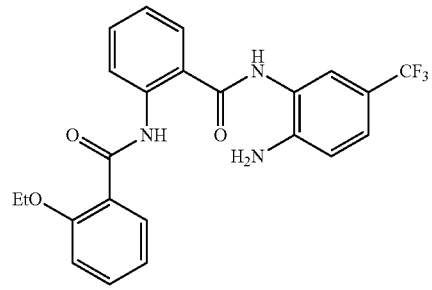 [SMILES: CCOc1ccccc1C(=O)Nc1ccccc1C(=O)Nc1cc(C(F)(F)F)ccc1N]

This example illustrates a synthesis of N-(2-amino-5-(trifluoromethyl)phenyl)-2-(2-ethoxybenzamido)benzamide (XJB11-063, NCGC00250125-01). The title compound was prepared according to general protocol A. LC-MS Retention Time: $t_1$ (Method 1)=6.408 min; $^1$H NMR (400 MHz, DMSO-$d_6$) δ ppm 11.43 (s, 1H), 9.89 (s, 1H), 8.48 (d, J=7.8 Hz, 1H), 7.88 (dd, J=7.8, 2.0 Hz, 2H), 7.53-7.61 (m, 1H), 7.49 (td, J=7.8, 2.0 Hz, 1H), 7.42 (d, J=7.8 Hz, 1H), 7.24 (t, J=7.6 Hz, 1H), 7.14 (d, J=8.2 Hz, 1H), 6.98-7.08 (m, 2H), 6.85 (dd, J=8.6, 2.3 Hz, 1H), 5.46 (s, 2H), 4.20 (q, J=6.9 Hz, 2H), 1.26 (t, J=6.8 Hz, 3H); $^{19}$F NMR (376 MHz, DMSO-$d_6$) δ ppm −60.99 (s, 3F); HRMS (ESI) m/z (M+H)$^+$ calcd. for $C_{23}H_{21}F_3N_3O_3$, 444.1530; found 444.1536.

EXAMPLE 174

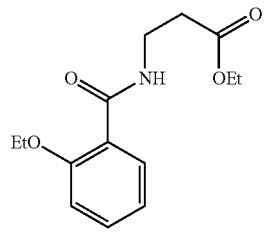

This example illustrates a synthesis of Ethyl 3-(2-ethoxybenzamido)propanoate (XJB11-061). A solution of ethyl 3-aminopropanoate, HCl salt (300 mg, 1.95 mmol) in dichloromethane (25.0 mL) and triethylamine (0.817 mL, 5.86 mmol) was treated at 0° C. with 2-ethoxybenzoyl chloride (361 mg, 1.95 mmol). The reaction mixture was stirred at 0° C. for 2 h and at room temperature for 2 h. The reaction mixture was concentrated and purified via silica gel chromatography using a gradient of 0-100% of EtOAc in hexanes to give 478 mg (92%) of the title product as a colorless oil which was used directly in the next reaction without further purification. LC-MS Retention Time: $t_2$ (Method 2)=3.346 min; m/z (M+H)$^+$ 266.1.

EXAMPLE 175

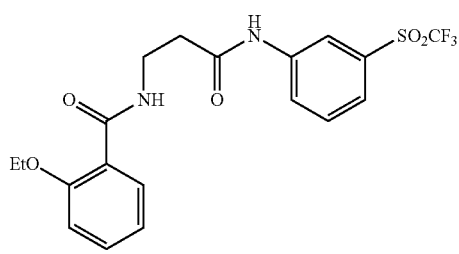

This example illustrates a synthesis of 2-Ethoxy-N-(3-oxo-3-((3-(((trifluoromethyl)sulfonyl)phenyl)amino)propyl)benzamide (XJB11-064, NCGC00250126-01, CID-56593338). The title compound was prepared according to general protocol A. LC-MS Retention Time: $t_1$ (Method 1)=5.985 min; $^1$H NMR (400 MHz, DMSO-d$_6$) δ ppm 10.62 (s, 1H), 8.62 (s, 1H), 8.39 (t, J=5.9 Hz, 1H), 7.93-8.07 (m, 1H), 7.82 (dd, J=7.8, 2.0 Hz, 1H), 7.78 (d, J=5.5 Hz, 2H), 7.38-7.48 (m, 1H), 7.08 (d, J=8.6 Hz, 1H), 6.96-7.04 (m, 1H), 4.09 (q, J=6.8 Hz, 2H), 3.61 (q, J=6.0 Hz, 2H), 2.68 (t, J=6.3 Hz, 2H), 1.29 (t, J=7.0 Hz, 3H); $^{19}$F NMR (376 MHz, DMSO-d$_6$) δ ppm −78.46 (s, 3F); HRMS (ESI) m/z (M+H)$^+$ calcd. for C$_{19}$H$_{20}$F$_3$N$_2$O$_5$S, 445.1040; found 445.1042.

EXAMPLE 176

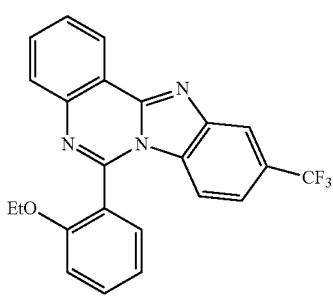

-continued

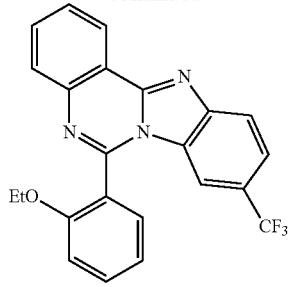

This example illustrates a synthesis of Mixture of 6-(2-ethoxyphenyl)-10-(trifluoromethyl)benzo[4,5]imidazo[1,2-c]quinazoline and 6-(2-ethoxyphenyl)-9-(trifluoromethyl)benzo[4,5]imidazo[1,2-c]quinazoline (XJB11-067-2, NCGC00250127-01). A solution of N-(2-amino-5-(trifluoromethyl)phenyl)-2-(2-ethoxybenzamido)benzamide (30.0 mg, 0.068 mmol) in glacial acetic acid (1.00 mL) was heated at 70° C. for 16 h. The mixture was concentrated, re-dissolved in 2.00 mL of DMSO, filtered and purified via C$_{18}$ reverse phase HPLC to give the final products as a mixture.

EXAMPLE 177

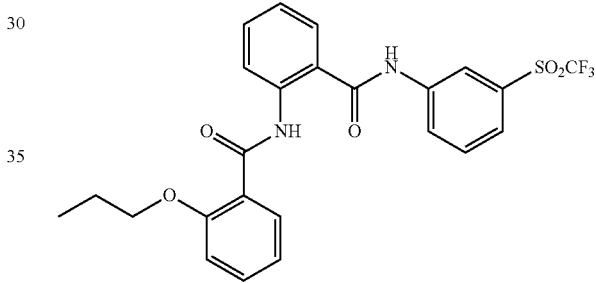

This example illustrates a synthesis of 2-Propoxy-N-(2-((3-(((trifluoromethyl)sulfonyl)phenyl)carbamoyl)phenyl)benzamide (XJB11-068, NCGC00250109-01, compound 179). The title compound was prepared according to general protocol H. LC-MS Retention Time: $t_1$ (Method 1)=7.147 min; HRMS (ESI) m/z (M+H)$^+$ calcd. for C$_{24}$H$_{22}$F$_3$N$_2$O$_5$S, 507.1196; found 507.1219.

EXAMPLE 178

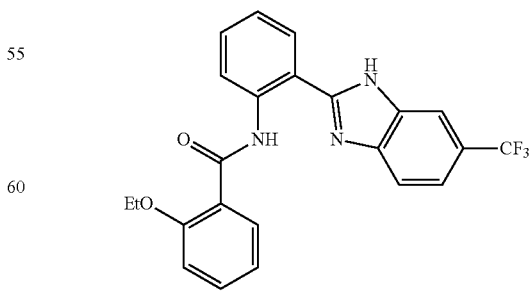

This example illustrates a synthesis of 2-Ethoxy-N-(2-(6-(trifluoromethyl)-1H- benzo[d]imidazol-2-yl)phenyl)benzamide (XJB11-069, NCGC00250108-01). A solution of N-(2-amino-5-(trifluoromethyl)phenyl)-2-(2-ethoxybenzamido)benzamide (30.0 mg, 0.068 mmol) in glacial acetic acid (1.00 mL) was stirred at room temperature for 24 h. The mixture was concentrated, re-dissolved in 2.00 mL of DMSO, filtered and purified via $C_{18}$ reverse phase HPLC to give the final products. LC-MS Retention Time: $t_1$ (Method 1)=6.588 min; HRMS (ESI) m/z (M+H)$^+$ calcd. for $C_{23}H_{19}F_3N_3O_2$, 426.1424; found 426.1437.

EXAMPLE 179

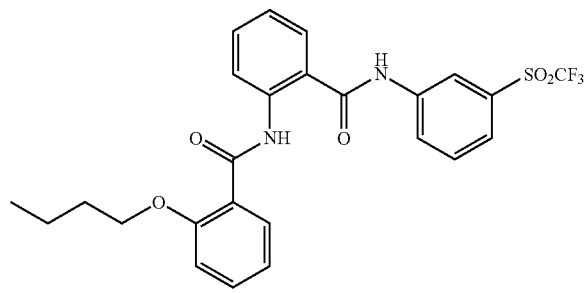

This example illustrates a synthesis of 2-Butoxy-N-(2-((3-((trifluoromethyl)sulfonyl)phenyl)carbamoyl)phenyl) benzamide (XJB11-070, NCGC00250110-01, compound 180). The title compound was prepared according to general protocol H. LC-MS Retention Time: $t_1$ (Method 1)=7.325 min; $t_2$ (Method 2)=3.971 min; $^1$H NMR (400 MHz, DMSO-$d_6$) δ ppm 11.25 (s, 1H), 11.09 (s, 1H), 8.69 (s, 1H), 8.53 (d, J=8.6 Hz, 1H), 8.24 (ddd, J=7.2, 2.2, 2.0 Hz, 1H), 7.91 (dd, J=7.8, 2.0 Hz, 1H), 7.77-7.89 (m, 3H), 7.60 (td, J=7.8, 1.6 Hz, 1H), 7.43-7.56 (m, 1H), 7.28 (td, J=7.5, 1.0 Hz, 1H), 7.20 (d, J=8.6 Hz, 1H), 7.00-7.11 (m, 1H), 4.18 (t, J=6.8 Hz, 2H), 1.54-1.75 (m, 2H), 1.21 (sxt, J=7.4 Hz, 2H), 0.69 (t, J=7.4 Hz, 3H); $^{19}$F NMR (376 MHz, DMSO-$d_6$) δ ppm −78.42 (s, 3F); HRMS (ESI) m/z (M+H)$^+$ calcd. for $C_{25}H_{24}F_3N_2O_5S$, 521.1353; found 521.1359.

EXAMPLE 180

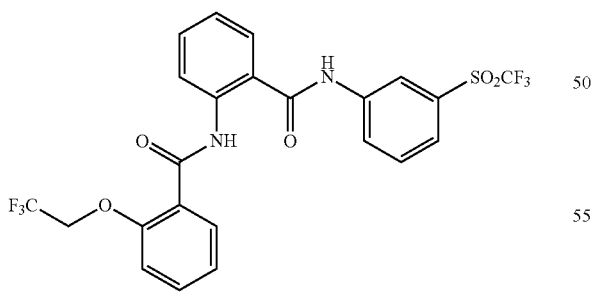

This example illustrates a synthesis of 2-(2,2,2-Trifluoroethoxy)-N-(2-((3-((trifluoromethyl)sulfonyl)phenyl)carbamoyl)phenyl)benzamide (XJB11-071, NCGC00250111-01, compound 177). The title compound was prepared according to general protocol H. LC-MS Retention Time: $t_1$ (Method 1)=6.804 min; $^1$H NMR (400 MHz, DMSO-$d_6$) δ ppm 11.07 (s, 1H), 11.03 (s, 1H), 8.61 (t, J=2.2 Hz, 1H), 8.41 (d, J=8.2 Hz, 1H), 8.19-8.33 (m, 1H), 7.70-7.94 (m, 4H), 7.58-7.67 (m, 1H), 7.47-7.58 (m, 1H), 7.35 (d, J=8.6 Hz, 1H), 7.26-7.33 (m, 1H), 7.17 (t, J=7.4 Hz, 1H), 4.92 (q, J=9.0 Hz, 2H); $^{19}$F NMR (376 MHz, DMSO-$d_6$) δ ppm −72.45 (s, 3F), −78.46 (s, 3F); HRMS (ESI) m/z (M+H)$^+$ calcd. for $C_{23}H_{17}F_6N_2O_5S$, 547.0757; found 547.0762.

EXAMPLE 181

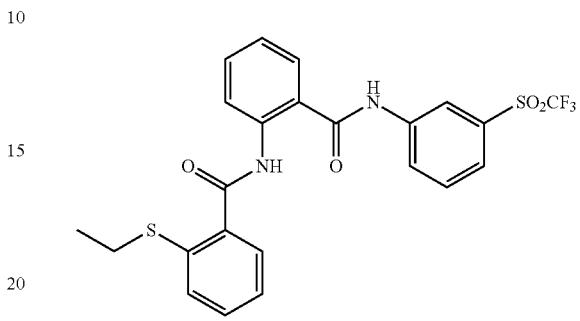

This example illustrates a synthesis of 2-(Ethylthio)-N-(2-((3-((trifluoromethyl)sulfonyl)phenyl)carbamoyl)phenyl)benzamide (XJB11-072, NCGC00250106-01, CID-56593341). A tube was charged with CuI (3.3 mg, 0.017 mmol), 1,10-phenanthroline (6.3 mg, 0.035 mmol), (56.7 mg, 0.174 mmol), 2-iodo-N-(2-(3-(trifluoromethylsulfonyl) phenylcarbamoyl)phenyl)benzamide (50.0 mg, 0.087 mmol) and ethanethiol (10.8 mg, 0.174 mmol) in toluene (1.50 mL) under $N_2$. The tube was sealed and the reaction mixture was stirred at 110° C. for 24 h. The resulting mixture was cooled to room temperature and treated with a small portion of Si-THIOL to get rid of copper. The mixture was concentrated, re-dissolved in 2.00 mL of DMSO, filtered and purified via $C_{18}$ reverse phase HPLC to give the final product. LC-MS Retention Time: $t_1$ (Method 1)=6.910 min; $^1$H NMR (400 MHz, DMSO-$d_6$) δ ppm 10.95 (s, 1H), 10.73 (s, 1H), 8.55 (s, 1H), 8.28 (dt, J=6.7, 2.0 Hz, 1H), 8.10 (d, J=7.8 Hz, 1H), 7.74-7.91 (m, 3H), 7.57-7.66 (m, 1H), 7.51-7.57 (m, 1H), 7.39-7.48 (m, 2H), 7.31 (td, J=7.6, 1.2 Hz, 1H), 7.24 (ddd, J=7.4, 4.9, 3.7 Hz, 1H), 2.90 (q, J=7.3 Hz, 2H), 1.13 (t, J=7.2 Hz, 3H); $^{19}$F NMR (376 MHz, DMSO-$d_6$) δ ppm −78.40 (s, 3F); HRMS (ESI) m/z (M+H)$^+$ calcd. for $C_{23}H_{20}F_3N_2O_4S_2$, 509.0811; found 509.0814.

EXAMPLE 182

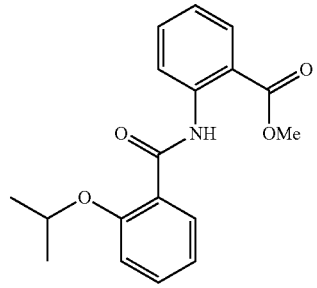 [SMILES: COC(=O)c1ccccc1NC(=O)c1ccccc1OC(C)C]

This example illustrates a synthesis of Methyl 2-(2-isopropoxybenzamido)benzoate (XJB12-040). A solution of methyl 2-aminobenzoate (0.245 mL, 1.89 mmol) in dichloromethane (8.00 mL) and triethylamine (0.53 mL, 3.78 mmol) was treated at 0° C. with 2-isopropoxybenzoyl chloride (250 mg, 1.26 mmol). The reaction mixture was stirred at 0° C. for 2 hours and then at room temperature for another 2 hours. The reaction mixture was concentrated in vacuo and the crude residue was purified via silica gel chromatography using a gradient of 0-50% of EtOAc in hexanes to give 320 mg (81%) of the title compound as a colorless oil. LC-MS Retention Time: $t_1$ (Method 1)=6.576 min; $t_2$ (Method 2)=3.825 min; $^1$H NMR (400 MHz, DMSO-$d_6$) δ ppm 11.59 (s, 1H), 8.63 (d, J=8.6 Hz, 1H), 7.98 (dd, J=7.8, 1.6 Hz, 1H), 7.83 (dd, J=7.8, 2.0 Hz, 1H), 7.64 (ddd, J=8.5, 7.1, 1.6 Hz, 1H), 7.45-7.56 (m, 1H), 7.13-7.27 (m, 2H), 6.94-7.09 (m, 1H), 4.82 (dq, J=6.3, 6.0 Hz, 1H), 3.85 (s, 3H), 1.35 (d, J=5.9 Hz, 6H); HRMS (ESI) m/z (M+H)$^+$ calcd. for $C_{18}H_{20}NO_4$, 314.1387; found 314.1399.

EXAMPLE 183

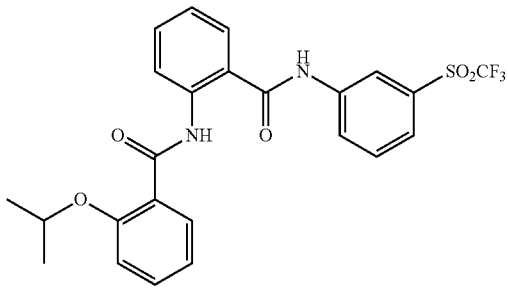

This example illustrates a synthesis of 2-Isopropoxy-N-(2-(3-(trifluoromethylsulfonyl)phenylcarbamoyl)phenyl)benzamide (XJB11-073, NCGC00250135-01, compound 178). A µW tube was charged with copper (I) iodide (3.3 mg, 0.017 mmol), 1,10-phenanthroline (6.3 mg, 0.035 mmol), cesium carbonate (56.7 mg, 0.174 mmol), 2-iodo-N-(2-(3-(trifluoromethylsulfonyl)phenylcarbamoyl)phenyl)benzamide (50.0 mg, 0.087 mmol), propan-2-ol (10.5 mg, 0.174 mmol), and dry toluene (1.50 mL). The tube was sealed, and the reaction mixture was stirred at 110° C. for overnight. The resulting suspension was cooled to room temperature and treated with Si-Thio. The reaction mixture was filtered and concentrated in vacuo to give an orange oil that was taken up in 1.5 mL of DMSO and purified via $C_{18}$ reverse phase HPLC to give 1.7 mg (4%) of the title compound as a white solid. LC-MS Retention Time: $t_1$ (Method 1)=6.974 min; $t_2$ (Method 2)=3.881 min; $^1$H NMR (400 MHz, DMSO-$d_6$) δ ppm 11.08 (br. s., 1H), 11.07 (s, 1H), 8.73 (s, 1H), 8.46 (d, J=8.2 Hz, 1H), 8.18 (dt, J=7.4, 2.0 Hz, 1H), 7.89 (dd, J=7.8, 1.6 Hz, 1H), 7.77-7.87 (m, 3H), 7.57-7.63 (m, 1H), 7.49 (ddd, J=8.7, 7.1, 1.8 Hz, 1H), 7.28 (td, J=7.5, 1.0 Hz, 1H), 7.19 (d, J=8.2 Hz, 1H), 7.03 (t, J=7.6 Hz, 1H), 4.79 (m, 1H), 1.31 (d, 6H); $^{19}$F NMR (376 MHz, DMSO-$d_6$) d ppm −78.36 (s, 3F); HRMS (ESI) m/z (M+H)$^+$ calcd. for $C_{24}H_{22}F_3N_2O_5S$, 507.1196; found 507.1221.

Or a solution of methyl 2-(2-isopropoxybenzamido)benzoate (110 mg, 0.351 mmol) in toluene (4.00 mL) was treated with 3-(trifluoromethylsulfonyl)aniline (119 mg, 0.527 mmol) at room temperature, followed by trimethylaluminum (0.503 mL, 2.0 M in toluene, 1.06 mmol). The reaction mixture was stirred at 100° C. for overnight. After cooling, the reaction mixture was concentrated in vacuo; and the crude residue was purified via silica gel chromatography using a gradient of 0-80% of EtOAc in hexanes to give 130 mg (73%) of the title compound as a white solid.

EXAMPLE 184

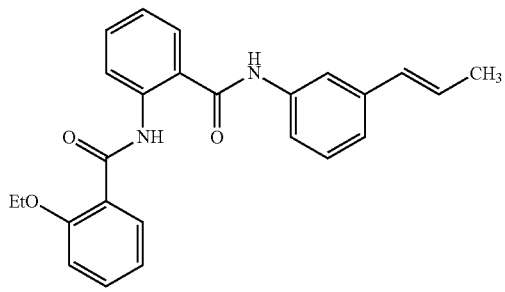 [SMILES: C/C=C/c1cccc(NC(=O)c2ccccc2NC(=O)c2ccccc2OCC)c1]

This example illustrates a synthesis of (E)-2-Ethoxy-N-(2-((3-(prop-1-en-1-yl)phenyl)carbamoyl)phenyl)benzamide (XJB11-074, NCGC00250131-01). A mixture of 2-ethoxy-N-(2-(3-iodophenylcarbamoyl)phenyl)benzamide (50.0 mg, 0.103 mmol), (E)-prop-1-enylboronic acid (13.3 mg, 0.154 mmol) and Pd(PPh$_3$)$_4$ (5.9 mg, 5.14 µmol) in DMF (1.50 mL) and 2.0 N Na$_2$CO$_3$ (0.500 mL) aqueous solution was heated in µW at 100° C. for 30 min. The reaction was cooled to room temperature, added a small portion of Si-THIOL to get rid of Palladium. The mixture was filtered and purified via $C_{18}$ reverse phase HPLC to give the final product. LC-MS Retention Time: $t_1$ (Method 1)=7.093 min; $^1$H NMR (400 MHz, DMSO-$d_6$) δ ppm 11.35 (s, 1H), 10.48 (s, 1H), 8.51 (d, J=8.2 Hz, 1H), 7.93 (dd, J=7.8, 2.0 Hz, 1H), 7.70-7.82 (m, 2H), 7.42-7.63 (m, 3H), 7.21-7.33 (m, 2H), 7.18 (d, J=8.6 Hz, 1H), 7.12 (d, J=7.8 Hz, 1H), 7.06 (t, J=7.4 Hz, 1H), 6.33-6.46 (m, 1H), 6.16-6.32 (m, 1H), 4.28 (q, J=7.0 Hz, 2H), 1.84 (dd, J=6.7, 1.6 Hz, 3H), 1.30 (t, J=7.0 Hz, 3H); HRMS (ESI) m/z (M+H)$^+$ calcd. for $C_{25}H_{25}N_2O_3$, 401.1860; found 401.1859.

EXAMPLE 185

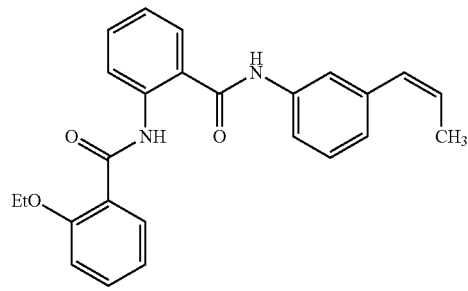 [SMILES: C/C=C\c1cccc(NC(=O)c2ccccc2NC(=O)c2ccccc2OCC)c1]

This example illustrates a synthesis of (Z)-2-Ethoxy-N-(2-((3-(prop-1-en-1-yl)phenyl)carbamoyl)phenyl)benzamide (XJB11-075, NCGC00250132-01). A mixture of 2-ethoxy-N-(2-(3-iodophenylcarbamoyl)phenyl)benzamide (50.0 mg, 0.103 mmol), (Z)-prop-1-enylboronic acid (13.3 mg, 0.154 mmol) and Pd(PPh$_3$)$_4$ (5.9 mg, 5.14 µmol) in DMF (1.50 mL) and 2.0 N Na$_2$CO$_3$ (0.500 mL) aqueous solution was heated in µW at 100° C. for 30 min. The reaction was cooled to room temperature, added a small portion of Si-THIOL to get rid of Palladium. The mixture was filtered and purified via $C_{18}$ reverse phase HPLC to give the final product. LC-MS Retention Time: $t_1$ (Method 1)=7.100 min; $^1$H NMR (400 MHz, DMSO-$d_6$) δ ppm 11.33 (s, 1H), 10.52 (s, 1H), 8.50 (d, J=8.2 Hz, 1H), 7.93 (dd, J=7.8, 2.0 Hz, 1H), 7.71-7.80 (m, 2H), 7.59-7.64 (m, 1H), 7.53-7.59 (m, 1H), 7.51 (ddd, J=8.5, 7.1, 2.0 Hz, 1H), 7.32 (t, J=7.8 Hz, 1H), 7.25 (t, J=7.8 Hz, 1H), 7.18 (d, J=8.6 Hz, 1H), 7.00-7.10 (m, 2H), 6.39 (dd, J=11.7, 2.3 Hz, 1H), 5.60-5.92 (m, 1H), 4.27 (q, J=6.9 Hz, 2H), 1.86 (dd, J=7.4, 2.0 Hz, 3H), 1.30 (t, J=6.8 Hz, 3H); HRMS (ESI) m/z (M+H)$^+$ calcd. for $C_{25}H_{25}N_2O_3$, 401.1860; found 401.1862.

EXAMPLE 186

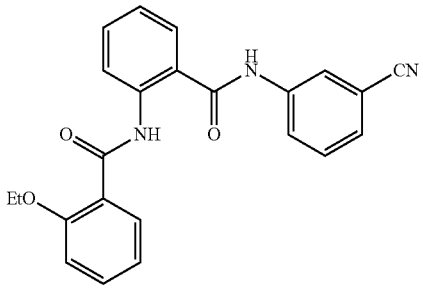 [SMILES: CCOc1ccccc1C(=O)Nc1ccccc1C(=O)Nc1cccc(C#N)c1]

This example illustrates a synthesis of N-(3-Cyanophenyl)-2-(2-ethoxybenzamido)benzamide (XJB11-080, NCGC00250133-01). The title compound was prepared according to general protocol A. LC-MS Retention Time: $t_1$ (Method 1)=6.342 min; $^1$H NMR (400 MHz, DMSO-$d_6$) δ ppm 11.28 (s, 1H), 10.83 (s, 1H), 8.49 (d, J=7.8 Hz, 1H), 8.22 (t, J=1.6 Hz, 1H), 7.95-8.04 (m, 1H), 7.93 (dd, J=7.8, 2.0 Hz, 1H), 7.78 (dd, J=7.8, 2.0 Hz, 1H), 7.54-7.63 (m, 3H), 7.51 (ddd, J=8.5, 7.1, 2.0 Hz, 1H), 7.23-7.33 (m, 1H), 7.19 (d, J=8.2 Hz, 1H), 7.00-7.13 (m, 1H), 4.29 (q, J=7.0 Hz, 2H), 1.30 (t, J=7.0 Hz, 3H); HRMS (ESI) m/z (M+H)$^+$ calcd. for $C_{23}H_{20}N_3O_3$, 386.1499; found 386.1515.

EXAMPLE 187

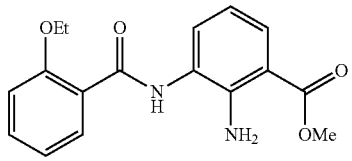 [SMILES: CCOc1ccccc1C(=O)Nc1cccc(C(=O)OC)c1N]

This example illustrates a synthesis of Methyl 2-amino-3-(2-ethoxybenzamido)benzoate (XJB11-082). A solution of 2,3-diaminobenzoate (100 mg, 0.602 mmol) in dichloromethane (5.00 mL) and TEA (0.252 mL, 1.81 mmol) was treated at 0° C. with 2-ethoxybenzoyl chloride (111 mg, 0.602 mmol). The reaction mixture was stirred at 0° C. for 1 h. The reaction mixture was concentrated in vacuo and the crude material was used directly in the next reaction.

EXAMPLE 188

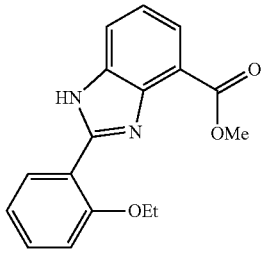 [SMILES: CCOc1ccccc1-c1nc2c(C(=O)OC)cccc2[nH]1]

This example illustrates a synthesis of Methyl 2-(2-ethoxyphenyl)-1H-benzo[d]imidazole-4-carboxylate (XJB11-083). A solution of methyl crude 2-amino-3-(2-ethoxybenzamido)benzoate (189 mg, 0.602 mmol) in glacial acetic acid (3.00 mL) was heated at 70° C. for 24 h. The reaction mixture was concentrated in vacuo; and the crude residue was purified via silica gel chromatography using a gradient of 0-20% of MeOH in dichloromethane to give 165 mg (92%) of the title compound as a white solid. LC-MS Retention Time: $t_2$ (Method 2)=3.088 min; m/z (M+H)$^+$ 297.1.

EXAMPLE 189

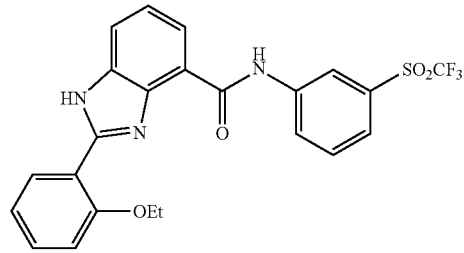

This example illustrates a synthesis of 2-(2-Ethoxyphenyl)-N-(3-((trifluoromethyl)sulfonyl)phenyl)-1H-benzo[d]imidazole-4-carboxamide (XJB11-086, NCGC00250115-01). The title compound was prepared according to general protocol A. LC-MS Retention Time: $t_1$ (Method 1)=6.265 min; HRMS (ESI) m/z (M+H)$^+$ calcd. for $C_{23}H_{19}F_3N_3O_4S$, 490.1043; found 490.1049.

EXAMPLE 190

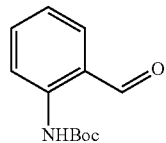 [SMILES: CC(C)(C)OC(=O)Nc1ccccc1C=O]

This example illustrates a synthesis of tert-Butyl (2-formylphenyl)carbamate (XJB11-088). A solution of tert-butyl 2-(hydroxymethyl)phenylcarbamate (0.370 g, 1.66 mmol) and Dess-Martin Periodinane (0.914 g, 2.15 mmol) in dichloromethane (15.0 mL) was stirred at 0° C. for 1 h. The reaction mixture was concentrated and the crude residue was purified via silica gel chromatography using 10% of EtOAc in hexanes to give 300 mg (82%) of the title compound as a colorless oil.

EXAMPLE 191

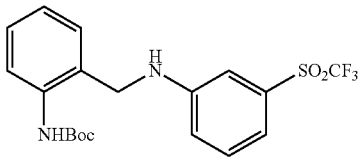

This example illustrates a synthesis of tert-Butyl (2-(((3-((trifluoromethyl)sulfonyl)phenyl)amino)methyl)phenyl)carbamate (XJB11-090). A mixture of tert-butyl 2-formylphenylcarbamate (80.0 mg, 0.362 mmol) and 3-(trifluoromethylsulfonyl)aniline (122 mg, 0.542 mmol) in MeOH (2.00 ml) was treated with Ti(O$^i$Pr)$_4$ (0.212 mL, 0.723 mmol). The reaction was stirred at room temperature for 6 h, then treated with NaBH$_4$ (20.5 mg, 0.542 mmol) and stirred overnight at room temperature. The reaction mixture was poured into 2N NH$_4$OH aqueous solution, the resulting inorganic precipitate was filtered off, and the filtrate was extracted with EtOAc. The organic layer was separated, dried and concentrated to give the final product as a colorless oil which was used directly in the next reaction. LC-MS Retention Time: t$_2$ (Method 2)=3.869 min; m/z (M+H)$^+$ 431.1.

EXAMPLE 192

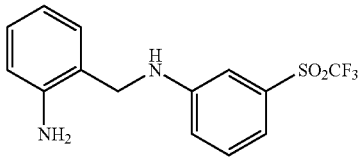

This example illustrates a synthesis of N-(2-Aminobenzyl)-3-((trifluoromethyl)sulfonyl)aniline (XJB11-091). A solution of tert-butyl 2-((3-(trifluoromethylsulfonyl)phenylamino)methyl)phenylcarbamate (0.156 g, 0.362 mmol) in dichloromethane (2.00 mL) was treated at 0° C. with TFA (2.00 mL, 26.0 mmol). The reaction mixture was stirred at room temperature for 1 h. The mixture was concentrated to give the final product which was used directly in the next reaction.

EXAMPLE 193

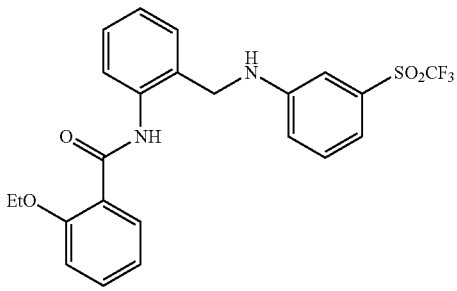

This example illustrates a synthesis of 2-Ethoxy-N-(2-(((3-((trifluoromethyl)sulfonyl)phenyl)amino)methyl)phenyl)benzamide (XJB11-097, NCGC00250112-01). A solution of N-(2-aminobenzyl)-3-(trifluoromethylsulfonyl)aniline (0.060 g, 0.181 mmol) in dichloromethane (2.00 mL) and TEA (0.075 mL, 0.535 mmol) was treated at 0° C. with 2-ethoxybenzoyl chloride (0.033 g, 0.181 mmol). The reaction mixture was stirred overnight at room temperature for 2 h. The mixture was concentrated, re-dissolved in 2.00 mL of DMSO, filtered and purified via C$_{18}$ reverse phase HPLC to give the final product. LC-MS Retention Time: t$_1$ (Method 1)=6.813 min; HRMS (ESI) m/z (M+H)' calcd. for C$_{23}$H$_{22}$F$_3$N$_2$O$_4$S, 479.1247; found 479.1249.

EXAMPLE 194

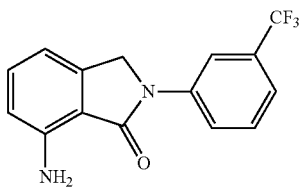 [SMILES: Nc1cccc2c1C(=O)N(c1cccc(C(F)(F)F)c1)C2]

This example illustrates a synthesis of 7-Amino-2-(3-(trifluoromethyl)phenyl)isoindolin-1-one (XJB11-098). A mixture of 7-aminoisoindolin-1-one (80.0 mg, 0.540 mmol), 1-iodo-3-(trifluoromethyl)benzene (176 mg, 0.648 mmol), (1S,2S)—N1,N2-dimethylcyclohexane-1,2-diamine (0.017 mL, 0.108 mmol), CuI (5.1 mg, 0.027 mmol) and K$_2$CO$_3$ (149 mg, 1.08 mmol) in toluene (3.00 mL) was stirred overnight at 110° C. The reaction mixture was concentrated and the crude residue was purified via silica gel chromatography using a gradient of 0-100% of EtOAc in hexanes to give 39.0 mg (25%) of the title compound as a white solid. LC-MS Retention Time: t$_2$ (Method 2)=3.736 min; m/z (M+H)$^+$ 293.1.

EXAMPLE 195

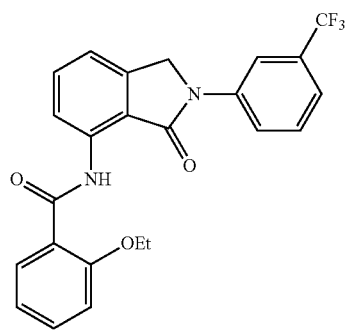 [SMILES: CCOc1ccccc1C(=O)Nc1cccc2c1C(=O)N(c1cccc(C(F)(F)F)c1)C2]

This example illustrates a synthesis of 2-Ethoxy-N-(3-oxo-2-(3-(trifluoromethyl)phenyl)isoindolin-4-yl)benzamide (XJB12-002, NCGC00250113-01). A solution of 7-amino-2-(3-(trifluoromethyl)phenyl)isoindolin-1-one (18.0 mg, 0.062 mmol) in dichloromethane (1.00 mL) and TEA (0.026 mL, 0.185 mmol) was treated at 0° C. with 2-ethoxybenzoyl chloride (17.1 mg, 0.092 mmol). The reaction mixture was stirred overnight at room temperature for 2 h. The mixture was concentrated, re-dissolved in 2.00 mL of DMSO, filtered and purified via $C_{18}$ reverse phase HPLC to give the final product. LC-MS Retention Time: $t_1$ (Method 1)=7.538 min; $^1$H NMR (400 MHz, DMSO-$d_6$) δ ppm 12.04 (s, 1H), 8.98 (d, J=8.2 Hz, 1H), 8.76 (s, 1H), 8.35 (dd, J=8.2, 2.7 Hz, 1H), 8.27 (dd, J=7.8, 2.0 Hz, 1H), 7.93-8.05 (m, 2H), 7.79-7.92 (m, 2H), 7.65 (d, J=7.8 Hz, 1H), 7.57 (d, J=8.2 Hz, 1H), 7.35-7.50 (m, 1H), 5.41 (s, 2H), 4.72 (q, J=6.8 Hz, 2H), 1.68-1.82 (t, J=7.2 Hz, 3H); $^{19}$F NMR (376 MHz, DMSO-$d_6$) δ ppm −61.34 (s, 3F); HRMS (ESI) m/z (M-FH)$^+$ calcd. for $C_{24}H_{20}F_3N_2O_3$, 441.1421; found 441.1429.

EXAMPLE 196

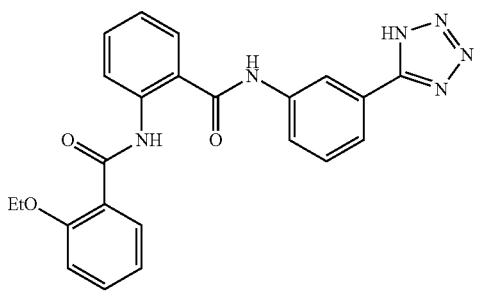 [SMILES: CCOc1ccccc1C(=O)Nc1ccccc1C(=O)Nc1cccc(-c2nnn[nH]2)c1]

This example illustrates a synthesis of N-(3-(1H-tetrazol-5-yl)phenyl)-2-(2-ethoxybenzamido)benzamide (XJB12-006, NCGC00250114-01). A solution of N-(3-cyanophenyl)-2-(2-ethoxybenzamido)benzamide (0.066 g, 0.171 mmol) in water (1.00 mL) was treated at room temperature with ZnBr$_2$ (0.058 g, 0.257 mmol) and NaN$_3$ (0.033 g, 0.513 mmol). The pH value of the solution was adjusted to ~7 by several drops of 1 N NaOH aqueous solution. The reaction mixture was heated at 120° C. for 60 hours. Another aliquot of reagents was added and the mixture was heated at 120° C. for an additional 24 h. The reaction mixture filtered and purified via $C_{18}$ reverse phase HPLC to give two products NCGC00250114-01 and NCGC00250134-01. LC-MS Retention Time: $t_1$ (Method 1)=5.547 min; $^1$H NMR (400 MHz, DMSO-$d_6$) δ ppm 11.36 (s, 1H), 10.77 (s, 1H), 8.61 (t, J=2.0 Hz, 1H), 8.52 (d, J=8.2 Hz, 1H), 7.93 (dd, J=7.8, 2.0 Hz, 1H), 7.85-7.91 (m, 1H), 7.81 (dd, J=7.8, 1.6 Hz, 1H), 7.74 (d, J=7.8 Hz, 1H), 7.53-7.63 (m, 2H), 7.50 (ddd, J=8.6, 7.0, 2.0 Hz, 1H), 7.23-7.31 (m, 1H), 7.18 (d, J=8.2 Hz, 1H), 7.01-7.10 (m, 1H), 4.30 (q, J=7.0 Hz, 2H), 1.28 (t, J=7.0 Hz, 3H); HRMS (ESI) m/z (M+H)$^+$ calcd. for $C_{23}H_{21}N_6O_3$, 429.1670; found 429.1673.

EXAMPLE 197

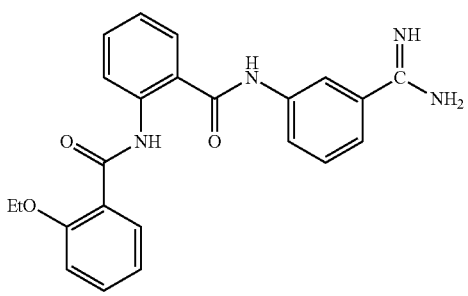 [SMILES: CCOc1ccccc1C(=O)Nc1ccccc1C(=O)Nc1cccc(C(=N)N)c1]

This example illustrates a synthesis of N-(3-Carbamimidoylphenyl)-2-(2-ethoxybenzamido)benzamide (XJB12-008, NCGC00250116-01). A suspension of ammonium chloride (267 mg, 5.00 mmol) in benzene (5.00 mL) at 5° C., was slowly added a trimethylaluminum (2.0 M in toluene, 2.50 mL, 5.00 mmol). After the addition was completed, the reaction mixture was allowed to warm to room temperature and was stirred for 1-2 hours until gas evolution has ceased. The solution was ready to use. 0.394 mL of above in situ solution was added to another solution of N-(3-cyanophenyl)-2-(2-ethoxybenzamido)benzamide (50.0 mg, 0.130 mmol) in toluene (1.00 mL) at room temperature. The reaction mixture was heated under argon at 80° C. for 4 h. The reaction mixture was filtered through a pad of celite and concentrated as a yellow oil. The crude material was re-dissolved in 2.00 mL of DMSO, filtered and purified via $C_{18}$ reverse phase HPLC to give the final product. LC-MS Retention Time: $t_1$ (Method 1)=4.349 min; $^1$H NMR (400 MHz, DMSO-$d_6$) δ ppm 11.36 (s, 1H), 10.78 (s, 1H), 8.58-8.64 (m, 1H), 8.52 (d, J=8.2 Hz, 1H), 7.93 (dd, J=7.6, 2.2 Hz, 1H), 7.87 (dd, J=8.2, 2.7 Hz, 1H), 7.81 (dd, J=7.8, 2.0 Hz, 1H), 7.74 (d, J=7.4 Hz, 1H), 7.53-7.62 (m, 2H), 7.50 (ddd, J=8.6, 7.0, 2.0 Hz, 1H), 7.24-7.32 (m, 1H), 7.18 (d, J=8.2 Hz, 1H), 7.06 (t, J=7.6 Hz, 1H), 4.30 (q, J=7.0 Hz, 2H), 1.28 (t, J=6.8 Hz, 3H) (3 N—H protons didn☐t show up); HRMS (ESI) m/z (M+H)$^+$ calcd. for $C_{23}H_{23}N_4O_3$, 403.1765; found 403.1766.

EXAMPLE 198

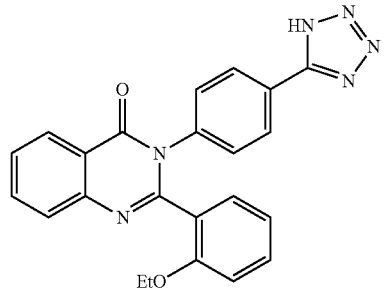 [SMILES: CCOc1ccccc1-c1nc2ccccc2c(=O)n1-c1ccc(-c2nnn[nH]2)cc1]

This example illustrates a synthesis of 3-(4-(1H-Tetrazol-5-yl)phenyl)-2-(2-ethoxyphenyl)quinazolin-4(3H)-one (XJB12-010, NCGC00250134-01). The title compound was prepared as a by-product of synthesizing N-(3-(1H-tetrazol-5-yl)phenyl)-2-(2-ethoxybenzamido)benzamide (XJB12-006, NCGC00250114-01). LC-MS Retention Time: $t_1$ (Method 1)=5.100 min; HRMS (ESI) m/z (M+H)$^+$ calcd. for $C_{23}H_{19}N_6O_2$, 411.1564; found 411.1569.

EXAMPLE 199

This example demonstrates activation of the RXFP1 receptor resulting in stimulation of cAMP production by several embodiments of the disclosure in the RXFP1 cAMP assay in HEK293-RXFP1 cells The RXFP1 receptor couples to the Gs protein, and activation of the receptor results in stimulation of cAMP production. To screen for agonists of the receptor, RXFP1 was stably expressed in human embryonic kidney cells (HEK293-RXFP1), which have previously been show to constitute a functional cell-based model for RXFP1-cAMP signaling pathway.[16,17] Cyclic AMP levels were detected using the HTRF cAMP assay kit.[18] This assay uses a europium cryptate labeled anti-cAMP antibody (K-α-cAMP) and d2 dye labeled cAMP (cAMP-d2) as a tracer in a time-resolved fluorescence energy transfer (TR-FRET) detection system. The TR-FRET between the K-α-cAMP and cAMP-d2 is disrupted by cAMP in the cell lysates, thus allowing TR-FRET detection in a homogenous format that is suitable for HTS. The assay was carried out in the presence of a phosphodiesterase 4 (PDE4) inhibitor, Ro 20-1724, to amplify cAMP signal. The primary screen was carried out in 1536-well format, however, because of a more robust signal to background ratio, all subsequent follow-up experiments were carried out in 384-well format.

For the primary screen, HEK293-RXFP1 cells were seeded at 2,000 cells/well in 3 µL/well media with a MultiDrop Combi dispenser (Thermo Scientific, Logan, Utah), and allowed to attach overnight at 37° C., 5% $CO_2$. Next, 1 µL/well of 400 µM Ro 20-1724 in PBS was added, followed by addition of 23 nL/well of compound solution in DMSO with a pintool transfer (Kalypsys, San Diego, Calif.). The cells were allowed to be stimulated with the compounds for 30 minutes at 37° C., 5% $CO_2$, after which, 1 µL/well of each HTRF detection reagent was dispensed with a Bio-RAPTR FRD dispenser. The detection reagents were diluted before addition as follows: K-α-cAMP antibody at 1:20 and cAMP-d2 at 1:18 in HTRF lysis buffer (supplied by the assay kit). The plates were incubated for 30 minute at room temperature, and then the signal was read on a ViewLux plate reader (PerkinElmer, Waltham, Mass.).

The assay was run according to the following protocol:

| Sequence | Parameter | Value | Description |
|---|---|---|---|
| 1 | Cells | 3 µL | 2,000 cells/well |
| 2 | Time | 16-24 h | Incubate at 37° C. and 5% $CO_2$ |
| 3 | Reagent | 1 µL | 400 µM Ro 20-1724 in PBS |
| 4 | Reagent | 23 nL | Compound library, forskolin as control |
| 5 | Time | 30 min | Incubate at 37° C. and 5% $CO_2$ |
| 6 | Reagent | 1 µL | cAMP-d2 diluted 1:18 in lysis buffer |
| 7 | Reagent | 1 µL | K-α-cAMP diluted 1:20 in lysis buffer |
| 8 | Time | 30 min | Room temperature incubation |
| 9 | Detector | TR-FRET | ViewLux plate reader |

The results are set forth in Tables 1-7, wherein $AC_{50}$ (µM) indicates the potency of the compound in micromolar, or more specifically the concentration at which the compound activates the functional activity of the receptor by its half-maximal amount. Max Response indicates what the maximal amount of functional activity induced by the compound is, as a percentage of the maximal receptor activation induced by high concentrations of forskolin.

TABLE 1

| # | $NHR_2$ | RXFP1 $AC_{50}$ (µM) | Max Response |
|---|---|---|---|
| 1 | NH-(3-CF₃-phenyl) | 1.88 | 92% |
| 2 | NH-phenyl | 94.0 | 57% |
| 3 | NH-(2-methylphenyl) | inactive | N/A |
| 4 | NH-(3-methylphenyl) | 37.4 | 65% |
| 5 | NH-(4-methylphenyl) | 187 | 32% |
| 6 | NH-(4-CF₃-phenyl) | 94.0 | 46% |
| 7 | NH-(3-tert-butylphenyl) | 2.65 | 70% |
| 8 | NH-(3,5-di-tert-butylphenyl) | inactive | N/A |
| 9 | NH-(3-methoxyphenyl) | 37.4 | 74% |

TABLE 1-continued

Core structure: cyclohexane-C(=O)-NH-(2-substituted phenyl)-C(=O)-NHR₂

| # | NHR₂ | RXFP1 AC₅₀ (μM) | Max Response |
|---|---|---|---|
| 10 | NH-(4-methoxyphenyl) | inactive | N/A |
| 11 | NH-(2-fluorophenyl) | inactive | N/A |
| 12 | NH-(3-fluorophenyl) | 13.3 | 81% |
| 13 | NH-(4-fluorophenyl) | 37.4 | 74% |
| 14 | NH-(2-bromophenyl) | inactive | N/A |
| 15 | NH-(3-bromophenyl) | 2.65 | 91% |
| 16 | NH-(4-bromophenyl) | 118 | 50% |
| 17 | NH-(2-nitrophenyl) | inactive | N/A |
| 18 | NH-(3-nitrophenyl) | 5.93 | 93% |
| 19 | NH-(4-nitrophenyl) | 74.7 | 56% |
| 20 | NH-(3-isopropylphenyl) | 5.29 | 66% |
| 21 | NH-(3-ethynylphenyl) | 6.66 | 85% |
| 22 | NH-(3-phenylphenyl) | inactive | N/A |
| 23 | NH-(3-chlorophenyl) | 3.34 | 89% |
| 24 | NH-(3-iodophenyl) | 2.97 | 84% |
| 25 | NH-(2-fluoro-5-CF₃-phenyl) | inactive | N/A |
| 26 | NH-(3-SMe-phenyl) | 5.29 | 84% |
| 27 | NH-(3-SO₂Me-phenyl) | 118 | 34% |
| 28 | NH-(3-SCF₃-phenyl) | 1.88 | 90% |

TABLE 1-continued

Structure: cyclohexyl-C(=O)-NH-phenyl(2-C(=O)NHR₂)

| # | NHR₂ | RXFP1 AC₅₀ (μM) | Max Response |
|---|---|---|---|
| 29 | -NH-C₆H₄-SO₂CF₃ (3-) | 1.06 | 87% |
| 30 | -NH-C₆H₄-(3-piperidinyl) | inactive | N/A |
| 31 | -NH-C₆H₄-(3-thiophen-2-yl) | 471 | 31% |
| 32 | -NH-C₆H₄-(3-(2-CF₃-phenyl)) | 2.65 | 74% |
| 33 | -NH-C₆H₄-(3-(3-CF₃-phenyl)) | inactive | N/A |
| 34 | -NH-C₆H₄-(3-(4-CF₃-phenyl)) | inactive | N/A |
| 35 | -NH-indanyl | 9.40 | 46% |
| 36 | -NH-benzo[1,3]dioxol-5-yl | 74.7 | 58% |
| 37 | -NH-(1H-indol-6-yl) | inactive | N/A |
| 38 | -NH-CH₂-C₆H₄-4-CF₃ | inactive | N/A |
| 39 | -NH-CH₂-C₆H₄-3-CF₃ | inactive | N/A |
| 40 | -NH-CH₂-C₆H₄-2-CF₃ | inactive | N/A |
| 41 | -NH-CH₂-furan-2-yl | inactive | N/A |
| 42 | -NH-CH₂-(5-methylfuran-2-yl) | 149 | 31% |
| 43 | -NH-CH₂-thiophen-2-yl | 118 | 40% |
| 44 | -NH-C₆H₄-2-(C(=O)NH-CH₂-furan-2-yl) | 9.40 | 45% |

TABLE 2

[Structure: 2-(R3-C(O)NH)-N-(3-trifluoromethylphenyl)benzamide]

| # | COR3 | RXFP1 AC50 (μM) | Max Response |
|---|------|-----------------|--------------|
| 45 | cyclohexyl-C(O)- | 1.88 | 92% |
| 46 | H-C(O)- | 47.1 | 78% |
| 47 | CH3-C(O)- | 74.7 | 51% |
| 48 | (Et)2CH-C(O)- | 5.29 | 59% |
| 49 | n-butyl-CH2-C(O)- | 5.29 | 94% |
| 50 | t-BuO-C(O)- | 5.29 | 79% |
| 51 | cyclopropyl-C(O)- | 8.38 | 79% |
| 52 | cyclobutyl-C(O)- | 2.97 | 75% |
| 53 | cyclopentyl-C(O)- | 2.36 | 88% |

TABLE 2-continued

| # | COR3 | RXFP1 AC50 (μM) | Max Response |
|---|------|-----------------|--------------|
| 54 | 4-methylcyclohexyl-C(O)- | 2.36 | 92% |
| 55 | 1-adamantyl-C(O)- | 4.71 | 87% |
| 56 | cycloheptyl-C(O)- | 2.11 | 75% |
| 57 | phenyl-C(O)- | 1.32 | 64% |
| 58 | benzyl-C(O)- | 8.38 | 86% |
| 59 | 1-naphthyl-C(O)- | 5.93 | 81% |
| 60 | 2-naphthyl-C(O)- | 14.9 | 85% |
| 61 | benzo[1,3]dioxol-5-yl-C(O)- | 6.66 | 81% |

TABLE 2-continued

Structure: 2-(R3-C(O)NH)-N-(3-(trifluoromethyl)phenyl)benzamide

| # | COR3 | RXFP1 AC$_{50}$ (μM) | Max Response |
|---|---|---|---|
| 62 | (benzimidazol-4-yl)carbonyl | 11.8 | 90% |
| 63 | (isoxazol-5-yl)carbonyl | 14.9 | 93% |
| 64 | (furan-2-yl)carbonyl | 2.36 | 81% |
| 65 | (thiophen-2-yl)carbonyl | 1.88 | 88% |
| 66 | (pyridin-3-yl)carbonyl | 5.93 | 95% |
| 67 | (pyridin-4-yl)carbonyl | 7.47 | 51% |

TABLE 3

Structure: 2-(R3-C(O)NH)-N-(3-(trifluoromethyl)phenyl)benzamide

| # | COR3 | RXFP1 AC$_{50}$ (μM) | Max Response |
|---|---|---|---|
| 68 | cyclohexylcarbonyl | 1.88 | 92% |
| 69 | phenylcarbonyl | 1.32 | 64% |
| 70 | (2-(trifluoromethyl)phenyl)carbonyl | 7.47 | 70% |
| 71 | (3-(trifluoromethyl)phenyl)carbonyl | 2.97 | 95% |
| 72 | (4-(trifluoromethyl)phenyl)carbonyl | 5.93 | 93% |
| 73 | (3,5-bis(trifluoromethyl)phenyl)carbonyl | 4.20 | 94% |
| 74 | (2-methoxyphenyl)carbonyl | 0.334 | 99% |
| 75 | (3-methoxyphenyl)carbonyl | 1.88 | 94% |

TABLE 3-continued

Structure: 2-(R₃C(O)NH)-benzamide-N-(3-trifluoromethylphenyl)

| # | COR₃ | RXFP1 AC₅₀ (μM) | Max Response |
|---|---|---|---|
| 76 | 4-methoxyphenyl-C(O)- | 9.40 | 71% |
| 77 | 2-methylphenyl-C(O)- | 4.20 | 90% |
| 78 | 3-methylphenyl-C(O)- | 3.74 | 92% |
| 79 | 4-methylphenyl-C(O)- | 4.71 | 85% |
| 80 | 2-chlorophenyl-C(O)- | 3.74 | 92% |
| 81 | 3-chlorophenyl-C(O)- | 1.88 | 96% |
| 82 | 4-chlorophenyl-C(O)- | 2.65 | 95% |
| 83 | 2-bromophenyl-C(O)- | 7.47 | 78% |
| 84 | 3-bromophenyl-C(O)- | 1.67 | 97% |
| 85 | 4-bromophenyl-C(O)- | 4.20 | 93% |
| 86 | 2-iodophenyl-C(O)- | 7.47 | 80% |
| 87 | 3-nitrophenyl-C(O)- | 1.06 | 84% |
| 88 | 2-nitrophenyl-C(O)- | 188 | 30% |
| 89 | 4-nitrophenyl-C(O)- | 1.49 | 96% |
| 90 | 3-cyanophenyl-C(O)- | 2.10 | 96% |
| 91 | 4-cyanophenyl-C(O)- | 1.67 | 96% |

TABLE 3-continued

[Structure: 2-(R3CO-NH)-N-(3-trifluoromethylphenyl)benzamide]

| # | COR3 | RXFP1 AC50 (μM) | Max Response |
|---|---|---|---|
| 92 | 3-Ph-benzoyl | 5.29 | 89% |
| 93 | 3-(SO2Me)-benzoyl | 9.40 | 77% |
| 94 | 4-acetyl-benzoyl | 5.93 | 71% |

TABLE 4

[Structure: 2-(R3CO-NH)-N-(3-trifluoromethylphenyl)benzamide]

| # | COR3 | RXFP1 AC50 (μM) | Max Response |
|---|---|---|---|
| 95 | cyclohexylcarbonyl | 1.88 | 92% |
| 96 | benzoyl | 1.32 | 64% |
| 97 | 2-OMe-benzoyl | 0.334 | 99% |
| 98 | 2-OCF3-benzoyl | 1.18 | 96% |
| 99 | 2-OEt-benzoyl | 0.265 | 94% |
| 100 | 2-OiPr-benzoyl | 0.471 | 99% |
| 101 | 2-OPh-benzoyl | 0.747 | 97% |
| 102 | 2,6-diOMe-benzoyl | 7.47 | 42% |
| 103 | 2-(OCH2CH2OMe)-benzoyl | 0.747 | 98% |

TABLE 4-continued

[Structure: 2-(R3CONH)-N-(3-trifluoromethylphenyl)benzamide core]

| # | COR3 | RXFP1 AC50 (μM) | Max Response |
|---|---|---|---|
| 104 | 2-(2-(methylamino)ethoxy)benzoyl | 3.74 | 92% |
| 105 | 2-(3-(dimethylamino)propoxy)benzoyl | 59.3 | 66% |
| 106 | 2-(2-morpholinoethoxy)benzoyl | 4.71 | 98% |
| 107 | 2-(2-(piperidin-1-yl)ethoxy)benzoyl | 2.65 | 99% |
| 108 | 2-(2-(4-Boc-piperazin-1-yl)ethoxy)benzoyl | 1.33 | 94% |
| 109 | 2-(2-(piperazin-1-yl)ethoxy)benzoyl | inactive | N/A |

TABLE 5

[Structure: 2-R1-N-(3-trifluoromethylphenyl)benzamide core]

| # | R1 | RXFP1 AC50 (μM) | Max Response |
|---|---|---|---|
| 110 | cyclohexanecarboxamido (-NHC(O)Cy) | 1.88 | 92% |
| 111 | benzamido (-NHC(O)Ph) | 1.32 | 64% |
| 112 | 2-methoxybenzamido | 0.334 | 99% |
| 113 | (cyclohexylmethyl)amino | 5.93 | 77% |
| 114 | benzylamino | 47.1 | 69% |
| 115 | (2-methoxybenzyl)amino | 59.3 | 57% |
| 116 | phenylamino | 4.20 | 84% |

TABLE 5-continued

Structure: 2-R₁-benzamide with N-(3-trifluoromethylphenyl)

| # | R₁ | RXFP1 AC₅₀ (µM) | Max Response |
|---|---|---|---|
| 117 | 2-methoxyanilino (–NH–C₆H₄–OMe) | 4.71 | 77% |
| 118 | 3-(trifluoromethyl)anilino (–NH–C₆H₄–CF₃) | 4.20 | 93% |
| 119 | 3-(trifluoromethyl)benzylamino (–NH–CH₂–C₆H₄–CF₃) | 47.1 | 71% |
| 120 | phenethylamino (–NH–CH₂CH₂–C₆H₅) | 9.40 | 83% |
| 121 | –NH–CH₂CH₂–OMe | 59.3 | 63% |
| 122 | –O–CH₂CH₂–OMe | inactive | N/A |
| 123 | –O–CH₂CH₂CH₂–N(Me)₂ | inactive | N/A |
| 124 | –O–CH₂CH₂–N(Me)₂ | inactive | N/A |
| 125 | –O–CH₂CH₂–N(piperazine)–Boc | inactive | N/A |
| 126 | –O–CH₂CH₂–N(piperazine)–NH | inactive | N/A |
| 127 | –O–CH₂CH₂–N(morpholine) | inactive | N/A |
| 128 | –O–CH₂CH₂–N(piperidine) | inactive | N/A |
| 129 | phenyl (–C₆H₅) | inactive | N/A |
| 130 | 2-methoxyphenyl (–C₆H₄–OMe) | inactive | N/A |
| 131 | 2-(benzyloxy)phenyl (–C₆H₄–OBn) | inactive | N/A |

TABLE 6

| # | R_A | Linker 1 | R_B | RXFP1 AC$_{50}$ (μM) | Max Response |
|---|---|---|---|---|---|
| 132 | cyclohexyl | 2-aminobenzamide linker | CF$_3$ | 1.88 | 92% |
| 133 | | 3-aminobenzamide linker | CF$_3$ | inactive | N/A |
| 134 | | 4-(methylamino)benzamide linker | CF$_3$ | inactive | N/A |
| 135 | 2-methoxyphenyl | 2-aminobenzamide linker | CF$_3$ | 0.334 | 99% |
| 136 | | 3-aminobenzamide linker | CF$_3$ | inactive | N/A |
| 137 | | 4-(methylamino)benzamide linker | CF$_3$ | inactive | N/A |

TABLE 6-continued

| # | Structure | R | IC50 | % |
|---|---|---|---|---|
| 138 | [2-(N-methylamino)phenyl]-C(=O)-NH- linker | CF3 | inactive | N/A |
| 139 | [2-(NH)phenyl]-C(=O)-N(Me)- linker | CF3 | 29.7 | 77% |
| 140 | 2-OMe-phenyl ; [2-(N-methyl)phenyl]-C(=O)-N(Me)- linker | | inactive | N/A |
| 141 | 2-(2-ethoxybenzamido)phenyl-benzimidazole-5-CF3 | | 149 | 31% |
| 142 | 6-(2-ethoxyphenyl)-benzimidazo-quinazoline with CF3 | | 188 | 34% |
| 143 | 2-(2-ethoxyphenyl)-3-[3-(1H-tetrazol-5-yl)phenyl]-quinazolin-4(3H)-one | | 149 | 36% |

TABLE 6-continued

| # | R1 | R2 | R3 | Val1 | Val2 |
|---|----|----|----|------|------|
| 144 | 2-OEt-phenyl | 2-(NH)-benzamide | SO$_2$CF$_3$ | 0.118 | 99% |
| 145 | | 3-(NH)-benzamide | SO$_2$CF$_3$ | 2.65 | 77% |
| 146 | | 3-aminopropanamide | SO$_2$CF$_3$ | 4.71 | 90% |
| 147 | | 2-amino-2,3-dihydrothiophene-3-carboxamide | SO$_2$CF$_3$ | 2.36 | 95% |
| 148 | 2-OEt-phenyl | 7-amino-isoindolin-1-one | SO$_2$CF$_3$ | inactive | N/A |
| 149 | | 2-aminonicotinamide | SO$_2$CF$_3$ | 1.67 | 98% |
| 150 | | 3-aminoisonicotinamide | SO$_2$CF$_3$ | 2.97 | 99% |

TABLE 6-continued
| # | (structure) | | RXFP1 AC$_{50}$ (µM) | Max Response |
|---|---|---|---|---|
| 151 | (4-amino-N-pyridine-3-carboxamide) | SO$_2$CF$_3$ | 0.747 | 97% |
| 152 | (3-amino-N-pyridine-2-carboxamide) | SO$_2$CF$_3$ | 4.71 | 73% |
| 153 | (2-ethoxyphenylsulfonamido benzamide) | SO$_2$CF$_3$ | inactive | N/A |
| 154 | (2-(2-ethoxyphenyl)-1H-benzimidazole-4-carboxamide) | SO$_2$CF$_3$ | inactive | N/A |
TABLE 7
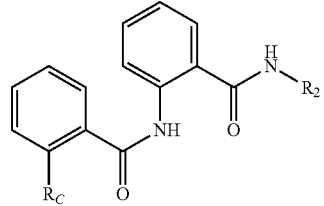
| # | R$_C$ | R$_2$ | RXFP1 AC$_{50}$ (µM) | Max Response |
|---|---|---|---|---|
| 155 | OMe | 3-CF$_3$-phenyl | 0.334 | 99% |
| 156 | OMe | 3-SCH$_3$-phenyl | 1.33 | 94% |
| 157 | OMe | 3-SO$_2$CH$_3$-phenyl | 6.66 | 95% |

TABLE 7-continued
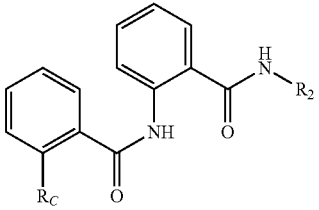
| # | R_C | R_2 | RXFP1 AC$_{50}$ (μM) | Max Response |
|---|---|---|---|---|
| 158 | OMe | 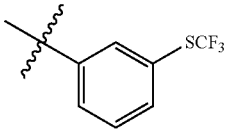 | 0.297 | 99% |
| 159 | OMe | 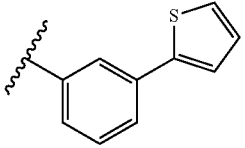 [SMILES: *c1cccc(-c2cccs2)c1] | 0.188 | 99% |
| 160 | OMe | 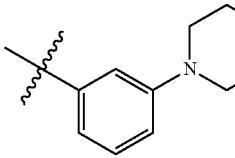 | inactive | N/A |
| 161 | OMe | 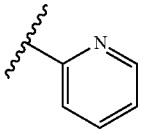 [SMILES: *c1ccccn1] | 5.29 | 77% |
| 162 | OEt | 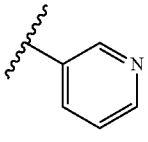 [SMILES: *c1cccnc1] | 29.7 | 74% |
| 163 | OEt | 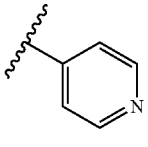 [SMILES: *c1ccncc1] | 149 | 37% |
| 164 | OEt | 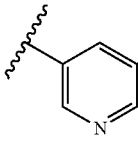 | 74.7 | 64% |
| 165 | OEt | 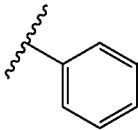 | 11.8 | 72% |
| 166 | OEt | | 0.747 | 96% |

TABLE 7-continued
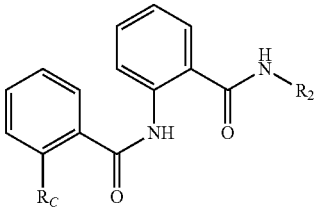
| # | $R_C$ | $R_2$ | RXFP1 $AC_{50}$ (μM) | Max Response |
|---|---|---|---|---|
| 167 | OEt | 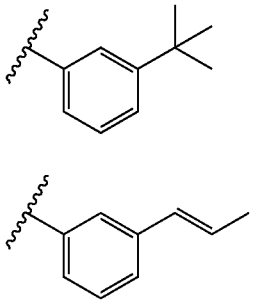 | 1.06 | 93% |
| 168 | OEt | 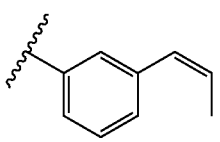 [SMILES: *c1cccc(/C=C\C)c1] | 2.11 | 84% |
| 169 | OEt | 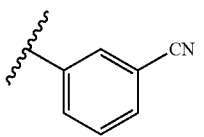 [SMILES: *c1cccc(C#N)c1] | 1.49 | 91% |
| 170 | OEt | 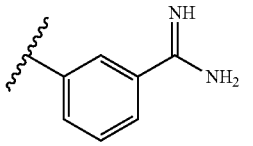 [SMILES: *c1cccc(C(=N)N)c1] | 0.666 | 96% |
| 171 | OEt | 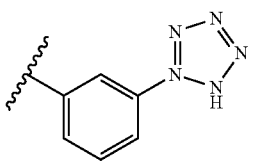 | inactive | N/A |
| 172 | OEt | 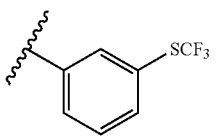 | inactive | N/A |
| 173 | OEt | 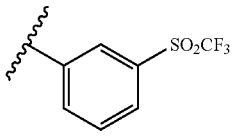 | 0.666 | 98% |
| 174 | OEt | | 0.188 | 99% |

TABLE 7-continued

Structure: two linked benzamide cores with $R_C$ on one ring and $R_2$ amide substituent.

| # | $R_C$ | $R_2$ | RXFP1 $AC_{50}$ (µM) | Max Response |
|---|---|---|---|---|
| 175 | I | 3-($SO_2CF_3$)phenyl | 4.20 | 85% |
| 176 | SEt | 3-($SO_2CF_3$)phenyl | 0.529 | 95% |
| 177 | $OCH_2CF_3$ | 3-($SO_2CF_3$)phenyl | 0.067 | 97% |
| 178 | $OCH(CH_3)_2$ | 3-($SO_2CF_3$)phenyl | 0.094 | 98% |
| 179 | $OCH_2CH_2CH_3$ | 3-($SO_2CF_3$)phenyl | 0.052 | 98% |
| 180 | $OCH_2CH_2CH_2CH_3$ | 3-($SO_2CF_3$)phenyl | 0.047 | 98% |

EXAMPLE 200

This example illustrates the activation of VEGF expression in THP1 cells by several embodiments of the disclosure.

THP1 cells (human acute monocytic leukemia cell line) were used to analyze the stimulation of VEGF gene expression after treatment with relaxin or compounds. The VEGF stimulation in these cultured endometrial cells is a well-established property of relaxin.[19] This effect is most probably responsible for the observed angiogenic and neovascularization properties of relaxin in various settings.[20] 400,000 THP1 cells (0.4 mL at 1×10$^6$ cells/mL) in test media (RPMI-1640 without phenol red, 0.5% FBS, 1× Pen/Strep, 0.05 mM of 2-mercaptoethanol) were seeded in each well on a 24-well plate. After 24 hours incubation at 37° C., 5% $CO_2$, relaxin or compounds were added for 2 hours. The cells were harvested and RNA was extracted by the Trizol (Invitrogen, Carlsbad, Calif.) method according to manufacturers instructions. cDNA was synthesized by using Verso cDNA kit (Thermo Scientific, Waltham, Mass.) according to manufacturers protocol. Quantitative real time RT-PCR for VEGF and GAPDH gene expression was done using a Roche LightCycler 480 (Roche Diagnostics, Indianapolis, Ind.) with the appropriate set of primers and probes spanning different exons. The relative fold change in VEGF mRNA level was calculated by the comparative $C_t$ ($2^{\Box \Delta \Delta^{Ct}}$) method using GAPDH expression for normalization of RNA.

The results are set forth in Table 8 as relative VEGF gene expression relative to control.

TABLE 8

| Compound | Relative VEGF gene expression (control = 1.0) |
|---|---|
| Relaxin | 2.5 |
| 158 | 1.2 |
| 177 | 1.3 |
| 179 | 1.5 |
| 180 | 1.6 |
| 99 | 1.9 |
| 174 | 2.3 |
| 178 | 2.8 |
| 159 | 1.4 |

As is apparent from the results set forth, all of the compounds with the possible exception of compound 158 exhibited a significant upregulation of VEGF expression. Compound 178 exhibited a greater upregulation of VEGF expression than did relaxin.

EXAMPLE 201

It was previously shown that relaxin increases cell impedance in RXFP1 transfected cells. Cell-substrate impedance was measured using a Roche DP RTCA xCELLigence Analyzer (Roche Diagnostics, Indianapolis, Ind.) on E-Plates. Real Time Cell Analyzer (RTCA) allows for continuous time-resolved measurement of cellular index without additional labeling. Cell number, cellular adherence to the plate, and intracellular interactions all contribute to the total cellular impedance. The effect of the compound treatment is only measured within the first hour, changes in cellular density are unlikely to contribute to the overall effect, and therefore cellular impedance is most likely caused by intercellular interactions, or signaling.

Cell Index (CI) was calculated by subtracting impedance at the beginning of experiment $Z_0$ from impedance at each individual time point $Z_t$, divided by 15Ω [$CI_t=(Z_0-Z_t)/15Ω$]. Delta Cellular Indices were calculated as the change of impedance at a given time t, from the time of compound addition ($CI_{compound}$) $\Delta CI_t = CI_t - CI_{compound}$. Impedance at each time point was then normalized to the average of quadruplicate CI of cells treated with vehicle (V1, V2, V3, and V4), to calculate normalized delta Cell Index $N\Delta CI= (CI_t - CI_{compound})/\text{Average}[\Delta CI_{V1}, \Delta CI_{V2}, \Delta CI_{V3}, \Delta CI_{V4}]$. Maximal relaxin activity was assigned a value of 100% and all other values adjusted proportionally.

The cell line stably transfected with RXFP1 receptor HEK293-RXFP1 was used for cell impedance assay to confirm relaxin-like properties of the compounds. To equilibrate the plates, 100 μL of test media (DMEM, 1% FBS, 1× Pen/Strep) was added to each well of E-Plate (Roche Diagnostics, Indianapolis, Ind.) and the plate was incubated at room temperature for 30 minutes at which point baseline impedance was measures. Then 20,000 HEK293-RXFP1 cell or HEK293 cells (parental control cell line) were added per well in a volume of 100 μL test media and allowed to sediment at room temperature for 30 minutes. The plate was placed into xCELLigence RTCA DP Instrument in the $CO_2$ incubator overnight to allow the cells to attach. Relaxin (10 ng/mL), vehicle, or compounds at different concentrations (250, 500, and 750 nM) were added to the wells and the cellular impedance was measured every 10-30 seconds for 1 hour. The protocol was as follows:

| Sequence | Parameter | Value | Description |
|---|---|---|---|
| 1 | Cells | 200 μL | 20,000 cells/well |
| 2 | Time | Overnight | Incubate at 37° C. and 5% $CO_2$ |
| 3 | Reagent | 50 μL | Compounds in DMEM and 1% FBS, relaxin as positive control, and vehicle as a baseline |
| 4 | Time | 1 h | Incubate at 37° C. and 5% $CO_2$ |
| 5 | Detector | impedance | RTCA DP Instrument |
| 6 | Cells | 200 μL | 20,000 cells/well |

The results are set forth in FIG. 8.

EXAMPLE 202

This Example illustrates the cyclic AMP assay in THP-1 cells. THP-1 cells were propagated in RPMI-1640 supplemented with 20% FBS, 0.05 mM β-mercaptoethanol, 100 U/mL penicillin and 100 μg/mL streptomycin at 37° C. in 5% $CO_2$. Before assaying for cAMP response, cells were serum starved in RPMI-1640 supplemented with 0.05 mM β-mercaptoethanol, 100 U/mL penicillin and 100 μg/mL streptomycin at 37° C. in 5% $CO_2$ for 16 hrs. For 384-well format assays, cells were seeded as 30,000 cells/well in 30 μL/well media with a MultiDrop Combi dispenser (Thermo Scientific, Waltham, Mass.). Subsequently, 2 μL/well of 1.6 mM Ro 20-1724 and 160 uM forskolin in PBS+ (DPBS, 1 mM $CaCl_2$, 0.5 mM $MgCl_2$, 0.05% BSA, 0.005% Tween 20) was dispensed using a BioRAPTR FRD dispenser (Beckman Coulter, Brea, Calif.). Immediately after, 0.25 μL/well of compound solutions in DMSO was dispensed with CyBi-well dispenser (CyBio, Jena, Germany). The cells were allowed to be stimulated with compounds for 30 min at 37° C. in 5% $CO_2$, after which, 8 μL/well of each HTRF cAMP HiRange kit (CisBio, Bedford, Mass.) detection reagent was dispensed with a BioRAPTR FRD dispenser. The detection reagents were diluted as such: K-α-cAMP antibody at 1:20 and cAMP-d2 at 1:18 in HTRF lysis buffer (supplied by the assay kit). The plates were incubated for 30 min at room temperature before the signal was read on an Envision plate reader (PerkinElmer, Waltham, Mass.). The $EC_{50}$ values for selected embodiments are set forth in Table 9.

TABLE 9

| Compound | $EC_{50}$ |
|---|---|
| 99 | 0.4711 |
| 158 | 0.5231 |
| 159 | 0.3585 |
| 174 | 0.3622 |
| 177 | 0.1073 |
| 178 | 0.1999 |
| 179 | 0.1051 |
| 180 | 0.1237 |

EXAMPLE 203

This example demonstrates the RXFP2 cAMP assay in HEK293-RXFP2 cells. HEK293 cells stably transfected with RXFP2, the cognate receptor for another relaxin family peptide, insulin-like 3, (HEK293-RXFP2) was used to test compound specificity towards the RXFP1 receptor. For this assay, cells were seeded at 8,000 cells/well in 30 μL/well of media with a MultiDrop Combi dispenser (Thermo Scientific), and allowed to attach overnight at 37° C., 5% $CO_2$. Next, 2 μL/well of 1.6 mM Ro 20-1724 solution in PBS+

(DPBS, 1 mM CaCl$_2$, 0.5 mM MgCl$_2$, 0.05% BSA, 0.005% Tween 20) were dispensed using a BioRAPTR FRD dispenser (Beckman Coulter, Brea, Calif.), followed addition of 0.25 μL/well of compound solution in DMSO with CyBi-well dispenser (CyBio, Jena, Germany). The cells were allowed to be stimulated with the compounds for 30 minutes at 37° C., 5% CO$_2$, after which, 8 μL/well of each HTRF detection reagent (diluted according to assay kit directions in HTRF lysis buffer) was dispensed with a BioRAPTR FRD dispenser. The plates were incubated for 30 minute at 37° C., and then the signal was read on a ViewLux plate reader (PerkinElmer, Waltham, Mass.). The protocol was as follows:

| Sequence | Parameter | Value | Description |
|---|---|---|---|
| 1 | Cells | 30 μL | 8,000 cells/well |
| 2 | Time | 16-24 h | Incubate at 37° C. and 5% CO$_2$ |
| 3 | Reagent | 2 μL | 1600 μM Ro 20-1724 in PBS |
| 4 | Reagent | 2.5 μL | Compounds in DMSO, forskolin as control |
| 5 | Time | 30 min | Incubate at 37° C. and 5% CO$_2$ |
| 6 | Reagent | 8 μL | cAMP-d2 diluted 1:18 in lysis buffer |
| 7 | Reagent | 8 μL | K-α-cAMP diluted 1:20 in lysis buffer |
| 8 | Time | 30 min | Room temperature incubation |

EXAMPLE 204

This example demonstrates the V1b cAMP assay in HEK293-V1b cells. HEK293 stably transfected with a non-related G protein coupled receptor, vasopressin receptor 1b (HEK293-V1b), were used as an additional counter screen to eliminate compounds that increase cAMP HTRF signal through non-RXFP1 dependent mechanisms. For this assay, cells were seeded at 8,000 cells/well in 30 μL/well media with a MultiDrop Combi dispenser (Thermo Scientific, Logan, Utah), and allowed to attach overnight at 37° C., 5% CO$_2$. Next, 2 μL/well of 1.6 mM Ro 20-1724 solution in PBS+(DPBS, 1 mM CaCl$_2$, 0.5 mM MgCl$_2$, 0.05% BSA, 0.005% Tween 20) was dispensed using a BioRAPTR FRD dispenser (Beckman Coulter, Brea, Calif.), followed by additional of 0.25 μL/well of compound solution in DMSO with CyBi-well dispenser (CyBio, Jena, Germany). The cells were allowed to be stimulated with the compounds for 30 minutes at 37° C., 5% CO$_2$, after which, 8 μL/well of each HTRF detection reagent (diluted according to assay kit directions in HTRF lysis buffer) was dispensed with a BioRAPTR FRD dispenser. The plates were incubated for 30 minute at room temperature, and then the signal was read on a ViewLux plate reader (PerkinElmer, Waltham, Mass.). The protocol was as follows:

| Sequence | Parameter | Value | Description |
|---|---|---|---|
| 1 | Cells | 30 μL | 8,000 cells/well |
| 2 | Time | 16-24 h | Incubate at 37° C. and 5% CO$_2$ |
| 3 | Reagent | 2 μL | 1,600 μM Ro 20-1724 in PBS |
| 4 | Reagent | 2.5 μL | Compounds in DMSO, forskolin as control |
| 5 | Time | 30 min | Incubate at 37° C. and 5% CO$_2$ |
| 6 | Reagent | 8 μL | cAMP-d2 diluted 1:18 in lysis buffer |
| 7 | Reagent | 8 μL | K-α-cAMP diluted 1:20 in lysis buffer |
| 8 | Time | 30 min | Room temperature incubation |
| 9 | Detector | TR-FRET | EnVision plate reader |

EXAMPLE 205

This example demonstrates the ATP Cytotoxicity assay in HEK293-RXFP1 cells. This follow-up assay was conducted to measure the effect of compounds on cell viability by measuring ATP levels (ATPLite™). ATPLite™ is an Adenosine TriPhosphate (ATP) monitoring system based on firefly (*Photinus pyralis*) luciferase. The level of ATP in a metabolically active cell is a general marker for its viability. ATP levels are often reduced during necrosis or apoptosis. In this assay, the luciferase enzyme catalyzes the conversion of the added substrate D-luciferin to oxyluciferin and light with ATP. Thus, the emitted light is proportional to the ATP concentration. To evaluate the cytotoxic properties of the compounds, HEK293-RXFP1 cells were incubated with compounds for 72 hours in growth media (DMEM 10% FBS, 1× Pen/Strep, 0.5 mg/mL of G418) in 384-well format. After compound incubation, the levels of ATP in each well were measured with the addition of the ATPLite assay reagent. The protocol was as follows:

| Sequence | Parameter | Value | Description |
|---|---|---|---|
| 1 | Cells | 30 μL | 1,000 cells/well |
| 2 | Time | 16-24 h | Incubate at 37° C. and 5% CO$_2$ |
| 3 | Reagent | 2.5 μL | Compounds in DMSO |
| 4 | Time | 72 h | Incubate at 37° C. and 5% CO$_2$ |
| 5 | Reagent | 20 μL | ATPLite (PerkinElmer) |
| 6 | Time | 15 min | Room temperature incubation |
| 7 | Detector | Luminescence | ViewLux plate reader |

EXAMPLE 206

This example illustrates the activity of several embodiments of the disclosure in the RXFP1 assay (Example 199), the RXFP2 assay (Example 203), the V1b assay (Example 204), and the ATP toxicity (Example 202), as well as the PBS solubility and the mouse liver microsome (MLM) stability. The results are set forth in Table 10.

TABLE 10

| Entry | Internal ID | RXFP1 AC$_{50}$ (μM, Max. Resp.) | RXFP2 AC$_{50}$ (μM, Max. Resp.) | V1b AC$_{50}$ (μM, Max. Resp.) | ATP Tox. EC$_{50}$ (μM, Max. Resp.) | PBS Solubility (μM) | MLM Stability ($t_{1/2}$ in min.) |
|---|---|---|---|---|---|---|---|
| 37 | 99 | 0.297 (95%) | 9.40 (47%) | inactive[a] | inactive[a] | 1.7 | N/A |
| 61 | 158 | 0.297 (99%) | 3.34 (54%) | inactive[a] | 3.74 (−31%) | 2.9 | N/A |
| 62 | 159 | 0.188 (99%) | inactive[a] | inactive[a] | 29.7 (−76%) | 6.3 | N/A |
| 63 | 174 | 0.188 (99%) | 7.47 (38%) | inactive[a] | 18.8 (−73%) | <1.1 | 1732 |
| 65 | 177 | 0.067 (97%) | inactive[a] | inactive[a] | 29.7 (−78%) | 3.3 | 100 |
| 66 ML290 | 178 | 0.094 (98%) | inactive[a] | inactive[a] | 9.4 (−85%) | 7.0 | 122 |
| 67 | 179 | 0.052 (98%) | inactive[a] | inactive[a] | 9.4 (−83%) | 17.0 | 133 |
| 68 | 180 | 0.047 (98%) | inactive[a] | inactive[a] | 59.3 (−53%) | 5.3 | 178 |

[a]Maximum response less than 30%.

EXAMPLE 207

Referring to FIG. 9, 1-3ECL are extracellular loops of transmembrane domains of RXFP1. This example demonstrates the ability of compound to activate human but not mouse relaxin receptor transfected in HEK293 cells as measured by cAMP accumulation. The compound was inactive against related to RXFP1 mouse relaxin family receptor 2, RXFP2. The chimeric mouse/human RXFP1 receptors were activated by compounds only if they contained the region encoded by human exon 17 plus two humanized codons from exon 18. The 3□-end of mouse and human exon 17 encodes the 3$^{rd}$ ECL. There are 4 amino acid differences between human and mouse 3EXL. Two mouse site-specific mutants were tested, one where isoleucine 646 and leucine 647 were substituted by two valines specific for human sequence (M10), and the other one where aspartic acid (position 659) and serine (660) were substituted by glycine and threonine (M11). Both did not respond to the compound stimulation.

EXAMPLE 208

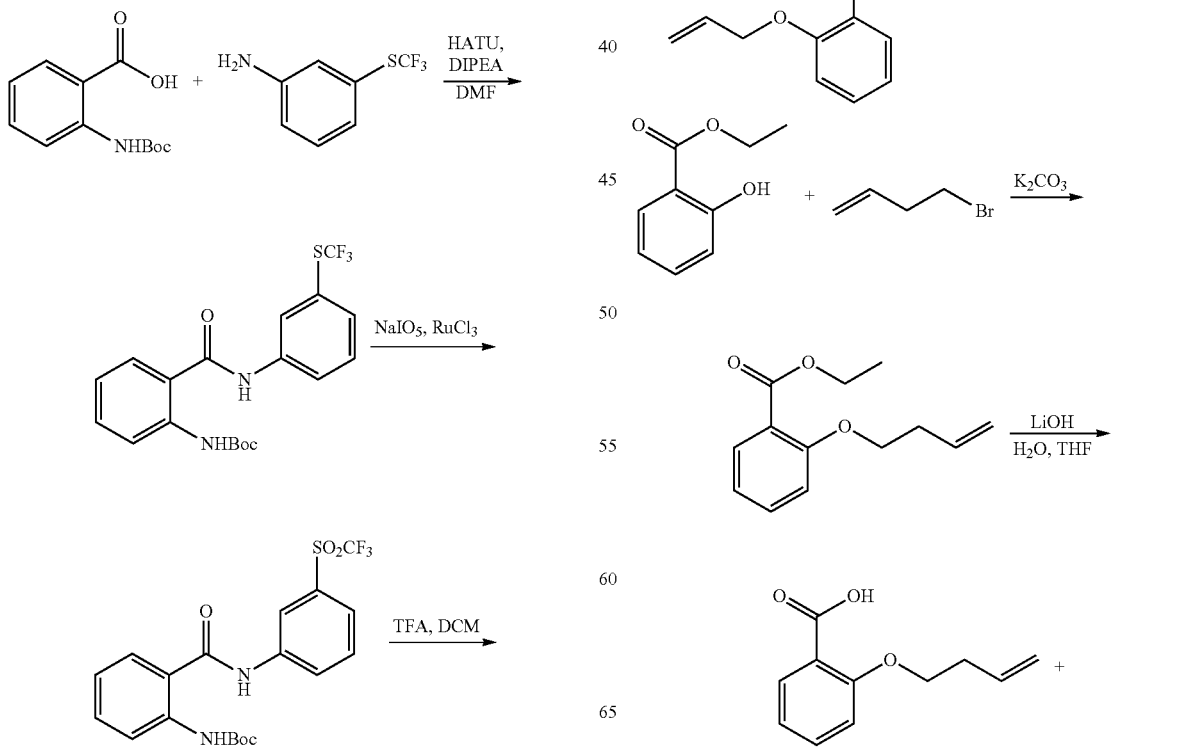

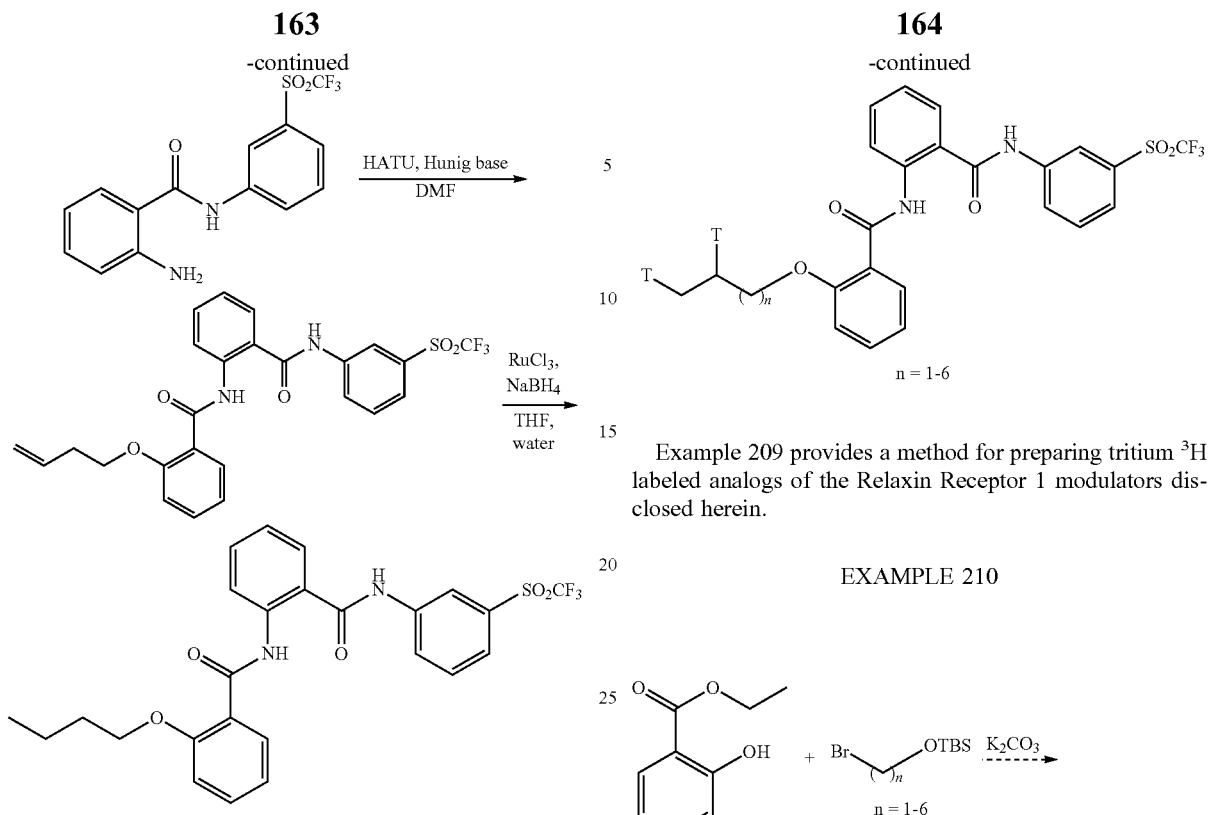
Example 208 provides a method for synthesizing radiolabelled precursors.
EXAMPLE 209
Example 209 provides a method for preparing tritium $^3$H labeled analogs of the Relaxin Receptor 1 modulators disclosed herein.
EXAMPLE 210
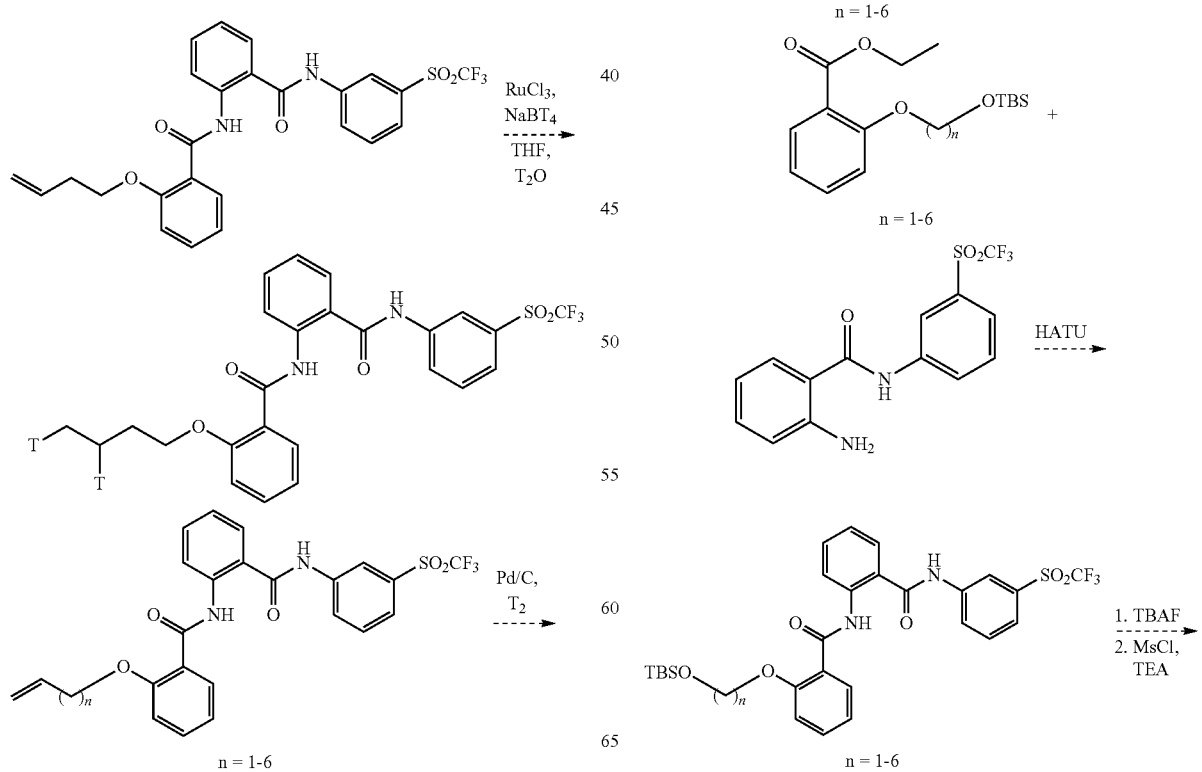

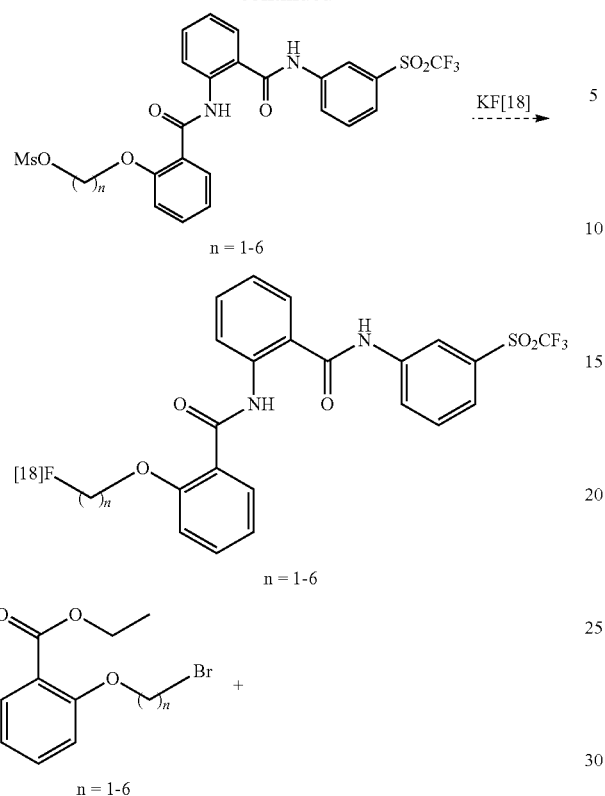

n = 1-6

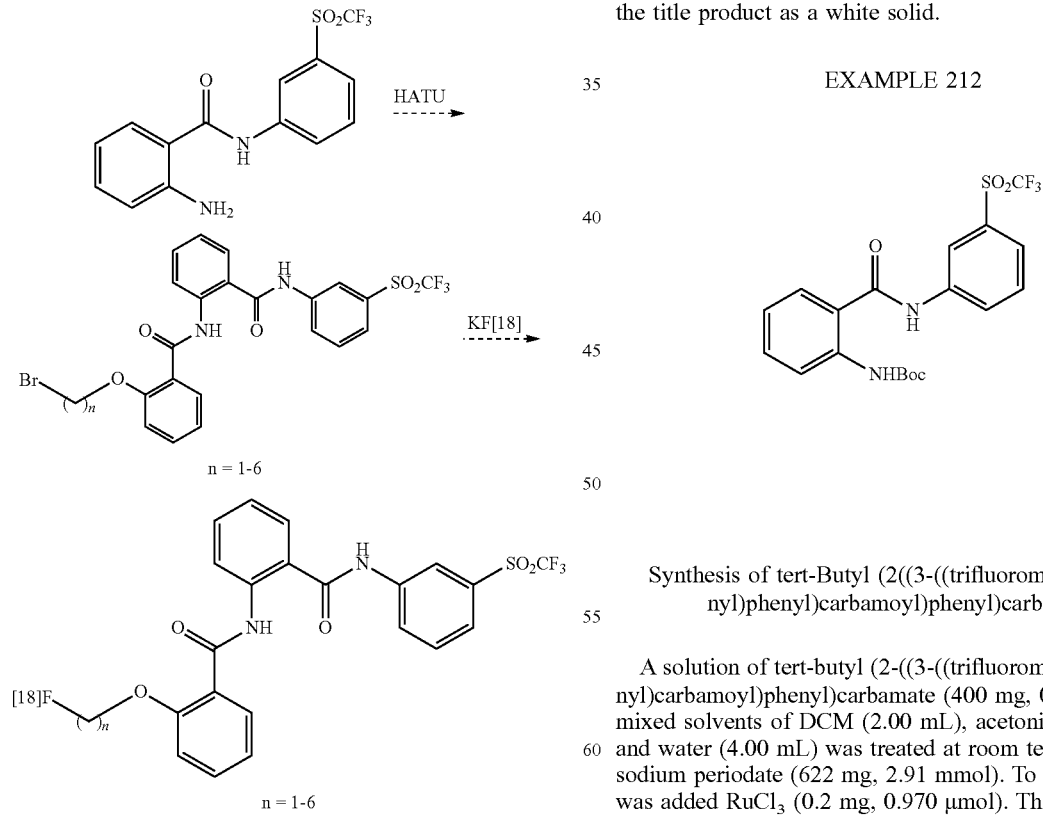

Example 210 provides a method for preparing fluorine-18 ($^{18}$F) labeled analogs of the Relaxin Receptor 1 modulators disclosed herein.

EXAMPLE 211

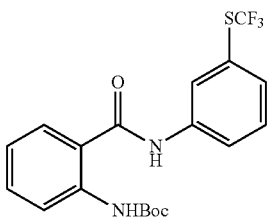

Synthesis of tert-Butyl (2-((3-((trifluoromethyl)thio)phenyl)carbamoyl)phenyl)carbamate A mixture of 2-((tert-butoxycarbonyl)amino)benzoic acid (2.50 g, 10.5 mmol) and 3-((trifluoromethyl)thio)aniline (2.44 g, 12.6 mmol) in DMF (40.0 mL) was treated at room temperature with HATU (4.01 g, 10.5 mmol) and DIPEA (5.52 mL, 31.6 mmol). The reaction mixture was stirred at room temperature overnight. The reaction mixture was poured into ice water and extracted with EtOAc. The organic layer was separated, dried and concentrated as a brown oil. The crude material was purified on silica gel with a gradient of 0-100% EtOAc in hexanes to give 3.20 g (yield 74%) of the title product as a white solid.

EXAMPLE 212

Synthesis of tert-Butyl (2((3-((trifluoromethyl)sulfonyl)phenyl)carbamoyl)phenyl)carbamate A solution of tert-butyl (2-((3-((trifluoromethyl)thio)phenyl)carbamoyl)phenyl)carbamate (400 mg, 0.970 mmol) in mixed solvents of DCM (2.00 mL), acetonitrile (2.00 mL) and water (4.00 mL) was treated at room temperature with sodium periodate (622 mg, 2.91 mmol). To this suspension was added RuCl$_3$ (0.2 mg, 0.970 µmol). The reaction mixture was stirred at room temperature overnight. The mixture was concentrated and re-dissolved in water and DCM. The organic layer was separated, dried and concentrated to give a grey powder which was used directly in the next reaction without further purification.

EXAMPLE 213

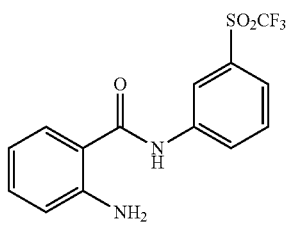

Synthesis of 2-Amino-N-(3-((trifluoromethyl)sulfonyl)phenyl)benzamide

A solution of crude tert-butyl (2((3-(((trifluoromethyl)sulfonyl)phenyl)carbamoyl)phenyl)carbamate (0.430 g, 0.970 mmol) in DCM (10.0 mL) was treated with TFA (5.00 mL) at room temperature. The reaction mixture was stirred at room temperature for 30 minutes. The reaction mixture was concentrated and purified using ISCO on reverse phase column to give the desired product as a TFA salt.

EXAMPLE 214

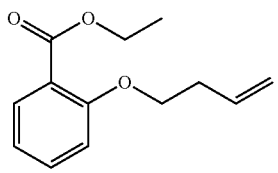 [SMILES: C=CCCOc1ccccc1C(=O)OCC]

Synthesis of Ethyl 2-(but-3-en-1-yloxy)benzoate

A solution of ethyl 2-hydroxybenzoate (0.442 mL, 3.01 mmol) and 4-bromobut-1-ene (1.22 g, 9.03 mmol) in DMF (30.0 mL) was treated at room temperature with $K_2CO_3$ (4.16 g, 30.1 mmol). The reaction mixture was stirred at room temperature overnight. The reaction mixture was filtered and concentrated to give a yellow oil which was used directly in the next reaction without further purification.

EXAMPLE 215

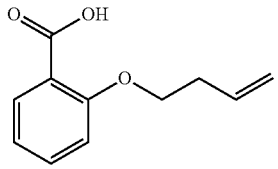

Synthesis of 2-(But-3-en-1-yloxy)benzoic acid

A solution of ethyl 2-(but-3-en-1-yloxy)benzoate (0.66 g, 3.01 mmol) in MeOH (15.0 mL) and water (15.0 mL) was treated at room temperature with LiOH (0.72 g, 30.1 mmol). The reaction mixture was stirred at room temperature overnight. The mixture was cooled to 0° C. and acidified with 1 N HCl until pH=1. The reaction mixture was extracted with DCM and the organic layer was separated, dried and concentrated to give a colorless oil. The crude product was purified on silica gel with a gradient of 5-20% MeOH in DCM to give a colorless oil.

EXAMPLE 216

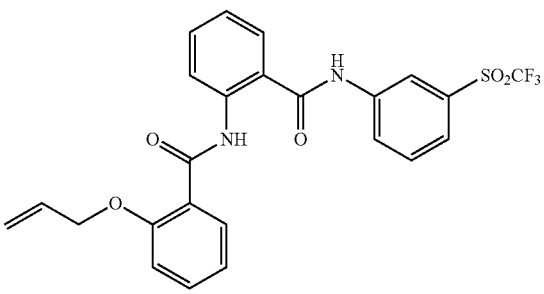

Synthesis of 2-(Allyloxy)-N-(2-((3-((trifluoromethyl)sulfonyl)phenyl)carbamoyl)phenyl)benzamide A solution of 2-amino-N-(3-((trifluoromethyl)sulfonyl)phenyl)benzamide, TFA salt (30.5 mg, 0.067 mmol) in DMF (2.00 mL) was treated at room temperature with 2-(allyloxy)benzoic acid (23.7 mg, 0.13 mmol), HATU (25.3 mg, 0.067 mmol) and DIPEA (0.058 mL, 0.33 mmol). The reaction mixture was stirred at room temperature for 2 days. The crude mixture was purified on ISCO under reverse phase column to give the title product as a grey solid.

EXAMPLE 217

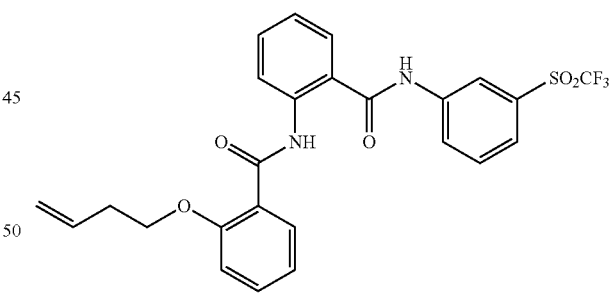

Synthesis of 2-(But-3-en-1-yloxy)-N-(2-((3-((trifluoromethyl)sulfonyl)phenyl)carbamoyl)phenyl)benzamide A solution of 2-amino-N-(3-((trifluoromethyl)sulfonyl)phenyl)benzamide, TFA salt (10.0 mg, 0.022 mmol) in DMF (2.00 mL) was treated at room temperature with 2-(but-3-en-1-yloxy)benzoic acid (8.4 mg, 0.044 mmol), HATU (8.3 mg, 0.022 mmol) and DIPEA (0.019 mL, 0.109 mmol). The reaction mixture was stirred at room temperature for 2 days. The crude mixture was purified on ISCO under reverse phase column to give the title product as a grey solid.

EXAMPLE 218

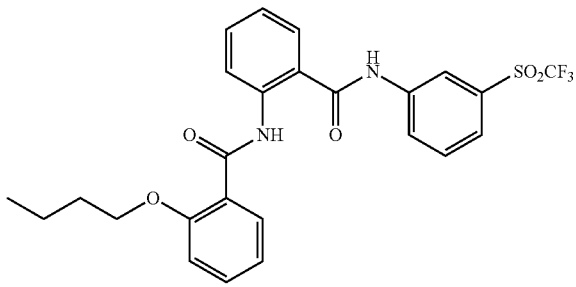

Synthesis of 2-Butoxy-N-(2-((3-((trifluoromethyl) sulfonyl)phenyl) carbamoyl)phenyl)benzamide A solution of 2-(but-3-en-1-yloxy)-N-(2-((3-((trifluoromethyl) sulfonyl)phenyl)carbamoyl)phenyl)benzamide (1.8 mg, 3.47 µmol) in a mixed solvents of THF (0.60 mL) and water (0.20 mL) was treated at 0° C. with ruthenium (III) chloride (1.0 mg, 4.8 µmol). NaBH$_4$ (2.0 mg, 15.2 µmol) was added slowly into the mixture. The reaction mixture was stirred at room temperature for 15 minutes. The reaction mixture was filtered through a pad of celite and purified using reverse phase column to give the desired product as a white powder. In the scaled up reaction, ruthenium (III) chloride can be catalytic and NaBH$_4$ will be 2 equivalents.

EXAMPLE 219

Figure 11:
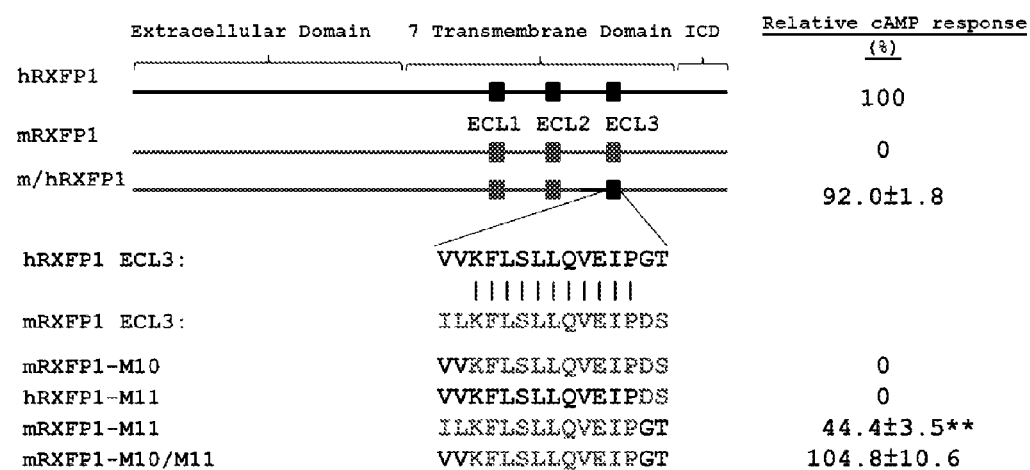
FIG. 11 depicts the identification of a human RXFP1 region responsible for activation by compound 178.

Identification of a Human RXFP1 Region Responsible for Activation by Compound 178 (FIG. 11)

Human RXFP1 (hRXFP1) is fully activated (100%) after treatment with relaxin or compound 178. Mouse RXFP1 (mRXFP1) does not respond to compound 178 (marked as 0%) at 66 µM. The RXFP1 contains the extracellular, 7 transmembrane, and intracellular (ICD) domains. Using chimeric mouse-human receptors (m/hRXFP1) the region responsible for RXFP1 activation by compound 178 was mapped to the part containing extracellular loop 3 (ECL3) of 7 transmembrane domain. Alignment of hRXFP1 and mRXFP1 shows two pairs of diverse amino acids within ECL3. The N-terminal IL to VV substitution in mRXFP1 (mRXFP1-M10) did not change mouse receptor response, whereas C-terminal GT to DS substitution in hRXFP1 (hRXFP1-M11) abolished its compound 178 dependent activation. The mRXFP1-M11 mutant was partially active and the mouse receptor with humanized ECL3 (mRXFP1-M10/M11) was fully active after stimulation with compound 178. The cAMP response to compound 178 (66 µM) in cells transfected with a specific construct was normalized to the response of the same cells to relaxin (15 nM). The results represent the average of 3 independent experiments±s.e.m. repeated in quadruplicates. **P<0.01 vs hRXFP1 by Student's t-test.

EXAMPLE 220

Pharmacokinetics of Compound 178 (NCGC00250135)

The pharmacokinetics of compound 178 (NCGC00250135) were determined in male C57/Bl6 mice after a single intravenous (IV) administration of 3 mg/kg and oral (PO) administration of 30 mg/kg of compound 178. The data is present in TABLE 11.

TABLE 11

| Parameter | Units | IV (plasma) | PO (plasma) | IV (heart) | PO (heart) |
|---|---|---|---|---|---|
| AUClast | hr*ng/mL | 703 | 980 | 5190 | 2630 |
| AUCINF_obs | hr*ng/mL | 745 | 1000 | 5690 | 2680 |
| Cl_obs | mL/min/kg | 67.2 | | 8.78 | |
| AUMClast | hr*hr*ng/mL | 3110 | 2990 | 28300 | 5780 |
| MRTlast | hr | 4.4 | 3.1 | 5.5 | 2.2 |
| Vss_obs | L/kg | 24.5 | | 4.2 | |
| t½ | hr | 6.6 | 5.5 | 6.3 | 1.0 |
| C0 | ng/mL | 499 | | 2930 | |
| Tmax | hr | | 0.5 | | 1.5 |
| Cmax | ng/mL | | 306 | | 1030 |
| Bioavailablity (BA) | | | 14% | | |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Embodiments of this disclosure are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A compound or pharmaceutically acceptable salt thereof, having the formula

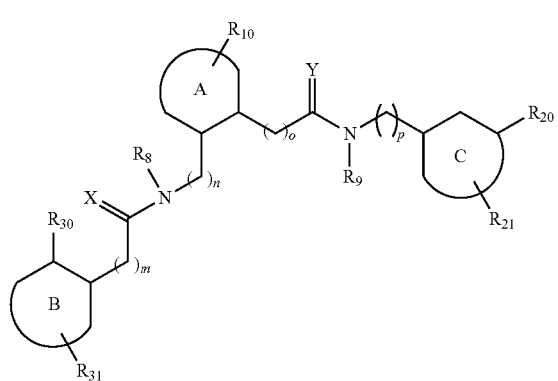

where

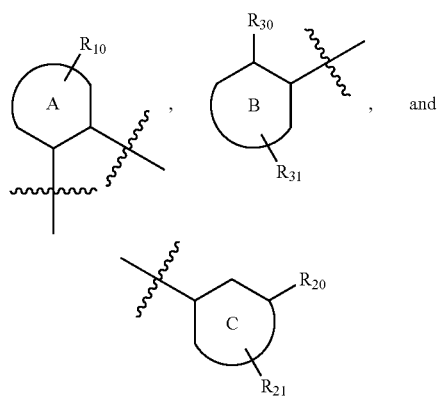

are each phenyl;

m, n, o, and p are integers independently chosen from 0, 1, and 2 and each of

is unsubstituted or substituted with one or more substituents independently chosen from halogen, hydroxyl, $C_1$-$C_2$alkyl, and $C_1$-$C_2$alkoxy;

X and Y are independently chosen from O and S;

$R_8$ and $R_9$ are independently chosen from hydrogen and $C_1$-$C_4$alkyl;

$R_{10}$, $R_{21}$, and $R_{31}$ are each 0 to 3 substituents independently chosen from hydroxyl, halogen, nitro, cyano, amino, $C_1$-$C_4$alkyl, $C_1$-$C_4$alkoxy, mono- and di-($C_1$-$C_2$alkyl)amino-, $C_1$-$C_2$haloalkyl, and $C_1$-$C_2$haloalkoxy;

$R_{20}$ is $C_1$-$C_{10}$haloalkyl, $C_1$-$C_{10}$haloalkoxy, —$SR_7$, —$SOR_7$, or —$SO_2R_7$, where $R_7$ is $C_1$-$C_{10}$carbyhdryl or $C_1$-$C_{10}$haloalkyl;

$R_{30}$ is hydrogen or $R_{30}$ is $C_1$-$C_8$carbhydryloxy or $C_1$-$C_8$carbhydrylthio- each or which is substituted with 0 to 3 substituents independently chosen from hydroxyl, halogen, nitro, cyano, $C_1$-$C_4$alkyl, $C_1$-$C_4$alkoxy, $C_1$-$C_2$haloalkyl, and $C_1$-$C_2$haloalkoxyl.

2. The compound or salt of claim 1, wherein the compound is selected from the group consisting of:

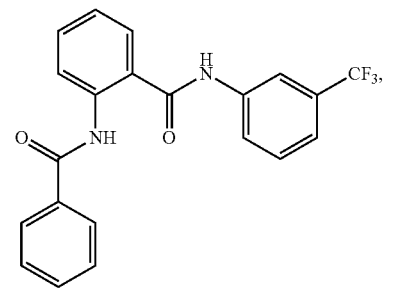

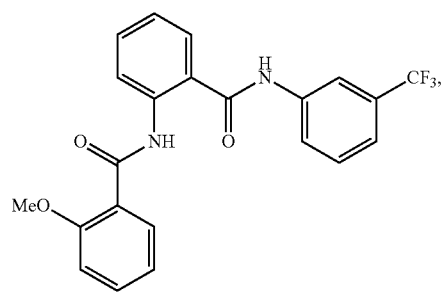

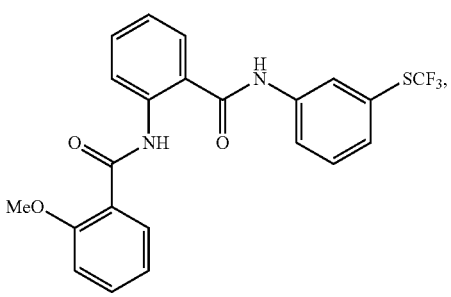

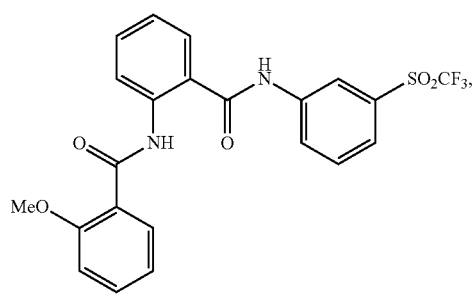

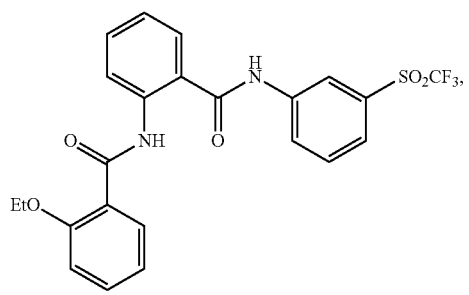

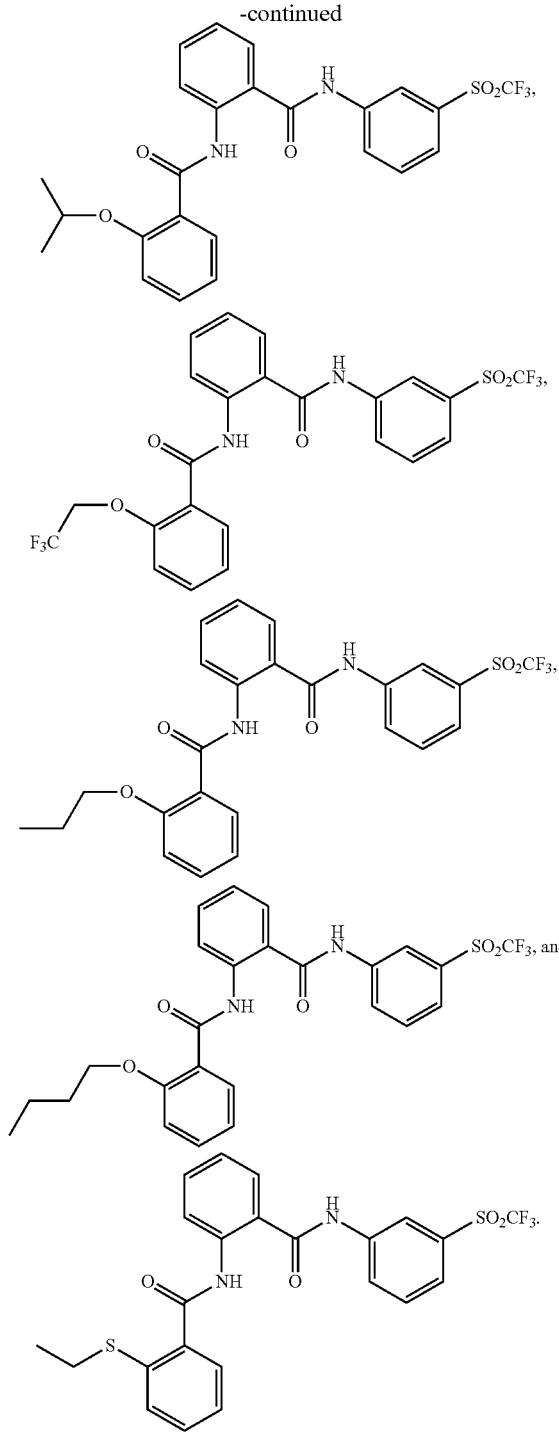
3. A method for treating myocardial ischemia-reperfusion injury, cardiac fibrosis, acute congestive heart failure, post-infarction heart, or myocardial infarction in a patient, the method comprising administering to the patient an effective amount of a compound or salt of claim 1.
4. The method of claim 2, wherein the compound is selected from the group consisting of:
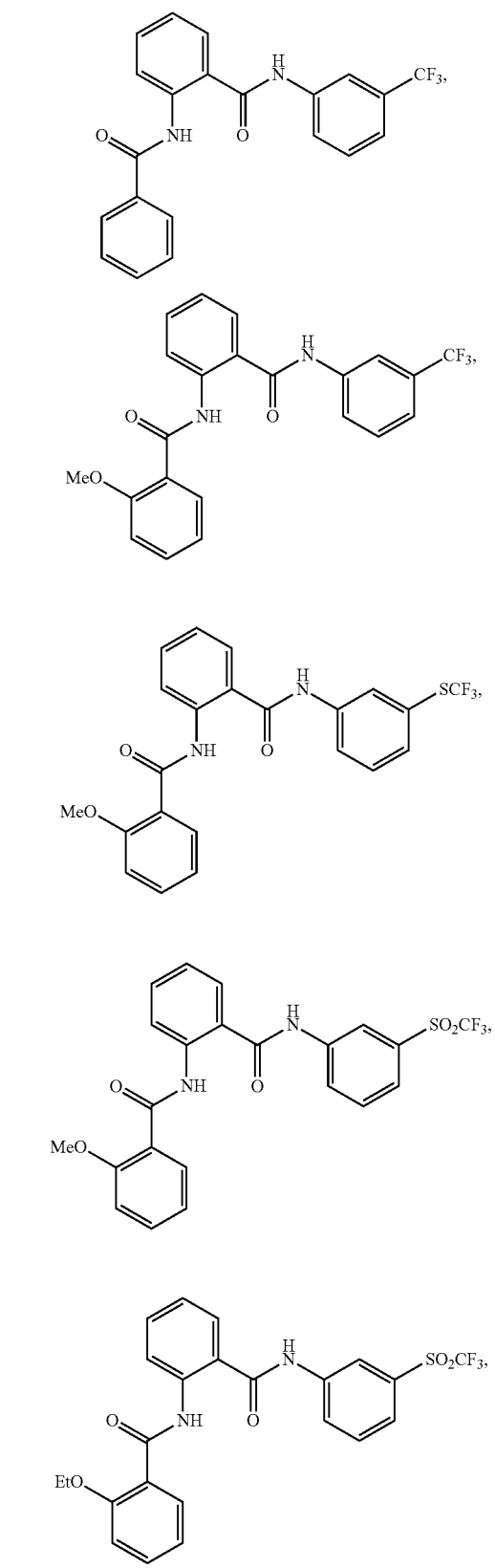

-continued

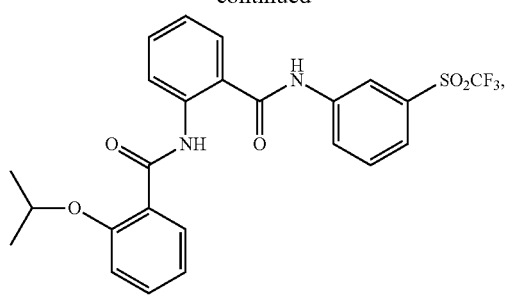

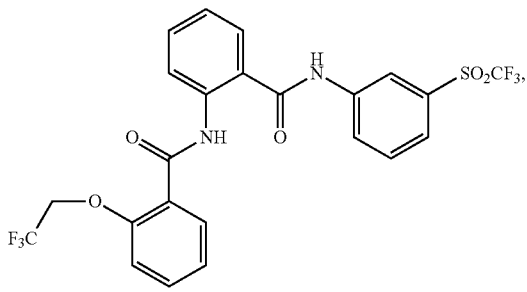

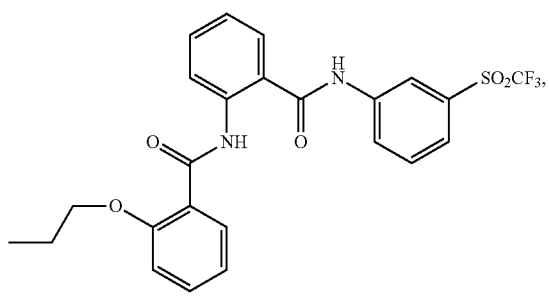

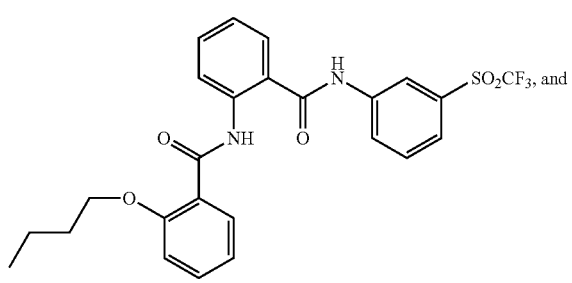

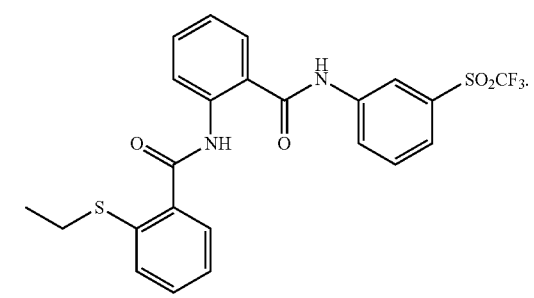

5. A compound or salt thereof of claim 1, having the formula

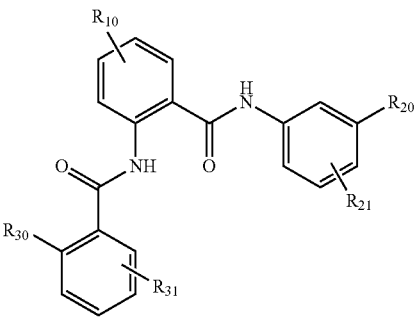

where:
R$_{10}$, R$_{21}$, and R$_{31}$ are each 0 to 3 substitutents independently chosen from hydroxyl, halogen, nitro, cyano, amino, C$_1$-C$_4$alkyl, C$_1$-C$_4$alkoxy, mono- and di-(C$_1$-C$_2$alkyl)amino-, C$_1$-C$_2$haloalkyl, and C$_1$-C$_2$haloalkoxy;
R$_{20}$ is C$_1$-C$_{10}$haloalkyl, C$_1$-C$_{10}$haloalkoxy, —SR$_7$, —SOR$_7$, or —SO$_2$R$_7$, where R$_7$ is C$_1$-C$_{10}$alkyl or C$_1$-C$_{10}$haloalkyl;
R$_{30}$ is hydrogen or R$_{30}$ is C$_1$-C$_8$alkoxy or C$_1$-C$_8$alkylthio- each or which is substituted with 0 to 3 substituents independently chosen from hydroxyl, halogen, nitro, cyano, C$_1$-C$_4$alkyl, C$_1$-C$_4$alkoxy, C$_1$-C$_2$haloalkyl, and C$_1$-C$_2$haloalkoxy.

6. A compound or salt thereof of claim 5, wherein R$_{20}$ is SO$_2$CF$_3$.

7. A compound or pharmaceutically acceptable salt thereof of claim 1, having the formula

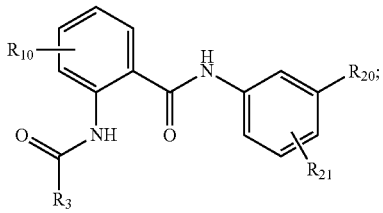

where:
R$_{10}$ and R$_{21}$ are each 0 to 3 substituents independently chosen from hydroxyl, halogen, nitro, cyano, amino, C$_1$-C$_4$alkyl, C$_1$-C$_4$alkoxy, mono- and di-(C$_1$-C$_2$alkyl) amino-, C$_1$-C$_2$haloalkyl, and C$_1$-C$_2$haloalkoxy;
R$_{20}$ is C$_1$-C$_{10}$haloalkyl, C$_1$-C$_{10}$haloalkoxy, —SR$_7$, —SOR$_7$, or —SO$_2$R$_7$, where R$_7$ is C$_1$-C$_{10}$carbhydryl or C$_1$-C$_{10}$haloalkyl; and
R$_3$ is phenyl substituted with one or more substituents independently chosen from hydroxyl, halogen, nitro, cyano, amino, SCF$_3$, SO$_2$CF$_3$, C$_1$-C$_6$alkyl, C$_2$-C$_6$alkenyl, C$_2$-C$_6$alkynyl, phenyl mono- and di-C$_1$-C$_6$alkylamino, C$_1$-C$_6$alkylthio, C$_1$-C$_6$alkylsulfonyl, C$_1$-C$_4$alkoxy, C$_1$-C$_2$haloalkyl, and C$_1$-C$_2$haloalkoxy.

8. A compound or salt of claim 1, wherein m, n, o, and p are all 0, X and Y are both 0; and R$_8$ and R$_9$ are both hydrogen.

9. A compound or salt of claim 1, wherein R$_{20}$ is C$_1$-C$_6$haloalkyl, —S(C$_1$-C$_6$haloalkyl), or —SO$_2$(C$_1$-C$_6$haloalkyl).

10. A compound or salt thereof of claim 9 wherein R$_{10}$, R$_{21}$, and R$_{31}$ are each 0 substituents.

11. A compound or salt thereof of claim 9, wherein $R_{20}$ is $CF_3$, $SCF_3$, or $SO_2CF_3$, and $R_{30}$ is $C_2$-$C_6$alkoxy or $C_2$-$C_6$alkylthio-, each of which is substituted with 0 to 2 substituents independently chosen from halogen and —$CF_3$.

12. A compound or salt of claim 1, where $R_{30}$ is $C_1$-$C_8$alkoxy or $C_1$-$C_8$alkylthio, and $R_{31}$ is absent or cyano.

13. A compound or salt of claim 1, where $R_{20}$ is $C_1$-$C_6$haloalkyl, —S($C_1$-$C_6$haloalkyl), or —$SO_2$($C_1$-$C_6$haloalkyl); and $R_{21}$ is absent.

14. A compound or salt thereof of claim 5, wherein $R_{10}$, $R_{21}$, and $R_{31}$ are each 0 substituents; $R_{20}$ is $CF_3$, $SCF_3$, or $SO_2CF_3$, and $R_{30}$ is $C_2$-$C_6$alkoxy or $C_2$-$C_6$alkylthio-, each of which is substituted with 0 to 2 substituents independently chosen from halogen and —$CF_3$.

15. A compound or salt of claim 7, wherein $R_{10}$ and $R_{21}$ are both 0 substituents and $R_3$ is phenyl substituted with one meta-position substituent.

16. A compound or salt of claim 7, wherein $R_{10}$ and $R_{21}$ are both 0 substituents and $R_{20}$ is $CF_3$, $SCF_3$, or $SO_2CF_3$.

17. A compound or salt of claim 7, wherein $R_{20}$ is $CF_3$ or $SO_2CF_3$; and $R_3$ is phenyl substituted with one or more substituents independently chosen from hydroxyl, halogen, nitro, cyano, amino, $SCF_3$, $SO_2CF_3$, $C_1$-$C_6$alkyl, $C_2$-$C_6$alkenyl, $C_2$-$C_6$alkynyl, phenyl mono- and di-$C_1$-$C_6$alkylamino, $C_1$-$C_6$alkylthio, $C_1$-$C_6$alkylsulfonyl, $C_1$-$C_4$alkoxy, $C_1$-$C_2$haloalkyl, and $C_1$-$C_2$haloalkoxy.

18. A compound or salt thereof, wherein the compound is selected from

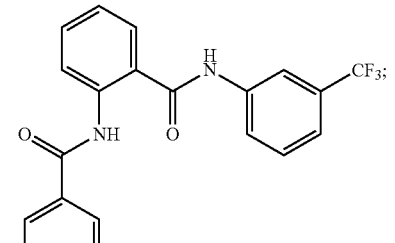

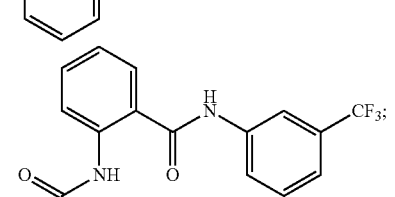

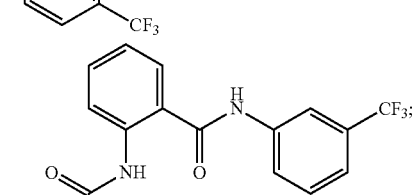

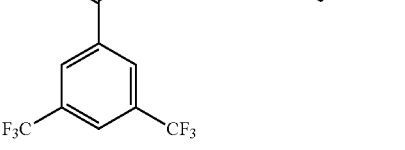

-continued

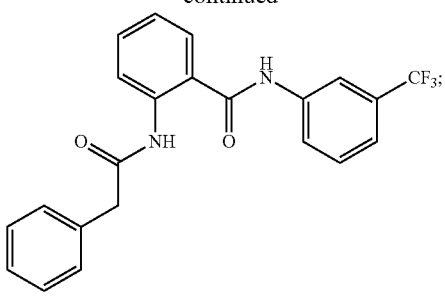

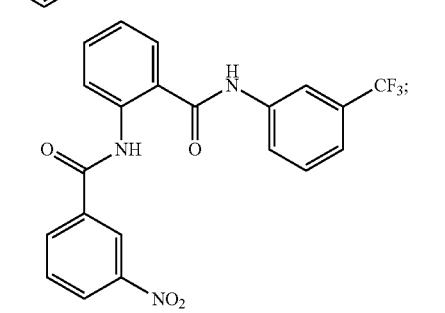

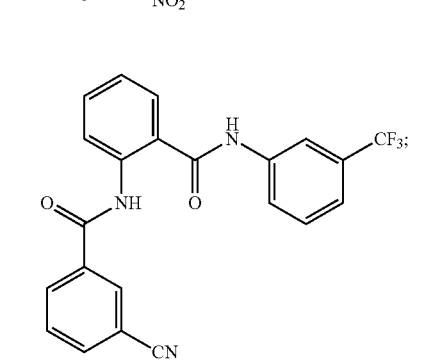

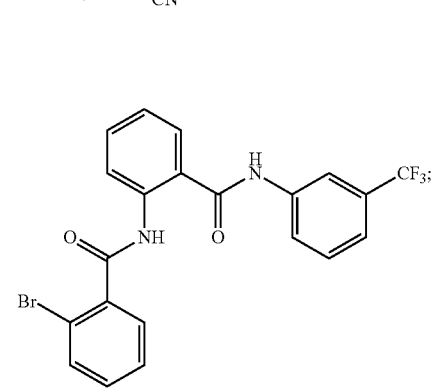

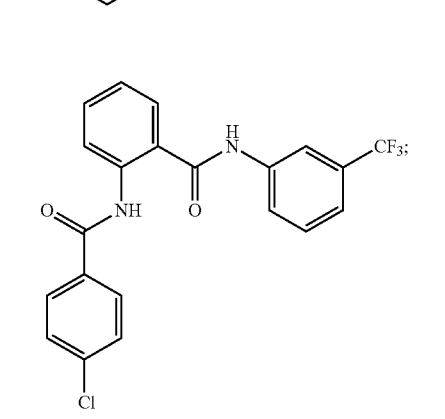

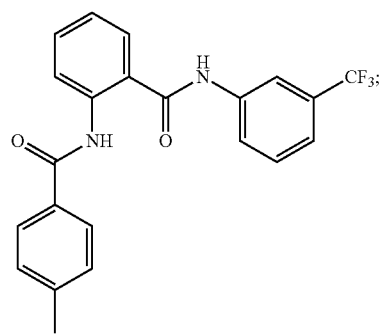
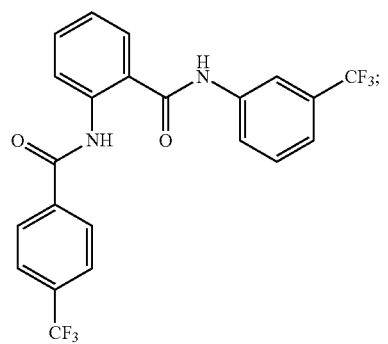
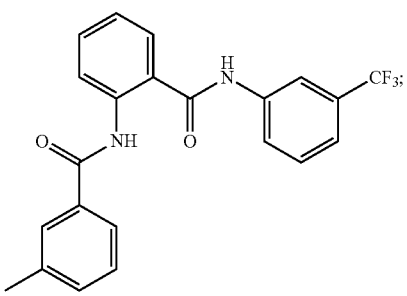
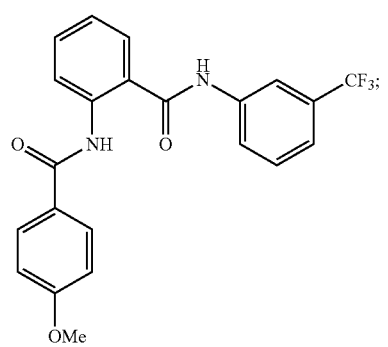
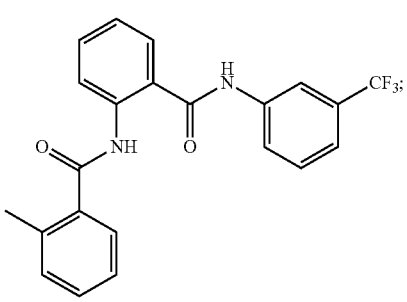
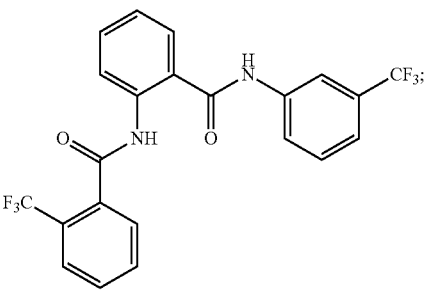
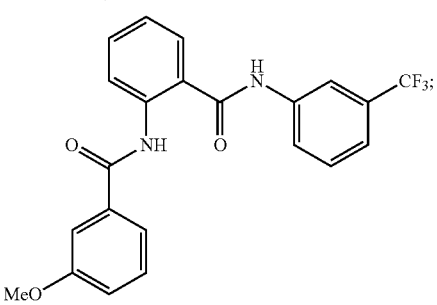
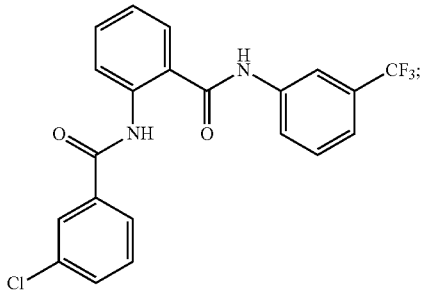
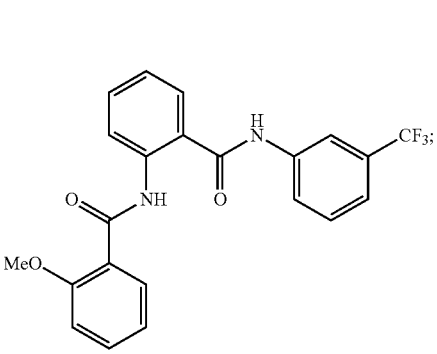
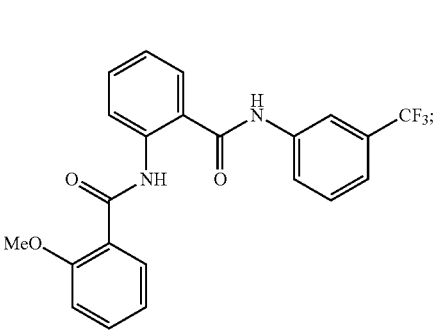

-continued
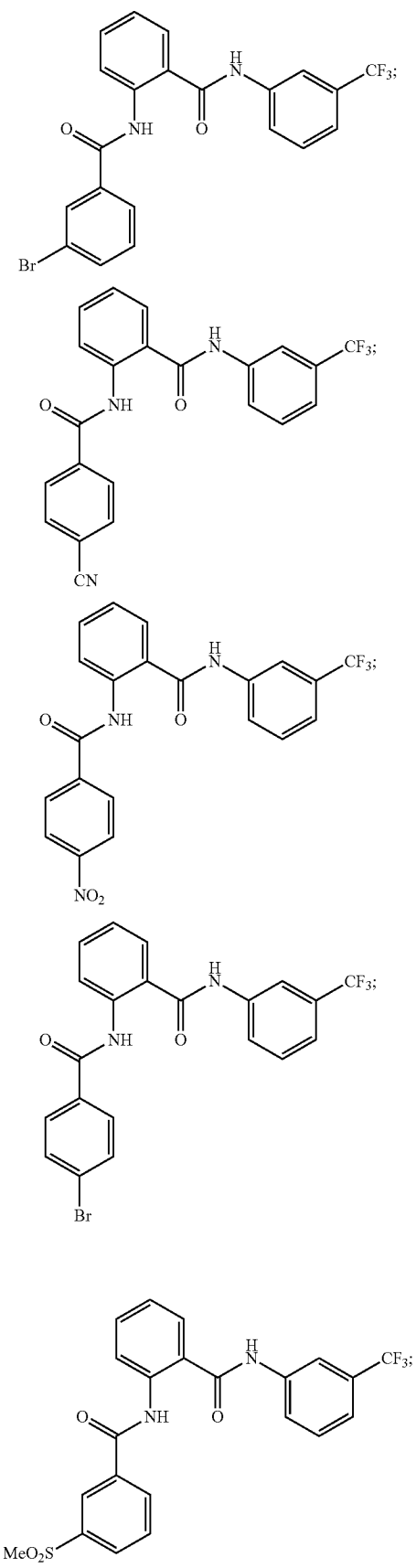
-continued
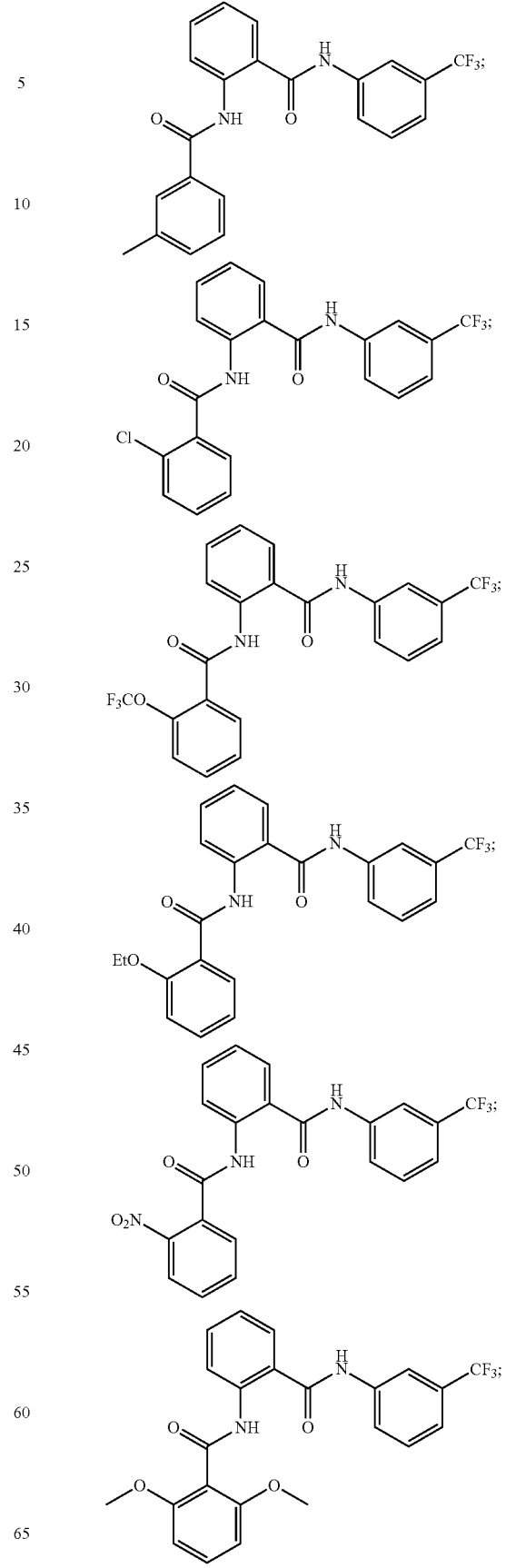

183
-continued
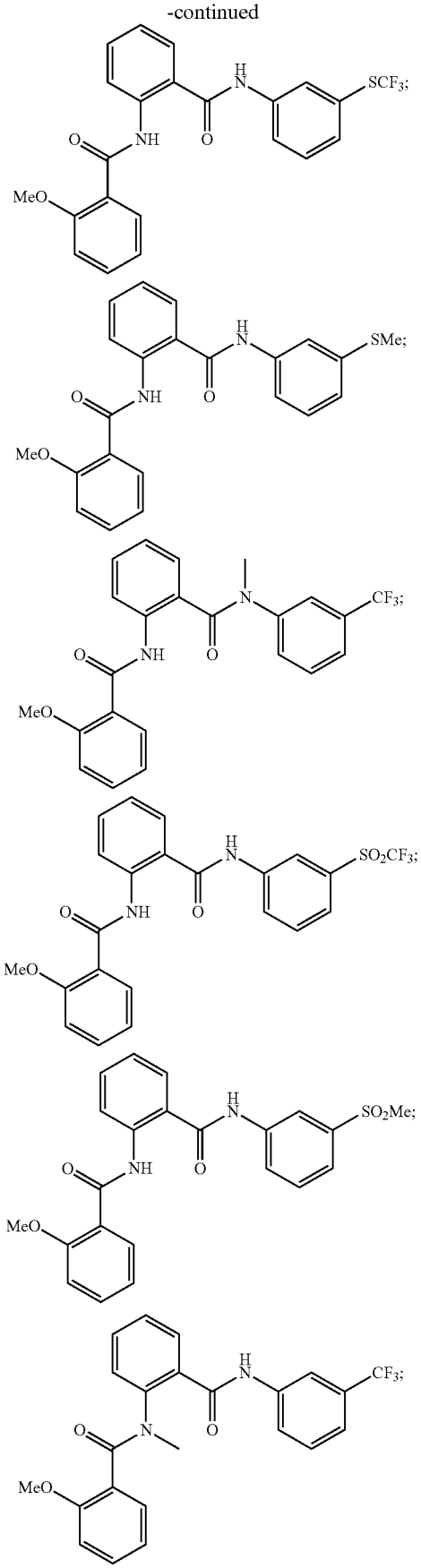
184
-continued
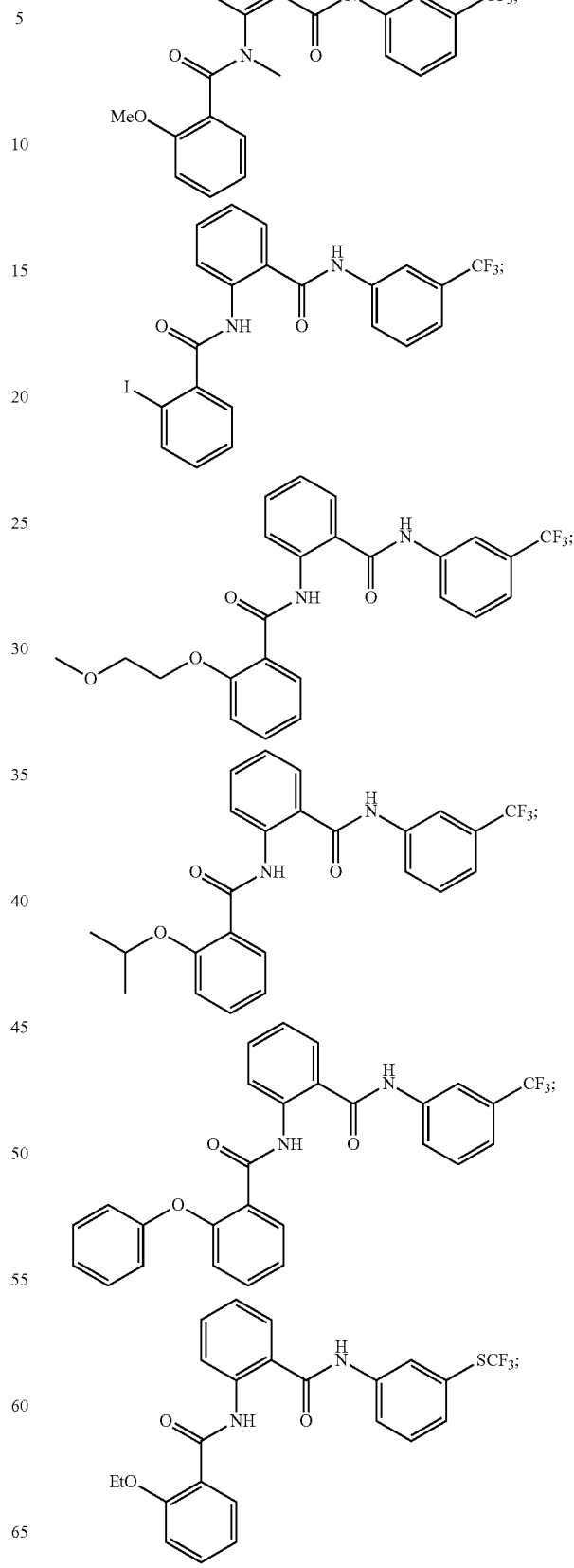

185
-continued
186
-continued
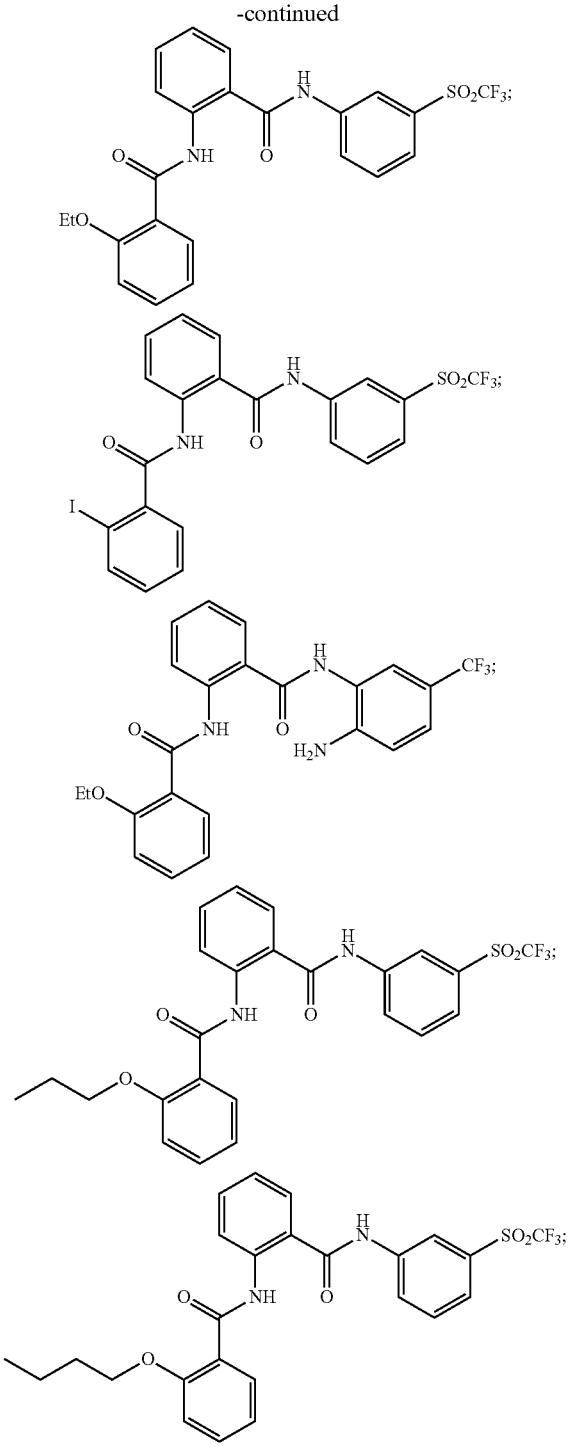
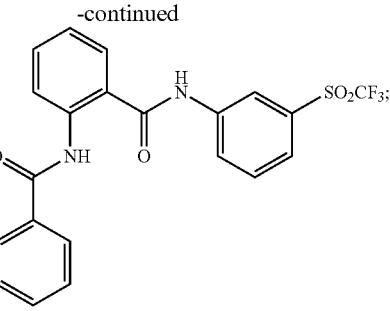
* * * * *

UNITED STATES PATENT AND TRADEMARK OFFICE
CERTIFICATE OF CORRECTION

| | | |
|---|---|---|
| PATENT NO. | : 9,452,973 B2 | Page 1 of 1 |
| APPLICATION NO. | : 14/398830 | |
| DATED | : September 27, 2016 | |
| INVENTOR(S) | : Juan Jose Marugan et al. | |

It is certified that error appears in the above-identified patent and that said Letters Patent is hereby corrected as shown below:

In Column 1, Line 15, please make the following change:
"This invention was made in part with government support from the National Institutes of Health."
should be changed to "This invention was made with government support under R03 MH085705 awarded by the National Institutes of Health."

Signed and Sealed this
Fifteenth Day of May, 2018

Andrei Iancu
*Director of the United States Patent and Trademark Office*